(12) United States Patent
Langenbach et al.

(10) Patent No.: US 12,215,332 B2
(45) Date of Patent: Feb. 4, 2025

(54) METHOD OF INCREASING RESISTANCE AGAINST SOYBEAN RUST IN TRANSGENIC PLANTS BY INCREASING THE SCOPARONE

(71) Applicant: BASF PLANT SCIENCE COMPANY GMBH, Ludwigshafen (DE)

(72) Inventors: Caspar Langenbach, Aachen (DE); Uwe Conrath, Aachen (DE); Patrick Schwinges, Aachen (DE); Sebastian Beyer, Aachen (DE); Holger Schultheiss, Einbeck (DE); David Spencer, Aachen (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 126 days.

(21) Appl. No.: 17/413,037

(22) PCT Filed: Dec. 13, 2019

(86) PCT No.: PCT/EP2019/085118
§ 371 (c)(1),
(2) Date: Jun. 11, 2021

(87) PCT Pub. No.: WO2020/120753
PCT Pub. Date: Jun. 18, 2020

(65) Prior Publication Data
US 2023/0022475 A1    Jan. 26, 2023

(30) Foreign Application Priority Data
Dec. 14, 2018   (EP) ..................... 18212497

(51) Int. Cl.
C12N 15/82    (2006.01)
A61K 8/49    (2006.01)

(52) U.S. Cl.
CPC .......... *C12N 15/8282* (2013.01); *A61K 8/498* (2013.01); *C12Y 201/01068* (2013.01)

(58) Field of Classification Search
CPC ............ C12Y 201/01068; A61K 8/498; C12N 15/8282
See application file for complete search history.

(56) References Cited

U.S. PATENT DOCUMENTS 10,570,412 B2 *   2/2020   Schultheiss ............ C12Y 114/11

FOREIGN PATENT DOCUMENTS

| WO | WO-0071736 A1 * | 11/2000 | ......... C12N 15/8243 |
|---|---|---|---|
| WO | WO-2007/047518 A2 | 4/2007 | |
| WO | WO-2016124515 A1 * | 8/2016 | ......... C07K 14/415 |

OTHER PUBLICATIONS

GenBank_ID_U19911.1., Submitted Jan. 17, 1995.*
Van de Mortel et al., 2007, Distinct biphasic mRNA changes in response to Asian soybean rust infection. Molecular Plant-Microbe Interactions, 20(8), 887-899. (Year: 2007).*
Kai et al., 2008, Scopoletin is biosynthesized via ortho-hydroxylation of feruloyl CoA by a 2-oxoglutarate-dependent dioxygenase in *Arabidopsis thaliana*. The Plant Journal, 55(6), 989-999. (Year: 2008).*
Lam et al., 2007, Structure, function, and evolution of plant O-methyltransferases. Genome, 50(11), 1001-1013. (Year: 2007).*
Panday et al., 2011, Functional analysis of the Asian soybean rust resistance pathway mediated by Rpp2. Molecular Plant-Microbe Interactions, 24(2), 194-206. (Year: 2011).*
Definition of Derivative. National Cancer Institute Dictionary. https://www.cancer.gov/publications/dictionaries/cancer-terms/def/derivative. Accessed Jul. 28, 2023. (Year: 2023).*
Tal et al., 1985, The induction, by fungal inoculation, of ayapin and scopoletin biosynthesis in *Helianthus annuus*. Phytochemistry, 25(1), 77-79. (Year: 1985).*
Guo et al., 2004, Protein tolerance to random amino acid change. Proceedings of the National Academy of Sciences, 101(25), 9205-9210. (Year: 2004).*
Goellner et al., 2010, *Phakopsora pachyrhizi*, the causal agent of Asian soybean rust. Molecular plant pathology, 11(2), 169-177. (Year: 2010).*
Dubery et al., 6,7-Dimethoxycoumarin: a stress metabolite with antifungal activity in gamma-irradiated citrus peel, South African Journal of Science, vol. 83, pp. 440-441 (1987).
International Application No. PCT/EP2019/085118, International Search Report and Written Opinion, mailed Apr. 7, 2020.
Jeandet et al., Modulation of phytoalexin biosynthesis in engineered plants for disease resistance, Int. J. Mol. Sci., 14(7):14136-70 (2013).
Kim et al., Production of three O-methhylated esculetins with *Escherichia coli* expressing O-methyltransferase from poplar, Biosci. Biotechnol. Biochem., 70(5):1269-72 (2006).
Langenbach et al., Fighting Asian Soybean Rust, Front Plant Sci., 7:797 (2016).

(Continued)

*Primary Examiner* — David H Kruse
*Assistant Examiner* — Santosh Sharma
(74) *Attorney, Agent, or Firm* — MARSHALL, GERSTEIN & BORUN LLP

(57) ABSTRACT

The present invention pertains to the field of imparting or increasing resistance against fungal pathogens, in particular soy-beanrust, in plants, plant parts, and/or plant cells. This is achieved by increasing the content of scopoletin, scopolin and/or, most preferably, scoparone (6,7-di-methoxycoumarin) in a plant, plant part and/or plant cell. This can in particular be achieved by establishing and/or increasing the expression of an OMT3 enzyme and an F6H1 protein in the respective plant, plant part and/or plant cell; a further way would be to apply a formulation or solution containing scopoletin and/or, most preferably, scoparone to the plant, plant part and/or plant cell. The invention correspondingly also provides proteins, enzymes, expression constructs, plants, plant parts and/or plant cells. In this respect the invention also provides variants of the OMT3 enzyme.

Figure 1:
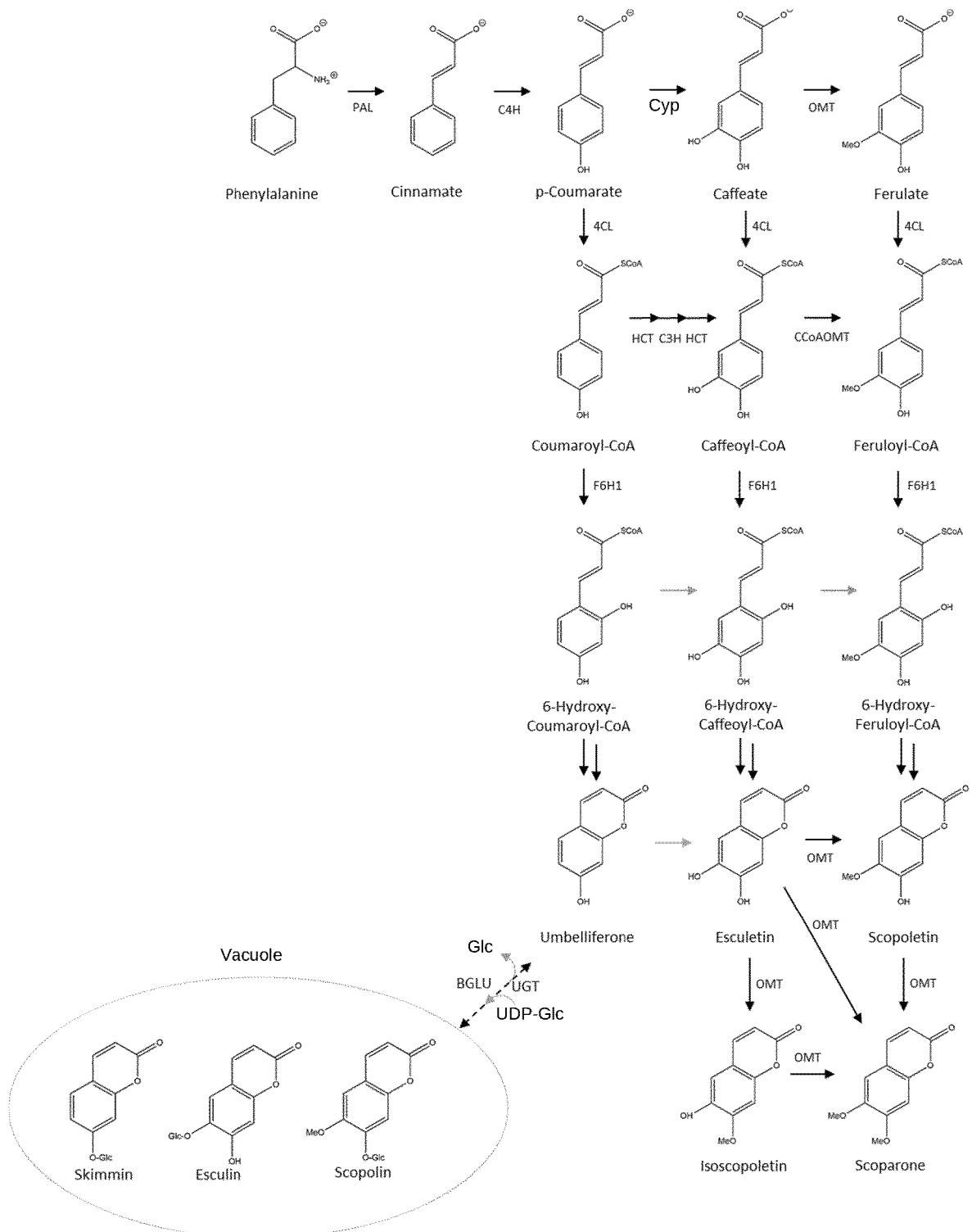

2 Claims, 6 Drawing Sheets
Specification includes a Sequence Listing.

(56) References Cited

OTHER PUBLICATIONS

Soria-Guerra et al., Transcriptome analysis of resistant and susceptible genotypes of *Glycine tomentella* during *Phakopsora pachyrhizi* infection reveals novel rust resistance genes, Theor. Appl. Genet., 120(7):1315-33 (2010).
UniProtKB—A0A251U7E8, downloaded from the Internet: <https://www.uniprot.org/uniprot/A0A251U7E8> (2017).
Stringlis, et al., "MYB72-dependent coumarin exudation shapes root microbiome assembly to promote plant health", Proceedings of the National Academy of Sciences of the United States of America, vol. 115, Issue 22, Apr. 23, 2018, pp. E5213-E5222.

* cited by examiner

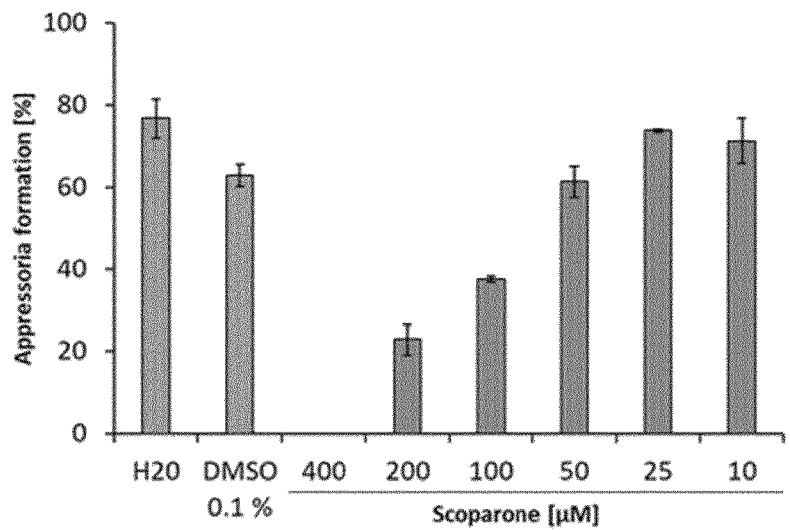
Figure 2
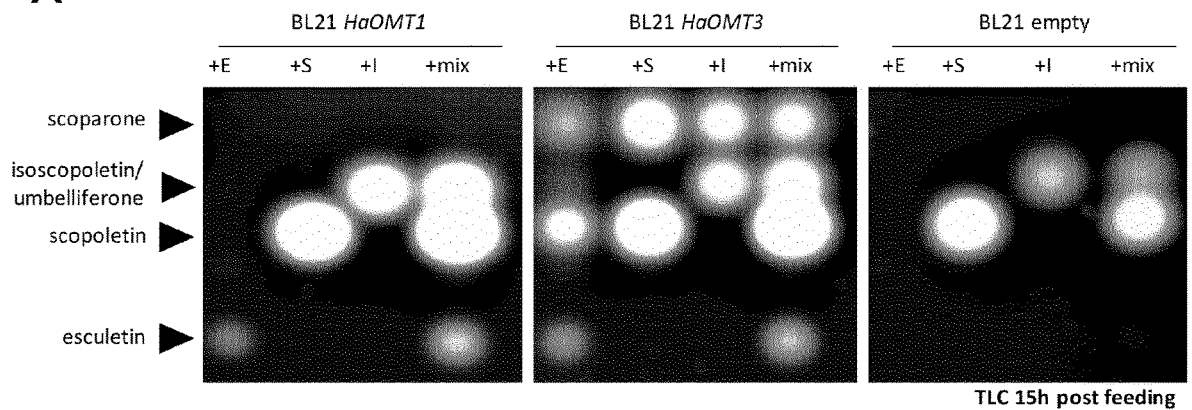
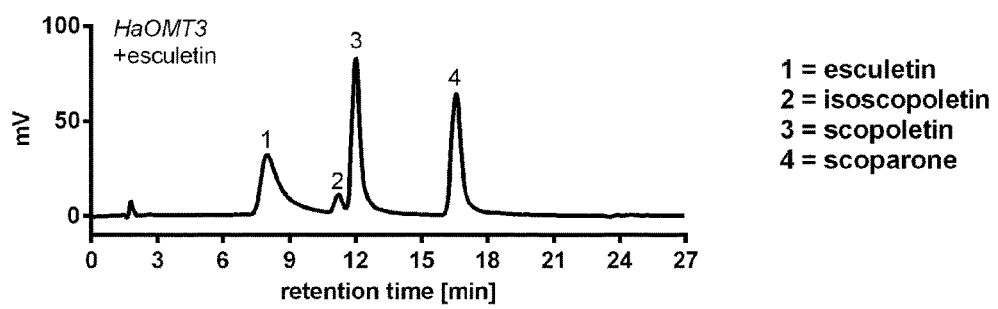
Figure 3

A

```
AtF6H1    1  maptlltqfsmpaevdfvvykgngvkglsetgikalpeqriqpleerlinkfvnstde-aipvrldmsnpdedrvaeavcdaaekrgftqvihgvplevlddvkaathkffnlpveekrkftkenslstc
IbF6H1    1  mpsttlstvls---dinefvvkqghghgvkglseiglqtlpndgvhppeerlsmdv-vsdd-sipvrldvsnwedpkvaklicdaaekrgtqivnhgiplemlekakaetyrffrepaekkkyekencptsh
HaF6H1    1  mapsismcp-snpldildfvvnkghgvkgladigliktiphqrlqppqerfdhtsneelnedsipvldlsnsddpkvakavcdaaqkrgtiinhgiplhvlgnvkdathkffelpaeekkkyskeqsgtnnr AtF6H1  160  aaaeqfspdicrnetleyinkskkmavrrlleylgktninvkeidetkeslfmqsirvnlnypicppditvgrhsdvssltillqddqigglhvrslasgnvvhvppyragsfvrinigdamqimsnglyksv
IbF6H1  156  eaadyvppscrddaleylkscemvsrklleaimqginvneiddakesllmgsrrininyypkcpnpditvgrhsdistltillqddigglvvrklcheawshvppvkgalvrinigdalqimsngryksl
HaF6H1  160  dsaaslvpaicrneqleylrsseetvvhrllkiimngivnvkidstkeslmgskrininyypkcpnpelvgvgrhsdvstltillqddigglyrntkcmeavhvppyngslvinvgdalqimsngkyksv AtF6H1  320  plpeviangeeplyrdvlysdykyffrkahdgkktvdyaki-
IbF6H1  316  plpevlasgekpyykpvvlysdyakhfyrkahngkdtiafarie
HaF6H1  320  plvemvesgekpiykhvlysdyvkhffrkahdgkatidfakv-
```

Global Protein alignment. Reference molecule: AtF6H1, Region 1 to 361
Sequences: 3. Scoring matrix: BLOSUM 62

| Sequence | Start | End | #Match | NonMatch | %Match |
|---|---|---|---|---|---|
| AtF6H1 | 1 | 361 | | | |
| IbF6H1 | 1 | 358 | 218 | 144 | 60 |
| HaF6H1 | 1 | 361 | 242 | 120 | 66 |

B

Figure 5

SEQUENCE LISTING

<160> NUMBER OF SEQ ID NOS: 57

<210> SEQ ID NO 1
<211> LENGTH: 1117
<212> TYPE: DNA
<213> ORGANISM: Helianthus annuus
<220> FEATURE:
<221> NAME/KEY: misc_feature
<223> OTHER INFORMATION: OMT3

<400> SEQUENCE: 1

```
atgggttcaa catcagcctc tgtgaacgtt ctactggaag caaaccaaga tgatcaatct      60
ttcctgtttg caatgcaatt ggcatctgca tctgtcttgc caatggtgtt gaaaaccgcc     120
atcgagcttg atttgcttga gaccattgcg aaagctggtc caggtggttc gctttcgtct     180
tctgaactgg tggctcagct tcccaaggtt aacaaccccg aagcaccagt gatggtggac     240
cggatttgta gacttttggc tagctattct gtgctcacat gtactctcaa ggagaccatg     300
gatgggtgcg ctgagcggtt ctatggtgtg gctccggtgt gcaagttctt gaccaagaat     360
gatagtggtg tttcgttagc acccttgttg ctcatgaacc aggacaaggt tttcatggag     420
agctggtact ttctaaaaga cgcggttttg gatggtggaa tcccatccaa caaagcttat     480
ggtatgccgg cattcgaata ttatgggaaa gatcaaagat ttaacaaggt tttcaatagt     540
```

```
gcaatgttta atcattccac catgacgatg aaaaagatta tagatttgta cgatggtttt      600
agtagtctcg aaacactagt tgatgttggt ggtggcactg gtgcaagcct taacatgatc      660
acctctaaac atacttcact caagggtata aactttgatt tgccacatgt tattgaagat      720
gccacaactt atcatggtat tgagcatgtt ggaggagata tgtttgaaag tgtaccgaaa      780
ggagatgcta tatttatgaa gtggatactt catgactgga gtgatgcact ctgcctgcaa      840
gttcttaaga actgctacaa atcacttcca aaaaatggga agtcattgt ggcagaatgc       900 attctttctg aggcacccga ctcgactcca gctacccaaa atgtaataca tatcgacgcg      960
attatgttgg ttcacagcct gggtggcaaa gagagaactg agaaagaatt tgaggcttta     1020
gctaaagcag caggttttaa aggtttcaac aaggctgctt gtgctctcaa tacatgggtt     1080
atggaatttt gcaaataggc ggccgcatcg tgactga                              1117
```

<210> SEQ ID NO 2
<211> LENGTH: 365
<212> TYPE: PRT
<213> ORGANISM: Helianthus annuus
<220> FEATURE:
<221> NAME/KEY: MISC_FEATURE
<223> OTHER INFORMATION: OMT3

<400> SEQUENCE: 2

```
Met Gly Ser Thr Ser Ala Ser Val Asn Val Leu Leu Glu Ala Asn Gln
1               5                   10                  15

Asp Asp Gln Ser Phe Leu Phe Ala Met Gln Leu Ala Ser Ala Ser Val
            20                  25                  30

Leu Pro Met Val Leu Lys Thr Ala Ile Glu Leu Asp Leu Leu Glu Thr
        35                  40                  45

Ile Ala Lys Ala Gly Pro Gly Gly Ser Leu Ser Ser Glu Leu Val
    50                  55                  60

Ala Gln Leu Pro Lys Val Asn Asn Pro Glu Ala Pro Val Met Val Asp
65                  70                  75                  80

Arg Ile Cys Arg Leu Leu Ala Ser Tyr Ser Val Leu Thr Cys Thr Leu
                85                  90                  95

Lys Glu Thr Met Asp Gly Cys Ala Glu Arg Phe Tyr Gly Val Ala Pro
            100                 105                 110

Val Cys Lys Phe Leu Thr Lys Asn Asp Ser Gly Val Ser Leu Ala Pro
        115                 120                 125

Leu Leu Leu Met Asn Gln Asp Lys Val Phe Met Glu Ser Trp Tyr Phe
    130                 135                 140

Leu Lys Asp Ala Val Leu Asp Gly Gly Ile Pro Ser Asn Lys Ala Tyr
145                 150                 155                 160

Gly Met Pro Ala Phe Glu Tyr Tyr Gly Lys Asp Gln Arg Phe Asn Lys
                165                 170                 175

Val Phe Asn Ser Ala Met Phe Asn His Ser Thr Met Thr Met Lys Lys
            180                 185                 190

Ile Ile Asp Leu Tyr Asp Gly Phe Ser Ser Leu Glu Thr Leu Val Asp
        195                 200                 205

Val Gly Gly Gly Thr Gly Ala Ser Leu Asn Met Ile Thr Ser Lys His
    210                 215                 220

Thr Ser Leu Lys Gly Ile Asn Phe Asp Leu Pro His Val Ile Glu Asp
225                 230                 235                 240

Ala Thr Thr Tyr His Gly Ile Glu His Val Gly Gly Asp Met Phe Glu
                245                 250                 255
```

Ser Val Pro Lys Gly Asp Ala Ile Phe Met Lys Trp Ile Leu His Asp
            260                 265                 270

Trp Ser Asp Ala Leu Cys Leu Gln Val Leu Lys Asn Cys Tyr Lys Ser
        275                 280                 285

Leu Pro Lys Asn Gly Lys Val Ile Val Ala Glu Cys Ile Leu Ser Glu
    290                 295                 300

Ala Pro Asp Ser Thr Pro Ala Thr Gln Asn Val Ile His Ile Asp Ala
305                 310                 315                 320

Ile Met Leu Val His Ser Leu Gly Gly Lys Glu Arg Thr Glu Lys Glu
                325                 330                 335

Phe Glu Ala Leu Ala Lys Ala Ala Gly Phe Lys Gly Phe Asn Lys Ala
            340                 345                 350

Ala Cys Ala Leu Asn Thr Trp Val Met Glu Phe Cys Lys
        355                 360                 365

<210> SEQ ID NO 3
<211> LENGTH: 1653
<212> TYPE: DNA
<213> ORGANISM: Helianthus annuus
<220> FEATURE:
<221> NAME/KEY: misc_feature
<223> OTHER INFORMATION: 4CL2

<400> SEQUENCE: 3
atgccaactt tgtacaaaaa agcaggctca atggcgccgg agaaggagat aattttccgt      60
tcaaagctcc cagatatata cataccaaaa cacctaccgt acactcata ctgtttcgaa     120 aacatttcta ccttcaataa ccgcccctgt ttaatcgacg gagccaccgg tgtggtacac     180
acctacgctg acgtcgagct cacctcacga aaagttgctt ccgcttttca ccagcacggc     240
atcaacaaag gtgatgtcat catgatacta cttccgaatt caccagaatt cgtgtactcg     300 tttttttggtg catcgtacct cggtgcggtt tccaccatgg caaatccgtt cttcacctct     360
gctgaaatca ttaaacaagc aaaagcttct aacgctaaaa tcatcgtgac gcaagcgtca     420
cacgtaccga aaataaaaga gtacgcagct gaaaactcaa tcaaaatcgt atgcatagat     480
tccgctccag aaggttgctt gcacttcacg gaactagttt ctggagacga aacgaaatta     540
ccagaagttg agatctcgcc agacgacgtc gtggcgttgc cgtactcatc gggaacgacg     600
ggattgccta aggagttat gttaactcac aaggggctcg tgacgagcgt agcgcaacaa     660
gtggatggag aaaatccgaa tttgtggata cacagtgaag atgtgttgat gtgtgtgttg     720
ccactttttc acatctactc gttgaattcg attttgttgt gtgggttgcg ggccggtgcg     780
gcgattttga tcatgcagaa gtttgatata gtgccgtttt tggagttgat tgagaagtat     840
aaagtgacga tcgggccgtt tgtgccgccg atcgtgttgg cgattgcgaa taatgaggaa     900
gtggtggata agtatgattt gtcgtcgatg aggacggtga tgtccggtgc ggcaccgttg     960
gggaaagagc ttgaagatat ggttaggagg aagtttccga atgcgaaact ggacagggt    1020 tacggtatga cagaggctgg accggtgcta gcaatgtgtt tagcctttgc taaggagccc    1080
tatgagatca gtccggagc atgtggcact gtggtgcgca acgccgagat gaagatcgtt    1140
gaccccgaga caggtttgtc gctccctagg aaccaacgag agagatttg tattcgtggc    1200 gatcaaatca tgaaaggtta tcttaatgac ccggaatcga caaagacaac aatagactca    1260
gatgggtggc tacacacagg tgatataggg ttgattgacg acgatgatga gctcttcata    1320
gtggatcgac tcaaggagtt gattaaatac aaaggatttc aagtagcacc tgctgagctt    1380

```
gaagcgttat tactaactca tcctcaaatt tcggatgttg cagtagtccc tatggtaaac    1440
gaagcagctg gagaggttcc ggttgctttt gtggtgaaaa ctaaagactc aagtgtgaca    1500
gaggacgata tcaagcaatt cgtacacaaa caggtggtat tctataagag aataaatcgt    1560
gtgttcttta cgacacgat tccaaaatca ccagcaggga aaattcttcg caaagagttg    1620
agagcgaagc ttgcagctgg tgtcccaaat taa                                 1653
```

<210> SEQ ID NO 4
<211> LENGTH: 550
<212> TYPE: PRT
<213> ORGANISM: Helianthus annuus
<220> FEATURE:
<221> NAME/KEY: MISC_FEATURE
<223> OTHER INFORMATION: 4CL2

<400> SEQUENCE: 4

```
Met Pro Thr Leu Tyr Lys Lys Ala Gly Ser Met Ala Pro Glu Lys Glu
1               5                   10                  15

Ile Ile Phe Arg Ser Lys Leu Pro Asp Ile Tyr Ile Pro Lys His Leu
            20                  25                  30

Pro Leu His Ser Tyr Cys Phe Glu Asn Ile Ser Thr Phe Asn Asn Arg
        35                  40                  45

Pro Cys Leu Ile Asp Gly Ala Thr Gly Val Val His Thr Tyr Ala Asp
    50                  55                  60

Val Glu Leu Thr Ser Arg Lys Val Ala Ser Ala Phe His Gln His Gly
65                  70                  75                  80

Ile Asn Lys Gly Asp Val Ile Met Ile Leu Leu Pro Asn Ser Pro Glu
                85                  90                  95

Phe Val Tyr Ser Phe Phe Gly Ala Ser Tyr Leu Gly Ala Val Ser Thr
            100                 105                 110

Met Ala Asn Pro Phe Phe Thr Ser Ala Glu Ile Ile Lys Gln Ala Lys
        115                 120                 125

Ala Ser Asn Ala Lys Ile Ile Val Thr Gln Ala Ser His Val Pro Lys
    130                 135                 140

Ile Lys Glu Tyr Ala Ala Glu Asn Ser Ile Lys Ile Val Cys Ile Asp
145                 150                 155                 160

Ser Ala Pro Glu Gly Cys Leu His Phe Thr Glu Leu Val Ser Gly Asp
                165                 170                 175

Glu Thr Lys Leu Pro Glu Val Glu Ile Ser Pro Asp Asp Val Val Ala
            180                 185                 190

Leu Pro Tyr Ser Ser Gly Thr Thr Gly Leu Pro Lys Gly Val Met Leu
        195                 200                 205

Thr His Lys Gly Leu Val Thr Ser Val Ala Gln Gln Val Asp Gly Glu
    210                 215                 220

Asn Pro Asn Leu Trp Ile His Ser Glu Asp Val Leu Met Cys Val Leu
225                 230                 235                 240

Pro Leu Phe His Ile Tyr Ser Leu Asn Ser Ile Leu Leu Cys Gly Leu
                245                 250                 255

Arg Ala Gly Ala Ala Ile Leu Ile Met Gln Lys Phe Asp Ile Val Pro
            260                 265                 270

Phe Leu Glu Leu Ile Glu Lys Tyr Lys Val Thr Ile Gly Pro Phe Val
        275                 280                 285

Pro Pro Ile Val Leu Ala Ile Ala Asn Asn Glu Glu Val Val Asp Lys
    290                 295                 300

Tyr Asp Leu Ser Ser Met Arg Thr Val Met Ser Gly Ala Ala Pro Leu
```

```
                    305                 310                 315                 320
        Gly Lys Glu Leu Glu Asp Met Val Arg Arg Lys Phe Pro Asn Ala Lys
                        325                 330                 335

Leu Gly Gln Gly Tyr Gly Met Thr Glu Ala Gly Pro Val Leu Ala Met
                        340                 345                 350

Cys Leu Ala Phe Ala Lys Glu Pro Tyr Glu Ile Lys Ser Gly Ala Cys
                        355                 360                 365

Gly Thr Val Val Arg Asn Ala Glu Met Lys Ile Val Asp Pro Glu Thr
        370                 375                 380

Gly Leu Ser Leu Pro Arg Asn Gln Arg Gly Glu Ile Cys Ile Arg Gly
        385                 390                 395                 400

Asp Gln Ile Met Lys Gly Tyr Leu Asn Asp Pro Glu Ser Thr Lys Thr
                        405                 410                 415

Thr Ile Asp Ser Asp Gly Trp Leu His Thr Gly Asp Ile Gly Leu Ile
                        420                 425                 430

Asp Asp Asp Asp Glu Leu Phe Ile Val Asp Arg Leu Lys Glu Leu Ile
                        435                 440                 445

Lys Tyr Lys Gly Phe Gln Val Ala Pro Ala Glu Leu Glu Ala Leu Leu
                        450                 455                 460

Leu Thr His Pro Gln Ile Ser Asp Val Ala Val Val Pro Met Val Asn
        465                 470                 475                 480

Glu Ala Ala Gly Glu Val Pro Val Ala Phe Val Val Lys Thr Lys Asp
                        485                 490                 495

Ser Ser Val Thr Glu Asp Asp Ile Lys Gln Phe Val His Lys Gln Val
                        500                 505                 510

Val Phe Tyr Lys Arg Ile Asn Arg Val Phe Phe Ile Asp Thr Ile Pro
                        515                 520                 525

Lys Ser Pro Ala Gly Lys Ile Leu Arg Lys Glu Leu Arg Ala Lys Leu
                        530                 535                 540

Ala Ala Gly Val Pro Asn
        545                 550

<210> SEQ ID NO 5
<211> LENGTH: 1236
<212> TYPE: DNA
<213> ORGANISM: Rhodopseudomonas palustris
<220> FEATURE:
<221> NAME/KEY: misc_feature
<223> OTHER INFORMATION: CYP199A2 F185L

<400> SEQUENCE: 5
atgactaccg ctccatctct tgttccagtg actactccat ctcagcatgg tgctggtgtt      60
ccacaccttg gaattgatcc attcgctctc gactacttcg ctgacccata tccagagcaa     120
gagactctta gagaggctgg cccagttgtt tacctcgaca gtggaacgtt tacggtgtg      180 gctaggtacg ctgaggttta cgctgttctt aacgaccctc tcaccttctg ctcatctaga     240
ggtgtgggac tctccgactt caagaaagaa aagccttgga ggccaccaag cctcattctt     300
gaagctgatc accagctcta tccaggact agggctgtgc tttctaaggt gttgtctcca     360
gctaccatga gaggctcag atggattc gctgctgctg ccgatgctaa gattgatgag      420
cttcttgctc gcggaggcaa catcgatgct attgctgatc ttgctgaggc ttacccactc     480
agcgttttcc cagatgctat ggacttaag caagagggac gcgagaacct tcttccatac     540
gctggacttg tgctcaacgc tttcggacca ccaaacgagc ttaggcagtc tgctattgag     600 ggtctgctc cacatcaggc ttatgttgct gagcaatgcc agaggccaaa ccttgctcct     660
```

```
ggtggattcg gagcttgcat tcacgctttc tctgataccg gtgagatcac cccagaagag      720
gcaccacttc ttgtgcgctc acttctttct gctggtcttg ataccaccgt gaacggaatt      780
gctgctgcag tttactgcct tgctaggttc cctgatgagt tcgctagact tagggctgat      840
ccatccttgg ctaggaacgc attcgaagag gctgttaggt tcgagtctcc tgtgcagact      900
ttcttcagga ctaccaccag ggatgttgag cttgctggtg ctactattgg agagggtgag      960
aaggtgctca tgttcctcgg atctgctaac agggatccta aaggtgggat gatccagac     1020 aggtacgata tcaccagaaa gacctctgga cacgttggat tcggttctgg tgttcatatg     1080
tgcgtgggac agcttgttgc taggcttgag ggtgaagttg tgcttgctgc tctcgctaga     1140
aaggtggcag caattgagat tgctggccca ctcaagaggc gcttcaacaa cactcttagg     1200
ggacttgagt ccctgccaat tcaacttact ccagcc                               1236
```

<210> SEQ ID NO 6
<211> LENGTH: 412
<212> TYPE: PRT
<213> ORGANISM: Rhodopseudomonas palustris
<220> FEATURE:
<221> NAME/KEY: MISC_FEATURE
<223> OTHER INFORMATION: CYP199A2 F185L

<400> SEQUENCE: 6

```
Met Thr Thr Ala Pro Ser Leu Val Pro Val Thr Thr Pro Ser Gln His
1               5                   10                  15

Gly Ala Gly Val Pro His Leu Gly Ile Asp Pro Phe Ala Leu Asp Tyr
                20                  25                  30

Phe Ala Asp Pro Tyr Pro Glu Gln Glu Thr Leu Arg Glu Ala Gly Pro
            35                  40                  45

Val Val Tyr Leu Asp Lys Trp Asn Val Tyr Gly Val Ala Arg Tyr Ala
        50                  55                  60

Glu Val Tyr Ala Val Leu Asn Asp Pro Leu Thr Phe Cys Ser Ser Arg
65                  70                  75                  80

Gly Val Gly Leu Ser Asp Phe Lys Lys Glu Lys Pro Trp Arg Pro Pro
                85                  90                  95

Ser Leu Ile Leu Glu Ala Asp Pro Pro Ala His Thr Arg Thr Arg Ala
            100                 105                 110

Val Leu Ser Lys Val Leu Ser Pro Ala Thr Met Lys Arg Leu Arg Asp
        115                 120                 125

Gly Phe Ala Ala Ala Ala Asp Ala Lys Ile Asp Glu Leu Leu Ala Arg
    130                 135                 140

Gly Gly Asn Ile Asp Ala Ile Ala Asp Leu Ala Glu Ala Tyr Pro Leu
145                 150                 155                 160

Ser Val Phe Pro Asp Ala Met Gly Leu Lys Gln Glu Gly Arg Glu Asn
                165                 170                 175

Leu Leu Pro Tyr Ala Gly Leu Val Leu Asn Ala Phe Gly Pro Pro Asn
            180                 185                 190

Glu Leu Arg Gln Ser Ala Ile Glu Arg Ser Ala Pro His Gln Ala Tyr
        195                 200                 205

Val Ala Glu Gln Cys Gln Arg Pro Asn Leu Ala Pro Gly Gly Phe Gly
    210                 215                 220

Ala Cys Ile His Ala Phe Ser Asp Thr Gly Glu Ile Thr Pro Glu Glu
225                 230                 235                 240

Ala Pro Leu Leu Val Arg Ser Leu Leu Ser Ala Gly Leu Asp Thr Thr
                245                 250                 255
```

Val Asn Gly Ile Ala Ala Val Tyr Cys Leu Ala Arg Phe Pro Asp
              260                 265                 270

Glu Phe Ala Arg Leu Arg Ala Asp Pro Ser Leu Ala Arg Asn Ala Phe
            275                 280                 285

Glu Glu Ala Val Arg Phe Glu Ser Pro Val Gln Thr Phe Phe Arg Thr
        290                 295                 300

Thr Thr Arg Asp Val Glu Leu Ala Gly Ala Thr Ile Gly Glu Gly Glu
305                 310                 315                 320

Lys Val Leu Met Phe Leu Gly Ser Ala Asn Arg Asp Pro Arg Arg Trp
                325                 330                 335

Asp Asp Pro Asp Arg Tyr Asp Ile Thr Arg Lys Thr Ser Gly His Val
            340                 345                 350

Gly Phe Gly Ser Gly Val His Met Cys Val Gly Gln Leu Val Ala Arg
        355                 360                 365

Leu Glu Gly Glu Val Val Leu Ala Ala Leu Ala Arg Lys Val Ala Ala
370                 375                 380

Ile Glu Ile Ala Gly Pro Leu Lys Arg Arg Phe Asn Asn Thr Leu Arg
385                 390                 395                 400

Gly Leu Glu Ser Leu Pro Ile Gln Leu Thr Pro Ala
                405                 410

<210> SEQ ID NO 7
<211> LENGTH: 891
<212> TYPE: DNA
<213> ORGANISM: Arabidopsis thaliana
<220> FEATURE:
<221> NAME/KEY: misc_feature
<223> OTHER INFORMATION: MYB72

<400> SEQUENCE: 7

| | | | | | |
|---|---|---|---|---|---|
| atggggaaag | gaagagcacc | atgctgcgac | aagaacaaag | tgaagagagg | gccatggagc | 60 |
| cctcaagaag | atctcactct | catcactttt | attcaaaaac | atggccatca | aaactggaga | 120 |
| tctcttccca | agcttgctgg | attgttgaga | tgtgggaaaa | gttgccgact | aagatggata | 180 |
| aactatctga | gaccggacgt | gaagcgaggc | aactttagca | aaaaggagga | agatgctatc | 240 |
| attcactacc | atcaaaccct | tggaaacaag | tggtcaaaga | tcgcgtcctt | cttgccggga | 300 |
| agaactgaca | cgagatcaa | aaacgtgtgg | aacacgcatc | tcaagaaacg | actcactcca | 360 |
| tcttcttctt | cttcatccct | ctctagcact | catgaccaaa | gcacaaaagc | agatcatgac | 420 |
| aagaactgtg | acggggctca | agaagaaata | cattcagggt | taaatgagag | ccaaaactca | 480 |
| gctacttcgt | cacatcacca | aggcgagtgt | atgcacacaa | aaccagagct | tcatgaggtt | 540 |
| aatggactca | acgagatcca | gttcctgctc | gaccatgatg | actttgatga | tataacctct | 600 |
| gagtttcttc | aggataacga | tatcttattt | ccgctagact | ctcttcttca | taaccaccaa | 660 |
| actcacattt | caacccaaga | aatgactcga | gaggtaacca | aatcgcaatc | atttgatcat | 720 |
| cctcaaccgg | atatcccatg | cggatttgaa | gacacaaacg | aagaatccga | cttgaggaga | 780 |
| cagctggttg | aatcaaccac | acctaacaat | gagtacgacg | agtggttcaa | cttcattgac | 840 |
| aaccaaactt | actttgatga | tttttaatttc | gtcggagaag | tatgtctatg | a | 891 |

<210> SEQ ID NO 8
<211> LENGTH: 296
<212> TYPE: PRT
<213> ORGANISM: Arabidopsis thaliana
<220> FEATURE:
<221> NAME/KEY: MISC_FEATURE

<223> OTHER INFORMATION: MYB72

<400> SEQUENCE: 8

```
Met Gly Lys Gly Arg Ala Pro Cys Cys Asp Lys Asn Lys Val Lys Arg
1               5                   10                  15
Gly Pro Trp Ser Pro Gln Glu Asp Leu Thr Leu Ile Thr Phe Ile Gln
            20                  25                  30
Lys His Gly His Gln Asn Trp Arg Ser Leu Pro Lys Leu Ala Gly Leu
        35                  40                  45
Leu Arg Cys Gly Lys Ser Cys Arg Leu Arg Trp Ile Asn Tyr Leu Arg
    50                  55                  60
Pro Asp Val Lys Arg Gly Asn Phe Ser Lys Lys Glu Glu Asp Ala Ile
65                  70                  75                  80
Ile His Tyr His Gln Thr Leu Gly Asn Lys Trp Ser Lys Ile Ala Ser
                85                  90                  95
Phe Leu Pro Gly Arg Thr Asp Asn Glu Ile Lys Asn Val Trp Asn Thr
            100                 105                 110
His Leu Lys Lys Arg Leu Thr Pro Ser Ser Ser Ser Ser Ser Leu Ser
        115                 120                 125
Ser Thr His Asp Gln Ser Thr Lys Ala Asp His Asp Lys Asn Cys Asp
    130                 135                 140
Gly Ala Gln Glu Glu Ile His Ser Gly Leu Asn Glu Ser Gln Asn Ser
145                 150                 155                 160
Ala Thr Ser Ser His His Gln Gly Glu Cys Met His Thr Lys Pro Glu
                165                 170                 175
Leu His Glu Val Asn Gly Leu Asn Glu Ile Gln Phe Leu Leu Asp His
            180                 185                 190
Asp Asp Phe Asp Asp Ile Thr Ser Glu Phe Leu Gln Asp Asn Asp Ile
        195                 200                 205
Leu Phe Pro Leu Asp Ser Leu Leu His Asn His Gln Thr His Ile Ser
    210                 215                 220
Thr Gln Glu Met Thr Arg Glu Val Thr Lys Ser Gln Ser Phe Asp His
225                 230                 235                 240
Pro Gln Pro Asp Ile Pro Cys Gly Phe Glu Asp Thr Asn Glu Glu Ser
                245                 250                 255
Asp Leu Arg Arg Gln Leu Val Glu Ser Thr Thr Pro Asn Asn Glu Tyr
            260                 265                 270
Asp Glu Trp Phe Asn Phe Ile Asp Asn Gln Thr Tyr Phe Asp Asp Phe
        275                 280                 285
Asn Phe Val Gly Glu Val Cys Leu
    290                 295
```

<210> SEQ ID NO 9
<211> LENGTH: 1095
<212> TYPE: DNA
<213> ORGANISM: Artificial
<220> FEATURE:
<223> OTHER INFORMATION: OMT3 variant 1

<400> SEQUENCE: 9

```
atgggatcta cttctgcttc tgttaacgtt cttcttgagg ctaaccaaga tgatcaatct      60 tttcttttg ctatgcaact tgcttctgct tctatgcttc caatggttct tagaactgct      120
attgagcttg atcttcttga gactattgct aaggctggac caggaggatc tctttcttct      180
tctgagcttg ttgctcaact tccaaaggtt aacaacccag aggctccagt tcttgttgat      240
```

| | |
|---|---|
| agaatttgta gagttcttgc ttcttattct gttcttactt gtactgttaa ggagactatg | 300 |
| gatggatgtg ctgatagata ttatggagtt gctccacttt gtaagtatct tactagaaac | 360 |
| gattctggag tttctcttgc tccacttctt cttcttaacc aagataagat ttttatggag | 420 |
| tcttggtatt ttcttaagga tgctgttctt gatggaggaa ttccatctaa caaggcttat | 480 |
| ggaatgccag cttttgagta ttatggaaag gatcaaagat ttaacaaggt ttttaactct | 540 |
| gctatgttta accattctac tcttactatg aagaagatta ttgatcttta tgatggattt | 600 |
| tcttctgttg agactcttgt tgatgttgga ggaggatctg gagcttctct taaccttatt | 660 |
| acttctaagc atacttctct taagggaatt aactttgatc ttccacatgt tattgatgat | 720 |
| gctactactt atcatggaat tgagcatgtt ggaggagata tgtttgagtc tgttccaaag | 780 |
| ggagatgcta tttttatgag atggattctt catgattggt ctgatgctct ttgtcttcaa | 840 |
| gttcttaaga actgttataa gtctcttcca agaacggaa aggttattgt tgctgagtgt | 900 |
| attatttctg aggctccaga ttctactcca gctactcaaa acgttattca tattgatgct | 960 |
| attatgcttg ttcattctct tggaggaaag gagagaactg agaaggagtt tgaggctctt | 1020 |
| gctaaggctg ctggatttaa gggatttaac aaggctgctt gtgctcttaa cacttgggtt | 1080 |
| atggagtttt gtaag | 1095 |

```
<210> SEQ ID NO 10
<211> LENGTH: 365
<212> TYPE: PRT
<213> ORGANISM: Artificial
<220> FEATURE:
<223> OTHER INFORMATION: OMT3 variant 1

<400> SEQUENCE: 10
```

Met Gly Ser Thr Ser Ala Ser Val Asn Val Leu Leu Glu Ala Asn Gln
1               5                   10                  15

Asp Asp Gln Ser Phe Leu Phe Ala Met Gln Leu Ala Ser Ala Ser Met
                20                  25                  30

Leu Pro Met Val Leu Arg Thr Ala Ile Glu Leu Asp Leu Leu Glu Thr
            35                  40                  45

Ile Ala Lys Ala Gly Pro Gly Gly Ser Leu Ser Ser Glu Leu Val
        50                  55                  60

Ala Gln Leu Pro Lys Val Asn Asn Pro Glu Ala Pro Val Leu Val Asp
65                  70                  75                  80

Arg Ile Cys Arg Val Leu Ala Ser Tyr Ser Val Leu Thr Cys Thr Val
                85                  90                  95

Lys Glu Thr Met Asp Gly Cys Ala Asp Arg Tyr Tyr Gly Val Ala Pro
                100                 105                 110

Leu Cys Lys Tyr Leu Thr Arg Asn Asp Ser Gly Val Ser Leu Ala Pro
            115                 120                 125

Leu Leu Leu Leu Asn Gln Asp Lys Ile Phe Met Glu Ser Trp Tyr Phe
        130                 135                 140

Leu Lys Asp Ala Val Leu Asp Gly Gly Ile Pro Ser Asn Lys Ala Tyr
145                 150                 155                 160

Gly Met Pro Ala Phe Glu Tyr Tyr Gly Lys Asp Gln Arg Phe Asn Lys
                165                 170                 175

Val Phe Asn Ser Ala Met Phe Asn His Ser Thr Leu Thr Met Lys Lys
            180                 185                 190

Ile Ile Asp Leu Tyr Asp Gly Phe Ser Ser Val Glu Thr Leu Val Asp
        195                 200                 205

```
Val Gly Gly Ser Gly Ala Ser Leu Asn Leu Ile Thr Ser Lys His
210                 215                 220

Thr Ser Leu Lys Gly Ile Asn Phe Asp Leu Pro His Val Ile Asp Asp
225                 230                 235                 240

Ala Thr Thr Tyr His Gly Ile Glu His Val Gly Gly Asp Met Phe Glu
                245                 250                 255

Ser Val Pro Lys Gly Asp Ala Ile Phe Met Arg Trp Ile Leu His Asp
            260                 265                 270

Trp Ser Asp Ala Leu Cys Leu Gln Val Leu Lys Asn Cys Tyr Lys Ser
                275                 280                 285

Leu Pro Lys Asn Gly Lys Val Ile Val Ala Glu Cys Ile Ile Ser Glu
            290                 295                 300

Ala Pro Asp Ser Thr Pro Ala Thr Gln Asn Val Ile His Ile Asp Ala
305                 310                 315                 320

Ile Met Leu Val His Ser Leu Gly Gly Lys Glu Arg Thr Glu Lys Glu
                325                 330                 335

Phe Glu Ala Leu Ala Lys Ala Ala Gly Phe Lys Gly Phe Asn Lys Ala
                340                 345                 350

Ala Cys Ala Leu Asn Thr Trp Val Met Glu Phe Cys Lys
                355                 360                 365

<210> SEQ ID NO 11
<211> LENGTH: 1095
<212> TYPE: DNA
<213> ORGANISM: Artificial
<220> FEATURE:
<223> OTHER INFORMATION: OMT3 variant 2

<400> SEQUENCE: 11
atgggatcta cttctgcttc tgttaacgtt cttcttgagg ctaaccaaga tgatcaatct      60 tttcttttg ctatgcaact tgcttctgct tctcttgttc caatggttct taagactgct     120
attgagcttg atcttcttga gactattgct aaggctggac caggaggatc tctttcttct     180
tctgagcttg ttgctaacct tccaaaggtt aacaacccag aggctccagt tcttgttgat     240
agaatttgta gagttcttgc ttcttattct gttcttactt gtactcttaa ggagactatg     300
gatggatgtg ctgagagatt ttatgctgtt gctccagttt gtaagtttct tactaagaac     360
gattctggag tttctcttgc tccaatggtt attatgaacc aagataaggt ttttgttgag     420
tcttggtatt tccttaagga tgctgttctt gagggagcta ttccatctaa caaggcttgg     480
ggaatgccag cttttgagta ttatggaaga gatcaaagat taacaaggt ttttaactct     540 gctatgttta accatacttc tatgactctt aagaagattc ttgatcttta tgatggattt     600
tcttctcttg agactcttgt tgatgttgga ggaggaactg agcttctct taacatgatt     660 acttctaagc atacttctct taagggaatt aactttgatc ttccacatgt tattgaggag     720
gctacttctt atcatggaat tgagcatgtt ggagggagata tgtttgagtc tgttccaaag     780
ggagatgcta ttttatgaa gtggattctt catgattggt ctgatgctct tgtattcaa     840 gttcttagaa actgttatag atctcttcca aagaacggaa gagttattgt tgctgagtgt     900 gttgttctg aggctccaga ttctactcca gctactcaaa acgttattca tattgatgct     960
gttatgcttg ttcatactct tggaggaaga gagagaactg agaaggagtt tgaggctctt    1020
gctaaggctg ctggatttaa gggatttaac aaggctgctt gtgctcttaa ctcttgggtt    1080
atggagtttt gtaag                                                    1095
```

```
<210> SEQ ID NO 12
<211> LENGTH: 365
<212> TYPE: PRT
<213> ORGANISM: Artificial
<220> FEATURE:
<223> OTHER INFORMATION: OMT3 variant 2

<400> SEQUENCE: 12

Met Gly Ser Thr Ser Ala Ser Val Asn Val Leu Leu Glu Ala Asn Gln
1               5                   10                  15

Asp Asp Gln Ser Phe Leu Phe Ala Met Gln Leu Ala Ser Ala Ser Leu
            20                  25                  30

Val Pro Met Val Leu Lys Thr Ala Ile Glu Leu Asp Leu Leu Glu Thr
        35                  40                  45

Ile Ala Lys Ala Gly Pro Gly Gly Ser Leu Ser Ser Glu Leu Val
50                  55                  60

Ala Asn Leu Pro Lys Val Asn Asn Pro Glu Ala Pro Val Leu Val Asp
65                  70                  75                  80

Arg Ile Cys Arg Val Leu Ala Ser Tyr Ser Val Leu Thr Cys Thr Leu
                85                  90                  95

Lys Glu Thr Met Asp Gly Cys Ala Glu Arg Phe Tyr Ala Val Ala Pro
            100                 105                 110

Val Cys Lys Phe Leu Thr Lys Asn Asp Ser Gly Val Ser Leu Ala Pro
        115                 120                 125

Met Val Ile Met Asn Gln Asp Lys Val Phe Val Glu Ser Trp Tyr Phe
130                 135                 140

Leu Lys Asp Ala Val Leu Glu Gly Ala Ile Pro Ser Asn Lys Ala Trp
145                 150                 155                 160

Gly Met Pro Ala Phe Glu Tyr Tyr Gly Arg Asp Gln Arg Phe Asn Lys
                165                 170                 175

Val Phe Asn Ser Ala Met Phe Asn His Thr Ser Met Thr Leu Lys Lys
            180                 185                 190

Ile Leu Asp Leu Tyr Asp Gly Phe Ser Ser Leu Glu Thr Leu Val Asp
        195                 200                 205

Val Gly Gly Gly Thr Gly Ala Ser Leu Asn Met Ile Thr Ser Lys His
210                 215                 220

Thr Ser Leu Lys Gly Ile Asn Phe Asp Leu Pro His Val Ile Glu Glu
225                 230                 235                 240

Ala Thr Ser Tyr His Gly Ile Glu His Val Gly Gly Asp Met Phe Glu
                245                 250                 255

Ser Val Pro Lys Gly Asp Ala Ile Phe Met Lys Trp Ile Leu His Asp
            260                 265                 270

Trp Ser Asp Ala Leu Cys Ile Gln Val Leu Arg Asn Cys Tyr Arg Ser
        275                 280                 285

Leu Pro Lys Asn Gly Arg Val Ile Val Ala Glu Cys Val Val Ser Glu
290                 295                 300

Ala Pro Asp Ser Thr Pro Ala Thr Gln Asn Val Ile His Ile Asp Ala
305                 310                 315                 320

Val Met Leu Val His Thr Leu Gly Gly Arg Glu Arg Thr Glu Lys Glu
                325                 330                 335

Phe Glu Ala Leu Ala Lys Ala Ala Gly Phe Lys Gly Phe Asn Lys Ala
            340                 345                 350

Ala Cys Ala Leu Asn Ser Trp Val Met Glu Phe Cys Lys
        355                 360                 365
```

<210> SEQ ID NO 13
<211> LENGTH: 1095
<212> TYPE: DNA
<213> ORGANISM: Artificial
<220> FEATURE:
<223> OTHER INFORMATION: OMT3 variant 3

<400> SEQUENCE: 13

```
atgggatcta cttctgcttc tgttaacgtt cttcttgagg ctaaccaaga tgataactct      60
tatcttttg ctcttcaact tgcttctgct tctatgcttc caatggttct taagactgct     120
cttgagcttg atcttcttga gactattgct aaggctggac caggaggatc tgtttcttct     180
tctgagcttg ttgctcaact tccaaaggtt aacaacccag aggctccagt tatggttgag     240
agaatttgta gacttcttgc tacttattct gttcttactt gttctcttaa ggagactatg     300
gatggatgtg ctgagagatt ttatgctgtt gctccagttt gtaagtatct tactaagaac     360
gattctggag tttctcttgc tccacttgtt cttatgaacc aagataaggt ttttatggag     420
tcttattatt atcttaagga tgctgttctt gatggaggaa ttccatctaa caaggctttt     480
ggacttccag cttttgagta ttatggaaag gatcaaagat ttaacaaggt tttaactct     540
gctatgttta accattctac tatgactatg aagaagatta ttgatctttt tgatggattt     600
tcttctgttg agactcttgt tgatgttgga ggaggatctg gagcttctct taacatgatt     660
acttctaagc atacttctct taagggaatt aactttgatc ttccacatgt tattgaggat     720
gcttcttctt atcatggaat tgagcatgtt ggaggagata tgtttgagtc tgttccaaag     780
gctgatgcta tttttatgaa gtggattctt catgattgga ctgatgctct tgtcttcaa     840
gttcttagaa actgttatag atctcttcca agaacggaa aggttattgt tgctgagtgt     900
attctttctg aggctccaga gtctactcca gctactcaaa accttattca tcttgatgct     960
attatgcttg ttcattctct tggaggaaag gagagaactg agaaggagtg ggaggctctt    1020
gctaaggctg ctggatttaa gggatttaac aaggctgctt gtgctgttaa cacttgggtt    1080
atggagttt gtaag                                                      1095
```

<210> SEQ ID NO 14
<211> LENGTH: 365
<212> TYPE: PRT
<213> ORGANISM: Artificial
<220> FEATURE:
<223> OTHER INFORMATION: OMT3 variant 3

<400> SEQUENCE: 14

```
Met Gly Ser Thr Ser Ala Ser Val Asn Val Leu Leu Glu Ala Asn Gln
1               5                   10                  15

Asp Asp Asn Ser Tyr Leu Phe Ala Leu Gln Leu Ala Ser Ala Ser Met
            20                  25                  30

Leu Pro Met Val Leu Lys Thr Ala Leu Glu Leu Asp Leu Leu Glu Thr
        35                  40                  45

Ile Ala Lys Ala Gly Pro Gly Gly Ser Val Ser Ser Glu Leu Val
    50                  55                  60

Ala Gln Leu Pro Lys Val Asn Asn Pro Glu Ala Pro Val Met Val Glu
65                  70                  75                  80

Arg Ile Cys Arg Leu Leu Ala Thr Tyr Ser Val Leu Thr Cys Ser Leu
                85                  90                  95

Lys Glu Thr Met Asp Gly Cys Ala Glu Arg Phe Tyr Ala Val Ala Pro
            100                 105                 110

Val Cys Lys Tyr Leu Thr Lys Asn Asp Ser Gly Val Ser Leu Ala Pro
```

```
              115                 120                 125
Leu Val Leu Met Asn Gln Asp Lys Val Phe Met Glu Ser Tyr Tyr Tyr
            130                 135                 140
Leu Lys Asp Ala Val Leu Asp Gly Gly Ile Pro Ser Asn Lys Ala Phe
145                 150                 155                 160
Gly Leu Pro Ala Phe Glu Tyr Tyr Gly Lys Asp Gln Arg Phe Asn Lys
                165                 170                 175
Val Phe Asn Ser Ala Met Phe Asn His Ser Thr Met Thr Met Lys Lys
            180                 185                 190
Ile Ile Asp Leu Phe Asp Gly Phe Ser Ser Val Glu Thr Leu Val Asp
            195                 200                 205
Val Gly Gly Gly Ser Gly Ala Ser Leu Asn Met Ile Thr Ser Lys His
            210                 215                 220
Thr Ser Leu Lys Gly Ile Asn Phe Asp Leu Pro His Val Ile Glu Asp
225                 230                 235                 240
Ala Ser Ser Tyr His Gly Ile Glu His Val Gly Gly Asp Met Phe Glu
                245                 250                 255
Ser Val Pro Lys Ala Asp Ala Ile Phe Met Lys Trp Ile Leu His Asp
                260                 265                 270
Trp Thr Asp Ala Leu Cys Leu Gln Val Leu Arg Asn Cys Tyr Arg Ser
            275                 280                 285
Leu Pro Lys Asn Gly Lys Val Ile Val Ala Glu Cys Ile Leu Ser Glu
            290                 295                 300
Ala Pro Glu Ser Thr Pro Ala Thr Gln Asn Leu Ile His Leu Asp Ala
305                 310                 315                 320
Ile Met Leu Val His Ser Leu Gly Gly Lys Glu Arg Thr Glu Lys Glu
                325                 330                 335
Trp Glu Ala Leu Ala Lys Ala Ala Gly Phe Lys Gly Phe Asn Lys Ala
            340                 345                 350
Ala Cys Ala Val Asn Thr Trp Val Met Glu Phe Cys Lys
            355                 360                 365

<210> SEQ ID NO 15
<211> LENGTH: 1095
<212> TYPE: DNA
<213> ORGANISM: Artificial
<220> FEATURE:
<223> OTHER INFORMATION: OMT3 variant 4

<400> SEQUENCE: 15
atgggatcta cttctgcttc tgttaacgtt cttcttgagg ctaaccaaga tgatcaatct      60 tttcttttg ctatgcaaat tgcttctgct tctgttgttc caatggttct taagactgct     120
cttgagcttg atcttcttga gactattgga aaggctggac caggaggatc tatgtcttct     180
tctgagcttg ttgctcaact tccaaagatt aacaacccag aggctccagt tatggttgat     240
agaatttgta gacttcttgc ttcttattct gttcttactt gtactattaa ggagactatg     300
gagggatgtg ctgagagata ttatggagtt gctccacttt gtaagtatct tactaagaac     360
gagtctggac tttctcttgg accacttctt atgcttaacc aagataaggt ttttatggat     420
tcttggtatt atcttaagga tgctgttctt gaggaggaa ttccatctaa caaggcttat     480
ggaatgccag cttttgagtg gtttggaaga gatcaaagat taacaaggt ttttcaatct     540 gctatgttta accattctac tcttactatg aagaagattc ttgatcttta tgatggattt     600
tcttctcttg agtctcttgt tgatgttgga ggaggaactg gagcttctct taacatgatt     660
```

```
acttctaagc atacttctct tagaggaatt aactttgatc ttccacatgt tattgaggag    720
gctactactt atcatggaat tgagcatgtt ggaggagata tgtttgagtc tcttccaaag    780
gctgatgcta ttttatgaa gtggattctt catgattggt ctgatgctct tgtcttcaa     840 gttcttagaa actgttataa gtctcttcca agaacggaa gagttattgt tgctgagtgt    900
attgttactg atgctccaga ttcttctcca gcttctcaac aacttattca tattgatgct   960
attatgcttg ttcattctat tggaggaaag gagagaactg agagagagtg ggaggctctt   1020
gctagagctg ctggatttaa gggatttaac aaggctgctt gtggacttaa cacttgggtt   1080
atggagtttt gtaag                                                    1095
```

<210> SEQ ID NO 16
<211> LENGTH: 365
<212> TYPE: PRT
<213> ORGANISM: Artificial
<220> FEATURE:
<223> OTHER INFORMATION: OMT3 variant 4

<400> SEQUENCE: 16

```
Met Gly Ser Thr Ser Ala Ser Val Asn Val Leu Leu Glu Ala Asn Gln
1               5                   10                  15

Asp Asp Gln Ser Phe Leu Phe Ala Met Gln Ile Ala Ser Ala Ser Val
            20                  25                  30

Val Pro Met Val Leu Lys Thr Ala Leu Glu Leu Asp Leu Leu Glu Thr
        35                  40                  45

Ile Gly Lys Ala Gly Pro Gly Gly Ser Met Ser Ser Glu Leu Val
    50                  55                  60

Ala Gln Leu Pro Lys Ile Asn Asn Pro Glu Ala Pro Val Met Val Asp
65                  70                  75                  80

Arg Ile Cys Arg Leu Leu Ala Ser Tyr Ser Val Leu Thr Cys Thr Ile
                85                  90                  95

Lys Glu Thr Met Glu Gly Cys Ala Glu Arg Tyr Tyr Gly Val Ala Pro
            100                 105                 110

Leu Cys Lys Tyr Leu Thr Lys Asn Glu Ser Gly Leu Ser Leu Gly Pro
        115                 120                 125

Leu Leu Met Leu Asn Gln Asp Lys Val Phe Met Asp Ser Trp Tyr Tyr
    130                 135                 140

Leu Lys Asp Ala Val Leu Glu Gly Gly Ile Pro Ser Asn Lys Ala Tyr
145                 150                 155                 160

Gly Met Pro Ala Phe Glu Trp Phe Gly Arg Asp Gln Arg Phe Asn Lys
                165                 170                 175

Val Phe Gln Ser Ala Met Phe Asn His Ser Thr Leu Thr Met Lys Lys
            180                 185                 190

Ile Leu Asp Leu Tyr Asp Gly Phe Ser Ser Leu Glu Ser Leu Val Asp
        195                 200                 205

Val Gly Gly Gly Thr Gly Ala Ser Leu Asn Met Ile Thr Ser Lys His
    210                 215                 220

Thr Ser Leu Arg Gly Ile Asn Phe Asp Leu Pro His Val Ile Glu Glu
225                 230                 235                 240

Ala Thr Thr Tyr His Gly Ile Glu His Val Gly Gly Asp Met Phe Glu
                245                 250                 255

Ser Leu Pro Lys Ala Asp Ala Ile Phe Met Lys Trp Ile Leu His Asp
            260                 265                 270

Trp Ser Asp Ala Leu Cys Leu Gln Val Leu Arg Asn Cys Tyr Lys Ser
        275                 280                 285
```

Leu Pro Lys Asn Gly Arg Val Ile Val Ala Glu Cys Ile Val Thr Asp
        290                 295                 300

Ala Pro Asp Ser Ser Pro Ala Ser Gln Gln Leu Ile His Ile Asp Ala
305                 310                 315                 320

Ile Met Leu Val His Ser Ile Gly Gly Lys Glu Arg Thr Glu Arg Glu
                325                 330                 335

Trp Glu Ala Leu Ala Arg Ala Ala Gly Phe Lys Gly Phe Asn Lys Ala
                340                 345                 350

Ala Cys Gly Leu Asn Thr Trp Val Met Glu Phe Cys Lys
                355                 360                 365

<210> SEQ ID NO 17
<211> LENGTH: 1095
<212> TYPE: DNA
<213> ORGANISM: Artificial
<220> FEATURE:
<223> OTHER INFORMATION: OMT3 variant 5

<400> SEQUENCE: 17

```
atgggatcta cttctgcttc tgttaacgtt cttcttgagg ctaaccaaga tgatcaatct    60
tttcttttg ctatgcaact tgcttctgct tctgttcttc agttgttct taagactgct    120
attgagcttg atcttcttga gactattgct aagggaggac caggaggatc tgtttcttct    180
tctgagcttg ttgctcaact tccaaagatt aacaacccag atgctccagt tatggttgat    240
agaatttgta gagttcttgc ttcttattct gttctttctt gtactattaa ggagactatg    300
gagggatgtg agagagagatt ttatggagtt gctccacttt gtagatttct tactaagaac    360
gattctgctg tttctcttgg accagttgtt cttatgaacc aagatagagt ttatatggag    420
tcttggtatt tcttagaga tgctgttctt gatggagcta ttccatctaa cagagctttt    480
ggaatgccag cttttgagtg gtatgctaag gatcaaagat ttaacaagct ttttaactct    540
gctatgttta accattctac tatgactatg aagaagatta ttgagattta tgatggattt    600
tcttctcttg agactcttgt tgatgttgga ggaggatctg gagcttctct tcaaatgatt    660
actactaagc atacttctct taagggaatt aactttgatc ttccacatgt tattgatgat    720
gctacttctt atcatggaat tgagcatgtt ggaggagata tgtttgagtc tgttccaaag    780
gctgatgcta tttatatgaa gtggattctt catgattggt ctgatgctct tgtcttcaa    840
gttcttaaga actgttataa gtctcttcca agaacggaa aggttattgt tgctgagtgt    900
gttattctg atgctccaga ttctactcca gctactcaaa cgttattca tcttgatgct    960
attatgctta tgcattctat gggaggaaag gatagaactg agaaggagtg ggaggctctt   1020
gctaaggctg ctggatttag agcttttaac aaggctgctt gtgctcttaa cacttgggtt   1080
atggagtttt gtaag                                                    1095
```

<210> SEQ ID NO 18
<211> LENGTH: 365
<212> TYPE: PRT
<213> ORGANISM: Artificial
<220> FEATURE:
<223> OTHER INFORMATION: OMT3 variant 5

<400> SEQUENCE: 18

Met Gly Ser Thr Ser Ala Ser Val Asn Val Leu Leu Glu Ala Asn Gln
1               5                   10                  15

Asp Asp Gln Ser Phe Leu Phe Ala Met Gln Leu Ala Ser Ala Ser Val
                20                  25                  30

Leu Pro Val Val Leu Lys Thr Ala Ile Glu Leu Asp Leu Leu Glu Thr
    35                  40                  45

Ile Ala Lys Gly Gly Pro Gly Ser Val Ser Ser Ser Glu Leu Val
50                  55                  60

Ala Gln Leu Pro Lys Ile Asn Asn Pro Asp Ala Pro Val Met Val Asp
65                  70                  75                  80

Arg Ile Cys Arg Val Leu Ala Ser Tyr Ser Val Leu Ser Cys Thr Ile
                85                  90                  95

Lys Glu Thr Met Glu Gly Cys Gly Glu Arg Phe Tyr Gly Val Ala Pro
            100                 105                 110

Leu Cys Arg Phe Leu Thr Lys Asn Asp Ser Ala Val Ser Leu Gly Pro
        115                 120                 125

Val Val Leu Met Asn Gln Asp Arg Val Tyr Met Glu Ser Trp Tyr Phe
    130                 135                 140

Leu Arg Asp Ala Val Leu Asp Gly Ala Ile Pro Ser Asn Arg Ala Phe
145                 150                 155                 160

Gly Met Pro Ala Phe Glu Trp Tyr Ala Lys Asp Gln Arg Phe Asn Lys
                165                 170                 175

Leu Phe Asn Ser Ala Met Phe Asn His Ser Thr Met Thr Met Lys Lys
            180                 185                 190

Ile Ile Glu Ile Tyr Asp Gly Phe Ser Ser Leu Glu Thr Leu Val Asp
        195                 200                 205

Val Gly Gly Gly Ser Gly Ala Ser Leu Gln Met Ile Thr Thr Lys His
    210                 215                 220

Thr Ser Leu Lys Gly Ile Asn Phe Asp Leu Pro His Val Ile Asp Asp
225                 230                 235                 240

Ala Thr Ser Tyr His Gly Ile Glu His Val Gly Gly Asp Met Phe Glu
                245                 250                 255

Ser Val Pro Lys Ala Asp Ala Ile Tyr Met Lys Trp Ile Leu His Asp
            260                 265                 270

Trp Ser Asp Ala Leu Cys Leu Gln Val Leu Lys Asn Cys Tyr Lys Ser
        275                 280                 285

Leu Pro Lys Asn Gly Lys Val Ile Val Ala Glu Cys Val Ile Ser Asp
    290                 295                 300

Ala Pro Asp Ser Thr Pro Ala Thr Gln Asn Val Ile His Leu Asp Ala
305                 310                 315                 320

Ile Met Leu Met His Ser Met Gly Gly Lys Asp Arg Thr Glu Lys Glu
                325                 330                 335

Trp Glu Ala Leu Ala Lys Ala Ala Gly Phe Arg Ala Phe Asn Lys Ala
            340                 345                 350

Ala Cys Ala Leu Asn Thr Trp Val Met Glu Phe Cys Lys
        355                 360                 365

<210> SEQ ID NO 19
<211> LENGTH: 1095
<212> TYPE: DNA
<213> ORGANISM: Artificial
<220> FEATURE:
<223> OTHER INFORMATION: OMT3 variant 6

<400> SEQUENCE: 19
atgggatcta cttctgcttc tgttaacgtt cttcttgagg ctaaccaaga tgagcaatct    60 tttcttttg ctcttcaaat tgctactgct actgttcttc caatggttct taagactgct   120
attgagcttg atcttcttga gactattgct aaggctggac caggaggatc tatttcttct   180

```
tctgagcttg ttgctcaact tccaaagctt aacaacccag atgctccagt tcttgttgat    240
agaatttgta gagttcttgc ttcttattct gttcttactt gttctatgaa ggagactatg    300
gagggatgtg ctgatagatt ttatgctgtt gctccacttt gtagatttct tactagaaac    360
gattctgctg tttctattgc tccaatggtt attcttaaca acgagaagat ttatatggag    420
acttattatt atcttaagga tggagttctt gagggaggaa ttccatctca aaaggctttt    480
ggaatgccag cttttgagtg gtatgctaag gatcaaaagt ataacagaat ttttcaaact    540
gctatgttta accatacttc tcttactatg aagagaattc ttgatatttt tgatggattt    600
tcttctattg agactcttgt tgatgttgga ggaggatctg gagctactct taacgttatt    660
acttctaagc atactactct tagaggaatt aactttgatc ttccacatgt tattgatgag    720
gctacttctt atcatggaat tgagcatatt ggaggagata tgtttgagtc tgttccaaag    780
gctgatgcta ttttttatga gatggattct tcatgattggt ctgatgctct ttgtattcaa    840
gttcttaaga actgttataa gtctcttcca aagaacggaa gagttattgt tgctgagtgt    900
cttctttctg atgctccaga ttcttctcca gcttctcaac aaattgttca tcttgatgct    960
gttatgcttc ttcattctat gggaggaaag gatagaactg agagagagtg ggaggctctt   1020
gctaaggctg ctggatttaa ggcttttcaa aaggctgctt gtgctcttaa ctcttgggtt   1080
atggagtttt gtaag                                                    1095
```

<210> SEQ ID NO 20
<211> LENGTH: 365
<212> TYPE: PRT
<213> ORGANISM: Artificial
<220> FEATURE:
<223> OTHER INFORMATION: OMT3 variant 6

<400> SEQUENCE: 20

```
Met Gly Ser Thr Ser Ala Ser Val Asn Val Leu Leu Glu Ala Asn Gln
1               5                   10                  15

Asp Glu Gln Ser Phe Leu Phe Ala Leu Gln Ile Ala Thr Ala Thr Val
            20                  25                  30

Leu Pro Met Val Leu Lys Thr Ala Ile Glu Leu Asp Leu Leu Glu Thr
        35                  40                  45

Ile Ala Lys Ala Gly Pro Gly Gly Ser Ile Ser Ser Ser Glu Leu Val
    50                  55                  60

Ala Gln Leu Pro Lys Leu Asn Asn Pro Asp Ala Pro Val Leu Val Asp
65                  70                  75                  80

Arg Ile Cys Arg Val Leu Ala Ser Tyr Ser Val Leu Thr Cys Ser Met
                85                  90                  95

Lys Glu Thr Met Glu Gly Cys Ala Asp Arg Phe Tyr Ala Val Ala Pro
            100                 105                 110

Leu Cys Arg Phe Leu Thr Arg Asn Asp Ser Ala Val Ser Ile Ala Pro
        115                 120                 125

Met Val Ile Leu Asn Asn Glu Lys Ile Tyr Met Glu Thr Tyr Tyr Tyr
    130                 135                 140

Leu Lys Asp Gly Val Leu Glu Gly Gly Ile Pro Ser Gln Lys Ala Phe
145                 150                 155                 160

Gly Met Pro Ala Phe Glu Trp Tyr Ala Lys Asp Gln Lys Tyr Asn Arg
                165                 170                 175

Ile Phe Gln Thr Ala Met Phe Asn His Thr Ser Leu Thr Met Lys Arg
            180                 185                 190
```

```
Ile Leu Asp Ile Phe Asp Gly Phe Ser Ser Ile Glu Thr Leu Val Asp
            195                 200                 205

Val Gly Gly Ser Gly Ala Thr Leu Asn Val Ile Thr Ser Lys His
210                 215                 220

Thr Thr Leu Arg Gly Ile Asn Phe Asp Leu Pro His Val Ile Asp Glu
225                 230                 235                 240

Ala Thr Ser Tyr His Gly Ile Glu His Ile Gly Gly Asp Met Phe Glu
                245                 250                 255

Ser Val Pro Lys Ala Asp Ala Ile Phe Met Arg Trp Ile Leu His Asp
            260                 265                 270

Trp Ser Asp Ala Leu Cys Ile Gln Val Leu Lys Asn Cys Tyr Lys Ser
        275                 280                 285

Leu Pro Lys Asn Gly Arg Val Ile Val Ala Glu Cys Leu Leu Ser Asp
    290                 295                 300

Ala Pro Asp Ser Ser Pro Ala Ser Gln Gln Ile Val His Leu Asp Ala
305                 310                 315                 320

Val Met Leu Leu His Ser Met Gly Gly Lys Asp Arg Thr Glu Arg Glu
                325                 330                 335

Trp Glu Ala Leu Ala Lys Ala Ala Gly Phe Lys Ala Phe Gln Lys Ala
            340                 345                 350

Ala Cys Ala Leu Asn Ser Trp Val Met Glu Phe Cys Lys
        355                 360                 365

<210> SEQ ID NO 21
<211> LENGTH: 1095
<212> TYPE: DNA
<213> ORGANISM: Artificial
<220> FEATURE:
<223> OTHER INFORMATION: OMT3 variant 7

<400> SEQUENCE: 21
atgggatcta cttctgcttc tgttaacgtt cttcttgagg ctaaccaaga tgataactct      60 tttcttttg ctattcaaat tggaactgct tctatggttc caattgttct tagaactgct     120
gttgagcttg atcttcttga gactattgct aaggctggac caggaggatc tatgtcttct     180
tctgagcttg ttgctcaact tccaaagctt aaccaaccag atgctccagt tcttgttgag     240
agaatttgta gacttcttgc ttcttattct gttctttctt gtactcttag agagtctctt     300
gatggatgtg gagatagata ttatggagtt gctccacttt gtagatatct tactagaaac     360
gagtctgctc tttctatggg accacttatt cttcttcaaa acgagaagat gtatgttgag     420 tcttttatt ttcttaagga ggctgttgtt gatggaggag ttccaactaa caaggcttat     480
ggacttccag cttttgagta ttttgctaag gatcaaagat ggaacagaat ttttcaatct     540
ggaatgttta accattctac tgttactatg agaaagatta ttgagcttta tgatggattt     600
tcttctattg agtctcttgt tgatgttgga ggaggaactg gagcttctct tcaacttatt     660
acttctagac atactactct tagaggaatt aactttgatc ttccacatgt tattgaggag     720
gctactactt atcatggaat tgagcatctt gctggagata tgtttaactc tattccaaag     780
gctgatgcta tttatatgaa gtggattctt catgattgga ctgatgctct tgtcttcaa      840 gttcttagaa actgttatag atctcttcca agaacggaa aggttattgt tgctgagtgt      900
atgatgtctg atgctccaga gtcttctcca gctactcaaa accttcttca tcttgatgct     960
attatgctta ttcatactat tggaggaaag gatagaactg agaaggagtt taaggctctt    1020
gctagagctg ctggatttaa gggatataac aaggctgctt gtggaatgca atcttgggtt    1080
```
atggagtttt gtaag                                              1095

<210> SEQ ID NO 22
<211> LENGTH: 365
<212> TYPE: PRT
<213> ORGANISM: Artificial
<220> FEATURE:
<223> OTHER INFORMATION: OMT3 variant 7

<400> SEQUENCE: 22

```
Met Gly Ser Thr Ser Ala Ser Val Asn Val Leu Leu Glu Ala Asn Gln
1               5                   10                  15

Asp Asp Asn Ser Phe Leu Phe Ala Ile Gln Ile Gly Thr Ala Ser Met
            20                  25                  30

Val Pro Ile Val Leu Arg Thr Ala Val Glu Leu Asp Leu Leu Glu Thr
        35                  40                  45

Ile Ala Lys Ala Gly Pro Gly Gly Ser Met Ser Ser Ser Glu Leu Val
    50                  55                  60

Ala Gln Leu Pro Lys Leu Asn Gln Pro Asp Ala Pro Val Leu Val Glu
65                  70                  75                  80

Arg Ile Cys Arg Leu Leu Ala Ser Tyr Ser Val Leu Ser Cys Thr Leu
                85                  90                  95

Arg Glu Ser Leu Asp Gly Cys Gly Asp Arg Tyr Tyr Gly Val Ala Pro
            100                 105                 110

Leu Cys Arg Tyr Leu Thr Arg Asn Glu Ser Ala Leu Ser Met Gly Pro
        115                 120                 125

Leu Ile Leu Leu Gln Asn Glu Lys Met Tyr Val Glu Ser Phe Tyr Phe
    130                 135                 140

Leu Lys Glu Ala Val Val Asp Gly Gly Val Pro Thr Asn Lys Ala Tyr
145                 150                 155                 160

Gly Leu Pro Ala Phe Glu Tyr Phe Ala Lys Asp Gln Arg Trp Asn Arg
                165                 170                 175

Ile Phe Gln Ser Gly Met Phe Asn His Ser Thr Val Thr Met Arg Lys
            180                 185                 190

Ile Ile Glu Leu Tyr Asp Gly Phe Ser Ser Ile Glu Ser Leu Val Asp
        195                 200                 205

Val Gly Gly Gly Thr Gly Ala Ser Leu Gln Leu Ile Thr Ser Arg His
    210                 215                 220

Thr Thr Leu Arg Gly Ile Asn Phe Asp Leu Pro His Val Ile Glu Glu
225                 230                 235                 240

Ala Thr Thr Tyr His Gly Ile Glu His Leu Ala Gly Asp Met Phe Asn
                245                 250                 255

Ser Ile Pro Lys Ala Asp Ala Ile Tyr Met Lys Trp Ile Leu His Asp
            260                 265                 270

Trp Thr Asp Ala Leu Cys Leu Gln Val Leu Arg Asn Cys Tyr Arg Ser
        275                 280                 285

Leu Pro Lys Asn Gly Lys Val Ile Val Ala Glu Cys Met Met Ser Asp
    290                 295                 300

Ala Pro Glu Ser Ser Pro Ala Thr Gln Asn Leu Leu His Leu Asp Ala
305                 310                 315                 320

Ile Met Leu Ile His Thr Ile Gly Gly Lys Asp Arg Thr Glu Lys Glu
                325                 330                 335

Phe Lys Ala Leu Ala Arg Ala Gly Phe Lys Gly Tyr Asn Lys Ala
            340                 345                 350

Ala Cys Gly Met Gln Ser Trp Val Met Glu Phe Cys Lys
```

<210> SEQ ID NO 23
<211> LENGTH: 1061
<212> TYPE: DNA
<213> ORGANISM: Arabidopsis thaliana
<220> FEATURE:
<221> NAME/KEY: misc_feature
<223> OTHER INFORMATION: MYB72 genomic sequence

<400> SEQUENCE: 23

```
atggggaaag gaagagcacc atgctgcgac aagaacaaag tgaagagagg gccatggagc      60
cctcaagaag atctcactct catcactttt attcaaaaac atggccatca aaactggaga     120
tctcttccca agcttgctgg ttagtattta ttcacatgca tgtttcggta atactataaa     180
gttttaaata actaagagaa ataatgattg atatatatac ataggattgt tgagatgtgg     240
gaaaagttgc cgactaagat ggataaacta tctgagaccg acgtgaagc gaggcaactt      300
tagcaaaaag gaggaagatg ctatcattca ctaccatcaa acccttggaa caagtttgt      360
actctaccta ttcatctaat ttctttataa taagacaata tatagtatgt agagactaat     420
tgatatatgt gatcatcagg tggtcaaaga tcgcgtcctt cttgccggga agaactgaca     480
acgagatcaa aaacgtgtgg aacacgcatc tcaagaaacg actcactcca tcttcttctt     540
cttcatccct ctctagcact catgaccaaa gcacaaaagc agatcatgac aagaactgtg     600
acggggctca agaagaaata cattcagggt taaatgagag ccaaaactca gctacttcgt     660
cacatcacca aggcgagtgt atgcacacaa aaccagagct tcatgaggtt aatggactca     720
acgagatcca gttcctgctc gaccatgatg actttgatga tataacctct gagtttcttc     780
aggataacga tatcttattt ccgctagact ctcttcttca taaccaccaa actcacattt     840
caacccaaga aatgactcga gaggtaacca atcgcaatc atttgatcat cctcaaccgg      900
atatcccatg cggatttgaa gacacaaacg aagaatccga cttgaggaga cagctggttg     960
aatcaaccac acctaacaat gagtacgacg agtggttcaa cttcattgac aaccaaactt    1020
actttgatga ttttaatttc gtcggagaag tatgtctatg a                        1061
```

<210> SEQ ID NO 24
<211> LENGTH: 53
<212> TYPE: PRT
<213> ORGANISM: Artificial
<220> FEATURE:
<223> OTHER INFORMATION: dimerization domain PF08100

<400> SEQUENCE: 24

```
Met Val Leu Lys Thr Ala Ile Glu Leu Asp Leu Leu Glu Thr Ile Ala
1               5                   10                  15
Lys Ala Gly Pro Gly Gly Ser Leu Ser Ser Ser Glu Leu Val Ala Gln
                20                  25                  30
Leu Pro Lys Val Asn Asn Pro Glu Ala Pro Val Met Val Asp Arg Ile
            35                  40                  45
Cys Arg Leu Leu Ala
        50
```

<210> SEQ ID NO 25
<211> LENGTH: 206
<212> TYPE: PRT
<213> ORGANISM: Artificial
<220> FEATURE:
<223> OTHER INFORMATION: O-methyltransferase domain PF00891

<400> SEQUENCE: 25

```
Trp Tyr Phe Leu Lys Asp Ala Val Leu Asp Gly Gly Ile Pro Ser Asn
1               5                   10                  15
Lys Ala Tyr Gly Met Pro Ala Phe Glu Tyr Tyr Gly Lys Asp Gln Arg
            20                  25                  30
Phe Asn Lys Val Phe Asn Ser Ala Met Phe Asn His Ser Thr Met Thr
        35                  40                  45
Met Lys Lys Ile Ile Asp Leu Tyr Asp Gly Phe Ser Ser Leu Glu Thr
    50                  55                  60
Leu Val Asp Val Gly Gly Thr Gly Ala Ser Leu Asn Met Ile Thr
65                  70                  75                  80
Ser Lys His Thr Ser Leu Lys Gly Ile Asn Phe Asp Leu Pro His Val
                85                  90                  95
Ile Glu Asp Ala Thr Thr Tyr His Gly Ile Glu His Val Gly Gly Asp
            100                 105                 110
Met Phe Glu Ser Val Pro Lys Gly Asp Ala Ile Phe Met Lys Trp Ile
        115                 120                 125
Leu His Asp Trp Ser Asp Ala Leu Cys Leu Gln Val Leu Lys Asn Cys
    130                 135                 140
Tyr Lys Ser Leu Pro Lys Asn Gly Lys Val Ile Val Ala Glu Cys Ile
145                 150                 155                 160
Leu Ser Glu Ala Pro Asp Ser Thr Pro Ala Thr Gln Asn Val Ile His
                165                 170                 175
Ile Asp Val Ile Met Leu Val His Ser Leu Gly Gly Lys Glu Arg Thr
            180                 185                 190
Glu Lys Glu Phe Glu Ala Leu Ala Lys Ala Ala Gly Phe Lys
        195                 200                 205
```

<210> SEQ ID NO 26
<211> LENGTH: 1080
<212> TYPE: DNA
<213> ORGANISM: Ipomea batatas
<220> FEATURE:
<221> NAME/KEY: misc_feature
<223> OTHER INFORMATION: F6H1 (IbF6H1)

<400> SEQUENCE: 26

```
atgatgcctt caacaacact ctccactgtt ctctccgaca tcaatgactt cgtcgtgaaa     60
caaggccacg gagtgaaggg cctttcggag cttggcctcc aaacacttcc caaccaatat    120
gtccacccgc cggaggagag ctatccagca tggacgtcg ttaccgacga ctccattccg    180
gtcattgacg tctcaaactg ggaggacccg aaggtgtcta agctcatttg cgacgccgct    240
gagaagaggg gtttcttcca gattgtgaac catgggattc cccttgagat gctggagaag    300
gctaaggcgg ccacttaccg gttcttcagg gagccggccg aggaaaagaa gaagtattct    360
aaggagaact gtccgactag ccatgtgagg tatagcacaa gctttcttcc acaaatagag    420
aaagctttgg agtggaaaga tcacctcagt atgttctatg tttccgacga ggaagctgct    480
caatattggc ctccttcttg cagggatgat gcactggagt acctgaaaag ctgtgaaatg    540
gtgagtagga agctattaga ggcattgatg caaggactaa acgtgaatga aattgacgat    600
tccaaagaat cacttctaat gggttcacgt aggatcaaca tcaactacta cccaaagtgc    660
cccaaccccgg atctcaccgt cggcgtgggc cgtcactccg acatctccac cctcacactc    720
ctcctccagg acgacatcgg aggcctgtac gtgcgcaaac tggagcacga ggcctggtca    780
cacgtgcccc cagtaaaggg cgctctggtt atcaacatcg gcgacgctct ccagataatg    840
```

```
agcaacggtc gatacaagag catcgaacat cgcgttatgg ccaatgagac caacgacagg    900
atctccgtcc ctgttttcgt gaaccccagg cctaacgaca ttgtgggggcc actcccggag    960 gttctggcca gtggggagaa gccggtatac aagccggttc tctactccga ctacgccaag   1020
catttctacc ggaaagctca caacggaaaa gacactattg ccttcgccag aatagaatag   1080
```

```
<210> SEQ ID NO 27
<211> LENGTH: 359
<212> TYPE: PRT
<213> ORGANISM: Ipomea batatas
<220> FEATURE:
<221> NAME/KEY: MISC_FEATURE
<223> OTHER INFORMATION: F6H1 (IbF6H1)

<400> SEQUENCE: 27
```

Met Met Pro Ser Thr Thr Leu Ser Thr Val Leu Ser Asp Ile Asn Asp
1               5                   10                  15

Phe Val Val Lys Gln Gly His Gly Val Lys Gly Leu Ser Glu Leu Gly
            20                  25                  30

Leu Gln Thr Leu Pro Asn Gln Tyr Val His Pro Glu Glu Arg Leu
        35                  40                  45

Ser Ser Met Asp Val Val Thr Asp Ser Ile Pro Val Ile Asp Val
    50                  55                  60

Ser Asn Trp Glu Asp Pro Lys Val Ser Lys Leu Ile Cys Asp Ala Ala
65                  70                  75                  80

Glu Lys Arg Gly Phe Phe Gln Ile Val Asn His Gly Ile Pro Leu Glu
                85                  90                  95

Met Leu Glu Lys Ala Lys Ala Ala Thr Tyr Arg Phe Phe Arg Glu Pro
            100                 105                 110

Ala Glu Glu Lys Lys Lys Tyr Ser Lys Glu Asn Cys Pro Thr Ser His
        115                 120                 125

Val Arg Tyr Ser Thr Ser Phe Leu Pro Gln Ile Glu Lys Ala Leu Glu
    130                 135                 140

Trp Lys Asp His Leu Ser Met Phe Tyr Val Ser Asp Glu Glu Ala Ala
145                 150                 155                 160

Gln Tyr Trp Pro Pro Ser Cys Arg Asp Asp Ala Leu Glu Tyr Leu Lys
                165                 170                 175

Ser Cys Glu Met Val Ser Arg Lys Leu Leu Glu Ala Leu Met Gln Gly
            180                 185                 190

Leu Asn Val Asn Glu Ile Asp Asp Ser Lys Glu Ser Leu Leu Met Gly
        195                 200                 205

Ser Arg Arg Ile Asn Ile Asn Tyr Tyr Pro Lys Cys Pro Asn Pro Asp
    210                 215                 220

Leu Thr Val Gly Val Gly Arg His Ser Asp Ile Ser Thr Leu Thr Leu
225                 230                 235                 240

Leu Leu Gln Asp Asp Ile Gly Gly Leu Tyr Val Arg Lys Leu Glu His
                245                 250                 255

Glu Ala Trp Ser His Val Pro Pro Val Lys Gly Ala Leu Val Ile Asn
            260                 265                 270

Ile Gly Asp Ala Leu Gln Ile Met Ser Asn Gly Arg Tyr Lys Ser Ile
        275                 280                 285

Glu His Arg Val Met Ala Asn Glu Thr Asn Asp Arg Ile Ser Val Pro
    290                 295                 300

Val Phe Val Asn Pro Arg Pro Asn Asp Ile Val Gly Pro Leu Pro Glu
305                 310                 315                 320

```
Val Leu Ala Ser Gly Glu Lys Pro Val Tyr Lys Pro Val Leu Tyr Ser
                325                 330                 335

Asp Tyr Ala Lys His Phe Tyr Arg Lys Ala His Asn Gly Lys Asp Thr
            340                 345                 350

Ile Ala Phe Ala Arg Ile Glu
        355

<210> SEQ ID NO 28
<211> LENGTH: 1086
<212> TYPE: DNA
<213> ORGANISM: Arabidopsis thaliana
<220> FEATURE:
<221> NAME/KEY: misc_feature
<223> OTHER INFORMATION: F6H1 (AtF6H1)

<400> SEQUENCE: 28
atggctccaa cactcttgac aacccaattc tcaaatccag ctgaagtaac cgactttgta      60
gtctacaaag gaatggtgt taagggttta tcagaaacag gaatcaaagc tcttccagaa     120
caatacattc agccacttga agaacgactc atcaacaaat cgtcaacga acagatgaa      180 gccattccag ttatcgatat gtcgaaccct gatgaggaca gagtcgctga agctgtttgt     240
gatgctgctg agaaatgggg gttctttcaa gtgatcaatc atggagttcc tttggaagtt    300
cttgatgacg tcaaggctgc gactcacaag ttcttcaatc tccctgttga agagaagcgc    360
aagttcacta agagaattc gctgtcgacg actgttaggt ttgggacgag ttttagtcct     420
cttgcagagc aagcgcttga gtggaaagat tatctcagcc tcttctttgt ctctgaagct     480
gaagctgaac agttctggcc tgatatctgc aggaatgaaa cgttagagta cattaacaag    540
tcaaagaaga tggtgaggag gcttctagag tatttgggaa agaatctcaa tgttaaagag    600
cttgacgaga cgaaagaatc actctttatg ggctcgattc gagtcaacct taactactac    660
cccatctgcc ctaatccgga cctaacagtt ggtgttggtc gccactcaga cgtctcttct    720
ctcaccattc tcttacaaga ccagatcggt ggtctacacg tgcgttctct ggcttcaggg    780
aactgggttc acgtgcctcc ggttgctgga tcttttgtga tcaacatcgg agatgcgatg    840
cagatcatga gcaatggtct gtacaagagc gtggagcatc gtgtcttagc caatggttac    900
aataatagaa tctctgttcc tatctttgtg aacccaaaac cagagtcagt tattggtcct    960
ctacctgagg tgattgcaaa cggagaggaa ccgatttaca gagacgtcct gtactctgat   1020
tacgtcaagt atttcttcag gaaggcacac gatggaaaga aaccgtcga ttacgccaag   1080 atctga                                                              1086

<210> SEQ ID NO 29
<211> LENGTH: 361
<212> TYPE: PRT
<213> ORGANISM: Arabidopsis thaliana
<220> FEATURE:
<221> NAME/KEY: MISC_FEATURE
<223> OTHER INFORMATION: F6H1 (AtF6H1)

<400> SEQUENCE: 29

Met Ala Pro Thr Leu Leu Thr Thr Gln Phe Ser Asn Pro Ala Glu Val
1               5                   10                  15

Thr Asp Phe Val Val Tyr Lys Gly Asn Gly Val Lys Gly Leu Ser Glu
            20                  25                  30

Thr Gly Ile Lys Ala Leu Pro Glu Gln Tyr Ile Gln Pro Leu Glu Glu
        35                  40                  45
```

Arg Leu Ile Asn Lys Phe Val Asn Glu Thr Asp Glu Ala Ile Pro Val
 50                  55                  60

Ile Asp Met Ser Asn Pro Asp Glu Asp Arg Val Ala Glu Ala Val Cys
 65                  70                  75                  80

Asp Ala Ala Glu Lys Trp Gly Phe Phe Gln Val Ile Asn His Gly Val
                 85                  90                  95

Pro Leu Glu Val Leu Asp Asp Val Lys Ala Ala Thr His Lys Phe Phe
            100                 105                 110

Asn Leu Pro Val Glu Glu Lys Arg Lys Phe Thr Lys Glu Asn Ser Leu
            115                 120                 125

Ser Thr Thr Val Arg Phe Gly Thr Ser Phe Ser Pro Leu Ala Glu Gln
        130                 135                 140

Ala Leu Glu Trp Lys Asp Tyr Leu Ser Leu Phe Phe Val Ser Glu Ala
145                 150                 155                 160

Glu Ala Glu Gln Phe Trp Pro Asp Ile Cys Arg Asn Glu Thr Leu Glu
                165                 170                 175

Tyr Ile Asn Lys Ser Lys Lys Met Val Arg Arg Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Ala Ser Gly Asn Trp Val His Val Pro Pro Val Ala Gly Ser Phe
            260                 265                 270

Val Ile Asn Ile Gly Asp Ala Met Gln Ile Met Ser Asn Gly Leu Tyr
        275                 280                 285

Lys Ser Val Glu His Arg Val Leu Ala Asn Gly Tyr Asn Asn Arg Ile
290                 295                 300

Ser Val Pro Ile Phe Val Asn Pro Lys Pro Glu Ser Val Ile Gly Pro
305                 310                 315                 320

Leu Pro Glu Val Ile Ala Asn Gly Glu Glu Pro Ile Tyr Arg Asp Val
                325                 330                 335

Leu Tyr Ser Asp Tyr Val Lys Tyr Phe Arg Lys Ala His Asp Gly
            340                 345                 350

Lys Lys Thr Val Asp Tyr Ala Lys Ile
        355                 360

<210> SEQ ID NO 30
<211> LENGTH: 1086
<212> TYPE: DNA
<213> ORGANISM: Helianthus annuus
<220> FEATURE:
<221> NAME/KEY: misc_feature
<223> OTHER INFORMATION: F6H1 (HaF6H1)

<400> SEQUENCE: 30
atggctccat caatctccat gacccccctca aacccactcg acattctcga tttcgtggtg      60
aacaaaggtc atggagttaa aggcttagca gacctggggc tcaagacact accacaccaa     120
tacattcaac caccacaaga acggtttgat cacactagca tgaagaact  gaatgaagat     180 tccatcccgg ttattgattt gtccaactcg gatgacccga agtagcaaa agcggtatgt     240

-continued

```
gatgcagcac agaaatgggg attctttcag ataataaacc atgggatccc tattcatgtt     300
cttggaaatg tcaaagatgc aactcacaag ttttttgagt tgccagctga agaaaagaag     360
aaatactcga agaacaatc gggtaccaat aacgttagat ttggtacgag ttttacgcct      420
gaagccgaga agctctaga gtggaaggat tatctcagcc tgttctttgt ctcggatgat      480
gaggctgctt ccctctggcc agccatttgc aggaatgaag ctttggaata taaggagt      540 tctgaaacgg ttgtcaagag gttgctcaag atcctgatga atgggctaaa tgtaaaagac    600
attgactcaa ccaaagaatc aattctaatg gggtccaaga ggattaaccct taactactat   660 cccaaatgtc ctaaccctga gcttactgtg ggtgtgggc gtcattcaga cgtgtccaca     720
ctcacaatac tacttcaaga tgacattggc gggctttacg tacgaaacac aaaaactatg    780
gaatgggttc atgtccctcc ggtaaatgga tctttggtga tcaatgttgg agatgcactt    840
caaatcatga gtaacggtaa gtacaaaagt gttgagcatc gcgtaactgc aaatggaaat    900
ggtaacagga tttcagtccc gatattcgtc aacccaaggc ctagtgacat tattggacct    960
ttggtagaaa tggttgagag tggggagaaa ccgatctaca acatgtact ctactcggat    1020 tatgtcaagc attttttcag aaaggcacat gatgggaaag ccacaattga ttttgcaaag   1080
gtgtaa                                                              1086
```

<210> SEQ ID NO 31
<211> LENGTH: 361
<212> TYPE: PRT
<213> ORGANISM: Helianthus annuus
<220> FEATURE:
<221> NAME/KEY: MISC_FEATURE
<223> OTHER INFORMATION: F6H1 (HaF6H1)

<400> SEQUENCE: 31

```
Met Ala Pro Ser Ile Ser Met Thr Pro Ser Asn Pro Leu Asp Ile Leu
 1               5                  10                  15

Asp Phe Val Val Asn Lys Gly His Gly Val Lys Gly Leu Ala Asp Leu
                20                  25                  30

Gly Leu Lys Thr Leu Pro His Gln Tyr Ile Gln Pro Gln Glu Arg
        35                  40                  45

Phe Asp His Thr Ser Asn Glu Glu Leu Asn Glu Asp Ser Ile Pro Val
    50                  55                  60

Ile Asp Leu Ser Asn Ser Asp Pro Lys Val Ala Lys Ala Val Cys
65                  70                  75                  80

Asp Ala Ala Gln Lys Trp Gly Phe Phe Gln Ile Ile Asn His Gly Ile
                85                  90                  95

Pro Ile His Val Leu Gly Asn Val Lys Asp Ala Thr His Lys Phe Phe
            100                 105                 110

Glu Leu Pro Ala Glu Glu Lys Lys Lys Tyr Ser Lys Glu Gln Ser Gly
        115                 120                 125

Thr Asn Asn Val Arg Phe Gly Thr Ser Phe Thr Pro Glu Ala Glu Lys
    130                 135                 140

Ala Leu Glu Trp Lys Asp Tyr Leu Ser Leu Phe Phe Val Ser Asp Asp
145                 150                 155                 160

Glu Ala Ala Ser Leu Trp Pro Ala Ile Cys Arg Asn Glu Ala Leu Glu
                165                 170                 175

Tyr Ile Arg Ser Ser Glu Thr Val Val Lys Arg Leu Leu Lys Ile Leu
            180                 185                 190

Met Asn Gly Leu Asn Val Lys Asp Ile Asp Ser Thr Lys Glu Ser Ile
        195                 200                 205
```

Leu Met Gly Ser Lys Arg Ile Asn Leu Asn Tyr Tyr Pro Lys Cys Pro
    210                 215                 220

Asn Pro Glu Leu Thr Val Gly Val Gly Arg His Ser Asp Val Ser Thr
225                 230                 235                 240

Leu Thr Ile Leu Leu Gln Asp Asp Ile Gly Gly Leu Tyr Val Arg Asn
            245                 250                 255

Thr Lys Thr Met Glu Trp Val His Val Pro Pro Val Asn Gly Ser Leu
                260                 265                 270

Val Ile Asn Val Gly Asp Ala Leu Gln Ile Met Ser Asn Gly Lys Tyr
        275                 280                 285

Lys Ser Val Glu His Arg Val Thr Ala Asn Gly Asn Gly Asn Arg Ile
    290                 295                 300

Ser Val Pro Ile Phe Val Asn Pro Arg Pro Ser Asp Ile Ile Gly Pro
305                 310                 315                 320

Leu Val Glu Met Val Glu Ser Gly Glu Lys Pro Ile Tyr Lys His Val
                325                 330                 335

Leu Tyr Ser Asp Tyr Val Lys His Phe Phe Arg Lys Ala His Asp Gly
            340                 345                 350

Lys Ala Thr Ile Asp Phe Ala Lys Val
        355                 360

<210> SEQ ID NO 32
<211> LENGTH: 49
<212> TYPE: DNA
<213> ORGANISM: Artificial Sequence
<220> FEATURE:
<223> OTHER INFORMATION: primer HaOMT3_attB1_F

<400> SEQUENCE: 32
ggggacaagt ttgtacaaaa aagcaggctc aatgggttca acatcagcc                49

<210> SEQ ID NO 33
<211> LENGTH: 54
<212> TYPE: DNA
<213> ORGANISM: Artificial Sequence
<220> FEATURE:
<223> OTHER INFORMATION: primer HaOMT3_attB2_R

<400> SEQUENCE: 33
ggggaccact ttgtacaaga aagctgggta ctatttgcaa aattccataa ccca          54

<210> SEQ ID NO 34
<211> LENGTH: 52
<212> TYPE: DNA
<213> ORGANISM: Artificial Sequence
<220> FEATURE:
<223> OTHER INFORMATION: primer HaOMT1_attB1_F

<400> SEQUENCE: 34
ggggacaagt ttgtacaaaa aagcaggctc aatgggttca acatcagcat ct            52

<210> SEQ ID NO 35
<211> LENGTH: 54
<212> TYPE: DNA
<213> ORGANISM: Artificial Sequence
<220> FEATURE:
<223> OTHER INFORMATION: primer HaOMT1_attB2_R

<400> SEQUENCE: 35
ggggaccact ttgtacaaga aagctgggta ctatttgcaa aattccataa ccca          54

<210> SEQ ID NO 36
<211> LENGTH: 51
<212> TYPE: DNA
<213> ORGANISM: Artificial Sequence
<220> FEATURE:
<223> OTHER INFORMATION: primer HaF6H1_attB1_F

<400> SEQUENCE: 36
ggggacaagt tgtacaaaa aagcaggctc aatggctcca tcaatctcca t    51

<210> SEQ ID NO 37
<211> LENGTH: 50
<212> TYPE: DNA
<213> ORGANISM: Artificial Sequence
<220> FEATURE:
<223> OTHER INFORMATION: primer HaF6H1_attB2_R

<400> SEQUENCE: 37
ggggaccact tgtacaaga aagctgggta ttacaccttt gcaaaatcaa    50

<210> SEQ ID NO 38
<211> LENGTH: 52
<212> TYPE: DNA
<213> ORGANISM: Artificial Sequence
<220> FEATURE:
<223> OTHER INFORMATION: primer IbF6H1_attB1_F

<400> SEQUENCE: 38
ggggacaagt tgtacaaaa aagcaggctc aatgccttca acaacactct cc    52

<210> SEQ ID NO 39
<211> LENGTH: 50
<212> TYPE: DNA
<213> ORGANISM: Artificial Sequence
<220> FEATURE:
<223> OTHER INFORMATION: primer IbF6H1_attB2_R

<400> SEQUENCE: 39
ggggaccact tgtacaaga aagctgggta ctattctatt ctggcgaagg    50

<210> SEQ ID NO 40
<211> LENGTH: 51
<212> TYPE: DNA
<213> ORGANISM: Artificial Sequence
<220> FEATURE:
<223> OTHER INFORMATION: primer AtF6H1_GWY_F

<400> SEQUENCE: 40
ggggacaagt tgtacaaaa aagcaggctt aatggctcca acactcttga c    51

<210> SEQ ID NO 41
<211> LENGTH: 49
<212> TYPE: DNA
<213> ORGANISM: Artificial Sequence
<220> FEATURE:
<223> OTHER INFORMATION: primer AtF6H1_GWY_R

<400> SEQUENCE: 41
ggggaccact tgtacaaga aagctgggta tcagatcttg gcgtaatcg    49

<210> SEQ ID NO 42
<211> LENGTH: 40
<212> TYPE: DNA
<213> ORGANISM: Artificial Sequence
<220> FEATURE:
<223> OTHER INFORMATION: primer HaOMT1_gbs_F

<400> SEQUENCE: 42
aaggtcgtgg gatccccagg atgggttcaa catcagcatc                                40

<210> SEQ ID NO 43
<211> LENGTH: 42
<212> TYPE: DNA
<213> ORGANISM: Artificial Sequence
<220> FEATURE:
<223> OTHER INFORMATION: primer HaOMT1_gbs_R

<400> SEQUENCE: 43
gtcagtcacg atgcggccgc ctatttgcaa aattccataa cc                            42

<210> SEQ ID NO 44
<211> LENGTH: 38
<212> TYPE: DNA
<213> ORGANISM: Artificial Sequence
<220> FEATURE:
<223> OTHER INFORMATION: primer HaOMT3_gbs_F

<400> SEQUENCE: 44
aaggtcgtgg gatccccagg atgggttcaa catcagcc                                 38

<210> SEQ ID NO 45
<211> LENGTH: 42
<212> TYPE: DNA
<213> ORGANISM: Artificial Sequence
<220> FEATURE:
<223> OTHER INFORMATION: primer HaOMT3_gbs_R

<400> SEQUENCE: 45
gtcagtcacg atgcggccgc ctatttgcaa aattccataa cc                            42

<210> SEQ ID NO 46
<211> LENGTH: 38
<212> TYPE: DNA
<213> ORGANISM: Artificial Sequence
<220> FEATURE:
<223> OTHER INFORMATION: primer IbF6H1_gbsA_F

<400> SEQUENCE: 46
aaggtcgtgg gatccccagg atgccttcaa caacactc                                 38

<210> SEQ ID NO 47
<211> LENGTH: 38
<212> TYPE: DNA
<213> ORGANISM: Artificial Sequence
<220> FEATURE:
<223> OTHER INFORMATION: primer IbF6H1_gbsA_R

<400> SEQUENCE: 47
ccattggtat atctccttct attctattct ggcgaagg                                 38

<210> SEQ ID NO 48
<211> LENGTH: 41
<212> TYPE: DNA
<213> ORGANISM: Artificial Sequence
<220> FEATURE:
<223> OTHER INFORMATION: primer Ha4Cl2_gbsAC_F

<400> SEQUENCE: 48
aatagaatag aaggagatat accaatggcg ccggagaagg a                             41

<210> SEQ ID NO 49

<211> LENGTH: 41
<212> TYPE: DNA
<213> ORGANISM: Artificial Sequence
<220> FEATURE:
<223> OTHER INFORMATION: primer Ha4Cl2_gbsABC_R

<400> SEQUENCE: 49
gtcagtcacg atgcggccgc ttaatttggg acaccagctg c    41

<210> SEQ ID NO 50
<211> LENGTH: 38
<212> TYPE: DNA
<213> ORGANISM: Artificial Sequence
<220> FEATURE:
<223> OTHER INFORMATION: primer AtF6H1_pGEX_fwd

<400> SEQUENCE: 50
aaggtcgtgg gatccccagg atggctccaa cactcttg    38

<210> SEQ ID NO 51
<211> LENGTH: 28
<212> TYPE: DNA
<213> ORGANISM: Artificial Sequence
<220> FEATURE:
<223> OTHER INFORMATION: primer AtF6H1_pGEX_rev

<400> SEQUENCE: 51
atatctcctt tcagatcttg gcgtaatc    28

<210> SEQ ID NO 52
<211> LENGTH: 29
<212> TYPE: DNA
<213> ORGANISM: Artificial Sequence
<220> FEATURE:
<223> OTHER INFORMATION: primer At1_RBS_Ha4Cl2_fwd

<400> SEQUENCE: 52
caagatctga aaggagatat accaatggc    29

<210> SEQ ID NO 53
<211> LENGTH: 38
<212> TYPE: DNA
<213> ORGANISM: Artificial Sequence
<220> FEATURE:
<223> OTHER INFORMATION: primer Ha4Cl2_pGEX_rev

<400> SEQUENCE: 53
gtcagtcacg atgcggccgc ttaatttggg acaccagc    38

<210> SEQ ID NO 54
<211> LENGTH: 38
<212> TYPE: DNA
<213> ORGANISM: Artificial Sequence
<220> FEATURE:
<223> OTHER INFORMATION: primer HaF6H1_gbsB_F

<400> SEQUENCE: 54
aaggtcgtgg gatccccagg atggctccat caatctcc    38

<210> SEQ ID NO 55
<211> LENGTH: 41
<212> TYPE: DNA
<213> ORGANISM: Artificial Sequence
<220> FEATURE:
<223> OTHER INFORMATION: primer HaF6H1_gbsB_R

<400> SEQUENCE: 55

-continued

```
ccattggtat atctcctttt acacctttgc aaaatcaatt g                          41

<210> SEQ ID NO 56
<211> LENGTH: 41
<212> TYPE: DNA
<213> ORGANISM: Artificial Sequence
<220> FEATURE:
<223> OTHER INFORMATION: primer Ha4Cl2_gbsB_F

<400> SEQUENCE: 56
aaaggtgtaa aaggagatat accaatggcg ccggagaagg a                          41

<210> SEQ ID NO 57
<211> LENGTH: 41
<212> TYPE: DNA
<213> ORGANISM: Artificial Sequence
<220> FEATURE:
<223> OTHER INFORMATION: primer Ha4Cl2_gbsABC_R

<400> SEQUENCE: 57
gtcagtcacg atgcggccgc ttaatttggg acaccagctg c                          41
```

METHOD OF INCREASING RESISTANCE AGAINST SOYBEAN RUST IN TRANSGENIC PLANTS BY INCREASING THE SCOPARONE

This application is a National Stage application of International Application No. PCT/EP2019/085118, filed Dec. 13, 2019, which claims priority to European Patent Application No. 18212497.4, filed Dec. 14, 2018.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "180663_Seqlisting.txt", which was created on Jun. 2, 2021 and is 78,538 bytes in size. The subject matter of the Sequence Listing is incorporated herein in its entirety by reference.

BACKGROUND OF THE INVENTION

The cultivation of agricultural crop plants serves mainly for the production of foodstuffs for humans and animals. Monocultures in particular, which are routine nowadays, are highly susceptible to an epidemic-like spread of diseases. The result is markedly reduced yields. To date, the pathogenic organisms have been controlled mainly by using pesticides. Nowadays, the possibility of directly modifying the genetic disposition of a plant or pathogen is also open to man. Alternatively, natural occurring fungicides produced by the plants after fungal infection can be synthesized and applied to the plants. Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms (Schopfer and Brennicke (1999) Pflanzenphysiologie, Springer Verlag, Berlin-Heidelberg, Germany).

With regard to the race specific resistance, a differentiation is made between compatible and incompatible interactions. In the compatible interaction, an interaction occurs between a virulent pathogen and a susceptible plant. The pathogen survives, and may build up reproduction structures, while the host is seriously hampered in development or dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is mostly specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. To counteract plants have developed physical barriers, such as wax layers, and chemical compounds having antifungal effects to inhibit spore germination, hyphal growth or penetration.

The soybean rust fungus *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasma membrane of the penetrated mesophyll cell stays intact.

Biotrophic phytopathogenic fungi depend for their nutrition on the metabolism of living cells of the plants. This type of fungi belong to the group of biotrophic fungi, like many rust fungi, powdery mildew fungi or oomycete pathogens like the genus Phytophthora or Peronospora. Necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus switches to an obligatory biotrophic lifestyle. The subgroup of the biotrophic fungal pathogens which follows essentially such an infection strategy are heminecrotrohic.

Scopoletin and scopolin are antimicrobial phenolic hydroxycumarins that accumulate in different plants upon infection with various pathogens such as fungi or bacteria or in response to insect feeding damage, mechanical injury, dehydration or various other abiotic stresses.

Scopoletin has broad-spectrum antimicrobial activity and can inhibit development and growth of various fungi and bacteria in vitro (Goy, P. A., Signer, H., Reist, R., Aichholz, R., Blum, W., Schmidt, E., and Kessmann, H. (1993). Accumulation of scopoletin is associated with the high disease resistance of the hybrid Nicotiana glutinosa x Nicotiana debneyi. Planta 41: 200-206.; Tal, B. and Robeson, D. J. (1986b). The Metabolism of Sunflower Phytoalexins Ayapin and Scopoletin: Plant-Fungus Interactions. Plant Physiology 82: 167-172.). Scopoletin and its glucoside scopolin originate from the phenylpropanoid pathway (FIG. 1; (Kai, K., Mizutani, M., Kawamura, N., Yamamoto, R., Tamai, M., Yamaguchi, H., Sakata, K., and Shimizu, B. (2008). Scopoletin is biosynthesized via ortho-hydroxylation of feruloyl CoA by a 2-oxoglutarate-dependent dioxygenase in *Arabidopsis thaliana*. Plant Journal 55: 989-99).

Key steps of scopoletin/scopolin biosynthesis comprise the ortho hydroxylation of feruloyl-CoA, trans/cis isomeration of the side chain, lactonization and—in case of scopolin synthesis-glycosylation (Kai et al., 2008). In *Arabidopsis* it has recently been shown that scopoletin production depends on ortho hydroxylation of feruloyl-CoA by the Fe(II)- and 2-oxoglutarate-dependent dioxygenase F6H1 (At3g13610). E-Z isomerisation of the side chain and lactonization were found to occur spontaneously (Kai et al., 2008).

In planta accumulating scopoletin can finally be glucosylated to produce scopolin. Several *Arabidopsis* glucosyltransferases (e.g. UGT71 C1) (Lim, E.-K., Baldauf, S., Li, Y., Elias, L, Worrall, D., Spencer, S. P., Jackson, R. G., Taguchi, G., Ross, J., and Bowles, D. J. (2003). Evolution of substrate recognition across a multigene family of glycosyltransferases in *Arabidopsis*. Glycobiology 13: 139-45.) as well as two different tobacco glucosyltransferases (Togt1 and Togt2) (Fraissinet-Tachet, L., Baltz, R., Chong, J., Kauffmann, S., Fritig, B., and Saindrenan, P. (1998). Two tobacco genes induced by pathogen infection or elicitor and salicylic acid treatment encode glucosyltransferases acting on phenylpropanoids and benzoic acid derivatives, including salicylic acid. FEBS letters 437: 319-23) have been identified that can catalyze glycosylation of scopoletin in vitro.

Scopolin is generally regarded a less potent antimicrobial agent than scopoletin. Following pathogen-induced mechanical injury or hypersensitive reactions (HR), decompartimentalization of scopolin-containing cells might lead to the release of scopolin from vacuoles into the cytoplasm and subsequent hydrolysis of the glucose conjugate by β-glucosidases.

Scopoletin and its glucoside scopolin are widely distributed among the plant kingdom and have been detected in various organs of approximately 80 different plant families. Interestingly, scopoletin biosynthesis seems to be lost in several economically important crops (e.g. soybean (*Glycine max*), corn/maize (*Zea mays*), wheat (*Triticum aestivum*), rice (*Oryza sativa*) etc.), indicating that the ability to synthesize this antimicrobial substance might have been lost during breeding. However, this does not apply to sweet potato, tobacco, sunflower, cotton, and cassava since scopoletin has been shown to accumulate in these crops in response to infection (summarized by Gnonlonfin, G. J. B., Sanni, A., and Brimer, L. (2012). Review Scopoletin—A Coumarin Phytoalexin with Medicinal Properties. Critical Reviews in Plant Sciences 31: 47-56).

Scoparone is an antimicrobial phenolic coumarin that (together with the antimicrobial hydroxycoumarin scopoletin) accumulates in the flavedo tissue of citrus fruits upon injury, heat treatment, gamma and ultraviolet C (UV-C) irradiation and has been associated with induced resistance to postharvest decay (cf. Guy, D. et al. Scoparone and Scopoletin Accumulation and Ultraviolet-C Induced Resistance to Postharvest Decay in Oranges as Influenced by Harvest Date. 124, 702-707 (1999)). Scoparone concentration in citrus bark is higher and increases more rapidly in resistant than in susceptible citrus species upon inoculation with the oomycete Phytophthora citrophthora. In addition, treatment of resistant citrus cultivars with a phenylalanine ammonia lyase (PAL) inhibitor was associated with a suppression of scoparone production and induced susceptibility to Phytophthora citrophthora (cf. Afek, U. Accumulation of Scoparone, a Phytoalexin Associated with Resistance of Citrus to Phytophthora citrophthora. Phytopathology 78, 1678 (1988)). Scoparone accumulation was also associated with resistance to Phytophthora parasitica and the ascomycete Penicillium digitatum, the causal agent of green mold which is responsible for substantial post-harvest losses in citrus fruits (cf. Ortuño, A. et al. Comparative study of flavonoid and scoparone accumulation in different Citrus species and their susceptibility to Penicillium digitatum. Food Chem. 125, 232-239 (2011)). Scoparone is also mentioned in a study of agents to reduce green mold incidence and severity on pre-treated oranges (cf. Sanzani, S. M., Schena, L. & Ippolito, A. Effectiveness of phenolic compounds against citrus green mould. Molecules 19, 12500-12508 (2014)).

A recent publication reports that a myb transcription factor, MYB72, is able to upregulate the complete coumarin biosynthesis pathway in the roots of *Arabidopsis* (Ioannis A. Stringlis, Ke Yu, Kirstin Feussner, Ronnie de Jonge, Sietske Van Bentum, Marcel C. Van Verk, Roeland L. Berendsen, Peter A. H. M. Bakker, Ivo Feussner, and Corné M. J. Pieterse (2018) MYB72-dependent coumarin exudation shapes root microbiome assembly to promote plant health PNAS, Apr. 23, 2018 doi.org/10.1073/pnas.1722335115). Its possible influence on scoparone and/or scopoletin synthesis has not been established.

Soybean rust has become increasingly important in recent times. The disease is caused by the biotrophic rusts *Phakopsora pachyrhizi* (Sydow) and *Phakopsora meibomiae* (Arthur). They both belong to the class Basidiomycota, order Uredinales, family Phakopsoraceae. Both rusts infect a wide spectrum of leguminosic host plants.

*P. pachyrhizi* is the more aggressive pathogen on soybean (*Glycine max*), and is therefore, at least currently, of great importance for agriculture. *P. pachyrhizi* can be found in nearly all tropical and subtropical soybean growing regions of the world. *P. pachyrhizi* is capable of infecting 31 species from 17 families of the Leguminosae in nature and is capable of growing on further 60 species in controlled conditions (Sinclair et al. (eds.), Proceedings of the rust workshop (1995), National Soybeana Research Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soybean plants with resistance to the entire spectrum of the isolates are not available. When searching for resistant soybean accessions, six dominant R genes of the NBS-LRR family, which mediate resistance of soybean to *P. pachyrhizi*, were discovered. The resistance they conferred was lost rapidly, as *P. pachyrhizi* develops new virulent races.

In recent years, fungal diseases, e.g. soybean rust, became more important in agricultural production. There was, therefore, a demand for developing methods to control fungi and to provide plants that resist fungal diseases.

A lot of research has been performed on powdery and downy mildew infecting the epidermal layer of plants. However, the problem to cope with soybean rust, which infects the mesophyll or with *Fusarium* fungi that infect inaccessible inner tissues remains unsolved.

The object of the present invention is inter alia to provide a method of increasing, preferably in crops and most preferably in soybean, resistance against fungal pathogens, preferably against fungal pathogens of the family Phakopsoraceae, more preferably against fungal pathogens of the genus *Phakopsora*, most preferably against *Phakopsora pachyrhizi* (Sydow) and/or *Phakopsora meibomiae* (Arthur), also known as soybean rust.

SHORT DESCRIPTION OF THE INVENTION

Surprisingly, we found that fungal pathogens, in particular of the genus *Phakopsora*, for example soybean rust, can be controlled by increased production or increased accumulation of scoparone or derivatives thereof in a plant and by direct application of scoparone or derivatives thereof to the plant. Furthermore, we surprisingly found a new pathway for scopoletin synthesis.

The invention therefore provides a method of increasing resistance against fungal pathogens, preferably against soybean rust, more specifically against fungal pathogens of the family Phakopsoraceae, more preferably against fungal pathogens of the genus *Phakopsora*, most preferably against *Phakopsora pachyrhizi* (Sydow), *Phakopsora meibomiae* (Arthur) in plants, plant parts, or plant cells
 by increasing the production and/or accumulation of scoparone and/or derivatives thereof or
 by exogenous application of scoparone and/or derivatives thereof to plants, plant parts, or plant cells.

The invention also provides a method of increasing resistance against fungal pathogens, preferably against soybean rust, more specifically against fungal pathogens of the family Phakopsoraceae, more preferably against fungal pathogens of the genus *Phakopsora*, most preferably against *Phakopsora pachyrhizi* (Sydow) and/or *Phakopsora meibomiae* (Arthur) in transgenic plants, plant parts, or transgenic plant cells by increasing the expression and/or activity of an OMT3 enzyme in said transgenic plant, plant part or plant cell.

The invention also provides transgenic plants resistant against fungal pathogens, preferably against soybean rust, more specifically of the family Phakopsoraceae, more preferably against fungal pathogens of the genus *Phakopsora*, most preferably against *Phakopsora pachyrhizi* (Sydow) and/or *Phakopsora meibomiae* (Arthur), a method for producing such plants as well as a recombinant nucleic acids, in particular expression cassettes and vector constructs, useful for the above methods.

The objects of the present invention, as outlined above, are achieved by the subject-matter of the main claims. Preferred embodiments of the invention are defined by the subject matter of the dependent claims. Brief description of the several views of the drawings

FIGURES

FIG. 1 is a schematic presentation of the coumarin biosynthesis pathway in plants. Phenylalanine is converted to three derivatives of p-hydroxycinnamate, namely p-coumaric acid (PC), caffeic acid (CA) and ferulic acid (FA). Coenzyme A is added to these metabolites by 4-coumarate-CoA ligases (4CLs). Hereafter, members of the feruloyl-CoA-6' hydroxylase (F6'H) family add a hydroxyl group to the 6' C atom. The 6'-hydroxylated CoA esters undergo spontaneous isomerisation and lactonisation to yield the simple coumarins umbelliferone, esculetin and scopoletin. Caffeic acid-O-methyltransferases (COMTs) modify coumarins by methoxylation. The OMT3 enzyme is involved in the synthesis of scopoletin from esculetin, in the synthesis of scoparone from scopoletin, isoscopoletin and/or esculetin and in the synthesis of isoscopoletin from esculetin.

FIG. 2 depicts the inhibition of *P. pachyrhitzi* appressoria formation by scoparone in a concentration-dependent manner. *P. pachyrhizi* uredospores were resuspended in $H_2O$ supplemented with Tween-20 and 10 µM, 25 µM, 50 µM, 100 µM, 200 µM and 400 µM scoparone (solved in 0.1% DMSO) and incubated on glass slides in high humidity conditions. Treatment with 0.1% DMSO and $H_2O$ served as controls. The appressoria formation rate was determined by quantitative microscopic analysis. Only spores showing germtube formation with a visible thickening of the germ tube tip were counted as appressoria formation. FIG. 2 clearly shows that scoparone is inhibiting appressoria formation in a dose dependent manner (see also Example 15)

FIG. 3 shows that sunflower HaOMT3 catalyzes methoxycoumarin formation and enables production of scoparone. Coumarin accumulation was analyzed by TLC (FIG. 3A) fifteen hours after feeding of different substrates to *E. coli* BL21 strains expressing either HaOMT3, HaOMT1 or the empty pGEX5X-3 vector. Coumarins were identified by comparing their retention times with those of authentic standard substances. E: esculetin, S: scopoletin, I: isoscopoletin, mix: mixture of all three precursors in equimolar amounts. TLC was developed in toluene:ethyl formate:formic acid 5:4:1 (v/v). FIG. 3B: Exemplary HPLC chromatogram of reaction products 15 h after feeding of esculetin to *E. coli* BL21 expressing HaOMT3 (UV absorbance at 342 nm).

Figure 4:
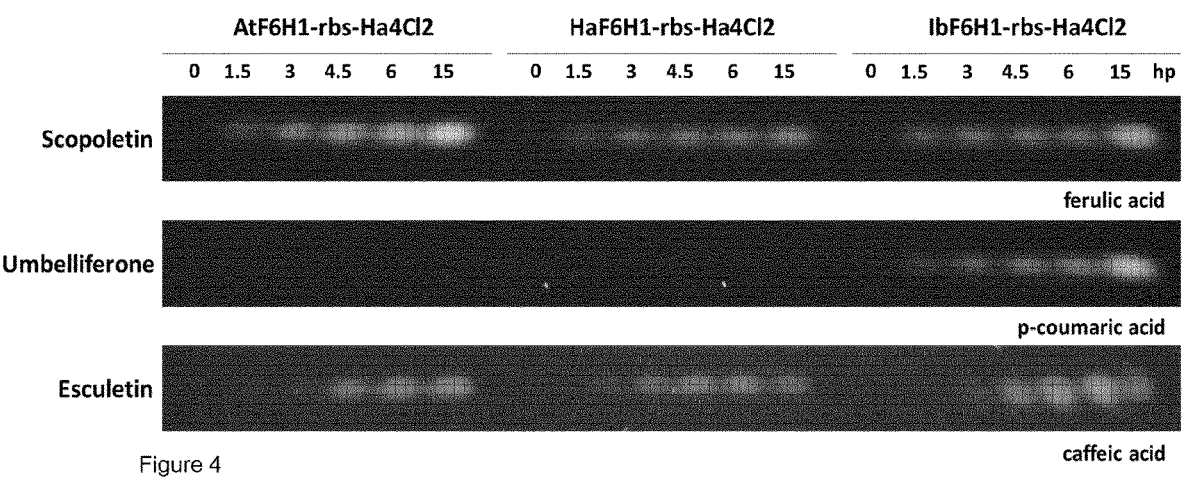

FIG. 4 shows that phylogenetically distinct F6H enzymes of *Arabidopsis*, sunflower and sweet potato all catalyze the production of the scoparone precursors scopoeltin and esculetin. Combinatorial expression of HaF6H1 and AtF6H1 with Ha4CL2 in *E. coli* BL21 cells causes the biosynthesis of esculetin and scopoletin from ferulic acid and caffeic acid, respectively. Besides catalyzing the biosynthesis of esculetin and scopoletin, simultaneous expression of IbF6H1 and Ha4CL2 also enables biotransformation of coumaric acid to umbelliferone. Coumarin accumulation was analysed by TLC in a timecourse after feeding of different substrates to *E. coli* BL21 strains expressing indicated gene combinations. Coumarins were identified by comparing their retention factors with those of authentic standard substances. TLC was developed in toluene:ethyl formate:formic acid 5:4:1 (v/v) and photos taken under UV-light.

FIG. 5 shows the sequence identity among F6H enzymes from sweet potato (IbF6H1), sunflower (HaF6H1) and *Arabidopsis* (AtF6H1). A) Alignment of amino acid sequences B) Alignment scores. Analyses were done with Clone Manager Professional Suite version 8.

Figure 6:
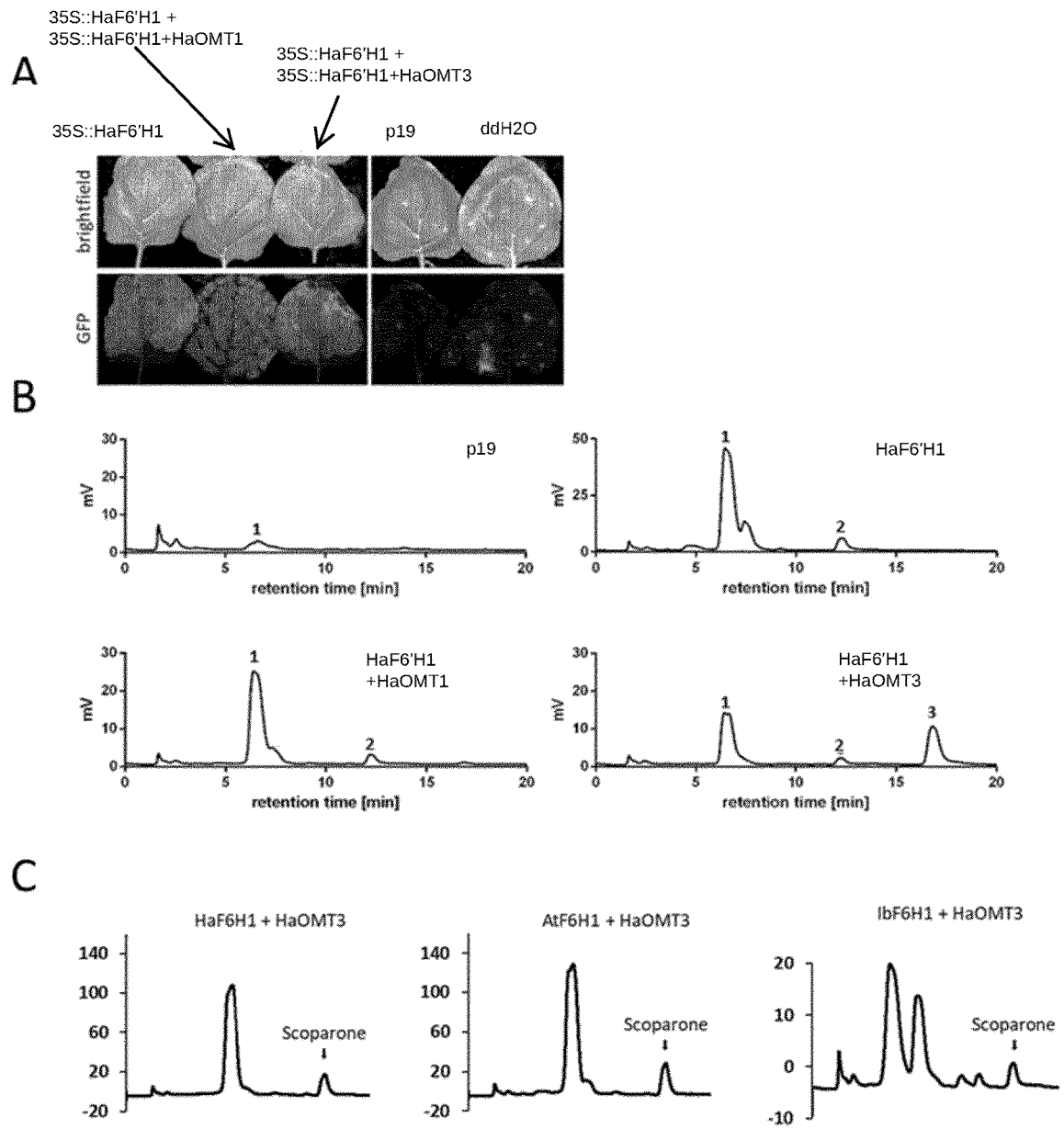

FIG. 6 shows that transient co-expression of HaOMT3 with either HaF6H1, AtF6H1 or IbF6H1 enables in planta accumulation of scoparone. FIG. 6A; eGFP fluorescence of *N. benthamiana* leaves 3 days after *Agrobacterium*-mediated transient transformation. Only leaves expressing the construct of interest (including an eGFP expression marker) but not control infiltrated leaves showed eGFP fluorescence. FIG. 6B: HPLC chromatograms (fluorescence excitation at 335 nm, detection at 460 nm) of extracts from *N. benthamiana* leaves transiently expressing either HaF6H1, HaF6H1 and HaOMT1 or HaF6H1 and HaOMT3, respectively. HaF6H1 expression alone only increases the concentration of scopolin (1) and scopoletin (2), whereas coexpression of HaF6H1 and HaOMT3 but not HaOMT1 also results in accumulation of scoparone (3). FIG. 6C: Combinatorial overexpression of HaOMT3 with either HaF6H1, AtF6H1 or IbF6H1 in *N. benthamiana* leads to simultaneous accumulation of scopoletin, scopolin and scoparone. Experimental conditions were as described in (B).

Figure 7:
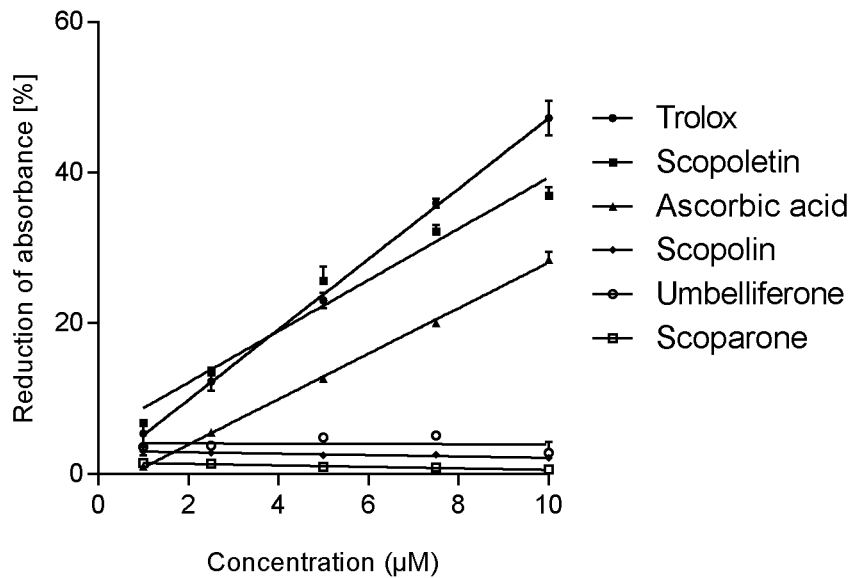

FIG. 7 shows that scoparone lacks antioxidant activity. Antioxidant activity of scoparone was determined in an 2,2'-azinobis-(3-ethylbenzothiazoline-6-sulfonic acid) (ABTS)-assay and compared to authentic analytical standards of scopoletin, scopolin, umbelliferone, ascorbic acid and Trolox (6-hydroxy-2,5,7,8-tetramethylchroman-2-carboxylic acid).

Figure 8:
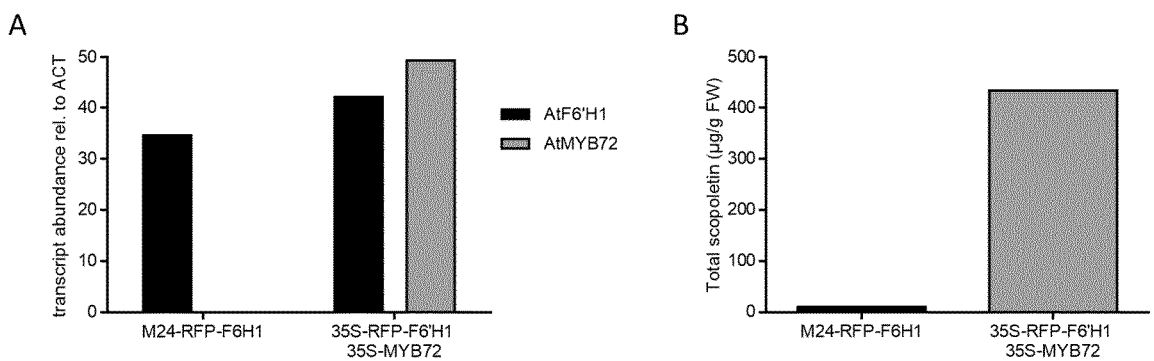

FIG. 8 shows that transient coexpression of AtMYB72 and AtF6H1 drastically increases scopoletin accumulation in *N. benthamiana* compared to plants only expressing AtF6H1. *N. benthamiana* plants were transiently transformed with constructs enabling overexpression of RFP-F6H1 only or simultaneous overexpression of RFP-F6H1 and MYB72. Three days after Agroinflitration transcript abundance of F6H1 and MYB72 was monitored by qRT-PCR (A) and scopoletin concentration in leaves determined by HPLC (B).

SEQUENCES

SEQ ID NO. 1 *Helianthus annuus*, OMT3, nucleic acid sequence
SEQ ID NO. 2 *Helianthus annuus*, OMT3, amino acid sequence
SEQ ID NO. 3 *Helianthus annuus* 4CL2, nucleic acid sequence
SEQ ID NO. 4 *Helianthus annuus*, 4CL2, amino acid sequence
SEQ ID NO. 5 *Rhodopseudomonas palustris*, CYP199A2 F185L, nucleic acid sequence
SEQ ID NO. 6 *Rhodopseudomonas palustris*, CYP199A2 F185L, amino acid sequence
SEQ ID NO. 7 *Arabidopsis thaliana*, MYB72, nucleic acid sequence
SEQ ID NO. 8 *Arabidopsis thaliana*, MYB72, amino acid sequence
SEQ ID NO. 9 artificial, OMT3 variant 1, nucleic acid sequence
SEQ ID NO. 10 artificial, OMT3 variant 1, amino acid sequence
SEQ ID NO. 11 artificial, OMT3 variant 2, nucleic acid sequence
SEQ ID NO. 12 artificial, OMT3 variant 2, amino acid sequence
SEQ ID NO. 13 artificial, OMT3 variant 3, nucleic acid sequence
SEQ ID NO. 14 artificial, OMT3 variant 3, amino acid sequence
SEQ ID NO. 15 artificial, OMT3 variant 4, nucleic acid sequence
SEQ ID NO. 16 artificial, OMT3 variant 4, amino acid sequence
SEQ ID NO. 17 artificial, OMT3 variant 5, nucleic acid sequence
SEQ ID NO. 18 artificial, OMT3 variant 5, amino acid sequence
SEQ ID NO. 19 artificial, OMT3 variant 6, nucleic acid sequence
SEQ ID NO. 20 artificial, OMT3 variant 6, amino acid sequence
SEQ ID NO. 21 artificial, OMT3 variant 7, nucleic acid sequence
SEQ ID NO. 22 artificial, OMT3 variant 7, amino acid sequence
SEQ ID NO. 23 *Arabidopsis thaliana*, MYB72 genomic sequence, nucleic acid sequence
SEQ ID NO. 24 artificial, dimerization domain PF08100, amino acid sequence
SEQ ID NO. 25 artificial, O-methyltransferase domain PF00891, amino acid sequence
SEQ ID NO. 26 *Ipomea batatas*, F6H1 (IbF6H1), nucleic acid sequence
SEQ ID NO. 27 *Ipomea batatas*, F6H1 (IbF6H1), amino acid sequence
SEQ ID NO. 28 *Arabidopsis thaliana*, F6H1 (AtF6H1), nucleic acid sequence
SEQ ID NO. 29 *Arabidopsis thaliana*, F6H1 (AtF6H1), amino acid sequence
SEQ ID NO. 30 *Helianthus annuus*, F6H1 (HaF6H1), nucleic acid sequence
SEQ ID NO. 31 *Helianthus annuus*, F6H1 (HaF6H1), amino acid sequence

DETAILED DESCRIPTION OF THE INVENTION

The present invention may be understood more readily by reference to the following detailed description of the preferred embodiments of the invention and the examples included herein.

Definitions Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101;

Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having the same, essentially the same biological activity or similar as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has the same, essentially the same or similar biological activity as the unmodified protein coded by the unmodified nucleic acid from which they are derived. In particular, homologues of a nucleic acid may encompass substitutions on the basis of the degenerative amino acid code. The terms "identity", "homology" and "similarity" are used herein interchangeably. "Identity" or "homology" or "similarity" between two nucleic acids sequences or amino acid sequences refers in each case over at least 70%, at least 80% or at least 90% of the entire length of the respective MYB72, 4-Coumarate-Coenzyme A ligase, ferulate 6-hydroxylase, CYP199A2, COSY, CCoAOMT, ABCG37 and UGT71C1 nucleic acid sequence or the respective OMT3, MYB72, 4-Coumarate-Coenzyme A ligase, ferulate 6-hydroxylase, CYP199A2, COSY, CCoAOMT, ABCG37 and UGT71C1 amino acid sequence, preferably over the entire length of the respective OMT3, MYB72, 4-Coumarate-Coenzyme A ligase, ferulate 6-hydroxylase, CYP199A2, COSY, CCoA-OMT, ABCG37 and UGT71C1 nucleic acid sequence or the respective OMT3, MYB72, 4-Coumarate-Coenzyme A ligase, ferulate 6-hydroxylase, CYP199A2, COSY, CCoA-OMT, ABCG37 and UGT71C1 amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively, the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13): 3497-500, the web page: ebi.ac.uk/Tools/clustalw/index.html and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

Sequence identity between the nucleic acid or protein useful according to the present invention and the OMT3, MYB72, 4-Coumarate-Coenzyme A ligase, ferulate 6-hydroxylase, CYP199A2, COSY, CCoAOMT, ABCG37 and UGT71C1 nucleic acids and the F6H1, CCoAOMT, ABCG37 and UGT71C1 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level, a substitution refers to a replacement of one or more nucleotides with other nucleotides within a nucleic acid, wherein the protein coded by the modified nucleic acid has essentially the same or a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986) The classification of amino acid conservation J Theor Biol., 119:205-18 and Table 1 below).

TABLE 1

Examples of conserved amino acid substitutions

| Residue | Conservative Substitutions | Residue | Conservative Substitutions |
|---|---|---|---|
| A | G, V, I, L, M | L | M, I, V, A, G |
| C | S, T | N | Q |
| E | D | Q | N |
| D | E | P | |
| G | A, V, I, L, M | S | T, C |
| F | Y, W | R | K, H |
| I | V, A, G, L, M | T | S, C |
| H | R, K | W | Y, F |
| K | R, H | V | I, A, G, L, M |
| M | L, I, V, A, G | Y | F, W |

Amino acid substitution, deletion and/or insertion may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, OH), QuickChange Site Directed mutagenesis (Stratagene, San Diego, CA), PCR-mediated site-directed mutagenesis or other site-directed mutagenesis protocols.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by non-coding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32: D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

The nucleic acids according to the present invention may comprise domains as defined herein below when analysed with the software tool InterProScan (version 4.8, (see Zdobnov E. M. and Apweiler R.; "InterProScan—an integration platform for the signature-recognition methods in InterPro."; Bioinformatics, 2001, 17(9): 847-8; InterPro database, release 42 (Apr. 4, 2013)).

As used herein the terms "fungal-resistance", "resistant to a fungus" and/or "fungal-resistant" mean reducing, preventing, or delaying an infection by fungi. Preferably, fungal resistance is soybean rust-resistance. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant. Preferably, the wild type plant is a plant of a similar, more preferably identical, genotype as the plant having increased resistance to fungi, in particular soybean rust, but does not comprise an exogenous OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acids. Preferably, the wildtype plant is not capable to produce more than 10 µM scoparone, scopoletin and/or a derivative thereof, more preferably more than 5 µM scoparone, scopoletin and/or a derivative thereof, most preferably the wildtype plant is not capable to produce scoparone, scopoletin and/or a derivative thereof.

As used herein the terms "soybean rust resistance", "resistant to a soybean rust", "soybean rust resistant", "rust resistance", "resistant to a rust", or "rust resistant" mean reducing or preventing or delaying an infection of a plant, plant part, or plant cell by Phacopsoracea, in particular

*Phakopsora*, more particularly soybean rust or Asian Soybean Rust (ASR), more particularly *Phakopsora pachyrhizi* and/or *Phakopsora meibomiae*, as compared to a wild type plant, wild type plant part, or wild type plant cell.

The level of fungal resistance of a plant can be determined in various ways, e.g. by scoring/measuring the infected leaf area or three-dimensional space in relation to the overall area or three-dimensional space. Another possibility to determine the level of resistance is to count the number of fusarium colonies on the plant or to measure the amount of spores produced by these colonies. Another way to resolve the degree of fungal infestation is to specifically measure the amount of fungal DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227). (Ni-colaisen M, Suproniene S, Nielsen L K, Lazzaro I, Spliid N H, Justesen A F. 2009 Real-time PCR for quantification of eleven individual *Fusarium* species in cereals. J Microbiol Methods. 2009 March; 76(3): 234-40.)

Another way of evaluating fungal biomass is to biochemically determining the amount of fungal specific compounds, such as ergosterol or chitin (L. M. Reid, R. W. Nicol, T. Ouellet, M. Savard, J. D. Miller, J. C. Young, D. W. Stewart, and A. W. Schaafsma (1999) Interaction of *Fusarium graminearum* and *F. moniliforme* in Maize Ears: Disease Progress, Fungal Biomass, and Mycotoxin Accumulation Phytopathology 89(11) 1028-1037; C A Roberts, R R Marquardt, A A Frohlich, R L McGraw, R G Rotter, J C Henning (1991) Chemical and spectral quantification of mold in contaminated barley; Cereal Chemistry 68(3):272-275).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole nucleic acids of exogenous OMT3, MYB72, 4-Coumarate-Coenzyme A ligase, ferulate 6-hydroxylase, CYP199A2, COSY, CCoA-OMT, ABCG37 and UGT71C1, respectively. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous OMT3 nucleic acid optionally in combination one or more nucleic acid selected from MYB72, 4-Coumarate-Coenzyme A ligase, ferulate 6-hydroxylase, CYP199A2, COSY, CCoA-OMT, ABCG37 and UGT71C1 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of gene technology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous OMT3 nucleic acid optionally in combination one or more exogenous nucleic acid(s) selected from MYB72, 4-Coumarate-Coenzyme A ligase, ferulate 6-hydroxylase, CYP199A2, COSY, CCoAOMT, ABCG37 and UGT71C1 nucleic acids integrated at any genetic loci and optionally the plant may also include the endogenous gene within the natural genetic background. Preferably the plant, plant part or plant cell does not include endogenous OMT3 nucleic acid optionally in combination with one or more endogenous nucleic acid(s) selected from MYB72, 4-Coumarate-Coenzyme A ligase, ferulate 6-hydroxylase, CYP199A2, COSY, CCoAOMT, ABCG37 and UGT71C1.

For the purposes of the invention, "recombinant" means with regard to, for example, a nucleic acid sequence, a nucleic acid molecule, an expression cassette or a vector construct comprising OMT3 nucleic acid optionally in combination with any one or more of MYB72, 4-Coumarate-Coenzyme A ligase, ferulate 6-hydroxylase, CYP199A2, COSY, CCoAOMT, ABCG37 and UGT71C1 nucleic acid(s), all those constructions brought about by man by gene technological methods in which either (a) the sequences of the OMT3, MYB72, 4-Coumarate-Coenzyme A ligase, ferulate 6-hydroxylase, CYP199A2, COSY, CCoAOMT, ABCG37 and UGT71C1 nucleic acids or a part thereof, or (b) genetic control sequence(s) which are operably linked with the OMT3, MYB72, 4-Coumarate-Coenzyme A ligase, ferulate 6-hydroxylase, CYP199A2, COSY, CCoAOMT, ABCG37 and UGT71C1 and/or UGT71C1 nucleic acid sequences according to the invention, for example a promoter, or (c) a) and b)

are not located in their natural genetic environment within the genome of the wild-type plant or have been modified by man by gene technological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

Preferably, the nucleic acids according to the invention or used according to the invention comprise OMT3 nucleic acids,
OMT3 and 4-Coumarate-Coenzyme A ligase nucleic acids,
OMT3 and F6H1 nucleic acids,
OMT3, 4-Coumarate-Coenzyme A ligase and CYP199A2 nucleic acids,
OMT3, F6H1 and CYP199A2 nucleic acids,
OMT3, 4-Coumarate-Coenzyme A ligase, F6H1 and CYP199A2 nucleic acids,
OMT3, F6H1 and CCoAOMT nucleic acids,
OMT3, F6H1 and ABCG37 nucleic acids,
OMT3, F6H1 and UGT71C1 nucleic acids,
OMT3, F6H1, CCoAOMT and ABCG37 nucleic acids
OMT3, F6H1, CCoAOMT, ABCG37 and UGT71C1 nucleic acids,
OMT3, 4-Coumarate-Coenzyme A ligase, F6H1 and CCoAOMT nucleic acids,
OMT3, 4-Coumarate-Coenzyme A ligase, F6H1 and ABCG37 nucleic acids,
OMT3, 4-Coumarate-Coenzyme A ligase, F6H1 and UGT71C1 nucleic acids,
OMT3, 4-Coumarate-Coenzyme A ligase, F6H1, CCoAOMT and ABCG37 nucleic acids
OMT3, 4-Coumarate-Coenzyme A ligase, F6H1, CCoAOMT, ABCG37 and UGT71C1 nucleic acids,
OMT3, CYP199A2, F6H1 and CCoAOMT nucleic acids,
OMT3, CYP199A2, F6H1 and ABCG37 nucleic acids,
OMT3, CYP199A2, F6H1 and UGT71C1 nucleic acids,
OMT3, CYP199A2, F6H1, CCoAOMT and ABCG37 nucleic acids
OMT3, CYP199A2, F6H1, CCoAOMT, ABCG37 and UGT71C1 nucleic acids,
OMT3, CYP199A2, 4-Coumarate-Coenzyme A ligase, F6H1 and CCoAOMT nucleic acids,
OMT3, CYP199A2, 4-Coumarate-Coenzyme A ligase, F6H1 and ABCG37 nucleic acids,
OMT3, CYP199A2, 4-Coumarate-Coenzyme A ligase, F6H1 and UGT71C1 nucleic acids,
OMT3, CYP199A2, 4-Coumarate-Coenzyme A ligase, F6H1, CCoAOMT and ABCG37 nucleic acids,
OMT3, CYP199A2, 4-Coumarate-Coenzyme A ligase, F6H1, CCoAOMT, ABCG37 and
UGT71C1 nucleic acids,
OMT3 and MYB72 nucleic acids,
OMT3, MYB72 and 4-Coumarate-Coenzyme A ligase nucleic acids,
OMT3, MYB72 and F6H1 nucleic acids,
OMT3, MYB72, 4-Coumarate-Coenzyme A ligase and CYP199A2 nucleic acids, OMT3, MYB72, F6H1 and CYP199A2 nucleic acids,
OMT3, MYB72, 4-Coumarate-Coenzyme A ligase, F6H1 and CYP199A2 nucleic acids,
OMT3, MYB72, F6H1 and CCoAOMT nucleic acids,
OMT3, MYB72, F6H1 and ABCG37 nucleic acids,
OMT3, MYB72, F6H1 and UGT71C1 nucleic acids,
OMT3, MYB72, F6H1, CCoAOMT and ABCG37 nucleic acids
OMT3, MYB72, F6H1, CCoAOMT, ABCG37 and UGT71C1 nucleic acids,
OMT3, MYB72, 4-Coumarate-Coenzyme A ligase, F6H1 and CCoAOMT nucleic acids,
OMT3, MYB72, 4-Coumarate-Coenzyme A ligase, F6H1 and ABCG37 nucleic acids,
OMT3, MYB72, 4-Coumarate-Coenzyme A ligase, F6H1 and UGT71C1 nucleic acids,
OMT3, MYB72, 4-Coumarate-Coenzyme A ligase, F6H1, CCoAOMT and ABCG37 nucleic acids
OMT3, MYB72, 4-Coumarate-Coenzyme A ligase, F6H1, CCoAOMT, ABCG37 and UGT71C1 nucleic acids,
OMT3, MYB72, CYP199A2, F6H1 and CCoAOMT nucleic acids,
OMT3, MYB72, CYP199A2, F6H1 and ABCG37 nucleic acids,
OMT3, MYB72, CYP199A2, F6H1 and UGT71C1 nucleic acids,
OMT3, MYB72, CYP199A2, F6H1, CCoAOMT and ABCG37 nucleic acids
OMT3, MYB72, CYP199A2, F6H1, CCoAOMT, ABCG37 and UGT71C1 nucleic acids,
OMT3, MYB72, CYP199A2, 4-Coumarate-Coenzyme A ligase, F6H1 and CCoAOMT nucleic acids,
OMT3, MYB72, CYP199A2, 4-Coumarate-Coenzyme A ligase, F6H1 and ABCG37 nucleic acids,
OMT3, MYB72, CYP199A2, 4-Coumarate-Coenzyme A ligase, F6H1 and UGT71C1 nucleic acids,
OMT3, MYB72, CYP199A2, 4-Coumarate-Coenzyme A ligase, F6H1, CCoAOMT and ABCG37 nucleic acids and
OMT3, MYB72, CYP199A2, 4-Coumarate-Coenzyme A ligase, F6H1, CCoAOMT, ABCG37 and UGT71C1 nucleic acids.

A transgenic plant, plants cell, or tissue for the purposes of the invention is thus understood as meaning that an exogenous OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acids is integrated into the genome by means of gene technology.

Most preferably, the transgenic plant, plant cell or tissue for the purposes of the invention comprises an expressible nucleic acid coding for OMT3 and ferulate 6-hydroxylase, even more preferably OMT3, ferulate 6-hydroxylase and at least one gene selected from 4-Coumarate-Coenzyme A ligase, CYP199A2, COSY, CCoAOMT, ABCG37 and UGT71C1, and most preferably OMT3, MYB72, ferulate 6-hydroxylase and at least one gene selected from 4-Coumarate-Coenzyme A ligase, CYP199A2, COSY, CCoA-OMT, ABCG37 and UGT71C1.

A recombinant construct, vector or expression cassette for the purposes of the invention comprises a OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acids and is prepared by means of gene technology.

A "wild type" plant, "wild type" plant part, or "wild type" plant cell means that said plant, plant part, or plant cell does not express exogenous OMT3, MYB72, 4-Coumarate-Coenzyme A ligase, ferulate 6-hydroxylase, CYP199A2, COSY, CCoAOMT, ABCG37 and UGT71C1 nucleic acids and exogenous OMT3, 4-Coumarate-Coenzyme A ligase, ferulate 6-hydroxylase, CYP199A2, COSY, CCoAOMT, ABCG37 and UGT71C1 proteins. Preferably, the wildtype plant is not capable to produce more than 10 µM scoparone, scopoletin and/or a derivative thereof, more preferably not more than 5 µM scoparone, scopoletin and/or a derivative thereof and most preferably the wildtype plant is not capable to produce scoparone, scopoletin and/or a derivative thereof. A derivative of scopoletin is e.g. scopolin. Preferably, the wild-type plant plant does not express endogenous OMT3, MYB72, 4-Coumarate-Coenzyme A ligase, ferulate 6-hydroxylase, CYP199A2, COSY, CCoAOMT, ABCG37 and UGT71C1 nucleic acids and endogenous OMT3, MYB72, 4-Coumarate-Coenzyme A ligase, ferulate 6-hydroxylase, CYP199A2, COSY, CCoA-OMT, ABCG37 and UGT71C1 proteins.

Natural locus means the location on a specific chromosome and/or the location between certain genes and/or the same sequence background as in the original plant which is transformed.

Preferably, the transgenic plant, plant cell or tissue thereof expresses the OMT3 nucleic acids optionally in combination with one or more nucleic acids selected from the group consisting MYB72, 4-Coumarate-Coenzyme A ligase, ferulate 6-hydroxylase, CYP199A2, COSY, CCoA-OMT, ABCG37 and UGT71C1 nucleic acids. Preferably, the transgenic plant, plant cell or tissue thereof is transformed with recombinant vector constructs comprising OMT3 nucleic acids optionally in combination with one or more nucleic acids selected from the group consisting of MYB72, 4-Coumarate-Coenzyme A ligase, ferulate 6-hydroxylase, CYP199A2, COSY, CCoA-OMT, ABCG37 and UGT71C1 nucleic acids described herein. OMT3, MYB72, 4-Coumarate-Coenzyme A ligase, ferulate 6-hydroxylase, CYP199A2, COSY, CCoAOMT, ABCG37 and UGT71C1 nucleic acids may be located on the same vector or different recombinant vectors.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers, or RNAa (Li et al 2006, PNAS 103(46) 17337-42). Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene. Instead of increasing expression of MYB72 it is also envisaged to increase expression of the enzymes of the shikimate pathway, in particular DAHP synthase, 3-dehydroquinate synthase, 3-dehydroquinate dehydratase, shikimate dehydrogenase, shikimate kinase, EPSP synthase, and chorismate synthase.

The term "functional fragment" refers to any nucleic acid or protein, which comprises merely a part of the full-length nucleic acid, or full-length protein, respectively, but still provides the essentially same or similar function, e.g., increased fungal resistance and/or the same, essentially the same or similar biological activity when expressed in a plant. Preferably, the fragment comprises at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the respective OMT3, MYB72, 4-Coumarate-Coenzyme A ligase, ferulate 6-hydroxylase, CYP199A2, COSY, CCoA-OMT, ABCG37 and UGT71C1 nucleic acids has an identity as defined above over a length of at least 70%, at least 75%, at least 90% of the nucleotides of the respective OMT3, MYB72, 4-Coumarate-Coenzyme A ligase, ferulate 6-hydroxylase, CYP199A2, COSY, CCoAOMT, ABCG37 and UGT71C1 nucleic acid.

The term "the same biological activity", "essentially the same biological activity", "similar biological activity" or increased biological activity preferably means leading to an increased production and/or accumulation compared to the wild-type plant, wild type plant part, or wild type plant cell of more than 0.1 µM, preferably more than 1 µM, preferably more than 2 µM, more preferably more than 5 µM, most preferably more than 10 µM scoparone, scopoletin and/or a derivative thereof when OMT3 and optionally MYB72, 4-Coumarate-Coenzyme A ligase, ferulate 6-hydroxylase, CYP199A2, COSY, CCoAOMT, ABCG37 and/or UGT71C1 nucleic acids or fragments thereof are expressed in a plant.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

The wild-type plant may express the respective endogenous OMT3, MYB72, 4-Coumarate-Coenzyme A ligase, ferulate 6-hydroxylase, CYP199A2, COSY, CCoAOMT, ABCG37 and/or UGT71C1 nucleic acids. As far as overexpression of exogenous OMT3, MYB72, 4-Coumarate-Coenzyme A ligase, ferulate 6-hydroxylase, CYP199A2, COSY, CCoAOMT, ABCG37 and/or UGT71C1 nucleic acids is concerned, for the purposes of this invention, the original wild-type expression level of the corresponding endogenous nucleic acids might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g. polyadenylation signals), in a manner which allows for expression of the nucleic acid (e.g. in a host plant cell when the vector is introduced into the host plant cell). Such regulatory sequences are described, for example, in Goeddel, Gene Expression Technology: Methods in Enzymology 185, Academic Press, San Diego, CA (1990) and Gruber and Crosby, in: Methods in Plant Molecular Biology and Biotechnology, Eds. Glick and Thompson, Chapter 7, 89-108, CRC Press: Boca Raton, Florida, including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

OMT3, MYB72, 4-Coumarate-Coenzyme A ligase, ferulate 6-hydroxylase, CYP199A2, COSY, CCoAOMT, ABCG37 and UGT71C nucleic acids The OMT3 nucleic acid to be overexpressed in order to achieve increased resistance to fungal pathogens, e.g., of the family Phacopsoraceae, for example soybean rust, is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO. 1 or a functional fragment, or a splice variant thereof;

(ii) a nucleic acid encoding a OMT3 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO. 2 or a functional fragment; preferably the OMT3 protein has the essentially same or similar biological activity as a OMT3 protein encoded by SEQ ID NO. 1; preferably the OMT3 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a OMT3 protein; preferably wherein the nucleic acid molecule codes for a polypeptide which has essentially identical properties to the polypeptide described in SEQ ID NO. 2; preferably the encoded protein confers enhanced fungal resistance relative to control plants; and (iv) a nucleic acid encoding the same OMT3 protein as the OMT3 nucleic acids of (i) to (iii) above, but differing from the OMT3 nucleic acids of (i) to (iii) above due to the degeneracy of the genetic code.

The OMT3 nucleic acid to be overexpressed in order to achieve increased resistance to fungal pathogens is for example a nucleic acid selected from SEQ ID No. 1, 9, 11, 13, 15, 17, 19 and 21. The OMT3 nucleic acid to be overexpressed in order to achieve increased resistance to fungal pathogens is for example a nucleic acid encoding a OMT3 protein selected from SEQ ID No. 2, 10, 12, 14, 16, 18, 20 and 22.

The OMT3 protein may comprise a dimerization domain according to PFAM id PF08100, preferably according to SEQ ID NO. 24, and an O-methyltransferase domain according to PFAM id PF00891, preferably according to SEQ ID No. 25, and having least 90%, at least 91%, at least 92%, at least 93%, at least 94%, at least 95%, at least 96%, at least 97%, at least 98%, at least 99% or 100% sequence identity to the protein sequence represented by the respective sequences.

Percentages of identity of a nucleic acid are indicated with reference to the entire nucleotide region given in a sequence specifically disclosed herein.

Preferably the portion of the OMT3 nucleic acid fragment is about 500-600, about 600-700, about 700-800, about 800-900, about 900-1000 or about 1000-1095 nucleotides, preferably consecutive nucleotides, preferably counted from the 5' or 3' end of the nucleic acid, in length, of the nucleic acid sequences given in SEQ ID NO. 1.

The ferulate 6-hydroxylase (F6H1), CCoAOMT, ABCG37 and UGT71C1 nucleic acids and proteins are those as described in WO2016/124515A1, in particular on pages 23-28 thereof. The COSY nucleic acid and protein is described in WO2018046526, in particular on pages 18-23.

The MYB72 nucleic acid to be overexpressed in order to achieve increased resistance to fungal pathogens, e.g., of the family Phacopsoraceae, for example soybean rust, is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO. 7 or SEQ ID NO. 23, or a functional fragment, or a splice variant thereof;

(ii) a nucleic acid encoding a MYB72 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO. 8 or a functional fragment; preferably the MYB72 protein has the essentially same or similar biological activity as a MYB72 protein encoded by SEQ ID NO. 7, preferably the MYB72 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MYB72 protein; preferably wherein the nucleic acid molecule codes for a polypeptide which has essentially identical properties to the polypeptide described in SEQ ID NO. 8, preferably the encoded protein confers enhanced fungal resistance relative to control plants; and (iv) a nucleic acid encoding the same MYB72 protein as the MYB72 nucleic acids of (i) to (iii) above, but differing from the MYB72 nucleic acids of (i) to (iii) above due to the degeneracy of the genetic code.

The nucleic acid sequence according to SEQ ID NO. 23 is a nucleic acid sequence encoding MYB72 and contains elements not found in the final protein according to SEQ ID NO. 8. It is advantageous to use the nucleic acid according to SEQ ID NO. 7, because this nucleic acid is shorter than that of SEQ ID NO. 23 and thus makes most efficient use of vector capacity.

Percentages of identity of a nucleic acid are indicated with reference to the entire nucleotide region given in a sequence specifically disclosed herein.

Preferably the portion of the MYB72 nucleic acid fragment is about 500-600, about 600-700, about 700-800 or about 800-888 nucleotides, preferably consecutive nucleotides, preferably counted from the 5' or 3' end of the nucleic acid, in length, of the nucleic acid sequence given in SEQ ID NO. 7.

The 4-Coumarate-Coenzyme A ligase (4CL2) nucleic acid is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO. 3 or a functional fragment, or a splice variant thereof;

(ii) a nucleic acid encoding a 4CL2 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO. 4 or a functional fragment; preferably the 4CL2 protein has the essentially same or similar biological activity as a 4CL2 protein encoded by SEQ ID NO. 3; preferably the 4CL2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a 4CL2 protein; preferably wherein the nucleic acid molecule codes for a polypeptide which has essentially identical properties to the polypeptide described in SEQ ID NO. 4; preferably the encoded protein confers enhanced fungal resistance relative to control plants; and (iv) a nucleic acid encoding the same 4CL2 protein as the 4CL2 nucleic acids of (i) to (iii) above, but differing from the 4CL2 nucleic acids of (i) to (iii) above due to the degeneracy of the genetic code.

The 4CL protein mediates coenzyme A esterification of caffeic acid and ferulic acid. Caffeoyl-CoA and feruloyl-CoA are then hydroxylated at position 6 by either of the above mentioned F6H1 enzymes followed by isomerization to esculetin and scopoletin, respectively.

The CYP199A2 nucleic acid and protein is described in Furuya, T., Arai, Y. & Kino, K. Biotechnological production of caffeic acid by bacterial cytochrome P450 CYP199A2. Appl. Environ. Microbiol. 78, 6087-6094 (2012). Most preferred is the F185L variant thereof, as described by the authors of the aforementioned publication.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The OMT3, MYB72, 4-Coumarate-Coenzyme A ligase, ferulate 6-hydroxylase, CYP199A2, COSY, CCoAOMT, ABCG37 and UGT71C nucleic acids described herein are useful in the constructs, methods, plants, harvestable parts and products of the invention.

OMT3, MYB72, 4-Coumarate-Coenzyme A ligase, ferulate 6-hydroxylase, CYP199A2, COSY, CCoAOMT, ABCG37 and UGT71C proteins In one embodiment of the invention, the OMT3 protein is encoded by a nucleic acid comprising an exogenous nucleic acid having (i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO. 1, a functional fragment thereof, or a splice variant thereof; or by (ii) an exogenous nucleic acid encoding a protein comprising an amino acid sequence having at least OMT3 homology with SEQ ID NO. 2, a functional fragment thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a OMT3 protein; preferably wherein the nucleic acid molecule codes for a polypeptide which has essentially identical properties to the polypeptide described in SEQ ID NO. 2; preferably the encoded protein confers enhanced fungal resistance relative to control plants; or by (iv) an exogenous nucleic acid encoding the same OMT3 protein as the nucleic acids of (i) to (iii) above, but differing from the nucleic acids of (i) to (iii) above due to the degeneracy of the genetic code.

Preferably, the OMT3 polypeptide comprises about 200-225, about 225-250, about 250-275, about 275-300, about 300-325, about 325-350, or about 350-365 amino acid residues, preferably consecutive amino acid residues, preferably counted from the N-terminus or C-terminus of the amino acid sequence, or up to the full length of any of the amino acid sequences encoded by the nucleic acid sequence set out in SEQ ID NO. 1.

Preferably, the OMT3 polypeptide amino acid sequence differs from the polypeptide described in SEQ ID NO. 2 only in substitutions according to table 1, even more preferably according to table Ts1. This table Ts1 lists, for each respective position in the polypeptide according to SEQ ID NO. 2, the preferred amino acids in decreasing order of preference. Thus, the sequence of the OMT3 polypeptide variant is aligned to the sequence according to SEQ ID NO.2, and then for each amino acid position according to the sequence described in SEQ ID NO. 2 it is checked if there exists an amino acid at this position in the aligned polypeptide variant sequence and if the respective amino acid in the polypeptide variant is listed as a preferred amino acid in the corresponding row of table Ts1. It is to be noted that insertions and deletions do not influence the outcome of this assessment. However, it is even more preferred that the polypeptide variant differs from the sequence according to SEQ ID NO. 2 only in substitutions according to table Ts1. Even more preferably the polypeptide variant differs from the sequence according to SEQ ID NO. 2 only in at most 20, even more preferably at most 15, even more preferably at most 10, even more preferably at most 8, even more preferably at most 5 and most preferably at most 3 substitutions according to table Ts1.

Preferably, the OMT3 polypeptide amino acid sequence differs from the polypeptide described in SEQ ID NO. 2 only in such way that the polypeptide variant, after alignment to the sequence according to SEQ ID NO. 2, comprises not more than 25 amino acid pairs, even more preferably not more than 20 amino acid pairs, even more preferably not more than 15 amino acid pairs, even more preferably not more than amino acid pairs, even more preferably not more than 8 amino acid pairs, even more preferably not more than 5 amino acid pairs, even more preferably not more than 3 amino acid pairs not found in table Ts2. The table lists, for each preferred amino acid position pairs, the amino acids pairs preferred at those positions. The table is sorted by decreasing desirability ("score") of the amino acid pairs given therein. For example, the amino acids at positions 253 and 256 according to SEQ ID NO. 2 are preferably chosen such that when the amino acid at position 253 is R, then the amino acid at position 256 is Q, and when the amino acid at position 253 is N, then the amino acid at position 256 is D or E, when the amino acid at position 253 is D, then the amino acid at position 256 is A, R, N, Q, H, L, K, S, T or V, when the amino acid at position 253 is E, then the amino acid at position 256 is A, when the amino acid at position 253 is L, then the amino acid at position 256 is A, when the amino acid at position 253 is K, then the amino acid at position 256 is Q, when the amino acid at position 253 is P, then the amino acid at position 256 is S, when the amino acid at position 253 is S, then the amino acid at position 256 is D or E, and when the amino acid at position 253 is T, then the amino acid at position 256 is D. It is again to be noted that insertions and deletions do not influence the outcome of this assessment. However, it is even more preferred that the polypeptide variant differs from the sequence according to SEQ ID NO. 2 only in substitutions according to table Ts2 and/or according to table Ts1.

In one embodiment of the invention, the MYB72 protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO. 7 or SEQ ID NO. 23, a functional fragment thereof, or a splice variant thereof; or by
(ii) an exogenous nucleic acid encoding a protein comprising an amino acid sequence having at least MYB72 homology with SEQ ID NO. 8, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MYB72 protein; preferably wherein the nucleic acid molecule codes for a polypeptide which has essentially identical properties to the polypeptide described in SEQ ID NO. 8, preferably the encoded protein confers enhanced fungal resistance relative to control plants; or by
(iv) an exogenous nucleic acid encoding the same MYB72 protein as the nucleic acids of (i) to (iii) above, but differing from the nucleic acids of (i) to (iii) above due to the degeneracy of the genetic code.

Preferably, the MYB72 polypeptide comprises, in ascending order of preference, about 200-225, about 225-250, about 250-275 or about 275-297 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO. 7

Homologs of the MYB72 protein are registered in the Uniprot database as of 11 Oct. 2018 under the accession identifiers F6H775_VITVI, A0A251U7E8_HELAN, A0A251U6N1_HELAN, A0A251U8S9_HELAN, A0A251U5T1_HELAN, A0A166FJW9_DAUCA and A0A2U1QGH9_ARTAN, in decreasing order of homology to the MYB72 protein of SEQ ID NO. 8.

Preferably the 4CL2 protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO. 3, a functional fragment thereof, or a splice variant thereof; or by
(ii) an exogenous nucleic acid encoding a protein comprising an amino acid sequence having at least 4CL2 homology with SEQ ID NO. 4, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a 4CL2 protein; preferably wherein the nucleic acid molecule codes for a polypeptide which has essentially identical properties to the polypeptide described in SEQ ID NO. 4; preferably the encoded protein confers enhanced fungal resistance relative to control plants; or by
(iv) an exogenous nucleic acid encoding the same 4CL2 protein as the nucleic acids of (i) to (iii) above, but differing from the nucleic acids of (i) to (iii) above due to the degeneracy of the genetic code.

The OMT3, MYB72, 4-Coumarate-Coenzyme A ligase, ferulate 6-hydroxylase, CYP199A2, COSY, CCoAOMT, ABCG37 and UGT71C proteins described herein are useful in the constructs, methods, plants, harvestable parts and products of the invention.

Methods for Increasing Fungal Resistance

One embodiment of the present invention is a method according to the present invention for increasing fungal resistance in a plant, a plant part, or a plant cell, wherein the method comprises the step of increasing the production of scoparone, scopoletin and/or a derivative thereof in the plant, plant part, or plant cell in comparison to a wild type plant, wild type plant part, or wild type plant cell. The derivative of the scopoletin may be scopolin.

Scoparone, also known as 6,7-dimethoxycoumarin, is defined by the chemical formula according to FIG. 1.

Scopoletin is defined by the structural formula:

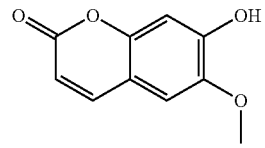

Scopolin is defined by the structural formula:

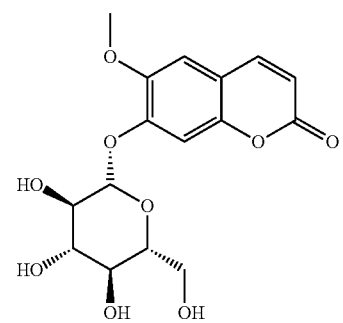

One embodiment of the present invention is a method for increasing fungal resistance in a plant, a plant part, or a plant cell, wherein the method comprises increasing the expression and/or biological activity of a OMT3 protein in the plant, plant part, or plant cell in comparison to a wild type plant, wild type plant part, or wild type plant cell, wherein said OMT3 protein is encoded by as defined above. In a preferred embodiment said method further comprises increasing the expression and/or biological activity of at least one or more additional protein(s) selected from the group consisting of a MYB72, 4-Coumarate-Coenzyme A ligase, ferulate 6-hydroxylase, CYP199A2, COSY, CCoAOMT, ABCG37 and UGT71C1 protein in the plant, plant part, or plant cell in comparison to a wild type plant, wild type plant part, or wild type plant cell, wherein said MYB72, 4-Coumarate-Coenzyme A ligase, ferulate 6-hydroxylase, CYP199A2, COSY, CCoAOMT, ABCG37 and UGT71C1 protein are defined as above. Preferably, said method comprises increasing the productions and/or accumulation of scoparone, scopoletin and/or a derivative thereof in a plant, plant part or plant cell.

One embodiment of the invention is a method for increasing fungal resistance, preferably resistance to Phacopsoracea, in a plant, plant part, or plant cell by increasing the expression and/or biological activity of a OMT3 protein, and optionally in combination with increasing the expression and/or biological activity of one or more of the protein(s) selected from the group consisting of MYB72, 4-Coumarate-Coenzyme A ligase, ferulate 6-hydroxylase, CYP199A2, COSY, CCoAOMT, ABCG37 and/or UGT71C1 protein(s) or a functional fragment, homologue thereof in comparison to wild-type plants, wild-type plant parts or wild-type plant cells. Preferably, the OMT3 protein is expressed from an exogenous nucleic acid. Preferably, OMT3 protein and one or more the proteins selected from the group consisting of MYB72, 4-Coumarate-Coenzyme A ligase, ferulate 6-hydroxylase, CYP199A2, COSY, CCoAOMT, ABCG37 and UGT71C1 protein(s), are expressed from an exogenous nucleic acid.

One embodiment of the invention is a method for increasing fungal resistance in a plant, a plant part, or a plant cell comprises
  (a) stably transforming a plant cell with an expression cassette comprising an exogenous nucleic acid encoding a OMT3 protein,
  (b) regenerating the plant from the plant cell; and (c) expressing said exogenous nucleic acid.

A preferred method according to the present invention comprises
  (a) stably transforming a plant cell with expression cassette(s) comprising an exogenous nucleic acid encoding a OMT3 protein and encoding one or more exogenous nucleic acid(s) encoding MYB72, 4-Coumarate-Coenzyme A ligase, ferulate 6-hydroxylase, CYP199A2, COSY, CCoAOMT, ABCG37 and/or UGT71C1 protein(s),
  (b) regenerating the plant from the plant cell; and
  (c) expressing said exogenous nucleic acids,
optionally wherein the nucleic acid(s) which codes for a MYB72, 4-Coumarate-Coenzyme A ligase, ferulate 6-hydroxylase, CYP199A2, COSY, CCoAOMT, ABCG37 and/or UGT71C1 protein(s) is expressed in an amount and for a period sufficient to generate or to increase fungal resistance in said plant.

Preferably the nucleic acid(s) encoding OMT3, MYB72, 4-Coumarate-Coenzyme A ligase, ferulate 6-hydroxylase, CYP199A2, COSY, CCoAOMT, ABCG37 and/or UGT71C1 protein(s) are in functional linkage with a promoter. Preferably, the promoter is a constitutive, pathogen inducible, preferably fungal inducible, mesophyll-specific promoter and/or epidermis-specific promoter and/or stalk specific, ear or kernel specific promoter Preferably, the production of scoparone, scopoletin and/or a derivative thereof in the plant, plant part, or plant cell in comparison to a wild type plant, wild type plant part, or wild type plant cell is increased.

In preferred embodiments, the protein amount and/or biological activity of the OMT3 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the OMT3 nucleic acid.

The exogenous nucleic acid encoding the OMT3, MYB72, 4-Coumarate-Coenzyme A ligase, ferulate 6-hydroxylase, CYP199A2, COSY, CCoAOMT, ABCG37 and UGT71C1 protein(s) are located on the same or different expression cassettes. Preferably, one expression cassette comprises exogenous nucleic acid encoding OMT3 and optionally in combination with one or more exogenous nucleic acid encoding MYB72, 4-Coumarate-Coenzyme A ligase, ferulate 6-hydroxylase, CYP199A2, COSY, CCoAOMT, ABCG37 and UGT71C1. Preferably, the expression cassette comprises exogenous nucleic acid encoding
  OMT3 protein,
  OMT3 and 4-Coumarate-Coenzyme A ligase protein,
  OMT3 and F6H1 protein,
  OMT3, 4-Coumarate-Coenzyme A ligase and CYP199A2 protein,
  OMT3, F6H1 and CYP199A2 protein,
  OMT3, 4-Coumarate-Coenzyme A ligase, F6H1 and CYP199A2 protein,
  OMT3, F6H1 and CCoAOMT protein,
  OMT3, F6H1 and ABCG37 protein,
  OMT3, F6H1 and UGT71C1 protein,
  OMT3, F6H1, CCoAOMT and ABCG37 protein
  OMT3, F6H1, CCoAOMT, ABCG37 and UGT71C1 protein,
  OMT3, 4-Coumarate-Coenzyme A ligase, F6H1 and CCoAOMT protein,
  OMT3, 4-Coumarate-Coenzyme A ligase, F6H1 and ABCG37 protein,
  OMT3, 4-Coumarate-Coenzyme A ligase, F6H1 and UGT71C1 protein,
  OMT3, 4-Coumarate-Coenzyme A ligase, F6H1, CCoAOMT and ABCG37 protein
  OMT3, 4-Coumarate-Coenzyme A ligase, F6H1, CCoAOMT, ABCG37 and UGT71C1 protein,
  OMT3, CYP199A2, F6H1 and CCoAOMT protein,
  OMT3, CYP199A2, F6H1 and ABCG37 protein,
  OMT3, CYP199A2, F6H1 and UGT71C1 protein,
  OMT3, CYP199A2, F6H1, CCoAOMT and ABCG37 protein
  OMT3, CYP199A2, F6H1, CCoAOMT, ABCG37 and UGT71C1 protein,
  OMT3, CYP199A2, 4-Coumarate-Coenzyme A ligase, F6H1 and CCoAOMT protein,
  OMT3, CYP199A2, 4-Coumarate-Coenzyme A ligase, F6H1 and ABCG37 protein,
  OMT3, CYP199A2, 4-Coumarate-Coenzyme A ligase, F6H1 and UGT71C1 protein,
  OMT3, CYP199A2, 4-Coumarate-Coenzyme A ligase, F6H1, CCoAOMT and ABCG37 protein,
  OMT3, CYP199A2, 4-Coumarate-Coenzyme A ligase, F6H1, CCoAOMT, ABCG37 and
  UGT71C1 protein,
  OMT3 and MYB72 protein,
  OMT3, MYB72 and 4-Coumarate-Coenzyme A ligase protein,
  OMT3, MYB72, and F6H1 protein,
  OMT3, MYB72, 4-Coumarate-Coenzyme A ligase and CYP199A2 protein,
  OMT3, MYB72, F6H1 and CYP199A2 protein, OMT3, MYB72, 4-Coumarate-Coenzyme A ligase, F6H1 and CYP199A2 protein,
OMT3, MYB72, F6H1 and CCoAOMT protein,
OMT3, MYB72, F6H1 and ABCG37 protein,
OMT3, MYB72, F6H1 and UGT71C1 protein,
OMT3, MYB72, F6H1, CCoAOMT and ABCG37 protein
OMT3, MYB72, F6H1, CCoAOMT, ABCG37 and UGT71C1 protein,
OMT3, MYB72, 4-Coumarate-Coenzyme A ligase, F6H1 and CCoAOMT protein,
OMT3, MYB72, 4-Coumarate-Coenzyme A ligase, F6H1 and ABCG37 protein,
OMT3, MYB72, 4-Coumarate-Coenzyme A ligase, F6H1 and UGT71C1 protein,
OMT3, MYB72, 4-Coumarate-Coenzyme A ligase, F6H1, CCoAOMT and ABCG37 protein
OMT3, MYB72, 4-Coumarate-Coenzyme A ligase, F6H1, CCoAOMT, ABCG37 and UGT71C1 protein,
OMT3, MYB72, CYP199A2, F6H1 and CCoAOMT protein,
OMT3, MYB72, CYP199A2, F6H1 and ABCG37 protein,
OMT3, MYB72, CYP199A2, F6H1 and UGT71C1 protein,
OMT3, MYB72, CYP199A2, F6H1, CCoAOMT and ABCG37 protein
OMT3, MYB72, CYP199A2, F6H1, CCoAOMT, ABCG37 and UGT71C1 protein,
OMT3, MYB72, CYP199A2, 4-Coumarate-Coenzyme A ligase, F6H1 and CCoAOMT protein,
OMT3, MYB72, CYP199A2, 4-Coumarate-Coenzyme A ligase, F6H1 and ABCG37 protein,
OMT3, MYB72, CYP199A2, 4-Coumarate-Coenzyme A ligase, F6H1 and UGT71C1 protein,
OMT3, MYB72, CYP199A2, 4-Coumarate-Coenzyme A ligase, F6H1, CCoAOMT and ABCG37 protein or
OMT3, MYB72, CYP199A2, 4-Coumarate-Coenzyme A ligase, F6H1, CCoAOMT, ABCG37 and
UGT71C1 protein.

In another embodiment the exogenous nucleic acid encoding
OMT3 protein,
OMT3 and 4-Coumarate-Coenzyme A ligase protein,
OMT3 and F6H1 protein,
OMT3, 4-Coumarate-Coenzyme A ligase and CYP199A2 protein,
OMT3, F6H1 and CYP199A2 protein,
OMT3, 4-Coumarate-Coenzyme A ligase, F6H1 and CYP199A2 protein,
OMT3, F6H1 and CCoAOMT protein,
OMT3, F6H1 and ABCG37 protein,
OMT3, F6H1 and UGT71C1 protein,
OMT3, F6H1, CCoAOMT and ABCG37 protein
OMT3, F6H1, CCoAOMT, ABCG37 and UGT71C1 protein,
OMT3, 4-Coumarate-Coenzyme A ligase, F6H1 and CCoAOMT protein,
OMT3, 4-Coumarate-Coenzyme A ligase, F6H1 and ABCG37 protein,
OMT3, 4-Coumarate-Coenzyme A ligase, F6H1 and UGT71C1 protein,
OMT3, 4-Coumarate-Coenzyme A ligase, F6H1, CCoAOMT and ABCG37 protein
OMT3, 4-Coumarate-Coenzyme A ligase, F6H1, CCoAOMT, ABCG37 and UGT71C1 protein,
OMT3, CYP199A2, F6H1 and CCoAOMT protein,
OMT3, CYP199A2, F6H1 and ABCG37 protein,
OMT3, CYP199A2, F6H1 and UGT71C1 protein,
OMT3, CYP199A2, F6H1, CCoAOMT and ABCG37 protein
OMT3, CYP199A2, F6H1, CCoAOMT, ABCG37 and UGT71C1 protein,
OMT3, CYP199A2, 4-Coumarate-Coenzyme A ligase, F6H1 and CCoAOMT protein,
OMT3, CYP199A2, 4-Coumarate-Coenzyme A ligase, F6H1 and ABCG37 protein,
OMT3, CYP199A2, 4-Coumarate-Coenzyme A ligase, F6H1 and UGT71C1 protein,
OMT3, CYP199A2, 4-Coumarate-Coenzyme A ligase, F6H1, CCoAOMT and ABCG37 protein,
OMT3, CYP199A2, 4-Coumarate-Coenzyme A ligase, F6H1, CCoAOMT, ABCG37 and
UGT71C1 protein,
OMT3 and MYB72 protein,
OMT3, MYB72 and 4-Coumarate-Coenzyme A ligase protein,
OMT3, MYB72, and F6H1 protein,
OMT3, MYB72, 4-Coumarate-Coenzyme A ligase and CYP199A2 protein,
OMT3, MYB72, F6H1 and CYP199A2 protein,
OMT3, MYB72, 4-Coumarate-Coenzyme A ligase, F6H1 and CYP199A2 protein,
OMT3, MYB72, F6H1 and CCoAOMT protein,
OMT3, MYB72, F6H1 and ABCG37 protein,
OMT3, MYB72, F6H1 and UGT71C1 protein,
OMT3, MYB72, F6H1, CCoAOMT and ABCG37 protein
OMT3, MYB72, F6H1, CCoAOMT, ABCG37 and UGT71C1 protein,
OMT3, MYB72, 4-Coumarate-Coenzyme A ligase, F6H1 and CCoAOMT protein,
OMT3, MYB72, 4-Coumarate-Coenzyme A ligase, F6H1 and ABCG37 protein,
OMT3, MYB72, 4-Coumarate-Coenzyme A ligase, F6H1 and UGT71C1 protein,
OMT3, MYB72, 4-Coumarate-Coenzyme A ligase, F6H1, CCoAOMT and ABCG37 protein
OMT3, MYB72, 4-Coumarate-Coenzyme A ligase, F6H1, CCoAOMT, ABCG37 and UGT71C1 protein,
OMT3, MYB72, CYP199A2, F6H1 and CCoAOMT protein,
OMT3, MYB72, CYP199A2, F6H1 and ABCG37 protein,
OMT3, MYB72, CYP199A2, F6H1 and UGT71C1 protein,
OMT3, MYB72, CYP199A2, F6H1, CCoAOMT and ABCG37 protein
OMT3, MYB72, CYP199A2, F6H1, CCoAOMT, ABCG37 and UGT71C1 protein,
OMT3, MYB72, CYP199A2, 4-Coumarate-Coenzyme A ligase, F6H1 and CCoAOMT protein,
OMT3, MYB72, CYP199A2, 4-Coumarate-Coenzyme A ligase, F6H1 and ABCG37 protein,
OMT3, MYB72, CYP199A2, 4-Coumarate-Coenzyme A ligase, F6H1 and UGT71C1 protein,
OMT3, MYB72, CYP199A2, 4-Coumarate-Coenzyme A ligase, F6H1, CCoAOMT and ABCG37 protein or
OMT3, MYB72, CYP199A2, 4-Coumarate-Coenzyme A ligase, F6H1, CCoAOMT, ABCG37 and
UGT71C1 proteins are located on different expression cassettes.

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
|---|---|
| Plume blotch | *Septoria (Stagonospora) nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* (teleomorph: *Glomerella graminicola* Politis); *Glomerella tucumanensis* |
| Anthracnose stalk rot | (anamorph: *Glomerella falcatum* Went) |
| *Curvularia* leaf spot | *Curvularia clavata, C. eragrostidis, = C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| Diplodia leaf spot or streak | *Stenocarpella macrospora = Diplodialeaf macrospora* |
| Brown stripe downy mildew | *Sclerophthora rayssiae* var. *zeae* |
| Crazy top downy mildew | *Sclerophthora macrospora = Sclerospora macrospora* |
| Green ear downy mildew (*graminicola* downy mildew) | *Sclerospora graminicola* |
| Leaf spots, minor | *Alternaria alternata, Ascochyta maydis, A. tritici, A. zeicola, Bipolaris victoriae = Helminthosporium victoriae* (teleomorph: *Cochliobolus victoriae*), *C. sativus* (anamorph: *Bipolaris sorokiniana = H. sorokinianum = H. sativum*), *Epicoccum nigrum, Exserohilum prolatum = Drechslera prolata* (teleomorph: *Setosphaeria prolata*) *Graphium penicillioides, Leptosphaeria maydis, Leptothyrium zeae, Ophiosphaerella herpotricha,* (anamorph: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorph: *Exserohilum turcicum = Helminthosporium turcicum*) |

TABLE 3-continued

Diseases caused by necrotrophic and/or hemibiotrophic fungi and Oomycetes

| Disease | Pathogen |
|---|---|
| Northern corn leaf spot *Helminthosporium* ear rot (race 1) | *Cochliobolus carbonum* (anamorph: *Bipolaris zeicola = Helminthosporium carbonum*) |
| *Phaeosphaeria* leaf spot | *Phaeosphaeria maydis = Sphaerulina maydis* |
| Rostratum leaf spot (*Helminthosporium* leaf disease, ear and stalk rot) | *Setosphaeria rostrata*, (anamorph: *xserohilum rostratum = Helminthosporium rostratum*) |
| Java downy mildew | *Peronosclerospora maydis = Sclerospora maydis* |
| Philippine downy mildew | *Peronosclerospora philippinensis = Sclerospora philippinensis* |
| Sorghum downy mildew | *Peronosclerospora sorghi = Sclerospora sorghi* |
| Spontaneum downy mildew | *Peronosclerospora spontanea = Sclerospora spontanea* |
| Sugarcane downy mildew | *Peronosclerospora sacchari = Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

Preferred fungal pathogens are of the order Pucciniales, in particular the family Phacopsoracea, in particular the genus *Phakopsora*, more particularly the species *Phakopsora pachyrhizi* and/or *Phakopsora meibomiae*—also known as soybean rust or Asian Soybean Rust (ASR).

OMT3, 4-Coumarate-Coenzyme A ligase, ferulate 6-hydroxylase, CYP199A2, COSY, CCoA-OMT, ABCG37 and UGT71C expression constructs and vector constructs One embodiment of the present invention is a recombinant vector construct comprising the nucleic acid encoding OMT3 protein as defined above operably linked with a promoter and a transcription termination sequence.

One embodiment of the present invention is a recombinant vector construct comprising the nucleic acid encoding 4CL2 protein as defined above operably linked with a promoter and a transcription termination sequence.

One embodiment of the present invention is a recombinant vector construct comprising the nucleic acid encoding CYP199A2 protein as defined above operably linked with a promoter and a transcription termination sequence.

One embodiment of the present invention is a recombinant vector construct comprising the nucleic acid encoding F6H1 protein as defined above operably linked with a promoter and a transcription termination sequence.

One embodiment of the present invention is a recombinant vector construct comprising the nucleic acid encoding COSY protein as defined above operably linked with a promoter and a transcription termination sequence.

One embodiment of the present invention is a recombinant vector construct comprising the nucleic acid encoding CCoAOMT protein as defined above operably linked with a promoter and a transcription termination sequence.

One embodiment of the present invention is a recombinant vector construct comprising the nucleic acid encoding ABCG37 protein as defined above operably linked with a promoter and a transcription termination sequence.

One embodiment of the present invention is a recombinant vector construct comprising the nucleic acid encoding UGT71C1 protein as defined above operably linked with a promoter and a transcription termination sequence.

In one embodiment the nucleic acid encoding OMT3, 4-Coumarate-Coenzyme A ligase, ferulate 6-hydroxylase, CYP199A2, COSY, CCoAOMT, ABCG37 and/or UGT71C1 protein are located on the same recombinant vector construct. In another embodiment the nucleic acid encoding OMT3, 4-Coumarate-Coenzyme A ligase, ferulate 6-hydroxylase, CYP199A2, COSY, CCoA-OMT, ABCG37 and/or UGT71C1 protein are located on different vector constructs. Preferably, one expression cassette comprises the exogenous nucleic acid(s) encoding OMT3 and optionally in combination with exogenous nucleic acids encoding one or more selected from the group of the exogenous nucleic acid(s) 4-Coumarate-Coenzyme A ligase, ferulate 6-hydroxylase, CYP199A2, COSY, CCoAOMT, ABCG37 and UGT71C1. Preferably, the recombinant vector construct comprises exogenous nucleic acid encoding.

OMT3 protein,
OMT3 and 4-Coumarate-Coenzyme A ligase protein,
OMT3 and F6H1 protein,
OMT3, 4-Coumarate-Coenzyme A ligase and CYP199A2 protein,
OMT3, F6H1 and CYP199A2 protein,
OMT3, 4-Coumarate-Coenzyme A ligase, F6H1 and CYP199A2 protein,
OMT3, F6H1 and CCoAOMT protein,
OMT3, F6H1 and ABCG37 protein,
OMT3, F6H1 and UGT71C1 protein,
OMT3, F6H1, CCoAOMT and ABCG37 protein
OMT3, F6H1, CCoAOMT, ABCG37 and UGT71C1 protein,
OMT3, 4-Coumarate-Coenzyme A ligase, F6H1 and CCoAOMT protein,
OMT3, 4-Coumarate-Coenzyme A ligase, F6H1 and ABCG37 protein,
OMT3, 4-Coumarate-Coenzyme A ligase, F6H1 and UGT71C1 protein,
OMT3, 4-Coumarate-Coenzyme A ligase, F6H1, CCoA-OMT and ABCG37 protein
OMT3, 4-Coumarate-Coenzyme A ligase, F6H1, CCoA-OMT, ABCG37 and UGT71C1 protein,
OMT3, CYP199A2, F6H1 and CCoAOMT protein,
OMT3, CYP199A2, F6H1 and ABCG37 protein,
OMT3, CYP199A2, F6H1 and UGT71C1 protein,
OMT3, CYP199A2, F6H1, CCoAOMT and ABCG37 protein
OMT3, CYP199A2, F6H1, CCoAOMT, ABCG37 and UGT71C1 protein,
OMT3, CYP199A2, 4-Coumarate-Coenzyme A ligase, F6H1 and CCoAOMT protein,
OMT3, CYP199A2, 4-Coumarate-Coenzyme A ligase, F6H1 and ABCG37 protein,
OMT3, CYP199A2, 4-Coumarate-Coenzyme A ligase, F6H1 and UGT71C1 protein,
OMT3, CYP199A2, 4-Coumarate-Coenzyme A ligase, F6H1, CCoAOMT and ABCG37 protein,
OMT3, CYP199A2, 4-Coumarate-Coenzyme A ligase, F6H1, CCoAOMT, ABCG37 and
UGT71C1 proteins,
OMT3 and MYB72 proteins,
OMT3, MYB72 and 4-Coumarate-Coenzyme A ligase proteins,
OMT3, MYB72 and F6H1 proteins,
OMT3, MYB72, 4-Coumarate-Coenzyme A ligase and CYP199A2 proteins,
OMT3, MYB72, F6H1 and CYP199A2 proteins,
OMT3, MYB72, 4-Coumarate-Coenzyme A ligase, F6H1 and CYP199A2 proteins,
OMT3, MYB72, F6H1 and CCoAOMT proteins,
OMT3, MYB72, F6H1 and ABCG37 proteins,
OMT3, MYB72, F6H1 and UGT71C1 proteins,
OMT3, MYB72, F6H1, CCoAOMT and ABCG37 proteins
OMT3, MYB72, F6H1, CCoAOMT, ABCG37 and UGT71C1 proteins,
OMT3, MYB72, 4-Coumarate-Coenzyme A ligase, F6H1 and CCoAOMT proteins,
OMT3, MYB72, 4-Coumarate-Coenzyme A ligase, F6H1 and ABCG37 proteins,
OMT3, MYB72, 4-Coumarate-Coenzyme A ligase, F6H1 and UGT71C1 proteins,
OMT3, MYB72, 4-Coumarate-Coenzyme A ligase, F6H1, CCoAOMT and ABCG37 proteins
OMT3, MYB72, 4-Coumarate-Coenzyme A ligase, F6H1, CCoAOMT, ABCG37 and UGT71C1 proteins,
OMT3, MYB72, CYP199A2, F6H1 and CCoAOMT proteins,
OMT3, MYB72, CYP199A2, F6H1 and ABCG37 proteins,
OMT3, MYB72, CYP199A2, F6H1 and UGT71C1 proteins,
OMT3, MYB72, CYP199A2, F6H1, CCoAOMT and ABCG37 proteins
OMT3, MYB72, CYP199A2, F6H1, CCoAOMT, ABCG37 and UGT71C1 proteins,
OMT3, MYB72, CYP199A2, 4-Coumarate-Coenzyme A ligase, F6H1 and CCoAOMT proteins,
OMT3, MYB72, CYP199A2, 4-Coumarate-Coenzyme A ligase, F6H1 and ABCG37 proteins,
OMT3, MYB72, CYP199A2, 4-Coumarate-Coenzyme A ligase, F6H1 and UGT71C1 proteins,
OMT3, MYB72, CYP199A2, 4-Coumarate-Coenzyme A ligase, F6H1, CCoAOMT and ABCG37 proteins or
OMT3, MYB72, CYP199A2, 4-Coumarate-Coenzyme A ligase, F6H1, CCoAOMT, ABCG37 and
UGT71C1 proteins.

Promoters according to the present invention may be constitutive, inducible, in particular pathogen-inducible, developmental stage-preferred, cell type-preferred, tissue-preferred or organ-preferred. Examples for suitable promoters and terminators are:
p-PcUbi::GENE::t-ocs
p-SUPER::GENE::t-nos
p-Glyma14g06680::GENE::t-StCATHD
p-SUPER::GENE::t-nos,
pGmUbi3::GENE::t-StCATHD
PCaMV35S::GENE::t35S wherein "GENE" is any gene selected from MYB72, OMT3, 4-Coumarate-Coenzyme A ligase, ferulate 6-hydroxylase, CYP199A2, COSY, CCoAOMT, ABCG37 and UGT71C1.

The PcUbi promoter regulates constitutive expression of the ubi4-2 gene (accession number X64345) of *Petroselinum crispum* (Kawalleck, P., Somssich, I. E., Feldbrügge, M., Hahlbrock, K., & Weisshaar, B. (1993). Polyubiquitin gene expression and structural properties of the ubi4-2 gene in *Petroselinum crispum*. Plant molecular biology, 21(4), 673-684. The p-Super promoter consists of three identical Octapine Synthase Enhancers followed by a MAS promoter (Lee et al., 2007 Plant Physiology Vol145 Issue 4 1294-1300). The p-Glyma14g06680 promoter has been identified in a screen for genes that are predominantly expressed in the leaf of soybean. The promoter regulates the expression of the gene Glyma14g06680, which is most likely a water channel protein (WO12127373). The pGmUbi3 promoter is a strong constitutive promoter in soybean (see U.S. Pat. No. 8,395,021). The Cauliflower mosaic virus 35S promoter (pCaMV35S) and the respective 35S terminator (t35S) is a well-known expression system in plants that leads to strong constitutive expression (Benfey and Chua N H 1990 The Cauliflower Mosaic Virus 35S Promoter: Combinatorial Regula-tion of Transcription in Plants. Science. 250(4983): 959-66.). T-ocs and t-NOS terminators are both derived from *Agrobacterium* (Gielen, J., et al. "The complete nucleotide sequence of the TL-DNA of the *Agrobacterium tumefaciens* plasmid pTiAch5." The EMBO journal 3.4 (1984): 835. T-ocs is the terminator of the octopine synthase gene and t-NOS is the terminator of the nopaline synthase gene of *Agrobacterium tumefaciens* The StCATHD-pA is the terminator of the cathepsin D inhibitor gene from *Solanum tuberosum* (t-StCat) (Herbers et al. 1994)

One type of recombinant vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular, the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic organisms; transgenic plants, plant parts, and plant cells

A preferred embodiment is a transgenic plant, transgenic plant part, or transgenic plant cell overexpressing an exogenous OMT3 protein, optionally in combination with overexpressing one or more of MYB72, 4-Coumarate-Coenzyme A ligase, ferulate 6-hydroxylase, CYP199A2, COSY, CCoAOMT, ABCG37 and UGT71C1 protein encoded by a nucleic acid as defined above.

In preferred embodiments the biological activity of the OMT3 protein optional the biological activity of one or more of MYB72, 4-Coumarate-Coenzyme A ligase, ferulate 6-hydroxylase, CYP199A2, COSY, CCoAOMT, ABCG37 and/or UGT71C1 protein is increased in said transgenic plant, transgenic plant part, or transgenic plant cell.

In preferred embodiments, the protein amount of a OMT3 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the OMT3 nucleic acid.

In preferred embodiments, the protein amount of a MYB72 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the MYB72 nucleic acid.

In preferred embodiments, the protein amount of a 4CL2 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the 4CL2 nucleic acid.

In preferred embodiments, the protein amount of a CYP199A2 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the CYP199A2 nucleic acid.

In preferred embodiments, the protein amount of a F6H1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the F6H1 nucleic acid.

In preferred embodiments, the protein amount of a CCoA-OMT1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the CCoAOMT1 nucleic acid.

In preferred embodiments, the protein amount of a ABCG37 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the ABCG37 nucleic acid.

In preferred embodiments, the protein amount of a UGT71C1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the ABCG37 nucleic acid.

In preferred embodiments, the protein amount of a COSY protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the COSY nucleic acid.

On preferred embodiments the amount of OMT3 protein in combination with MYB72, 4-Coumarate-Coenzyme A ligase, ferulate 6-hydroxylase, CYP199A2, COSY, CCoA-OMT, ABCG37 and/or UGT71C1 protein(s) in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the respective nucleic acid(s).

More preferably, the transgenic plant, transgenic plant part, or transgenic plant cell according to the present invention has been obtained by transformation with one or more recombinant vector construct(s) described herein. In one embodiment a transgenic plant, transgenic plant part, or transgenic plant cell is transformed with one or more recombinant vector construct(s) as described, wherein the nucleic acid(s) encoding a OMT3 protein, and/or a MYB72 protein and/or a 4CL2 protein, and/or a CYP199A2 protein, and/or a COSY protein, and/or a F6H1 protein, and/or a CCoAOMT1 protein, and/or a ABCG37 protein and/or a UGT71C1 protein are located on the same recombinant vector construct or different vector constructs. Preferably, the recombinant vector construct comprises an exogenous nucleic acid or nucleic acids encoding OMT3 and 4-Coumarate-Coenzyme A ligase protein, OMT3 and F6H1 protein, OMT3, 4-Coumarate-Coenzyme A ligase and CYP199A2 protein, OMT3, F6H1 and CYP199A2 protein, OMT3, 4-Coumarate-Coenzyme A ligase, F6H1 and CYP199A2 protein, OMT3, F6H1 and CCoAOMT protein, OMT3, F6H1 and ABCG37 protein, OMT3, F6H1 and UGT71C1 protein, OMT3, F6H1, CCoAOMT and ABCG37 protein OMT3, F6H1, CCoAOMT, ABCG37 and UGT71C1 protein, OMT3, 4-Coumarate-Coenzyme A ligase, F6H1 and CCoAOMT protein, OMT3, 4-Coumarate-Coenzyme A ligase, F6H1 and ABCG37 protein, OMT3, 4-Coumarate-Coenzyme A ligase, F6H1 and UGT71C1 protein, OMT3, 4-Coumarate-Coenzyme A ligase, F6H1, CCoAOMT and ABCG37 protein, OMT3, 4-Coumarate-Coenzyme A ligase, F6H1, CCoAOMT, ABCG37 and UGT71C1 protein, OMT3, CYP199A2, F6H1 and CCoAOMT protein, OMT3, CYP199A2, F6H1 and ABCG37 protein, OMT3, CYP199A2, F6H1 and UGT71C1 protein, OMT3, CYP199A2, F6H1, CCoAOMT and ABCG37 protein, OMT3, CYP199A2, F6H1, CCoAOMT, ABCG37 and UGT71C1 protein, OMT3, CYP199A2, 4-Coumarate-Coenzyme A ligase, F6H1 and CCoAOMT protein, OMT3, CYP199A2, 4-Coumarate-Coenzyme A ligase, F6H1 and ABCG37 protein, OMT3, CYP199A2, 4-Coumarate-Coenzyme A ligase, F6H1 and UGT71C1 protein, OMT3, CYP199A2, 4-Coumarate-Coenzyme A ligase, F6H1, CCoAOMT and ABCG37 protein or OMT3, CYP199A2, 4-Coumarate-Coenzyme A ligase, F6H1, CCoAOMT, ABCG37 and UGT71C1 protein, OMT3, MYB72 and 4-Coumarate-Coenzyme A ligase protein, OMT3, MYB72 and F6H1 protein, OMT3, MYB72, 4-Coumarate-Coenzyme A ligase and CYP199A2 protein, OMT3, MYB72, F6H1 and CYP199A2 protein, OMT3, MYB72, 4-Coumarate-Coenzyme A ligase, F6H1 and CYP199A2 protein, OMT3, MYB72, F6H1 and CCoAOMT protein, OMT3, MYB72, F6H1 and ABCG37 protein, OMT3, MYB72, F6H1 and UGT71C1 protein, OMT3, MYB72, F6H1, CCoA-OMT and ABCG37 protein OMT3, MYB72, F6H1, CCoAOMT, ABCG37 and UGT71C1 protein, OMT3, MYB72, 4-Coumarate-Coenzyme A ligase, F6H1 and CCoAOMT protein, OMT3, MYB72, 4-Coumarate-Coenzyme A ligase, F6H1 and ABCG37 protein, OMT3, MYB72, 4-Coumarate-Coenzyme A ligase, F6H1 and UGT71C1 protein, OMT3, MYB72, 4-Coumarate-Coenzyme A ligase, F6H1, CCoAOMT and ABCG37 protein, OMT3, MYB72, 4-Coumarate-Coenzyme A ligase, F6H1, CCoAOMT, ABCG37 and UGT71C1 protein, OMT3, MYB72, CYP199A2, F6H1 and CCoAOMT protein, OMT3, MYB72, CYP199A2, F6H1 and ABCG37 protein, OMT3, MYB72, CYP199A2, F6H1 and UGT71C1 protein, OMT3, MYB72, CYP199A2, F6H1, CCoAOMT and ABCG37 protein, OMT3, MYB72, CYP199A2, F6H1, CCoAOMT, ABCG37 and UGT71C1 protein, OMT3, MYB72, CYP199A2, 4-Coumarate-Coenzyme A ligase, F6H1 and CCoAOMT protein, OMT3, MYB72, CYP199A2, 4-Coumarate-Coenzyme A ligase, F6H1 and ABCG37 protein, OMT3, MYB72, CYP199A2, 4-Coumarate-Coenzyme A ligase, F6H1 and UGT71C1 protein, OMT3, MYB72, CYP199A2, 4-Coumarate-Coenzyme A ligase, F6H1, CCoAOMT and ABCG37 protein or OMT3, MYB72, CYP199A2, 4-Coumarate-Coenzyme A ligase, F6H1, CCoAOMT, ABCG37 and UGT71C1 proteins.

A preferred embodiment comprises a transgenic plant, transgenic plant part, or transgenic plant cell expressing an exogenous OMT3 protein optionally in combination with one or more additional exogenous protein(s) selected from the group consisting of a MYB72, 4-Coumarate-Co-enzyme A ligase, ferulate 6-hydroxylase, CYP199A2, COSY, CCoAOMT, ABCG37 and UGT71C1 protein, wherein the nucleic acid encodings the respective protein(s) is operably linked with a promoter and a transcription termination sequence.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyle-donous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Hofgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the OMT3, MYB72, 4-Coumarate-Coenzyme A ligase, ferulate 6-hydroxylase, CYP199A2, COSY, CCoAOMT, ABCG37 and UGT71C1 protein nucleic acid(s).

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques or crossed with appropriate tester lines to generate hybrids. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root-stock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of soybean, beans, pea, clover, kudzu, lucerne, lentils, lupins, vetches, groundnut, rice, wheat, barley, arabidopsis, lentil, banana, canola, cotton, potato, maize, sugar cane, alfalfa, sugar beet, sunflower, rapeseed, sorghum, rice, cabbage, tomato, peppers, sugarcane and tobacco.

In one embodiment of the present invention, the plant is selected from the group consisting of beans, soybean, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C. O. Lehm), sugar pea (*Pisum sativum* L. convar. axiphium Alef emend. C. O. Lehm), also called snow pea, edible-podded pea or mangetout, (*Pisum granda* sneida L. convar. sneidulo p. shneiderium)); peanut (*Arachis hypogaea*), clover (*Trifolium* spec.), medick (Medicago), kudzu vine (*Pueraria lobata*), common lucerne, alfalfa (*M. sativa* L.), chickpea (*Cicer*), lentils (*Lens*) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) MarAchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soybeana, pea, clover, kudzu, lucerne, lentils, lupins, vetches, and groundnut. Most preferably, the plant, plant part, or plant cell is or is derived from soybean and/or corn.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the production of transgenic plants

One embodiment according to the present invention provides a method for the production of a transgenic plant, transgenic plant part, or transgenic plant cell having increased fungal resistance, comprising introducing
- i) exogenous nucleic acid encoding the nucleic acid encoding OMT3 protein wherein said OMT3 protein is encoded a nucleic acid as defined above operably linked with a promoter and a transcription termination sequence, and further optionally introducing one or more nucleic acids selected from the group consisting of
- exogenous nucleic acids encoding MYB72 protein as defined above operably linked with a promoter and a transcription termination sequence,
- exogenous nucleic acids encoding 4-Coumarate-Coenzyme A ligase protein as defined above operably linked with a promoter and a transcription termination sequence,
- exogenous nucleic acids encoding CYP199A2 protein as defined above operably linked with a promoter and a transcription termination sequence,
- exogenous nucleic acids encoding COSY protein as defined above operably linked with a promoter and a transcription termination sequence,
- exogenous nucleic acids encoding F6H1 protein as defined above operably linked with a promoter and a transcription termination sequence,
- exogenous nucleic acids encoding CCoAOMT1 protein as defined above operably linked with a promoter and a transcription termination sequence,
- exogenous nucleic acids encoding ABCG37 protein as defined above operably linked with a promoter and a transcription termination sequence, and
- exogenous nucleic acids encoding UGT71C1 protein as defined above operably linked with a promoter and a transcription termination sequence into a plant, a plant part, or a plant cell,
wherein the exogenous nucleic acid encoding MYB72, 4-Coumarate-Coenzyme A ligase, ferulate 6-hydroxylase, CYP199A2, COSY, CCoAOMT, ABCG37 and/or UGT71C1 protein are located on the same or different vector constructs,
- ii) generating a transgenic plant, transgenic plant part, or transgenic plant cell from the plant, plant part or plant cell; and
- iii) expressing the protein(s) encoded by the recombinant vector construct(s).

In one embodiment, the present invention refers to a method for the production of a transgenic plant, transgenic plant part, or transgenic plant cell having increased fungal resistance, comprising
- (a) introducing a recombinant vector construct according to the present invention into a plant, a plant part or a plant cell and
- (b) generating a transgenic plant from the plant, plant part or plant cell and optionally
- (c) expressing the OMT3 protein and one or more proteins selected from the group consisting of MYB72, 4-Coumarate-Coenzyme A ligase, ferulate 6-hydroxylase, CYP199A2, COSY, CCoAOMT, ABCG37 and/or UGT71C1 protein(s).

Preferably, said introducing and expressing does not comprise an essentially biological process.

Preferably, the method for the production of the transgenic plant, transgenic plant part, or transgenic plant cell further comprises the step of selecting a transgenic plant expressing OMT3 protein and one or more proteins selected from the group consisting of MYB72, 4-Coumarate-Coenzyme A ligase, ferulate 6-hydroxylase, CYP199A2, COSY, CCoAOMT, ABCG37 and UGT71C1 protein(s).

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises a nucleic acid encoding OMT3 protein and one or more nucleic acids encoding proteins selected from the group consisting of MYB72, 4-Coumarate-Coenzyme A ligase, ferulate 6-hydroxylase, CYP199A2, COSY, CCoAOMT, ABCG37 and UGT71C1 protein(s) operably linked with a promoter and a transcription termination sequence.

Preferably, the step of harvesting the seeds of the transgenic plant and planting the seeds and growing the seeds to plants is repeated more than one time, preferably, 1, 2, 3, 4, 5, 6, 7, 8, 9, 10, 15, 20, 25, 30, 35, 40, 45, or 50 times.

The transgenic plants may be selected by known methods as described above (e.g., by screening for the presence of one or more markers which are encoded by plant-expressible genes cotransferred with the OMT3, MYB72, 4-Coumarate-Coenzyme A ligase, ferulate 6-hydroxylase, CYP199A2, COSY, CCoAOMT, ABCG37 and/or UGT71C1 gene(s) or by directly screening for the OMT3, MYB72, 4-Coumarate-Coenzyme A ligase, ferulate 6-hydroxylase, CYP199A2, COSY, CCoAOMT, ABCG37 and UGT71C1 nucleic acid(s)).

Furthermore, the use of the exogenous OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT1, ABCG37 and UGT71C1 nucleic acid(s) or use of the recombinant vector construct comprising the OMT3 nucleic acid optionally in combination with one or more nucleic acid(s) selected from the group MYB72, 4-Coumarate-Coenzyme A ligase, ferulate 6-hydroxylase, CYP199A2, COSY, CCoAOMT, ABCG37 and/or UGT71C1 nucleic acid(s) for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and/or UGT71C1 nucleic acid(s) or OMT3 protein optionally in combination with one or more protein(s) selected from the group consisting of 4-Coumarate-Coenzyme A ligase, ferulate 6-hydroxylase, CYP199A2, COSY, CCoAOMT, ABCG37 and/or UGT71C1 protein(s). The harvestable parts may be seeds, roots, leaves and/or flowers. Preferred parts of soybean plants are soybean beans. Preferred parts of corn plants are corn grains.

Products derived from a transgenic plant according to the present invention, parts thereof or harvestable parts thereof are part of the invention. A preferred product is oil, preferably, corn oil or soybean oil.

Preferred parts of soybean plants are soybean beans comprising the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and/or UGT71C1 nucleic acid(s) or OMT3 protein optionally in combination with one or more protein(s) selected from the group consisting of 4-Coumarate-Coenzyme A ligase, ferulate 6-hydroxylase, CYP199A2, COSY, CCoAOMT, ABCG37 and/or UGT71C1 protein(s).

Preferred parts of corn plants are soybean grains comprising the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid(s) or OMT3 protein optionally in combination with one or more protein(s) selected from the group consisting of MYB72, 4-Coumarate-Coenzyme A ligase, ferulate 6-hydroxylase, CYP199A2, COSY, CCoAOMT, ABCG37 and UGT71C1 protein(s).

In a preferred embodiment a product is derived from the plant described above or from the harvestable part of the plant described above, wherein the product is preferably soybean oil and/or corn oil.

Preferably the soybean oil comprises the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid(s) or OMT3 protein optionally in combination with one or more protein(s) selected from the group consisting of MYB72, 4-Coumarate-Coenzyme A ligase, ferulate 6-hydroxylase, CYP199A2, COSY, CCoAOMT, ABCG37 and UGT71C1 protein(s).

Preferably the corn oil comprises the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid(s) or OMT3 protein optionally in combination with one or more protein(s) selected from the group consisting of MYB72, 4-Coumarate-Coenzyme A ligase, ferulate 6-hydroxylase, CYP199A2, COSY, CCoAOMT, ABCG37 and UGT71C1 protein(s).

Methods for Manufacturing a Product

In one embodiment the method for the production of a product comprises
 a) growing the plants of the invention or obtainable by the methods of invention and
 b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid(s) and/or protein(s) according to the invention.

Method for the production of a product comprising
 a) growing a plant according to the invention or obtainable by the method according to the invention and
 b) producing said product from or by the plant and/or part, preferably seeds, of the plant,
wherein the product comprises the OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid(s) or the proteins encoded by said nucleic acids.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally, the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the OMT3 nucleic acid optionally in combination with nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid(s). The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
 (a) crossing a transgenic plant described herein or a plant obtainable by a method described herein with a second plant;
 (b) obtaining a seed or seeds resulting from the crossing step described in (a);

(c) planting said seed or seeds and growing the seed or seeds to plants; and (d) selecting from said plants the plants expressing a OMT3 protein optionally in combination with one or more proteins selected from the group consisting of MYB72, 4-Coumarate-Co-enzyme A ligase, ferulate 6-hydroxylase, CYP199A2, COSY, CCoAOMT, ABCG37 and UGT71C1 protein(s).

Another preferred embodiment is a method for plant improvement comprising (a) obtaining a transgenic plant by any of the methods of the present invention;

(b) combining within one plant cell the genetic material of at least one plant cell of the plant of (a) with the genetic material of at least one cell differing in one or more gene from the plant cells of the plants of (a) or crossing the transgenic plant of (a) with a second plant;

(c) obtaining seed from at least one plant generated from the one plant cell of (b) or the plant of the cross of step (b);

(d) planting said seeds and growing the seeds to plants; and (e) selecting from said plants, plants expressing the nucleic acid encoding OMT3 protein optionally in combination with one or more protein(s) selected from the group consisting of MYB72, 4-Coumarate-Coenzyme A ligase, ferulate 6-hydroxylase, CYP199A2, COSY, CCoAOMT, ABCG37 and UGT71C1 protein(s); and optionally (f) producing propagation material from the plants expressing the nucleic acid encoding OMT3 protein optionally in combination with one or more protein(s) selected from the group consisting of MYB72, 4-Coumarate-Coenzyme A ligase, ferulate 6-hydroxylase, CYP199A2, COSY, CCoAOMT, ABCG37 and UGT71C1 protein(s).

The transgenic plants may be selected by known methods as described above (e.g., by screening for the presence of one or more markers which are encoded by plant-expressible genes cotransferred with the OMT3, MYB72, 4-Coumarate-Coenzyme A ligase, ferulate 6-hydroxylase, CYP199A2, COSY, CCoAOMT, ABCG37 and/or UGT71C1 gene or screening for the OMT3, MYB72, 4-Coumarate-Coenzyme A ligase, ferulate 6-hydroxylase, CYP199A2, COSY, CCoAOMT, ABCG37 and/or UGT71C1 nucleic acid itself).

According to the present invention, the introduced OMT3 nucleic acid optionally in combination with one or more nucleic acids selected from the group consisting of MYB72, 4-Coumarate-Coenzyme A ligase, ferulate 6-hydroxylase, CYP199A2, COSY, CCoAOMT, ABCG37 and UGT71C1 nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous OMT3, MYB72, 4-Coumarate-Coenzyme A ligase, ferulate 6-hydroxylase, CYP199A2, COSY, CCoAOMT, ABCG37 and/or UGT71C1 nucleic acid preferably resides in one or more a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from Agrobacterium tumefaciens t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et. al, 1987, Nucl. Acids Research 15:8693-8711). Examples of plant expression vectors include those detailed in: Becker, D. et al, 1992, New plant binary vectors with selectable markers located proximal to the left border, Plant Mol. Biol. 20:1195-1197; Bevan, M. W., 1984, Binary Agrobacterium vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

A preferred method according to the invention is a method for applying a scoparone, scopoletin and/or a derivative thereof to a surface of a plant, plant part or plant cell, wherein the resistance to a fungal pathogen of the plant, plant part or plant cell is increased by applying scoparone, scopoletin and/or a derivative thereof to the surface of the plant, plant part or plant cell in comparison to a plant, plant part or plant cell to which surface scoparone, scopoletin and/or a derivative has not been applied, wherein the plant is soybean and/or corn.

In one embodiment according to the invention, a plant surface or plant part surface is coated with scopoletin and/or a derivative thereof, wherein the plant is soybean and/or corn.

In one embodiment according to the invention a plant, plant part or plant cell has a surface coated with scopoletin and/or a derivative thereof. Wherein the plant is soybean and/or corn.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1

General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of E. coli cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977).

Example 2

Cloning of Overexpression Vector Constructs for Transient N. benthamiana Transformation To obtain cDNA, RNA was extracted from detached *Helianthus annuus* leaves two days after treatment with 300 µM CuCl2.

Total sunflower RNA was isolated according to the Rapid CTAB protocol (modified from Gambino et al., 2008, DOI: 10.1002/pca.1078). Nine hundred microliters of preheated (65° C.) extraction buffer (2% cetyltrimethylammonium bromide (CTAB), 2.5% PVP-40, 2 M NaCl, 100 mM Tris-HCl pH 8.0, 25 mM EDTA pH 8.0 and freshly added 2% (v/v) β-mercaptoethanol) was added to a minimum of 150 mg ground leaf material in a 2 ml reaction tube. After an incubation of 10 min at 65° C. 900 µl chloroform:isoamyl alcohol (24:1 v/v) were added and mixed by mixing. The samples were centrifuged for 10 min at 11,000 rcf and 4° C. The supernatant was recovered and one volume of chloroform:isoamyl alcohol was quickly added. After mixing, the samples were again centrifuged for 10 min at 11,000 rcf and 4° C. The supernatant was recovered and LiCl was added to a final concentration of 3 M. The samples were mixed and incubated on ice for 30 min. After a centrifugation for 20 min at 21,000 rcf and 4° C. 500 µl of preheated (65° C.) SSTE buffer (10 mM Tris-HCl pH 8.0, 1 mM EDTA pH 8.0, 1% SDS, 1 M NaCl) were added to the pellet and the mix was incubated for 10 min at 65° C. An equal volume of chloroform:isoamyl alcohol was added, the samples were mixed and centrifuged for 10 min at 11,000 rcf and 4° C. Subsequently, the transferred supernatant was mixed with 0.7 volumes of ice-cold isopropanol. The solution was mixed and centrifuged for 15 min at 21,000 rcf and 4° C. The pellet was washed twice with 70% (v/v) ethanol and suspended in 20 µl ddH$_2$O.

cDNA was produced with oligo-dT primers using RevertAid H minus reverse tranrciptase (Thermo Scientific). All steps of cDNA preparation and purification were performed according as described in the manual.

The OMT3 of *Helianthus annuus* according to SEQ ID NO. 1 was amplified from the cDNA by PCR as described in the protocol of the Phusion High-Fidelity DNA Polymerase (Thermo Scientific) hot-start, Pfu Ultra, Pfu Turbo or Herculase DNA polymerase (Stratagene). The composition for the protocol of the Pfu Ultra, Pfu Turbo or Herculase DNA polymerase was as follows: 1× PCR buffer, 0.2 mM of each dNTP, 100 ng cDNA of *Arabidopsis thaliana* (var Columbia-0), 50 µmol forward primer, 50 µmol reverse primer, 1 u Phusion hot-start, Pfu Ultra, Pfu Turbo or Herculase DNA polymerase.

The amplification cycles were as follows:

1 cycle of 30 seconds at 98° C., followed by 35 cycles of in each case 10 seconds at 98° C., 30 seconds at 62° C. and 40 seconds at 72° C., followed by 1 cycle of 10 minutes at 72° C., then 4° C. The following primer sequences were used to specifically amplify the OMT3 full-length ORF for cloning purposes:

```
HaOMT3_attB1_F:
GGGGACAAGTTTGTACAAAAAA-GCAGGCTCAATGGGTTCAACATCAGCC

HaOMT3_attB2_R:
GGGGACCACTTTGTACAAGAAAGCTGGGTACTATTTGCAAAATTCCA-
TAACCCA
```

For expression in e.g. Nicotiana benthamiana, further primers are useful:

```
HaOMT1_attB1_F
GGGGACAAGTTTGTACAAAAAA-
GCAGGCTCAATGGGTTCAACATCAGCATCT

HaOMT1_attB2_R
GGGGACCACTTTGTACAAGAAAGCTGGGTACTATTT-
GCAAAATTCCATAACCCA

HaF6H1_attB1_F
GGGGACAAGTTTGTACAAAAAA-
GCAGGCTCAATGGCTCCATCAATCTCCAT

HaF6H1_attB2_R
GGGGACCACTTTGTACAAGAAAGCTGGGTATTACACCTTT-
GCAAAATCAA

IbF6H1_attB1_F
GGGGACAAGTTTGTACAAAAAA-
GCAGGCTCAATGCCTTCAACAACACTCTCC

IbF6H1_attB2_R
GGGGACCACTTTGTACAAGAAAGCTGGGTACTATTC-
TATTCTGGCGAAGG

AtF6H1_GWY_F
GGGGACAAGTTTGTACAAAAAAGCAGGCTTAATGGCTCCAACACTCTT-
GAC

AtF6H1_GWY_R
GGGGACCACTTTGTACAAGAAAGCTGGGTATCAGATCTTGGCGTAATCG
```

The amplified fragments were gel purified and cloned into the pDONR 207 entry vector (Invitrogen) using Gateway® cloning according to the manufacturer's instructions. Using this cloning technique the full-length OMT3 fragment is inserted in sense direction between the attL1 and attL2 recombination sites of the entry vector. To prepare an untagged OMT3 overexpression construct, a LR reaction (Gateway system, (Invitrogen, Life Technologies, Carlsbad, California, USA) was performed according to manufacturers protocol by using a pDONR207 vector containing the OMT3 fragment. As target a binary pB7WG2D (Ghent University, Belgium; Karimi, M., Inzé, D., Depicker, A., Gateway vectors for *Agrobacterium*-mediated plant transformation. Trends Plant Sci. 2002 May; 7(5): 193-195) vector was used, which is composed of: (1) a Spectinomycin resistance cassette for bacterial selection (2) a pVS1 origin for replication in Agrobacteria (3) a pBR322 origin of replication for stable maintenance in *E. coli* and (4) between the right and left border a bar selection gene under control of a pNos-promoter and (5) an eGFP expression marker under control of a CaMV 35S promoter. The recombination reaction was transformed into competent *E. coli* (DH5alpha), mini-prepped and screened by specific restriction digestions. A positive clone from each the vector construct was sequenced and used for transient Agrotransformation of *N. benthamiana*.

Example 3

Transient Transformation of N. benthamiana Leaves

Transient transformation of *N. benthamiana* leaves was done according to a slightly modified protocol from Popescu et al. 2007 (Popescu, S. C., Popescu, G. V., Bachan, S., Zhang, Z., Seay, M., Gerstein, M., Snyder, M., and Dinesh-Kumar, S. P. (2007). Differential binding of calmodulin-related proteinsto their targets revealed through high-density *Arabidopsis* protein microarrays Proc Natl Acad Sci USA 104, 4730-4735.) A single *Agrobacterium* colony (strain AGL01) carrying a DNA construct of interest (see FIGS. 2*a* and 2*b*) was cultured in YEB medium with appropriate antibiotics for 14-16 h at 28° C. Cells were harvested by centrifugation (5000 rpm 10 min), resuspended to an OD of 0.4-0.8 in buffer containing 10 mM MgCl2, 10 mM MES pH 5.6 and 150 µM acetosyringone and incubated for 2-5 h at room temperature. For transient gene expression Agrobacteria strains transformed with the DNA constructs of interest were mixed in equal ratios with Agrobacteria containing the p19 silencing suppressor gene from tomato bushy stunt virus (TBSV) and were syringae-infiltrated into leaves of 6-week-old *N. benthamiana* plants. Three days after *Agrobacterium* infiltration, leaves were frozen in liquid nitrogen and stored at −80° C. until analysis.

Example 4

Coumarin Extraction from *N. benthamiana* Leaf Tissue 500 mg lyophilised and ground *N. benthamiana* leaf material were mixed with 1 ml of methanol in a 15 ml reaction tube and vortexed vigorously. The samples were sealed with parafilm and incubated overnight at RT with gentle shaking. Subsequently, the samples were centrifuged for 10 min at 21,000 rcf. Seven-hundred microliters of clear supernatant were transferred to a fresh 2 ml reaction tube and evaporated in a vacuum concentrator. The dry pellet was resuspended in 300 µl methanol and stored at −20° C.

Cloning of Constructs for Heterologous Expression of GOIs in *E. coli*

For expressing GOIs in *E. coli*, single cDNA sequences were cloned from sunflower cDNA (see above) in pGEX-5X-3 via Gibson Assembly® using EcoRI and XhoI restriction sites. Gibson assembly was performed as described by (Gibson et al., 2009, Enzymatic assembly of DNA molecules up to several hundred kilobases. Nature Methods 6: 343-345). F6H and 4CL2 genes were expressed under control of the same promoter. To ensure translation of the 4CL2 gene at the second position a ribosomal binding site (rbs) was integrated at the 5' end of the 4CL2 gene.

Primers:

For cloning according to Gibson et al. of OMT3 and OMT1 single gene constructs, respectively:

```
HaOMT1_gbs_F
aaggtcgtgggatccccaggATGGGTTCAACATCAGCATC

HaOMT1_gbs_R
gtcagtcacgatgcggccgcCTATTTGCAAAATTCCATAACC

HaOMT3_gbs_F
aaggtcgtgggatccccaggATGGGTTCAACATCAGCC

HaOMT3_gbs_R
gtcagtcacgatgcggccgcCTATTTGCAAAATTCCATAACC
```

For cloning according to Gibson et al. of IbF6H1-rbs-Ha4CL2 double gene constructs (FIG. 4):

```
IbF6H1_gbsA_F
aaggtcgtgggatccccaggATGCCTTCAACAACACTC
```

```
IbF6H1_gbsA_R
ccattggtatatctccttCTATTCTATTCTGGCGAAGG

Ha4Cl2_gbsAC_F
aatagaatagaaggagatataccaATGGCGCCGGAGAAGGA

Ha4Cl2_gbsABC_R
gtcagtcacgatgcggccgcTTAATTTGGGACACCAGCTGC
```

For cloning according to Gibson et al. of AtF6H1-rbs-Ha4CL2 double gene constructs (FIG. 4):

```
AtF6H1_pGEX_fwd
aaggtcgtgggatccccaggATGGCTCCAACACTCTTG

AtF6H1_pGEX_rev
atatctccttTCAGATCTTGGCGTAATC

At1_RBS_Ha4Cl2_fwd
caagatctgaAAGGAGATATACCAATGGC

Ha4Cl2_pGEX_rev
gtcagtcacgatgcggccgcTTAATTTGGGACACCAGC
```

For cloning according to Gibson et al. of HaF6H1-rbs-Ha4CL2 double gene constructs (FIG. 4):

```
HaF6H1_gbsB_F
aaggtcgtgggatccccaggATGGCTCCATCAATCTCC

HaF6H1_gbsB_R
ccattggtatatctccTTTTACACCTTTGCAAAATCAATTG

Ha4Cl2_gbsB_F
aaaggtgtaaaaggagatataccaATGGCGCCGGAGAAGGA

Ha4Cl2_gbsABC_R
gtcagtcacgatgcggccgcTTAATTTGGGACACCAGCTGC
```

Example 5

Precursor Feeding Assays and Coumarin Extraction from GOI Expressing *E. coli*

Precursor feeding for coumarin production was conducted as described before (Yang et al., 2015, modified). For heterologous expression, *E. coli* BL21 cells were transformed with the DNA construct of interest in the pGEX-5X-3 vector. A single transformant was inoculated into 3 ml liquid LB medium containing ampicillin and incubated overnight at 37° C., 220 rpm. The next morning, 0.5 ml of preculture were used to inoculate 50 ml LB with ampicillin for selection. The main culture was incubated at 37° C., 220 rpm until it reached an OD600 of ~0.8. Isopropyl β-D-1-thio-galactopyranoside (IPTG) was added directly to the culture to a final concentration of 1 mM to induce the expression of the gene of interest. The cells were grown at 28° C. until an OD600 of around 3.0. Subsequently, 1 ml aliquots of the culture were distributed into a sterile 24-well plate. The number of aliquots depended on the number of tested precursor substances. Precursors were solved in DMSO and fed at a final concentration of 400 µM. The plate was incubated at 28° C. and 220 rpm until samples were taken. Five-hundred microliters of each sample were extracted twice with an equal volume of ethyl acetate. The organic phases were joined and evaporated in a vacuum concentrator. The extracts were resuspended in 150 µl methanol and analysed via HPLC and/or TLC

Example 6

HPLC Based Analytics

Samples (20 µl injection volume) were subsequently subjected to reverse-phase high-performance liquid chromatography (HPLC) analysis on a Nucleosil C18 column (EC 150/4,6 Nucleosil 100-5 C18; Macherey-Nagel) with a gradient mobile phase built with 1.5% (v/v) acetic acid in water (A) and 1.5% (v/v) formic acid in acetonitrile (B), and a flow rate of 1.0 ml/min at RT. The gradient program started at 10% B fand increased linearly to 25% for 10 min where it remained until minute 20. The gradient then increased to 90% B within 2 min. This proportion was maintained for 3 min and then returned to initial conditions in 2 min. Coumarin fluorescence was detected at $\lambda$=335 nm excitation and $\lambda$=460 nm emission (FP 920 Intelligent Fluorescence Detector, Jasco) or at $\lambda$=342 nm (UV absorbance). Coumarin peaks were identified by comparison to retention times of authentic commercial standards. For quantification, a standard curve of commercial standards with known concentrations was measured.

Example 7

Thin Layer Chromatography Based Analytics

Thin layer chromatography (TLC) was performed with pre-coated TLC sheets (ALUGRAM® SIL G, Macherey-Nagel, Duren, Germany) with a layer of 0.20 mm silica gel 60. Coumarin methanol extracts and corresponding standards were spun down and loaded onto the sheet at a maximal volume of 10 µl. TLC sheets were dried and placed upright in a chamber containing TLC running buffer (toluene:ethyl formate:formic acid 5:4:1 (v/v)). After approximately 45 min, the plate was dried and photographed under UV light. Metabolites were identified by comparison to retention factors of authentic commercial standards.

Example 8

Analysis of Coumarins' Antioxidant Activity (FIG. 7)

The 2,2'-azinobis-(3-ethylbenzothiazoline-6-sulfonic acid (ABTS)-assay10 was applied to compare the antioxidant activity of different coumarins to Trolox and ascorbic acid as references. The radical monocation of ABTS (ABTS·+) was generated by oxidation of ABTS with potassium persulfate ($K_2S_2O_8$) This was done by mixing aqueous ABTS (7 mM) and $K_2S_2O_8$ (2.4 mM) in a 1:1 ratio (v/v). The mixture was placed in the dark and incubated at room temperature for 16 hours and then diluted with ethanol to an absorbance of 0.7 (±0.02) at 734 nm. All solutions were brought to a temperature of 37° C. Next, 990 µl of ABTS·+ was mixed with 10 µl of a test solution containing different concentrations of a coumarin standard. Ascorbic acid and Trolox served as positive and ethanol as the blanc control. Mixtures were incubated at 37° C. in a thermomixer (700 rpm) for 7 minutes. Absorbance at 734 nm was measured in a spectrophotometer following incubation for 7 minutes at 37° C. in a thermomixer (700 rpm).

Example 9

In Vitro Germination Tests: Growth Inhibition of *Phakopsora pachyrhizi*

Uredospores of *P. pachyrhizi* (isolate BRO5) were harvested from heavily infected soybean leaves and equally suspended in water by shaking for 25 s at 5'000 rpm on a Precellys 24 homogenizer in the absence of homogenizing beads (Bertin instruments). For in vitro assays, spores were added to the adequate test solution at a density of 1 mg spores/mL. Using a diffuser (Carl Roth) uredospores were subsequently sprayed on glass slides that were coated with polyethylene foil. The slides were kept for 18 h at high humidity. Germination of spores and fungal development was evaluated by counting developing appressoria in the presence of 10-400 μM scoparone (in 0.1% DMSO) and compared to fungal proliferation in presence of $H_2O$ or 0.1% DMSO only (controls).

The germination rate and appressoria formation rate was determined by quantitative microscopic analysis. Spores showing a visible germ tube formation but no thickening of the germ tube tip were counted as "germinated", whereas the presence of a thickened germ tube tip indicated the formation of an appressoria.

Soybean

Example 10

Cloning of Overexpression Vector Constructs for Stable Soybean Transformation The DNA sequence of the OMT3, MYB72, 4-Coumarate-Coenzyme A ligase, ferulate 6-hydroxylase, CYP199A2, COSY, CCoAOMT, ABCG37 and UGT71C1 genes mentioned in this application were generated by DNA synthesis (Geneart, Regensburg, Germany).

To obtain the OMT3 F6H1 double gene construct the OMT3 DNA (SEQ ID NO. 1) was synthesized in a way that a PacI restriction site is located in front of the start-ATG and an AscI restriction site downstream of the stop codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, California, USA) in a way that the full-length fragment is located in sense direction between the pGmUbi3 promoter (see U.S. Pat. No. 8,395,021) and the *Solanum tuberosum* cathepsin D inhibitor (Herbers, Karin, Salomé Prat, and Lothar Willmitzer. "Functional analysis of a leucine aminopeptidase from *Solanum tuberosum* L." Planta 194.2 (1994): 230-240.). The pGmUbi promoter mediates a strong constitutive expression in soybean.

The F6H1 DNA was synthesized in a way that a PacI restriction site is located in front of the start-ATG and an AscI restriction site downstream of the stop-codon. The synthesized DNA was digested using the restriction enzymes PacI and AscI (NEB Biolabs) and ligated in a PacI/AscI digested Gateway pENTRY-C vector (Invitrogen, Life Technologies, Carlsbad, California, USA) in a way that the full-length fragment is located in sense direction between the parsley ubiquitin promoter and the *Agrobacterium tumefaciens* derived octopine synthase terminator (t-OCS). The PcUbi promoter regulates constitutive expression of the ubi4-2 gene (accession number X64345) of *Petroselinum crispum* (Kawalleck et al. 1993 Plant Molecular Biology 21 (4): 673-684).

To generate the binary plant transformation vector containing F6H1 and OMT3, a triple LR reaction (Gateway system, Invitrogen, Life Technologies, Carlsbad, California, USA) was performed according to manufacturer's protocol by using an empty pENTRY-A vector, the pSuper promoter::OMT3::nos-terminator in the above described pENTRY-B vector and the PcUbi promoter::F6H1::OCS-terminator in the above described pENTRY-C vector. As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of an AtAHASL-promoter (see FIG. 3). The recombination reaction was transformed into *E. coli* (DH5alpha), mini-prepped and screened by specific restriction digestions. A positive clone from each vector construct was sequenced and submitted soybean transformation.

To generate a triple construct, such as F6H1+OMT3+ MYB72, the MYB72 DNA (as shown in SEQ ID NO. 7) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-A vector (Invitrogen, Life Technologies, Carlsbad, California, USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300). The pSUPER promoter is mediating a medium strong constitutive expression in soybean.

To obtain the binary plant transformation vector containing OMT3, F6H1 and MYB72, a triple LR reaction (Gateway system, Invitrogen, Life Technologies, Carlsbad, California, USA) was performed according to manufacturer's protocol by using the pSUPER::MYB72::cathepsin inhibitor terminator in the pENTRY-A vector, as decribed above, the pGmUbi3 promoter::OMT3::nos-terminator in the above described pENTRY-B vector and the PcUbi promoter:: F6H1::OCS-terminator in the above described pENTRY-C vector.

As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of an AtAHASL promoter (see FIG. 4). The recombination reaction was transformed into *E. coli* (DH5alpha), mini-prepped and screened by specific restriction digestions. A positive clone from each vector construct was sequenced and submitted soybean transformation.

All other double and triple constructs were generated in a similar manner as described above.

For constructs that contain more than 3 genes, like F6H1+ OMT3+MYB72+ABCG37 all genes were cloned in between promoter and terminator using AscI and PacI restriction, as described above. The genes F6H1, OMT3 and MYB72 were cloned as described above into pENTRY A, pENTRY B and pENTRY C vectors respectively. The DNA of the remaining gene ABCG37 was also digested using the restriction enzymes PacI and AscI (NEB Biolabs) and ligated in a PacI/AscI digested intermediate pUC19 vectors in a way that the full-length fragment is located in sense direction between the Cauliflower mosaic virus 35S promoter (pCaMV35S) and the respective 35S terminator (t35S) (Benfey and Chua N H 1990 The Cauliflower Mosaic Virus 35S Promoter: Combinatorial Regulation of Transcription in Plants. Science. 250(4983):959-66.). The complete p35S::ABCG37::t35S cassette was then transferred into the pENTRY C vector containing the pPcUbi::F6H1:: tOCS1 cassette by using 8-base cutters (restrictions enzymes), such as NcoI, FseI and CasI, in a way that the p35S::ABCG37::t35S cassette is in head to tail orientation with the pPcUbi::F6H1::tOCS1.

To obtain the binary plant transformation vector containing F6H1, OMT3, MYB72 and ABCG37 a triple LR reaction (Gateway system, Invitrogen, Life Technologies, Carlsbad, California, USA) was performed as described above, using the above described pENTRY-A, pENTRY-B and pENTRY-C vectors.

All constructs containing 4 ore more genes were generated in a similar way as described above by combining 2 (or more) promoter::gene:terminator cassettes in a pENTRY vector. The final plant transformation vector was then generated by a triple LR Gateway reaction as described above.

The F6H1 DNA (as shown in SEQ ID 1) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-C vector (Invitrogen, Life Technologies, Carlsbad, California, USA) in a way that the full-length fragment is located in sense direction between the parsley ubiquitin promoter and the *Agrobacterium tumefaciens* derived octopine synthase terminator (t-OCS). The PcUbi promoter regulates constitutive expression of the ubi4-2 gene (accession number X64345) of *Petroselinum crispum* (Kawalleck et al. 1993 Plant Molecular Biology 21(4): 673-684).

To obtain the binary plant transformation vector, a triple LR reaction (Gateway system, Invitrogen, Life Technologies, Carlsbad, California, USA) was performed according to manufacturer's protocol by using an empty pENTRY-A vector, an empty pENTRY-C, and the PcUbi promoter:: F6H1::OCS-terminator in the above described pENTRY-C vector. As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 2). The recombination reaction was transformed into *E. coli* (DH5alpha), mini-prepped and screened by specific restriction digestions. A positive clone from each vector construct was sequenced and submitted soybean transformation.

To obtain the F6H1-CCoAOMT1 double gene construct the CCoAOMT1 DNA (as shown in SEQ ID 3) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, California, USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and CCoAOMT1, a triple LR reaction (Gateway system, Invitrogen, Life Technologies, Carlsbad, California, USA) was performed according to manufacturer's protocol by using an empty pENTRY-A vector, the pSuper promoter::CCoAOMT1::nos-terminator in the above described pENTRY-B vector and the PcUbi promoter::F6H1::OCS-terminator in the above described pENTRY-C vector. As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 3). The recombination reaction was transformed into *E. coli* (DH5alpha), mini-prepped and screened by specific restriction digestions. A positive clone from each vector construct was sequenced and submitted soybean transformation.

To obtain the F6H1-UGT71C1 double gene construct the UGT71C1 DNA (as shown in SEQ ID 7) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, California, USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and UGT71C1, a triple LR reaction (Gateway system, Invitrogen, Life Technologies, Carlsbad, California, USA) was performed according to manufacturer's protocol by using an empty pENTRY-A vector, the pSuper promoter::UGT71C1::nos-terminator in the above described pENTRY-B vector and the PcUbi promoter::F6H1::OCS-terminator in the above described pENTRY-C vector. As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 5). The recombination reaction was transformed into *E. coli* (DH5alpha), mini-prepped and screened by specific restriction digestions. A positive clone from each vector construct was sequenced and submitted soybean transformation.

To obtain the F6H1-CCoAOMT1-ABCG37 triple gene construct the ABCG37 DNA (as shown in SEQ ID NO. 5) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-A vector (Invitrogen, Life Technologies, Carlsbad, California, USA) in a way that the full-length fragment is located in sense direction between the pGlyma14g06680 promoter (see WO 2012/127373) and the *Solanum tuberosum* cathepsin D inhibitor (Herbers, Karin, Salomé Prat, and Lothar Willmitzer. "Functional analysis of a leucine aminopeptidase from *Solanum tuberosum* L." Planta 194.2 (1994): 230-240.). The pGlyma14g06680 promoter mediates a medium strong constitutive expression in soybean.

To obtain the binary plant transformation vector containing F6H1, CCoAOMT1 and ABCG37, a triple LR reaction (Gateway system, Invitrogen, Life Technologies, Carlsbad, California, USA) was performed according to manufacturer's protocol by using the Glyma14g06680 promoter::ABCG37::cathepsin inhibitor terminator in the pENTRY-A vector, as described above, the pSuper promoter::CCoAOMT1::nos-terminator in the above described pENTRY-B vector and the PcUbi promoter::F6H1::OCS-terminator in the above described pENTRY-C vector.

As target a binary pDEST vector was used which is composed of: (1) a spectinomycin/streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 4). The recombination reaction was transformed into *E. coli* (DH5alpha), mini-prepped and screened by specific restriction digestions. A positive clone from each vector construct was sequenced and submitted soybean transformation.

Example 11

Soybean Transformation

The expression vector constructs (see example 2) is transformed into soybean.

11.1 Sterilization and Germination of Soybean Seeds

Virtually any seed of any soybean variety can be employed in the method of the invention. A variety of soybean cultivar (including Jack, Williams 82, Jake, Stoddard, CD215 and Resnik) is appropriate for soybean transformation. Soybean seeds are sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds are removed and approximately 18 to 20 seeds are plated on solid GM medium with or without 5 μM 6-benzyl-aminopurine (BAP) in 100 mm Petri dishes. Seedlings without BAP are more elongated and roots develop especially secondary and lateral root formation. BAP strengthens the seedling by forming a shorter and stockier seedling.

Seven-day-old seedlings grown in the light (>100 μEinstein/m$^2$s) at 25 degree C. are used for explant material for the three-explant types. At this time, the seed coat was split, and the epicotyl with the unifoliate leaves are grown to, at minimum, the length of the cotyledons. The epicotyl should be at least 0.5 cm to avoid the cotyledonary-node tissue (since soybean cultivars and seed lots may vary in the developmental time a description of the germination stage is more accurate than a specific germination time).

For inoculation of entire seedlings, see Method A (example 8.3. and 8.3.2) or leaf explants see Method B (example 8.3.3).

For method C (see example 8.3.4), the hypocotyl and one and a half or part of both cotyledons are removed from each seedling. The seedlings are then placed on propagation media for 2 to 4 weeks. The seedlings produce several branched shoots to obtain explants from. The majority of the explants originated from the plantlet growing from the apical bud. These explants are preferably used as target tissue.

11.2—Growth and Preparation of *Agrobacterium* Culture

*Agrobacterium* cultures are prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone. 5 g NaCl. Adjust pH to 7.0, and bring final volume to 1 liter with H2O, for YEP agar plates add 20 g Agar, autoclave) and incubating at 25. degree C. until colonies appeared (about 2 days). Depending on the selectable marker genes present on the Ti or Ri plasmid, the binary vector, and the bacterial chromosomes, different selection compounds are to be used for *A. tumefaciens* and *A. rhizogenes* selection in the YEP solid and liquid media. Various *Agrobacterium* strains can be used for the transformation method.

After approximately two days, a single colony (with a sterile toothpick) is picked and 50 ml of liquid YEP is inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP are inoculated with 5 µl to 3 ml of working *Agrobacterium* stock in a 500 ml Erlenmeyer flask. The flask is shaken overnight at 25° C. until the $OD_{600}$ is between 0.8 and 1.0. Before preparing the soybean explants, the Agrobacteria ARE pelleted by centrifugation for 10 min at 5,500×g at 20° C. The pellet is suspended in liquid CCM to the desired density ($OD_{600}$ 0.5-0.8) and placed at room temperature at least 30 min before use.

11.3—Explant Preparation and Co-Cultivation (Inoculation)

11.3.1 Method A: Explant Preparation on the Day of Transformation.

Seedlings at this time had elongated epicotyls from at least 0.5 cm but generally between 0.5 and 2 cm. Elongated epicotyls up to 4 cm in length are successfully employed. Explants are then prepared with: i) with or without some roots, ii) with a partial, one or both cotyledons, all preformed leaves are removed including apical meristem, and the node located at the first set of leaves is injured with several cuts using a sharp scalpel.

This cutting at the node not only induces *Agrobacterium* infection but also distributes the axillary meristem cells and damaged pre-formed shoots. After wounding and preparation, the explants are set aside in a Petri dish and subsequently co-cultivated with the liquid CCM/*Agrobacterium* mixture for 30 minutes. The explants are then removed from the liquid medium and plated on top of a sterile filter paper on 15×100 mm Petri plates with solid co-cultivation medium. The wounded target tissues are placed such that they are in direct contact with the medium.

11.3.2 Modified Method A: Epicotyl Explant Preparation

Soybean epicotyl segments prepared from 4 to 8 d old seedlings are used as explants for regeneration and transformation. Seeds of soybean cv. L00106CN, 93-41131 and Jack are germinated in 1/10 MS salts or a similar composition medium with or without cytokinins for 4 to 8 d. Epicotyl explants are prepared by removing the cotyledonary node and stem node from the stem section. The epicotyl is cut into 2 to 5 segments. Especially preferred are segments attached to the primary or higher node comprising axillary meristematic tissue.

The explants are used for *Agrobacterium* infection. *Agrobacterium* AGL1 harboring a plasmid with the gene of interest (GOI) and the AHAS, bar or dsdA selectable marker gene is cultured in LB medium with appropriate antibiotics overnight, harvested and suspended in a inoculation medium with acetosyringone. Freshly prepared epicotyl segments are soaked in the *Agrobacterium* suspension for 30 to 60 min and then the explants were blotted dry on sterile filter papers. The inoculated explants are then cultured on a co-culture medium with L-cysteine and TTD and other chemicals such as acetosyringone for increasing T-DNA delivery for 2 to 4 d. The infected epicotyl explants are then placed on a shoot induction medium with selection agents such as imazapyr (for AHAS gene), glufosinate (for bar gene), or D-serine (for dsdA gene). The regenerated shoots are subcultured on elongation medium with the selective agent.

For regeneration of transgenic plants, the segments are then cultured on a medium with cytokinins such as BAP, TDZ and/or Kinetin for shoot induction. After 4 to 8 weeks, the cultured tissues are transferred to a medium with lower concentration of cytokinin for shoot elongation. Elongated shoots are transferred to a medium with auxin for rooting and plant development. Multiple shoots are regenerated.

Many stable transformed sectors showing strong cDNA expression are recovered. Soybean plants are regenerated from epicotyl explants. Efficient T-DNA delivery and stable transformed sectors are demonstrated.

11.3.3 Method B: Leaf Explants

For the preparation of the leaf explant the cotyledon is removed from the hypocotyl. The cotyledons are separated from one another and the epicotyl is removed. The primary leaves, which consist of the lamina, the petiole, and the stipules, are removed from the epicotyl by carefully cutting at the base of the stipules such that the axillary meristems are included on the explant. To wound the explant as well as to stimulate de novo shoot formation, any pre-formed shoots are removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soybean-explants. Wrap five plates with Parafilm™. "M" (American National Can, Chicago, Ill., USA) and incubate for three to five days in the dark or light at 25° C.

11.3.4 Method C: Propagated Axillary Meristem

For the preparation of the propagated axillary meristem explant propagated 3-4 week-old plantlets are used. Axillary meristem explants can be pre-pared from the first to the fourth node. An average of three to four explants could be obtained from each seedling. The explants are prepared from plantlets by cutting 0.5 to 1.0 cm below the axillary node on the internode and removing the petiole and leaf from the explant. The tip where the axillary meristems lie is cut with a scalpel to induce de novo shoot growth and allow access of target cells to the *Agrobacterium*. Therefore, a 0.5 cm explant included the stem and a bud.

Once cut, the explants are immediately placed in the *Agrobacterium* suspension for 20 to 30 minutes. After inoculation, the explants are blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soybean explants. Plates are wrapped with Parafilm™. "M" (American National Can, Chicago, Ill., USA) and incubated for two to three days in the dark at 25° C.

11.4—Shoot Induction

After 3 to 5 days co-cultivation in the dark at 25° C., the explants are rinsed in liquid SIM medium (to remove excess *Agrobacterium*) (SIM, see Olhoft et al 2007 A novel *Agrobacterium rhizogenes*-mediated transformation method of soybean using primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants are placed such that the target tissue was in direct contact with the medium. During the first 2 weeks, the explants could be cultured with or without selective medium. Preferably, explants are transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant is placed into the medium such that it is parallel to the surface of the medium (basipetal) with the explant partially embedded into the medium.

Wrap plates with Scotch 394 venting tape (3M, St. Paul, Minn., USA) are placed in a growth chamber for two weeks with a temperature averaging 25. degree. C. under 18 h light/6 h dark cycle at 70-100 µE/m$^2$s. The explants remains on the SIM medium with or without selection until de novo shoot growth occurred at the target area (e.g., axillary meristems at the first node above the epicotyl). Transfers to fresh medium can occur during this time. Explants are transferred from the SIM with or without selection to SIM with selection after about one week. At this time, there is considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation are removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

11.5—Shoot Elongation

After 2 to 4 weeks (or until a mass of shoots is formed) on SIM medium (preferably with selection), the explants are transferred to SEM medium (shoot elongation medium, see Olhoft et al 2007 A novel *Agrobacterium rhizogenes*-mediated transformation method of soybean using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants are transferred to fresh SEM medium (preferably containing selection) after carefully removing dead tissue. The explants should hold together and not fragment into pieces and retain somewhat healthy. The explants are continued to be transferred until the explant dies or shoots elongate. Elongated shoots >3 cm are removed and placed into RM medium for about 1 week (Methods A and B), or about 2 to 4 weeks depending on the cultivar (Method C) at which time roots began to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and produced on average 500 seeds per plant.

After 5 days of co-cultivation with *Agrobacterium tumefaciens* transient expression of the gene of interest (GOI) is widespread on the seedling axillary meristem explants especially in the regions wounding during explant preparation (Method A). Explants are placed into shoot induction medium without selection to see how the primary-node responds to shoot induction and regeneration. Thus far, greater than 70% of the explants were formed new shoots at this region. Expression of the GOI is stable after 14 days on SIM, implying integration of the T-DNA into the soybean genome. In addition, preliminary experiments results in the formation of cDNA expressing shoots forming after 3 weeks on SIM.

For Method C, the average regeneration time of a soybean plantlet using the propagated axillary meristem protocol is 14 weeks from explant inoculation. Therefore, this method has a quick regeneration time that leads to fertile, healthy soybean plants.

Example 12

Pathogen Assay for Soybean 12.1. Growth of Plants

10 T1 soybean plants per event are potted and grown for 3-4 weeks in the Phytochamber (16 h-day- und 8 h-night-Rhythm at a temperature of 16° and 22° C. und a humidity of 75%) till the first 2 trifoliate leaves were fully expanded.

12.2 Inoculation

The plants are inoculated with spores of *P. pachyrhizi*.

In order to obtain appropriate spore material for the inoculation, soybean leaves, which are infected with rust 15-20 days ago, are taken 2-3 days before the inoculation and transferred to agar plates (1% agar in H2O). The leaves are placed with their upper side onto the agar, which allowed the fungus to grow through the tissue and to produce very young spores. For the inoculation solution, the spores are knocked off the leaves and are added to a Tween-H2O solution. The counting of spores is performed under a light microscope by means of a Thoma counting chamber. For the inoculation of the plants, the spore suspension is added into a compressed-air operated spray flask and applied uniformly onto the plants or the leaves until the leaf surface is well moisturized. For macroscopic assays a spore density of $1-5\times10^5$ spores/ml is used. For the microscopy, a density of $>5\times10^5$ spores/ml is used. The inoculated plants are placed for 24 hours in a greenhouse chamber with an average of 22° C. and >90% of air humidity. The following cultivation is performed in a chamber with an average of 25° C. and 70% of air humidity.

Example 13

Microscopical Screening

For the evaluation of the pathogen development, the inoculated leaves of plants are stained with aniline blue 48 hours after infection.

The aniline blue staining serves for the detection of fluorescent substances. During the defense reactions in host interactions and non-host interactions, substances such as phenols, callose or lignin accumulate or are produced and are incorporated at the cell wall either locally in papillae or in the whole cell (hypersensitive reaction, HR). Complexes are formed in association with aniline blue, which lead e.g. in the case of callose to yellow fluorescence. The leaf material is transferred to falcon tubes or dishes containing destaining solution II (ethanol/acetic acid 6/1) and is incubated in a water bath at 90° C. for 10-15 minutes. The destaining solution II is removed immediately thereafter, and the leaves are washed 2× with water. For the staining, the leaves are incubated for 1.5-2 hours in staining solution II (0.05% aniline blue=methyl blue, 0.067 M di-potassium hydrogen phosphate) and analyzed by microscopy immediately thereafter.

The different interaction types are evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae can be recognized beneath the fungal appressorium by a green/yellow staining. The hypersensitive reaction (HR) is characterized by a whole cell fluorescence

Example 14

Evaluating the Susceptibility to Soybean Rust

The progression of the soybean rust disease is scored by the estimation of the diseased area (area which was covered by sporulating uredinia) on the backside (abaxial side) of the leaf. Additionally the yellowing of the leaf is taken into account. (for scheme see FIG. 11)

At all 50 T1 soybean plants per construct are inoculated with spores of *Phakopsora pachyrhizi*. The macroscopic disease symptoms of soybean against *P. pachyrhizi* of the inoculated soybean plants are scored 14 days after inoculation.

The average of the percentage of the leaf area showing fungal colonies or strong yellowing/browning on all leaves is considered as diseased leaf area. At all 50 soybean T1 plants per construct (expression checked by RT-PCR) are evaluated in parallel to non-transgenic control plants. Non-transgenic soybean plants grown in parallel to the transgenic plants are used as controls.

The expression of the OMT3 gene or combinations with OMT3 leads to enhanced resistance of soybean against *Phakopsora pachyrhizi*.

Example 15

In Vitro Growth Inhibition of *Phakopsora pachyrhizi*

Spores of *Phakopsora pachyrhizi* were resuspended in $H_2O$ supplemented with Tween-20 and 10 µM, 25 µM, 50 µM, 100 µM, 200 µM and 400 µM scoparone (solved in 0.1% DMSO). Spores of *Phakopsora pachyrhizi* resuspended in $H_2O$ supplemented with Tween-20 and 0.1% DMSO were used as control. All resuspended spores are transferred onto glass slides. After six hours incubation time the ASR spores were germinated and started to form appressoria.

The appressoria formation rate was determined by quantitative microscopic analysis. Only spores showing germ-tube formation with a visible thickening of the germ tube tip were counted as "appressoria formation (FIG. 2)".

Application of scoparone to ASR spores decreases the formation of appressoria in a dose dependent manner. At 400 µM concentration, scoparone completely abolishes the formation of appressoria in-vitro.

TABLE Ts1

| pos | wildtype | A | R | N | D | C | Q | E | G | H | I | L | K | M | F | P | S | T | W | Y | V |
|-----|----------|---|---|---|---|---|---|---|---|---|---|---|---|---|---|---|---|---|---|---|---|
| 1 | M | 2 | 2 | 2 | 2 | 2 | 2 | 2 | 2 | 2 | 2 | 6 | 2 | 51 | 2 | 2 | 2 | 2 | 2 | 2 | 2 |
| 2 | G | 11 | 3 | 3 | 12 | 3 | 7 | 3 | 20 | 3 | 3 | 3 | 3 | 3 | 3 | 3 | 7 | 3 | 3 | 3 | 3 |
| 3 | S | 3 | 3 | 6 | 7 | 3 | 3 | 3 | 3 | 3 | 3 | 7 | 3 | 3 | 7 | 32 | 3 | 3 | 3 | 3 | 3 |
| 4 | T | 3 | 3 | 3 | 3 | 3 | 3 | 8 | 3 | 11 | 8 | 3 | 3 | 3 | 3 | 7 | 3 | 12 | 3 | 12 | 3 |
| 5 | S | 3 | 3 | 3 | 3 | 3 | 3 | 7 | 3 | 3 | 3 | 7 | 3 | 3 | 3 | 26 | 11 | 3 | 3 | 3 | 3 |
| 6 | A | 21 | 3 | 3 | 3 | 3 | 3 | 8 | 3 | 3 | 3 | 3 | 3 | 8 | 3 | 7 | 11 | 3 | 3 | 3 | 3 |
| 7 | S | 16 | 7 | 3 | 8 | 3 | 3 | 3 | 3 | 3 | 8 | 3 | 3 | 3 | 3 | 3 | 13 | 7 | 3 | 3 | 3 |
| 8 | V | 20 | 3 | 3 | 3 | 3 | 3 | 3 | 3 | 3 | 8 | 3 | 3 | 3 | 3 | 3 | 3 | 12 | 3 | 3 | 12 |
| 9 | N | 11 | 3 | 12 | 3 | 3 | 3 | 8 | 3 | 3 | 8 | 3 | 3 | 3 | 3 | 8 | 7 | 3 | 3 | 3 | 3 |
| 10 | V | 2 | 2 | 8 | 8 | 2 | 2 | 2 | 5 | 2 | 2 | 2 | 2 | 19 | 2 | 5 | 12 | 2 | 2 | 2 | 13 |
| 11 | L | 5 | 2 | 2 | 4 | 6 | 2 | 5 | 5 | 2 | 11 | 17 | 5 | 4 | 7 | 7 | 2 | 4 | 2 | 2 | 7 |
| 12 | L | 9 | 2 | 2 | 7 | 2 | 4 | 7 | 4 | 2 | 15 | 10 | 4 | 6 | 5 | 2 | 4 | 4 | 2 | 2 | 6 |
| 13 | E | 11 | 2 | 3 | 10 | 1 | 2 | 24 | 5 | 3 | 2 | 5 | 5 | 6 | 2 | 1 | 7 | 4 | 1 | 1 | 4 |
| 14 | A | 17 | 3 | 2 | 5 | 3 | 4 | 5 | 3 | 3 | 3 | 19 | 1 | 6 | 2 | 4 | 9 | 7 | 1 | 2 | 4 |
| 15 | N | 4 | 2 | 8 | 6 | 1 | 3 | 10 | 1 | 2 | 2 | 5 | 4 | 4 | 3 | 15 | 11 | 6 | 1 | 2 | 11 |
| 16 | Q | 4 | 3 | 4 | 7 | 1 | 16 | 29 | 1 | 4 | 2 | 3 | 3 | 3 | 1 | 3 | 8 | 6 | 1 | 1 | 3 |
| 17 | D | 8 | 4 | 3 | 15 | 1 | 4 | 11 | 3 | 1 | 7 | 13 | 4 | 4 | 2 | 5 | 6 | 4 | 1 | 1 | 4 |
| 18 | D | 7 | 5 | 5 | 15 | 0 | 5 | 11 | 3 | 0 | 5 | 9 | 6 | 3 | 5 | 11 | 4 | 1 | 0 | 1 | 4 |
| 19 | Q | 11 | 4 | 5 | 9 | 1 | 12 | 14 | 4 | 2 | 2 | 3 | 3 | 1 | 1 | 8 | 8 | 6 | 0 | 1 | 3 |
| 20 | S | 20 | 1 | 3 | 6 | 0 | 3 | 4 | 6 | 1 | 2 | 3 | 1 | 2 | 7 | 18 | 12 | 4 | 1 | 2 | 5 |
| 21 | F | 10 | 11 | 1 | 0 | 1 | 10 | 3 | 4 | 2 | 4 | 7 | 3 | 3 | 13 | 6 | 7 | 4 | 1 | 7 | 3 |
| 22 | L | 12 | 7 | 3 | 9 | 1 | 6 | 11 | 4 | 2 | 2 | 17 | 5 | 3 | 2 | 2 | 7 | 3 | 0 | 1 | 4 |
| 23 | F | 5 | 14 | 3 | 3 | 0 | 11 | 7 | 3 | 3 | 3 | 5 | 9 | 2 | 4 | 7 | 6 | 7 | 1 | 3 | 4 |
| 24 | A | 13 | 0 | 0 | 0 | 0 | 0 | 0 | 1 | 1 | 18 | 34 | 0 | 7 | 5 | 1 | 1 | 1 | 1 | 1 | 14 |
| 25 | M | 5 | 5 | 2 | 3 | 1 | 5 | 3 | 1 | 4 | 6 | 19 | 1 | 13 | 9 | 0 | 5 | 3 | 4 | 6 | 5 |
| 26 | Q | 5 | 11 | 6 | 15 | 0 | 13 | 21 | 4 | 2 | 1 | 3 | 5 | 1 | 1 | 1 | 5 | 3 | 0 | 1 | 1 |
| 27 | L | 3 | 1 | 1 | 3 | 1 | 2 | 1 | 0 | 3 | 15 | 38 | 1 | 9 | 3 | 1 | 2 | 5 | 1 | 4 | 5 |
| 28 | A | 25 | 1 | 2 | 0 | 3 | 1 | 1 | 5 | 1 | 10 | 13 | 0 | 6 | 5 | 1 | 9 | 5 | 1 | 3 | 9 |
| 29 | S | 6 | 3 | 8 | 4 | 3 | 3 | 4 | 4 | 3 | 2 | 8 | 2 | 6 | 10 | 1 | 9 | 10 | 3 | 8 | 4 |
| 30 | A | 21 | 1 | 4 | 3 | 1 | 6 | 1 | 35 | 1 | 1 | 2 | 1 | 3 | 0 | 1 | 13 | 3 | 0 | 2 | 1 |
| 31 | S | 10 | 1 | 2 | 1 | 0 | 2 | 1 | 5 | 6 | 3 | 6 | 1 | 3 | 17 | 10 | 6 | 4 | 1 | 17 | 4 |
| 32 | V | 9 | 5 | 2 | 0 | 1 | 6 | 2 | 3 | 3 | 7 | 11 | 2 | 6 | 6 | 1 | 4 | 6 | 9 | 4 | 13 |
| 33 | L | 10 | 8 | 2 | 6 | 0 | 6 | 5 | 3 | 3 | 6 | 13 | 8 | 1 | 3 | 3 | 5 | 7 | 0 | 2 | 9 |

TABLE Ts1-continued

| pos | wildtype | A | R | N | D | C | Q | E | G | H | I | L | K | M | F | P | S | T | W | Y | V |
|---|---|---|---|---|---|---|---|---|---|---|---|---|---|---|---|---|---|---|---|---|---|
| 34 | P | 13 | 0 | 3 | 0 | 1 | 1 | 0 | 3 | 1 | 3 | 7 | 0 | 2 | 7 | 14 | 26 | 12 | 1 | 2 | 4 |
| 35 | M | 19 | 9 | 2 | 1 | 2 | 12 | 3 | 4 | 3 | 3 | 5 | 6 | 10 | 3 | 2 | 7 | 3 | 2 | 2 | 4 |
| 36 | V | 37 | 0 | 1 | 0 | 8 | 1 | 0 | 2 | 1 | 6 | 8 | 0 | 3 | 2 | 0 | 7 | 7 | 0 | 1 | 17 |
| 37 | L | 3 | 0 | 0 | 0 | 0 | 0 | 0 | 1 | 0 | 14 | 58 | 0 | 3 | 3 | 0 | 1 | 1 | 0 | 0 | 14 |
| 38 | K | 7 | 21 | 4 | 2 | 2 | 5 | 3 | 4 | 6 | 2 | 5 | 12 | 3 | 5 | 0 | 5 | 3 | 1 | 8 | 3 |
| 39 | T | 28 | 1 | 0 | 0 | 3 | 1 | 1 | 1 | 0 | 9 | 7 | 0 | 2 | 2 | 0 | 6 | 19 | 2 | 1 | 16 |
| 40 | A | 65 | 0 | 0 | 0 | 2 | 0 | 0 | 9 | 0 | 3 | 6 | 0 | 2 | 3 | 0 | 2 | 1 | 0 | 0 | 6 |
| 41 | I | 12 | 2 | 2 | 3 | 4 | 2 | 1 | 2 | 3 | 18 | 14 | 1 | 3 | 3 | 0 | 3 | 4 | 1 | 2 | 22 |
| 42 | E | 2 | 13 | 4 | 14 | 0 | 6 | 37 | 1 | 3 | 0 | 1 | 10 | 0 | 0 | 0 | 3 | 4 | 0 | 0 | 1 |
| 43 | L | 3 | 1 | 1 | 0 | 1 | 0 | 0 | 1 | 2 | 3 | 64 | 1 | 4 | 6 | 0 | 3 | 4 | 2 | 2 | 3 |
| 44 | D | 1 | 9 | 10 | 14 | 0 | 2 | 4 | 42 | 3 | 0 | 0 | 11 | 0 | 0 | 0 | 2 | 0 | 0 | 0 | 0 |
| 45 | L | 2 | 0 | 0 | 0 | 0 | 0 | 0 | 0 | 0 | 29 | 39 | 0 | 1 | 1 | 0 | 0 | 0 | 1 | 0 | 25 |
| 46 | L | 13 | 0 | 0 | 0 | 0 | 0 | 0 | 1 | 1 | 2 | 13 | 0 | 0 | 48 | 12 | 1 | 1 | 2 | 2 | 3 |
| 47 | E | 5 | 3 | 4 | 40 | 0 | 5 | 20 | 2 | 2 | 0 | 0 | 4 | 0 | 0 | 1 | 5 | 8 | 0 | 0 | 0 |
| 48 | T | 20 | 6 | 1 | 1 | 1 | 3 | 5 | 1 | 9 | 11 | 14 | 5 | 1 | 2 | 1 | 2 | 7 | 1 | 3 | 6 |
| 49 | I | 0 | 0 | 0 | 0 | 0 | 0 | 0 | 0 | 0 | 28 | 55 | 0 | 3 | 2 | 0 | 0 | 0 | 0 | 2 | 8 |
| 50 | A | 31 | 5 | 2 | 6 | 1 | 2 | 8 | 6 | 4 | 1 | 3 | 4 | 0 | 1 | 10 | 7 | 3 | 1 | 1 | 4 |
| 51 | K | 12 | 6 | 5 | 12 | 0 | 6 | 17 | 5 | 2 | 1 | 4 | 11 | 0 | 0 | 2 | 9 | 6 | 0 | 0 | 1 |
| 52 | A | 25 | 5 | 7 | 5 | 1 | 2 | 7 | 6 | 9 | 2 | 5 | 4 | 1 | 2 | 1 | 9 | 4 | 0 | 1 | 4 |
| 53 | G | 4 | 1 | 2 | 6 | 1 | 3 | 5 | 41 | 2 | 3 | 2 | 3 | 0 | 1 | 8 | 6 | 2 | 0 | 0 | 7 |
| 54 | P | 6 | 3 | 3 | 7 | 1 | 1 | 8 | 10 | 1 | 1 | 4 | 3 | 0 | 0 | 36 | 7 | 4 | 0 | 2 | 2 |
| 55 | G | 6 | 3 | 6 | 14 | 0 | 8 | 9 | 18 | 1 | 2 | 7 | 6 | 1 | 0 | 7 | 5 | 4 | 1 | 0 | 2 |
| 56 | G | 8 | 6 | 3 | 5 | 1 | 5 | 7 | 40 | 2 | 1 | 1 | 7 | 1 | 0 | 3 | 7 | 4 | 0 | 0 | 1 |
| 57 | S | 9 | 3 | 1 | 2 | 1 | 2 | 4 | 15 | 2 | 1 | 1 | 3 | 1 | 1 | 34 | 14 | 4 | 1 | 1 | 2 |
| 58 | L | 10 | 7 | 1 | 1 | 2 | 4 | 1 | 1 | 1 | 14 | 23 | 8 | 6 | 1 | 1 | 2 | 6 | 0 | 1 | 11 |
| 59 | S | 3 | 2 | 2 | 5 | 0 | 1 | 2 | 2 | 4 | 0 | 1 | 1 | 0 | 0 | 5 | 35 | 36 | 0 | 0 | 0 |
| 60 | S | 26 | 1 | 1 | 1 | 2 | 1 | 2 | 1 | 1 | 7 | 14 | 1 | 1 | 3 | 5 | 12 | 2 | 0 | 6 | 15 |
| 61 | S | 18 | 3 | 3 | 12 | 1 | 4 | 19 | 5 | 2 | 1 | 2 | 6 | 1 | 1 | 4 | 12 | 5 | 0 | 1 | 3 |
| 62 | E | 6 | 2 | 2 | 17 | 0 | 10 | 47 | 2 | 1 | 1 | 1 | 3 | 1 | 0 | 0 | 2 | 3 | 0 | 0 | 2 |
| 63 | L | 1 | 0 | 0 | 0 | 0 | 0 | 0 | 0 | 0 | 30 | 55 | 0 | 1 | 1 | 0 | 0 | 1 | 0 | 0 | 8 |
| 64 | V | 71 | 2 | 0 | 0 | 1 | 1 | 1 | 2 | 0 | 2 | 2 | 1 | 1 | 0 | 0 | 10 | 2 | 0 | 0 | 5 |
| 65 | A | 22 | 8 | 2 | 6 | 0 | 7 | 17 | 3 | 1 | 1 | 2 | 11 | 1 | 0 | 1 | 10 | 4 | 0 | 0 | 2 |
| 66 | Q | 16 | 17 | 1 | 2 | 0 | 7 | 11 | 2 | 2 | 3 | 5 | 19 | 1 | 1 | 1 | 5 | 4 | 0 | 1 | 3 |
| 67 | L | 8 | 1 | 1 | 0 | 6 | 1 | 1 | 1 | 1 | 7 | 36 | 1 | 2 | 2 | 1 | 4 | 19 | 0 | 1 | 7 |
| 68 | P | 4 | 4 | 8 | 6 | 1 | 5 | 5 | 40 | 2 | 0 | 1 | 8 | 0 | 0 | 6 | 7 | 2 | 0 | 0 | 1 |
| 69 | K | 12 | 1 | 3 | 1 | 3 | 1 | 1 | 4 | 0 | 9 | 29 | 3 | 2 | 3 | 1 | 5 | 10 | 3 | 1 | 9 |
| 70 | V | 15 | 3 | 2 | 5 | 7 | 2 | 5 | 2 | 3 | 8 | 4 | 4 | 1 | 2 | 6 | 6 | 11 | 0 | 1 | 11 |
| 71 | N | 6 | 5 | 16 | 6 | 1 | 3 | 3 | 18 | 2 | 2 | 3 | 7 | 1 | 1 | 7 | 5 | 8 | 1 | 1 | 3 |
| 72 | N | 7 | 3 | 20 | 10 | 3 | 2 | 2 | 8 | 6 | 3 | 7 | 4 | 1 | 1 | 3 | 6 | 3 | 0 | 1 | 10 |
| 73 | P | 6 | 2 | 6 | 13 | 1 | 3 | 2 | 25 | 2 | 2 | 2 | 6 | 1 | 0 | 15 | 8 | 4 | 0 | 1 | 2 |
| 74 | E | 27 | 1 | 1 | 2 | 6 | 2 | 7 | 4 | 1 | 4 | 8 | 1 | 2 | 1 | 1 | 5 | 9 | 0 | 1 | 14 |
| 75 | A | 7 | 3 | 10 | 26 | 1 | 4 | 8 | 1 | 10 | 1 | 2 | 6 | 0 | 0 | 7 | 9 | 3 | 0 | 0 | 2 |
| 76 | P | 13 | 4 | 0 | 2 | 0 | 3 | 19 | 2 | 1 | 1 | 5 | 3 | 1 | 1 | 32 | 4 | 3 | 0 | 1 | 4 |
| 77 | V | 7 | 15 | 3 | 14 | 1 | 4 | 12 | 5 | 3 | 2 | 4 | 4 | 1 | 1 | 5 | 8 | 4 | 0 | 1 | 5 |
| 78 | M | 13 | 7 | 5 | 2 | 1 | 3 | 1 | 7 | 2 | 3 | 19 | 7 | 2 | 3 | 4 | 6 | 3 | 1 | 6 | 4 |
| 79 | V | 4 | 0 | 0 | 0 | 1 | 0 | 0 | 0 | 0 | 8 | 53 | 0 | 3 | 1 | 1 | 1 | 9 | 0 | 0 | 17 |
| 80 | D | 9 | 18 | 2 | 7 | 1 | 6 | 12 | 9 | 4 | 2 | 3 | 5 | 1 | 2 | 1 | 6 | 4 | 0 | 6 | 4 |
| 81 | R | 4 | 64 | 1 | 2 | 1 | 2 | 4 | 1 | 2 | 2 | 3 | 3 | 1 | 1 | 1 | 3 | 1 | 0 | 1 | 3 |
| 82 | I | 1 | 0 | 0 | 0 | 1 | 0 | 0 | 0 | 0 | 18 | 39 | 0 | 5 | 9 | 0 | 0 | 3 | 6 | 1 | 16 |
| 83 | C | 4 | 0 | 0 | 0 | 4 | 0 | 1 | 0 | 0 | 4 | 62 | 0 | 15 | 2 | 0 | 0 | 1 | 0 | 0 | 5 |
| 84 | R | 3 | 57 | 5 | 9 | 1 | 2 | 5 | 3 | 2 | 1 | 1 | 4 | 0 | 0 | 1 | 3 | 2 | 1 | 1 | 0 |
| 85 | L | 24 | 0 | 1 | 0 | 2 | 2 | 0 | 3 | 5 | 3 | 22 | 0 | 4 | 8 | 1 | 3 | 3 | 0 | 8 | 9 |
| 86 | L | 5 | 0 | 0 | 0 | 3 | 1 | 0 | 2 | 0 | 1 | 82 | 0 | 3 | 1 | 0 | 1 | 0 | 0 | 0 | 1 |
| 87 | A | 35 | 2 | 1 | 1 | 5 | 1 | 3 | 1 | 0 | 4 | 3 | 1 | 3 | 1 | 0 | 6 | 10 | 1 | 1 | 21 |
| 88 | S | 25 | 2 | 2 | 1 | 3 | 2 | 2 | 8 | 3 | 1 | 2 | 1 | 1 | 1 | 1 | 25 | 15 | 0 | 1 | 4 |
| 89 | Y | 8 | 5 | 5 | 1 | 3 | 3 | 3 | 3 | 6 | 7 | 19 | 3 | 7 | 6 | 0 | 5 | 4 | 1 | 5 | 6 |
| 90 | S | 2 | 6 | 5 | 7 | 0 | 2 | 6 | 51 | 8 | 0 | 0 | 4 | 0 | 1 | 0 | 5 | 1 | 0 | 2 | 1 |
| 91 | V | 2 | 0 | 0 | 0 | 1 | 0 | 0 | 0 | 1 | 21 | 24 | 1 | 3 | 11 | 0 | 1 | 1 | 1 | 6 | 23 |
| 92 | L | 2 | 0 | 0 | 0 | 1 | 0 | 0 | 0 | 0 | 8 | 42 | 0 | 1 | 26 | 0 | 0 | 1 | 0 | 1 | 16 |
| 93 | T | 8 | 11 | 2 | 8 | 2 | 6 | 16 | 3 | 3 | 4 | 2 | 9 | 0 | 1 | 0 | 6 | 12 | 0 | 1 | 5 |
| 94 | C | 4 | 9 | 1 | 1 | 4 | 7 | 31 | 3 | 3 | 3 | 6 | 11 | 1 | 1 | 1 | 3 | 3 | 0 | 3 | 5 |
| 95 | T | 4 | 5 | 3 | 13 | 1 | 3 | 6 | 2 | 4 | 4 | 4 | 5 | 1 | 1 | 6 | 7 | 16 | 0 | 1 | 15 |
| 96 | L | 10 | 5 | 3 | 6 | 1 | 3 | 10 | 12 | 1 | 3 | 9 | 6 | 0 | 2 | 7 | 9 | 7 | 0 | 0 | 5 |
| 97 | K | 6 | 8 | 2 | 11 | 1 | 2 | 12 | 4 | 1 | 2 | 5 | 11 | 1 | 0 | 5 | 14 | 4 | 0 | 1 | 9 |
| 98 | E | 3 | 3 | 2 | 9 | 0 | 6 | 41 | 10 | 2 | 2 | 1 | 3 | 1 | 0 | 3 | 7 | 3 | 0 | 1 | 1 |
| 99 | T | 4 | 3 | 3 | 6 | 1 | 4 | 6 | 6 | 2 | 3 | 7 | 4 | 2 | 1 | 11 | 6 | 19 | 1 | 1 | 11 |
| 100 | M | 6 | 7 | 5 | 7 | 1 | 6 | 9 | 9 | 2 | 5 | 10 | 7 | 3 | 2 | 2 | 9 | 3 | 1 | 1 | 5 |
| 101 | D | 7 | 2 | 3 | 24 | 1 | 2 | 9 | 11 | 2 | 2 | 1 | 4 | 0 | 0 | 15 | 8 | 4 | 1 | 1 | 3 |
| 102 | G | 6 | 3 | 3 | 9 | 1 | 3 | 11 | 36 | 3 | 0 | 2 | 6 | 1 | 1 | 3 | 5 | 5 | 0 | 1 | 3 |
| 103 | C | 7 | 2 | 5 | 11 | 3 | 3 | 7 | 6 | 4 | 2 | 5 | 3 | 1 | 1 | 10 | 8 | 8 | 1 | 1 | 11 |
| 104 | A | 13 | 4 | 4 | 9 | 0 | 3 | 15 | 16 | 1 | 1 | 2 | 7 | 0 | 0 | 5 | 9 | 4 | 0 | 2 | 3 |
| 105 | E | 7 | 4 | 5 | 13 | 0 | 4 | 16 | 15 | 2 | 1 | 1 | 5 | 0 | 0 | 12 | 5 | 5 | 0 | 0 | 4 |
| 106 | R | 4 | 13 | 6 | 14 | 0 | 3 | 8 | 28 | 2 | 3 | 3 | 3 | 0 | 1 | 2 | 3 | 3 | 0 | 0 | 2 |
| 107 | F | 6 | 19 | 1 | 1 | 1 | 4 | 4 | 6 | 5 | 3 | 8 | 7 | 1 | 4 | 0 | 4 | 10 | 1 | 4 | 11 |
| 108 | Y | 1 | 1 | 0 | 0 | 1 | 0 | 0 | 0 | 0 | 3 | 3 | 0 | 0 | 26 | 0 | 1 | 1 | 2 | 53 | 7 |
| 109 | G | 23 | 12 | 1 | 1 | 2 | 5 | 6 | 8 | 2 | 2 | 2 | 6 | 0 | 2 | 0 | 14 | 7 | 1 | 1 | 4 |
| 110 | V | 7 | 1 | 18 | 0 | 0 | 1 | 0 | 1 | 13 | 2 | 38 | 1 | 1 | 1 | 6 | 3 | 2 | 0 | 0 | 3 |
| 111 | A | 7 | 1 | 12 | 2 | 0 | 1 | 1 | 3 | 0 | 1 | 1 | 2 | 0 | 0 | 4 | 17 | 47 | 0 | 0 | 1 |

TABLE Ts1-continued

| pos | wildtype | A | R | N | D | C | Q | E | G | H | I | L | K | M | F | P | S | T | W | Y | V |
|---|---|---|---|---|---|---|---|---|---|---|---|---|---|---|---|---|---|---|---|---|---|
| 112 | P | 15 | 7 | 3 | 5 | 0 | 2 | 12 | 3 | 2 | 1 | 2 | 5 | 0 | 1 | 33 | 6 | 2 | 0 | 0 | 1 |
| 113 | V | 11 | 4 | 1 | 3 | 1 | 2 | 7 | 3 | 2 | 9 | 20 | 3 | 5 | 5 | 1 | 4 | 6 | 0 | 1 | 13 |
| 114 | C | 16 | 2 | 1 | 2 | 2 | 1 | 2 | 17 | 1 | 1 | 2 | 1 | 1 | 1 | 1 | 36 | 10 | 0 | 1 | 2 |
| 115 | K | 13 | 18 | 2 | 4 | 1 | 6 | 11 | 2 | 2 | 2 | 5 | 14 | 2 | 1 | 2 | 6 | 5 | 1 | 1 | 2 |
| 116 | F | 11 | 3 | 1 | 1 | 4 | 2 | 3 | 2 | 3 | 3 | 17 | 2 | 3 | 16 | 2 | 3 | 4 | 3 | 11 | 7 |
| 117 | L | 2 | 1 | 0 | 0 | 1 | 0 | 0 | 0 | 0 | 4 | 68 | 0 | 4 | 11 | 0 | 0 | 1 | 1 | 3 | 2 |
| 118 | T | 14 | 11 | 1 | 3 | 3 | 2 | 1 | 2 | 1 | 3 | 15 | 2 | 1 | 1 | 1 | 6 | 11 | 0 | 1 | 20 |
| 119 | K | 5 | 12 | 5 | 12 | 0 | 4 | 7 | 4 | 2 | 1 | 3 | 13 | 1 | 1 | 6 | 12 | 8 | 0 | 1 | 2 |
| 120 | N | 4 | 5 | 10 | 22 | 0 | 2 | 8 | 12 | 2 | 1 | 1 | 3 | 1 | 1 | 9 | 10 | 4 | 0 | 2 | 1 |
| 121 | D | 6 | 4 | 6 | 16 | 1 | 4 | 10 | 11 | 6 | 1 | 2 | 8 | 1 | 1 | 7 | 8 | 6 | 0 | 1 | 3 |
| 122 | S | 8 | 4 | 5 | 4 | 1 | 2 | 3 | 11 | 7 | 3 | 3 | 4 | 1 | 2 | 5 | 28 | 5 | 1 | 1 | 4 |
| 123 | G | 9 | 4 | 2 | 4 | 0 | 4 | 7 | 8 | 1 | 2 | 4 | 4 | 1 | 1 | 34 | 4 | 5 | 1 | 1 | 3 |
| 124 | V | 13 | 6 | 5 | 8 | 1 | 5 | 7 | 10 | 4 | 2 | 6 | 3 | 2 | 5 | 3 | 7 | 5 | 2 | 4 | 5 |
| 125 | S | 6 | 1 | 5 | 4 | 2 | 2 | 2 | 11 | 1 | 1 | 2 | 1 | 1 | 3 | 4 | 34 | 5 | 1 | 12 | 2 |
| 126 | L | 5 | 1 | 1 | 0 | 1 | 5 | 1 | 2 | 1 | 8 | 34 | 2 | 9 | 6 | 1 | 1 | 2 | 3 | 5 | 10 |
| 127 | A | 18 | 15 | 2 | 1 | 1 | 2 | 2 | 19 | 3 | 4 | 7 | 4 | 1 | 3 | 1 | 4 | 3 | 1 | 2 | 5 |
| 128 | P | 14 | 3 | 5 | 13 | 1 | 2 | 4 | 10 | 4 | 2 | 2 | 2 | 1 | 2 | 15 | 10 | 4 | 1 | 2 | 2 |
| 129 | L | 7 | 1 | 2 | 1 | 2 | 1 | 1 | 3 | 2 | 6 | 21 | 1 | 8 | 14 | 1 | 3 | 3 | 8 | 9 | 5 |
| 130 | L | 11 | 1 | 1 | 0 | 2 | 1 | 0 | 1 | 3 | 14 | 26 | 0 | 4 | 8 | 1 | 3 | 4 | 1 | 2 | 17 |
| 131 | L | 5 | 9 | 2 | 5 | 1 | 5 | 7 | 7 | 3 | 4 | 20 | 4 | 5 | 4 | 1 | 7 | 4 | 1 | 3 | 4 |
| 132 | M | 5 | 2 | 2 | 4 | 1 | 2 | 4 | 3 | 10 | 4 | 16 | 1 | 10 | 17 | 1 | 3 | 3 | 3 | 6 | 4 |
| 133 | N | 7 | 3 | 7 | 2 | 3 | 5 | 4 | 3 | 4 | 7 | 12 | 1 | 7 | 7 | 1 | 6 | 6 | 2 | 4 | 7 |
| 134 | Q | 10 | 3 | 5 | 3 | 4 | 4 | 2 | 12 | 5 | 5 | 8 | 2 | 4 | 4 | 1 | 8 | 11 | 1 | 2 | 5 |
| 135 | D | 7 | 4 | 5 | 22 | 1 | 4 | 10 | 11 | 5 | 2 | 5 | 2 | 2 | 2 | 2 | 9 | 4 | 1 | 1 | 2 |
| 136 | K | 4 | 7 | 2 | 7 | 0 | 4 | 20 | 4 | 2 | 2 | 3 | 5 | 1 | 1 | 24 | 3 | 4 | 0 | 1 | 4 |
| 137 | V | 8 | 4 | 2 | 6 | 3 | 4 | 6 | 9 | 2 | 6 | 8 | 1 | 5 | 4 | 2 | 6 | 6 | 2 | 3 | 12 |
| 138 | F | 5 | 4 | 4 | 1 | 3 | 4 | 2 | 3 | 7 | 6 | 16 | 1 | 6 | 14 | 1 | 6 | 4 | 2 | 7 | 5 |
| 139 | M | 7 | 4 | 3 | 2 | 0 | 4 | 2 | 4 | 2 | 4 | 9 | 4 | 6 | 4 | 5 | 5 | 4 | 11 | 11 | 6 |
| 140 | E | 15 | 8 | 5 | 6 | 1 | 5 | 9 | 5 | 2 | 1 | 5 | 9 | 1 | 1 | 11 | 7 | 4 | 1 | 1 | 2 |
| 141 | S | 21 | 2 | 2 | 2 | 2 | 2 | 1 | 7 | 1 | 5 | 11 | 1 | 4 | 3 | 7 | 14 | 6 | 1 | 1 | 8 |
| 142 | W | 9 | 2 | 1 | 1 | 2 | 1 | 2 | 1 | 2 | 2 | 10 | 1 | 4 | 10 | 8 | 5 | 2 | 30 | 4 | 4 |
| 143 | Y | 10 | 6 | 4 | 8 | 0 | 4 | 10 | 10 | 4 | 2 | 6 | 4 | 2 | 3 | 3 | 10 | 6 | 1 | 5 | 2 |
| 144 | F | 6 | 11 | 7 | 7 | 1 | 7 | 6 | 8 | 8 | 1 | 3 | 9 | 1 | 8 | 1 | 6 | 2 | 1 | 7 | 1 |
| 145 | L | 3 | 1 | 0 | 0 | 0 | 1 | 0 | 0 | 0 | 8 | 60 | 0 | 6 | 7 | 0 | 1 | 2 | 0 | 2 | 5 |
| 146 | K | 16 | 3 | 2 | 4 | 0 | 1 | 8 | 5 | 3 | 3 | 7 | 9 | 1 | 1 | 13 | 7 | 9 | 1 | 2 | 7 |
| 147 | D | 6 | 3 | 3 | 21 | 0 | 7 | 34 | 2 | 5 | 0 | 1 | 5 | 0 | 0 | 1 | 5 | 4 | 0 | 1 | 1 |
| 148 | A | 30 | 2 | 3 | 1 | 3 | 1 | 1 | 5 | 1 | 3 | 5 | 2 | 2 | 2 | 2 | 11 | 12 | 3 | 4 | 8 |
| 149 | V | 3 | 1 | 0 | 1 | 1 | 0 | 1 | 1 | 1 | 15 | 29 | 0 | 4 | 9 | 0 | 2 | 3 | 0 | 3 | 25 |
| 150 | L | 4 | 32 | 1 | 6 | 1 | 7 | 6 | 2 | 1 | 1 | 8 | 15 | 1 | 1 | 1 | 5 | 5 | 0 | 1 | 2 |
| 151 | D | 5 | 5 | 7 | 9 | 0 | 3 | 12 | 5 | 3 | 1 | 2 | 9 | 1 | 1 | 2 | 10 | 23 | 0 | 1 | 1 |
| 152 | G | 4 | 2 | 6 | 6 | 1 | 1 | 4 | 51 | 2 | 1 | 1 | 3 | 0 | 1 | 7 | 5 | 4 | 0 | 1 | 1 |
| 153 | G | 6 | 9 | 6 | 7 | 0 | 7 | 12 | 12 | 4 | 2 | 2 | 11 | 1 | 1 | 6 | 4 | 5 | 0 | 1 | 3 |
| 154 | I | 9 | 2 | 6 | 3 | 3 | 2 | 2 | 7 | 1 | 2 | 3 | 2 | 1 | 0 | 16 | 16 | 19 | 0 | 0 | 5 |
| 155 | P | 26 | 3 | 2 | 3 | 1 | 5 | 1 | 7 | 1 | 3 | 4 | 2 | 1 | 0 | 28 | 6 | 3 | 0 | 1 | 6 |
| 156 | S | 5 | 3 | 2 | 2 | 1 | 2 | 2 | 3 | 2 | 2 | 7 | 1 | 2 | 42 | 2 | 3 | 3 | 5 | 7 | 4 |
| 157 | N | 9 | 3 | 11 | 6 | 1 | 14 | 14 | 5 | 3 | 1 | 3 | 4 | 2 | 2 | 4 | 8 | 5 | 1 | 1 | 3 |
| 158 | K | 7 | 10 | 1 | 4 | 0 | 3 | 6 | 3 | 4 | 5 | 13 | 13 | 4 | 5 | 2 | 4 | 4 | 1 | 4 | 5 |
| 159 | A | 37 | 5 | 2 | 4 | 0 | 2 | 4 | 6 | 2 | 2 | 4 | 2 | 1 | 2 | 3 | 5 | 6 | 1 | 2 | 9 |
| 160 | Y | 4 | 2 | 6 | 4 | 1 | 1 | 3 | 2 | 18 | 2 | 7 | 2 | 3 | 20 | 1 | 3 | 4 | 2 | 13 | 1 |
| 161 | G | 3 | 2 | 8 | 6 | 0 | 3 | 3 | 59 | 2 | 0 | 1 | 4 | 0 | 1 | 2 | 3 | 1 | 0 | 1 | 1 |
| 162 | M | 5 | 7 | 2 | 4 | 2 | 5 | 9 | 5 | 2 | 3 | 9 | 10 | 8 | 1 | 2 | 5 | 12 | 0 | 2 | 6 |
| 163 | P | 5 | 2 | 6 | 11 | 0 | 2 | 6 | 9 | 3 | 0 | 1 | 4 | 0 | 0 | 21 | 15 | 12 | 0 | 0 | 1 |
| 164 | A | 8 | 1 | 1 | 2 | 1 | 1 | 1 | 2 | 2 | 9 | 20 | 1 | 2 | 6 | 19 | 4 | 2 | 2 | 3 | 8 | 6 |
| 165 | F | 2 | 1 | 0 | 2 | 0 | 1 | 2 | 1 | 2 | 2 | 2 | 1 | 1 | 41 | 0 | 2 | 1 | 24 | 13 | 2 |
| 166 | E | 9 | 2 | 1 | 19 | 0 | 8 | 34 | 4 | 1 | 1 | 1 | 2 | 0 | 0 | 3 | 7 | 5 | 0 | 0 | 1 |
| 167 | Y | 4 | 4 | 1 | 3 | 0 | 2 | 3 | 2 | 7 | 5 | 6 | 1 | 1 | 8 | 1 | 3 | 3 | 13 | 30 | 4 |
| 168 | Y | 6 | 2 | 1 | 1 | 1 | 1 | 1 | 2 | 2 | 8 | 34 | 1 | 8 | 9 | 2 | 2 | 3 | 2 | 7 | 5 |
| 169 | G | 17 | 6 | 4 | 8 | 1 | 5 | 15 | 11 | 2 | 1 | 1 | 6 | 2 | 1 | 3 | 9 | 3 | 0 | 2 | 2 |
| 170 | K | 9 | 10 | 4 | 7 | 0 | 11 | 14 | 5 | 3 | 1 | 4 | 13 | 1 | 1 | 1 | 8 | 6 | 0 | 1 | 2 |
| 171 | D | 3 | 4 | 16 | 26 | 0 | 3 | 6 | 3 | 9 | 1 | 2 | 3 | 2 | 3 | 4 | 7 | 4 | 1 | 3 | 1 |
| 172 | Q | 9 | 2 | 1 | 5 | 0 | 3 | 7 | 5 | 1 | 1 | 1 | 5 | 0 | 1 | 45 | 5 | 4 | 0 | 1 | 2 |
| 173 | R | 12 | 9 | 2 | 11 | 0 | 4 | 27 | 4 | 1 | 1 | 2 | 7 | 1 | 1 | 2 | 4 | 3 | 2 | 1 | 3 |
| 174 | F | 8 | 14 | 2 | 3 | 0 | 5 | 7 | 3 | 3 | 3 | 13 | 5 | 4 | 10 | 1 | 4 | 3 | 2 | 5 | 5 |
| 175 | N | 15 | 6 | 7 | 4 | 1 | 5 | 5 | 9 | 2 | 3 | 11 | 4 | 4 | 4 | 1 | 6 | 5 | 3 | 2 | 4 |
| 176 | K | 16 | 14 | 4 | 7 | 0 | 8 | 13 | 4 | 2 | 1 | 2 | 11 | 0 | 0 | 3 | 4 | 5 | 0 | 1 | 3 |
| 177 | V | 10 | 16 | 5 | 6 | 0 | 5 | 4 | 3 | 3 | 6 | 11 | 3 | 2 | 2 | 1 | 5 | 6 | 1 | 1 | 9 |
| 178 | F | 1 | 1 | 0 | 0 | 1 | 0 | 0 | 1 | 1 | 2 | 6 | 0 | 2 | 71 | 0 | 1 | 1 | 2 | 6 | 2 |
| 179 | N | 10 | 2 | 21 | 10 | 0 | 8 | 2 | 7 | 6 | 5 | 4 | 1 | 3 | 2 | 1 | 7 | 4 | 1 | 2 | 3 |
| 180 | S | 11 | 16 | 6 | 8 | 1 | 7 | 9 | 5 | 3 | 2 | 5 | 9 | 2 | 1 | 1 | 8 | 5 | 0 | 0 | 2 |
| 181 | A | 44 | 1 | 1 | 0 | 1 | 1 | 1 | 13 | 2 | 1 | 4 | 1 | 2 | 5 | 1 | 7 | 3 | 2 | 4 | 3 |
| 182 | M | 1 | 1 | 0 | 0 | 0 | 2 | 1 | 2 | 0 | 2 | 6 | 1 | 77 | 2 | 0 | 1 | 1 | 0 | 1 | 2 |
| 183 | F | 19 | 8 | 3 | 5 | 0 | 5 | 6 | 6 | 7 | 2 | 2 | 5 | 2 | 2 | 1 | 10 | 9 | 1 | 2 | 5 |
| 184 | N | 17 | 4 | 6 | 6 | 2 | 4 | 8 | 16 | 2 | 2 | 4 | 2 | 1 | 2 | 3 | 12 | 4 | 1 | 1 | 4 |
| 185 | H | 6 | 6 | 3 | 4 | 0 | 7 | 3 | 3 | 5 | 6 | 12 | 1 | 2 | 5 | 9 | 1 | 6 | 5 | 3 | 6 | 8 |
| 186 | S | 15 | 6 | 5 | 4 | 1 | 2 | 2 | 6 | 2 | 2 | 4 | 2 | 2 | 2 | 1 | 26 | 13 | 1 | 1 | 3 |
| 187 | T | 11 | 13 | 4 | 5 | 0 | 6 | 6 | 7 | 2 | 3 | 6 | 6 | 3 | 3 | 2 | 10 | 6 | 1 | 2 | 5 |
| 188 | M | 10 | 6 | 3 | 3 | 1 | 3 | 4 | 7 | 2 | 7 | 12 | 2 | 5 | 5 | 6 | 6 | 5 | 3 | 4 | 6 |
| 189 | T | 9 | 4 | 3 | 5 | 1 | 5 | 7 | 5 | 3 | 4 | 9 | 4 | 3 | 4 | 5 | 9 | 10 | 1 | 2 | 8 |

TABLE Ts1-continued

| pos | wildtype | A | R | N | D | C | Q | E | G | H | I | L | K | M | F | P | S | T | W | Y | V |
|---|---|---|---|---|---|---|---|---|---|---|---|---|---|---|---|---|---|---|---|---|---|
| 190 | M | 21 | 4 | 3 | 2 | 1 | 3 | 3 | 7 | 2 | 7 | 9 | 2 | 7 | 3 | 3 | 6 | 8 | 0 | 3 | 8 |
| 191 | K | 9 | 8 | 4 | 8 | 1 | 6 | 10 | 5 | 2 | 1 | 5 | 7 | 1 | 1 | 16 | 6 | 4 | 0 | 1 | 3 |
| 192 | K | 17 | 5 | 4 | 5 | 1 | 4 | 9 | 7 | 5 | 2 | 4 | 6 | 1 | 2 | 7 | 7 | 5 | 1 | 2 | 5 |
| 193 | I | 6 | 0 | 0 | 0 | 1 | 1 | 1 | 1 | 1 | 22 | 29 | 0 | 4 | 5 | 1 | 1 | 3 | 8 | 1 | 16 |
| 194 | I | 15 | 1 | 0 | 1 | 1 | 1 | 1 | 2 | 1 | 13 | 26 | 1 | 2 | 4 | 3 | 3 | 4 | 1 | 2 | 17 |
| 195 | D | 11 | 7 | 6 | 18 | 0 | 5 | 16 | 5 | 2 | 1 | 2 | 8 | 0 | 0 | 3 | 9 | 5 | 0 | 1 | 1 |
| 196 | L | 17 | 4 | 3 | 6 | 2 | 3 | 5 | 10 | 4 | 4 | 10 | 6 | 3 | 2 | 1 | 7 | 3 | 1 | 3 | 6 |
| 197 | Y | 4 | 2 | 0 | 0 | 1 | 1 | 1 | 3 | 2 | 8 | 15 | 1 | 2 | 17 | 1 | 2 | 1 | 1 | 31 | 8 |
| 198 | D | 4 | 2 | 5 | 44 | 0 | 2 | 4 | 5 | 1 | 0 | 2 | 4 | 0 | 0 | 18 | 3 | 2 | 0 | 0 | 1 |
| 199 | G | 5 | 4 | 2 | 7 | 0 | 2 | 9 | 26 | 1 | 3 | 9 | 2 | 1 | 5 | 4 | 2 | 3 | 6 | 1 | 8 |
| 200 | F | 3 | 1 | 1 | 1 | 0 | 1 | 2 | 1 | 1 | 2 | 15 | 1 | 1 | 45 | 3 | 2 | 1 | 14 | 2 | 2 |
| 201 | S | 11 | 4 | 4 | 7 | 0 | 5 | 10 | 8 | 2 | 1 | 2 | 8 | 0 | 1 | 7 | 23 | 5 | 0 | 0 | 2 |
| 202 | S | 7 | 6 | 5 | 10 | 1 | 6 | 8 | 18 | 1 | 1 | 1 | 10 | 0 | 0 | 7 | 14 | 4 | 0 | 0 | 1 |
| 203 | L | 10 | 5 | 3 | 5 | 1 | 1 | 3 | 12 | 3 | 4 | 9 | 3 | 2 | 10 | 5 | 5 | 4 | 0 | 5 | 9 |
| 204 | E | 12 | 10 | 3 | 4 | 1 | 4 | 7 | 11 | 2 | 3 | 3 | 11 | 1 | 1 | 5 | 8 | 6 | 0 | 1 | 7 |
| 205 | T | 3 | 13 | 3 | 2 | 1 | 3 | 2 | 0 | 5 | 3 | 10 | 9 | 1 | 2 | 1 | 9 | 24 | 1 | 0 | 8 |
| 206 | L | 2 | 0 | 0 | 0 | 1 | 0 | 0 | 0 | 0 | 20 | 32 | 0 | 6 | 6 | 0 | 0 | 0 | 0 | 0 | 30 |
| 207 | V | 5 | 0 | 0 | 0 | 4 | 0 | 0 | 0 | 0 | 7 | 27 | 0 | 2 | 0 | 0 | 0 | 1 | 0 | 0 | 53 |
| 208 | D | 0 | 0 | 0 | 96 | 0 | 0 | 2 | 0 | 0 | 0 | 0 | 0 | 0 | 0 | 0 | 0 | 0 | 0 | 0 | 0 |
| 209 | V | 2 | 0 | 0 | 0 | 1 | 0 | 0 | 0 | 0 | 19 | 18 | 0 | 1 | 1 | 0 | 0 | 0 | 0 | 0 | 56 |
| 210 | G | 8 | 0 | 0 | 0 | 0 | 0 | 0 | 89 | 0 | 0 | 0 | 0 | 0 | 0 | 0 | 1 | 0 | 0 | 0 | 0 |
| 211 | G | 3 | 0 | 0 | 0 | 9 | 0 | 0 | 83 | 0 | 0 | 0 | 0 | 0 | 0 | 0 | 2 | 1 | 0 | 0 | 0 |
| 212 | G | 4 | 1 | 5 | 1 | 1 | 0 | 0 | 78 | 0 | 0 | 0 | 0 | 0 | 0 | 0 | 9 | 0 | 0 | 0 | 0 |
| 213 | T | 5 | 6 | 6 | 4 | 0 | 4 | 2 | 2 | 10 | 6 | 5 | 3 | 2 | 1 | 5 | 12 | 17 | 1 | 3 | 5 |
| 214 | G | 3 | 0 | 0 | 0 | 0 | 0 | 0 | 95 | 0 | 0 | 0 | 0 | 0 | 0 | 0 | 0 | 0 | 0 | 0 | 0 |
| 215 | A | 12 | 3 | 3 | 3 | 1 | 6 | 4 | 6 | 14 | 4 | 7 | 2 | 2 | 3 | 1 | 9 | 9 | 1 | 3 | 7 |
| 216 | S | 7 | 1 | 3 | 5 | 1 | 3 | 1 | 1 | 2 | 5 | 20 | 1 | 4 | 11 | 1 | 4 | 7 | 2 | 10 | 10 |
| 217 | L | 18 | 0 | 0 | 1 | 4 | 0 | 1 | 3 | 0 | 7 | 36 | 0 | 3 | 0 | 1 | 15 | 6 | 0 | 0 | 4 |
| 218 | N | 12 | 7 | 3 | 2 | 2 | 4 | 5 | 2 | 2 | 17 | 11 | 6 | 6 | 2 | 0 | 5 | 3 | 0 | 2 | 7 |
| 219 | M | 24 | 6 | 2 | 3 | 0 | 5 | 15 | 4 | 3 | 2 | 7 | 5 | 4 | 2 | 2 | 5 | 5 | 0 | 2 | 3 |
| 220 | I | 5 | 0 | 0 | 0 | 0 | 1 | 0 | 0 | 0 | 32 | 34 | 0 | 4 | 10 | 0 | 1 | 1 | 0 | 0 | 10 |
| 221 | T | 26 | 6 | 1 | 0 | 7 | 2 | 0 | 1 | 2 | 3 | 28 | 5 | 2 | 0 | 0 | 3 | 3 | 0 | 1 | 10 |
| 222 | S | 10 | 14 | 3 | 5 | 0 | 10 | 13 | 3 | 2 | 1 | 3 | 19 | 1 | 0 | 1 | 9 | 4 | 0 | 0 | 1 |
| 223 | K | 20 | 20 | 3 | 2 | 0 | 6 | 6 | 1 | 5 | 1 | 4 | 18 | 1 | 1 | 0 | 5 | 4 | 0 | 1 | 2 |
| 224 | H | 3 | 2 | 13 | 2 | 2 | 1 | 1 | 2 | 17 | 1 | 4 | 1 | 1 | 18 | 0 | 3 | 2 | 2 | 23 | 3 |
| 225 | T | 3 | 3 | 1 | 2 | 0 | 1 | 3 | 2 | 1 | 1 | 1 | 5 | 0 | 1 | 69 | 5 | 2 | 0 | 0 | 1 |
| 226 | S | 4 | 3 | 14 | 11 | 1 | 7 | 8 | 11 | 15 | 0 | 1 | 7 | 0 | 1 | 1 | 9 | 4 | 1 | 0 | 1 |
| 227 | L | 10 | 2 | 0 | 0 | 2 | 1 | 1 | 2 | 1 | 14 | 42 | 0 | 5 | 1 | 1 | 6 | 2 | 1 | 1 | 9 |
| 228 | K | 2 | 21 | 5 | 2 | 0 | 6 | 6 | 1 | 5 | 1 | 1 | 25 | 0 | 1 | 5 | 7 | 9 | 0 | 1 | 2 |
| 229 | G | 16 | 0 | 0 | 0 | 5 | 0 | 0 | 40 | 0 | 5 | 5 | 0 | 1 | 10 | 1 | 2 | 1 | 0 | 2 | 10 |
| 230 | I | 2 | 1 | 0 | 1 | 1 | 1 | 1 | 0 | 1 | 32 | 3 | 1 | 1 | 0 | 2 | 17 | 0 | 3 | 29 |
| 231 | N | 4 | 0 | 9 | 0 | 2 | 0 | 0 | 13 | 0 | 9 | 27 | 0 | 1 | 1 | 0 | 1 | 1 | 0 | 1 | 30 |
| 232 | F | 1 | 0 | 0 | 0 | 2 | 19 | 3 | 0 | 1 | 6 | 13 | 0 | 2 | 35 | 0 | 1 | 0 | 0 | 6 | 9 |
| 233 | D | 0 | 0 | 0 | 91 | 0 | 0 | 6 | 0 | 0 | 0 | 0 | 0 | 0 | 0 | 0 | 0 | 0 | 0 | 0 | 0 |
| 234 | L | 1 | 10 | 1 | 1 | 0 | 5 | 1 | 1 | 0 | 6 | 59 | 1 | 2 | 3 | 1 | 2 | 2 | 1 | 1 | 2 |
| 235 | P | 8 | 1 | 2 | 3 | 0 | 2 | 6 | 2 | 1 | 0 | 1 | 2 | 0 | 0 | 63 | 6 | 1 | 0 | 0 | 1 |
| 236 | H | 10 | 3 | 4 | 7 | 1 | 5 | 19 | 7 | 11 | 1 | 1 | 5 | 1 | 1 | 9 | 8 | 3 | 0 | 1 | 3 |
| 237 | V | 8 | 1 | 1 | 1 | 0 | 1 | 1 | 1 | 0 | 5 | 3 | 1 | 7 | 1 | 1 | 3 | 7 | 0 | 1 | 55 |
| 238 | I | 6 | 1 | 0 | 0 | 3 | 1 | 2 | 1 | 0 | 42 | 13 | 1 | 1 | 1 | 1 | 1 | 3 | 0 | 0 | 23 |
| 239 | E | 17 | 5 | 3 | 10 | 0 | 5 | 29 | 3 | 1 | 1 | 1 | 7 | 0 | 0 | 5 | 6 | 3 | 0 | 0 | 1 |
| 240 | D | 8 | 6 | 5 | 6 | 0 | 9 | 8 | 4 | 4 | 8 | 8 | 6 | 2 | 2 | 1 | 5 | 4 | 0 | 2 | 10 |
| 241 | A | 64 | 1 | 1 | 0 | 0 | 1 | 0 | 7 | 0 | 3 | 4 | 1 | 1 | 1 | 3 | 6 | 0 | 0 | 5 |
| 242 | T | 8 | 18 | 3 | 4 | 0 | 7 | 10 | 3 | 2 | 2 | 3 | 18 | 1 | 0 | 8 | 4 | 5 | 0 | 1 | 2 |
| 243 | T | 12 | 8 | 3 | 6 | 1 | 7 | 18 | 3 | 2 | 2 | 3 | 14 | 1 | 1 | 5 | 6 | 5 | 0 | 0 | 3 |
| 244 | Y | 6 | 9 | 6 | 4 | 1 | 4 | 6 | 3 | 3 | 5 | 12 | 7 | 1 | 6 | 4 | 6 | 6 | 0 | 7 | 5 |
| 245 | H | 8 | 3 | 4 | 18 | 1 | 3 | 11 | 9 | 5 | 2 | 2 | 7 | 1 | 1 | 9 | 8 | 4 | 3 | 0 | 1 |
| 246 | G | 4 | 41 | 10 | 3 | 0 | 4 | 2 | 19 | 1 | 1 | 1 | 5 | 0 | 1 | 3 | 1 | 0 | 0 | 2 |
| 247 | I | 4 | 0 | 0 | 0 | 5 | 0 | 0 | 0 | 0 | 31 | 10 | 0 | 1 | 3 | 0 | 1 | 1 | 0 | 2 | 38 |
| 248 | E | 3 | 9 | 3 | 6 | 0 | 7 | 26 | 1 | 2 | 1 | 1 | 9 | 0 | 1 | 0 | 12 | 13 | 0 | 0 | 3 |
| 249 | H | 6 | 2 | 1 | 1 | 2 | 1 | 1 | 1 | 4 | 5 | 14 | 2 | 1 | 33 | 2 | 1 | 6 | 2 | 6 | 10 |
| 250 | V | 3 | 5 | 0 | 1 | 1 | 11 | 6 | 0 | 3 | 11 | 7 | 3 | 10 | 2 | 0 | 1 | 3 | 0 | 1 | 31 |
| 251 | G | 26 | 2 | 1 | 2 | 1 | 3 | 9 | 15 | 2 | 2 | 2 | 2 | 0 | 0 | 13 | 8 | 4 | 0 | 0 | 8 |
| 252 | G | 5 | 1 | 0 | 1 | 2 | 3 | 1 | 62 | 12 | 1 | 2 | 1 | 1 | 1 | 0 | 1 | 1 | 0 | 4 | 1 |
| 253 | D | 1 | 1 | 13 | 68 | 0 | 1 | 1 | 1 | 0 | 0 | 1 | 0 | 0 | 0 | 1 | 11 | 1 | 0 | 0 | 0 |
| 254 | M | 7 | 0 | 0 | 0 | 1 | 0 | 0 | 0 | 0 | 6 | 6 | 0 | 13 | 53 | 1 | 1 | 0 | 1 | 5 | 4 |
| 255 | F | 2 | 3 | 2 | 1 | 0 | 1 | 3 | 1 | 2 | 1 | 9 | 1 | 2 | 61 | 0 | 1 | 4 | 1 | 2 | 1 |
| 256 | E | 7 | 4 | 4 | 10 | 1 | 9 | 17 | 2 | 2 | 1 | 1 | 14 | 0 | 0 | 0 | 6 | 18 | 0 | 0 | 3 |
| 257 | S | 7 | 2 | 2 | 13 | 0 | 3 | 15 | 3 | 1 | 1 | 3 | 3 | 1 | 1 | 26 | 12 | 3 | 1 | 1 | 3 |
| 258 | V | 2 | 1 | 2 | 2 | 0 | 23 | 2 | 1 | 0 | 14 | 14 | 1 | 0 | 8 | 3 | 2 | 2 | 2 | 3 | 15 |
| 259 | P | 2 | 1 | 0 | 2 | 0 | 1 | 2 | 5 | 0 | 1 | 3 | 2 | 0 | 1 | 72 | 3 | 3 | 1 | 0 | 1 |
| 260 | K | 8 | 4 | 6 | 4 | 0 | 4 | 11 | 8 | 1 | 6 | 2 | 9 | 0 | 1 | 5 | 7 | 6 | 0 | 1 | 15 |
| 261 | G | 36 | 1 | 2 | 1 | 3 | 2 | 2 | 21 | 2 | 1 | 1 | 3 | 0 | 6 | 2 | 2 | 1 | 0 | 10 | 3 |
| 262 | D | 4 | 4 | 2 | 74 | 0 | 2 | 2 | 3 | 1 | 0 | 1 | 3 | 0 | 0 | 0 | 2 | 1 | 0 | 1 | 1 |
| 263 | A | 31 | 1 | 0 | 1 | 4 | 0 | 0 | 2 | 1 | 10 | 17 | 1 | 1 | 4 | 0 | 1 | 3 | 1 | 2 | 20 |
| 264 | I | 4 | 1 | 0 | 0 | 1 | 0 | 0 | 0 | 2 | 27 | 2 | 0 | 1 | 7 | 0 | 1 | 0 | 0 | 31 | 21 |
| 265 | F | 1 | 0 | 0 | 0 | 1 | 0 | 0 | 0 | 1 | 11 | 27 | 0 | 5 | 19 | 0 | 1 | 6 | 3 | 11 | 12 |
| 266 | M | 4 | 0 | 0 | 0 | 3 | 0 | 0 | 0 | 0 | 7 | 48 | 0 | 15 | 9 | 0 | 4 | 2 | 0 | 2 | 4 |
| 267 | K | 5 | 22 | 2 | 0 | 2 | 2 | 1 | 5 | 3 | 2 | 1 | 25 | 1 | 6 | 1 | 18 | 2 | 0 | 1 | 2 |

TABLE Ts1-continued

| pos | wildtype | A | R | N | D | C | Q | E | G | H | I | L | K | M | F | P | S | T | W | Y | V |
|---|---|---|---|---|---|---|---|---|---|---|---|---|---|---|---|---|---|---|---|---|---|
| 268 | W | 5 | 10 | 14 | 7 | 1 | 5 | 1 | 5 | 13 | 1 | 6 | 1 | 4 | 5 | 0 | 9 | 3 | 6 | 3 | 1 |
| 269 | I | 3 | 0 | 1 | 0 | 4 | 0 | 0 | 0 | 0 | 40 | 3 | 0 | 2 | 3 | 1 | 3 | 3 | 0 | 0 | 36 |
| 270 | L | 1 | 0 | 0 | 0 | 2 | 0 | 0 | 1 | 0 | 7 | 72 | 0 | 3 | 7 | 1 | 0 | 1 | 0 | 0 | 3 |
| 271 | H | 1 | 1 | 1 | 1 | 0 | 1 | 1 | 1 | 86 | 0 | 1 | 0 | 1 | 0 | 1 | 1 | 1 | 0 | 2 | 1 |
| 272 | D | 2 | 1 | 11 | 63 | 1 | 1 | 2 | 3 | 6 | 1 | 1 | 0 | 1 | 1 | 0 | 2 | 1 | 0 | 2 | 1 |
| 273 | W | 1 | 1 | 1 | 0 | 0 | 2 | 1 | 0 | 2 | 1 | 6 | 0 | 2 | 10 | 0 | 1 | 1 | 64 | 6 | 1 |
| 274 | S | 7 | 2 | 10 | 15 | 1 | 1 | 2 | 7 | 1 | 1 | 1 | 1 | 1 | 0 | 21 | 22 | 6 | 0 | 1 | 1 |
| 275 | D | 2 | 3 | 3 | 70 | 0 | 1 | 6 | 1 | 1 | 0 | 2 | 2 | 0 | 1 | 4 | 1 | 1 | 0 | 1 | 1 |
| 276 | A | 13 | 2 | 2 | 15 | 0 | 4 | 31 | 3 | 3 | 1 | 1 | 7 | 0 | 0 | 9 | 4 | 2 | 0 | 0 | 2 |
| 277 | L | 6 | 5 | 3 | 19 | 0 | 10 | 16 | 3 | 3 | 1 | 3 | 11 | 2 | 1 | 1 | 4 | 4 | 0 | 5 | 4 |
| 278 | C | 21 | 3 | 5 | 1 | 35 | 1 | 0 | 1 | 0 | 3 | 5 | 4 | 1 | 1 | 0 | 8 | 2 | 0 | 0 | 8 |
| 279 | L | 7 | 11 | 1 | 3 | 1 | 4 | 4 | 2 | 2 | 15 | 14 | 6 | 1 | 0 | 2 | 2 | 5 | 0 | 0 | 19 |
| 280 | Q | 11 | 13 | 2 | 4 | 0 | 11 | 9 | 3 | 2 | 2 | 4 | 21 | 1 | 1 | 1 | 4 | 8 | 0 | 1 | 2 |
| 281 | V | 5 | 0 | 0 | 0 | 0 | 0 | 1 | 0 | 0 | 53 | 21 | 0 | 3 | 3 | 0 | 1 | 1 | 0 | 1 | 10 |
| 282 | L | 1 | 0 | 0 | 0 | 0 | 0 | 0 | 0 | 0 | 4 | 83 | 0 | 2 | 4 | 0 | 0 | 1 | 0 | 1 | 2 |
| 283 | K | 8 | 22 | 3 | 2 | 0 | 9 | 6 | 4 | 1 | 1 | 1 | 26 | 0 | 0 | 1 | 8 | 5 | 0 | 0 | 1 |
| 284 | N | 7 | 13 | 30 | 1 | 1 | 5 | 6 | 2 | 6 | 1 | 2 | 17 | 1 | 0 | 0 | 3 | 4 | 0 | 0 | 1 |
| 285 | C | 12 | 0 | 0 | 0 | 20 | 1 | 0 | 0 | 1 | 21 | 17 | 0 | 2 | 2 | 0 | 2 | 4 | 0 | 1 | 15 |
| 286 | Y | 13 | 23 | 1 | 0 | 2 | 1 | 0 | 2 | 8 | 3 | 3 | 7 | 0 | 5 | 0 | 3 | 2 | 1 | 19 | 6 |
| 287 | K | 12 | 16 | 5 | 10 | 0 | 6 | 13 | 4 | 1 | 0 | 2 | 12 | 0 | 0 | 10 | 5 | 3 | 0 | 0 | 1 |
| 288 | S | 58 | 1 | 1 | 0 | 2 | 1 | 0 | 2 | 1 | 2 | 3 | 1 | 1 | 0 | 0 | 13 | 2 | 1 | 0 | 10 |
| 289 | L | 5 | 0 | 0 | 0 | 2 | 0 | 0 | 0 | 0 | 6 | 64 | 0 | 16 | 1 | 0 | 1 | 1 | 0 | 0 | 2 |
| 290 | P | 9 | 13 | 6 | 4 | 0 | 1 | 4 | 6 | 1 | 1 | 1 | 21 | 0 | 0 | 17 | 6 | 6 | 0 | 0 | 3 |
| 291 | K | 7 | 3 | 2 | 6 | 0 | 3 | 7 | 3 | 2 | 1 | 1 | 10 | 0 | 0 | 42 | 9 | 3 | 0 | 1 | 1 |
| 292 | N | 2 | 2 | 10 | 15 | 0 | 2 | 4 | 43 | 3 | 0 | 1 | 5 | 0 | 0 | 0 | 4 | 3 | 0 | 2 | 1 |
| 293 | G | 7 | 1 | 1 | 1 | 1 | 0 | 0 | 70 | 0 | 0 | 0 | 0 | 0 | 0 | 1 | 13 | 3 | 0 | 0 | 0 |
| 294 | K | 3 | 29 | 0 | 1 | 1 | 3 | 2 | 1 | 2 | 4 | 6 | 29 | 1 | 1 | 1 | 2 | 7 | 1 | 1 | 7 |
| 295 | V | 1 | 0 | 0 | 0 | 1 | 0 | 0 | 0 | 0 | 16 | 41 | 0 | 2 | 8 | 0 | 0 | 0 | 1 | 1 | 29 |
| 296 | I | 5 | 0 | 0 | 0 | 0 | 0 | 0 | 0 | 0 | 24 | 40 | 0 | 3 | 4 | 0 | 1 | 1 | 1 | 4 | 15 |
| 297 | V | 3 | 0 | 2 | 1 | 1 | 0 | 0 | 0 | 0 | 40 | 14 | 0 | 3 | 1 | 0 | 3 | 2 | 0 | 0 | 30 |
| 298 | A | 10 | 1 | 7 | 3 | 4 | 3 | 1 | 3 | 7 | 12 | 9 | 1 | 4 | 4 | 0 | 5 | 3 | 1 | 3 | 18 |
| 299 | E | 1 | 0 | 1 | 39 | 0 | 1 | 51 | 2 | 1 | 0 | 0 | 0 | 0 | 0 | 1 | 2 | 0 | 0 | 0 | 0 |
| 300 | C | 7 | 5 | 3 | 1 | 2 | 5 | 2 | 4 | 4 | 8 | 6 | 2 | 8 | 10 | 7 | 5 | 6 | 3 | 5 | 7 |
| 301 | I | 3 | 1 | 1 | 2 | 3 | 0 | 1 | 2 | 1 | 17 | 17 | 2 | 4 | 5 | 1 | 1 | 3 | 1 | 1 | 33 |
| 302 | L | 5 | 4 | 1 | 1 | 1 | 2 | 1 | 2 | 1 | 12 | 32 | 3 | 7 | 3 | 4 | 2 | 3 | 1 | 2 | 12 |
| 303 | S | 5 | 3 | 6 | 13 | 0 | 3 | 6 | 7 | 2 | 1 | 2 | 2 | 0 | 1 | 35 | 8 | 3 | 0 | 1 | 1 |
| 304 | E | 7 | 3 | 4 | 19 | 0 | 2 | 26 | 4 | 1 | 1 | 2 | 2 | 0 | 1 | 11 | 7 | 3 | 0 | 2 | 2 |
| 305 | A | 10 | 6 | 7 | 13 | 0 | 4 | 9 | 7 | 2 | 2 | 3 | 5 | 1 | 0 | 10 | 7 | 8 | 1 | 1 | 4 |
| 306 | P | 5 | 9 | 7 | 5 | 1 | 2 | 5 | 18 | 2 | 3 | 4 | 6 | 1 | 1 | 17 | 5 | 3 | 1 | 1 | 4 |
| 307 | D | 13 | 6 | 3 | 9 | 2 | 2 | 11 | 7 | 2 | 3 | 3 | 4 | 1 | 2 | 5 | 8 | 14 | 1 | 1 | 4 |
| 308 | S | 8 | 4 | 4 | 7 | 0 | 5 | 7 | 12 | 4 | 2 | 5 | 3 | 1 | 2 | 13 | 12 | 6 | 1 | 2 | 3 |
| 309 | T | 6 | 5 | 6 | 7 | 1 | 3 | 5 | 9 | 5 | 2 | 10 | 2 | 2 | 1 | 12 | 8 | 5 | 5 | 1 | 5 |
| 310 | P | 6 | 4 | 2 | 5 | 0 | 3 | 5 | 3 | 1 | 3 | 9 | 3 | 2 | 3 | 33 | 7 | 3 | 2 | 2 | 3 |
| 311 | A | 20 | 4 | 3 | 4 | 1 | 3 | 5 | 5 | 2 | 6 | 12 | 3 | 3 | 3 | 4 | 7 | 6 | 1 | 2 | 7 |
| 312 | T | 16 | 5 | 6 | 6 | 1 | 3 | 10 | 7 | 3 | 1 | 5 | 2 | 2 | 6 | 4 | 7 | 9 | 2 | 3 | 2 |
| 313 | Q | 14 | 14 | 4 | 4 | 1 | 7 | 6 | 7 | 2 | 2 | 7 | 9 | 3 | 2 | 4 | 6 | 4 | 1 | 1 | 3 |
| 314 | N | 11 | 6 | 4 | 2 | 1 | 3 | 5 | 4 | 4 | 5 | 12 | 2 | 4 | 11 | 3 | 5 | 7 | 2 | 5 | 5 |
| 315 | V | 17 | 2 | 2 | 3 | 1 | 4 | 4 | 6 | 2 | 6 | 14 | 2 | 4 | 2 | 6 | 8 | 6 | 0 | 1 | 8 |
| 316 | I | 18 | 10 | 2 | 1 | 1 | 2 | 1 | 3 | 3 | 4 | 12 | 4 | 3 | 4 | 2 | 5 | 8 | 1 | 11 | 5 |
| 317 | H | 13 | 3 | 3 | 3 | 2 | 5 | 4 | 7 | 3 | 6 | 13 | 1 | 6 | 5 | 1 | 9 | 4 | 4 | 2 | 6 |
| 318 | I | 3 | 4 | 2 | 1 | 1 | 4 | 2 | 2 | 1 | 7 | 23 | 2 | 13 | 14 | 1 | 4 | 3 | 2 | 5 | 7 |
| 319 | D | 3 | 1 | 4 | 74 | 0 | 1 | 2 | 2 | 1 | 0 | 0 | 1 | 1 | 1 | 0 | 6 | 1 | 0 | 2 | 0 |
| 320 | A | 6 | 1 | 1 | 1 | 1 | 2 | 1 | 1 | 1 | 15 | 37 | 1 | 12 | 6 | 0 | 2 | 2 | 2 | 1 | 9 |
| 321 | I | 7 | 4 | 11 | 2 | 1 | 5 | 3 | 3 | 6 | 6 | 12 | 1 | 5 | 6 | 1 | 8 | 8 | 1 | 4 | 6 |
| 322 | M | 2 | 2 | 1 | 0 | 1 | 1 | 1 | 1 | 2 | 3 | 10 | 1 | 66 | 2 | 0 | 1 | 2 | 1 | 1 | 4 |
| 323 | L | 5 | 2 | 1 | 1 | 1 | 1 | 1 | 1 | 1 | 3 | 37 | 2 | 26 | 5 | 2 | 2 | 3 | 3 | 2 | 2 |
| 324 | V | 15 | 2 | 3 | 1 | 4 | 3 | 1 | 4 | 3 | 6 | 14 | 1 | 5 | 2 | 2 | 7 | 7 | 1 | 1 | 19 |
| 325 | H | 7 | 2 | 7 | 2 | 5 | 7 | 3 | 5 | 4 | 4 | 12 | 1 | 6 | 4 | 1 | 10 | 7 | 2 | 2 | 8 |
| 326 | S | 6 | 3 | 6 | 1 | 5 | 2 | 2 | 2 | 1 | 3 | 19 | 2 | 5 | 6 | 2 | 8 | 18 | 1 | 3 | 5 |
| 327 | L | 4 | 4 | 2 | 3 | 3 | 3 | 4 | 6 | 6 | 4 | 17 | 2 | 6 | 11 | 4 | 6 | 8 | 1 | 3 | 6 |
| 328 | G | 7 | 4 | 18 | 5 | 1 | 3 | 4 | 36 | 3 | 0 | 1 | 3 | 1 | 1 | 1 | 9 | 2 | 1 | 1 | 1 |
| 329 | G | 11 | 2 | 1 | 1 | 1 | 1 | 1 | 66 | 1 | 0 | 1 | 1 | 0 | 0 | 1 | 8 | 2 | 0 | 1 | 2 |
| 330 | K | 4 | 20 | 1 | 2 | 1 | 6 | 3 | 4 | 3 | 2 | 4 | 28 | 4 | 3 | 2 | 3 | 3 | 0 | 2 | 3 |
| 331 | E | 4 | 1 | 1 | 3 | 2 | 4 | 60 | 2 | 1 | 2 | 5 | 1 | 2 | 2 | 1 | 2 | 2 | 0 | 1 | 5 |
| 332 | R | 1 | 81 | 0 | 0 | 0 | 1 | 0 | 0 | 1 | 1 | 2 | 1 | 1 | 2 | 2 | 0 | 1 | 1 | 5 | 1 |
| 333 | T | 2 | 2 | 3 | 4 | 1 | 1 | 3 | 3 | 1 | 1 | 1 | 1 | 0 | 0 | 2 | 18 | 55 | 0 | 1 | 0 |
| 334 | E | 8 | 8 | 1 | 2 | 1 | 3 | 23 | 2 | 1 | 3 | 14 | 6 | 1 | 6 | 7 | 3 | 2 | 1 | 2 | 6 |
| 335 | K | 14 | 6 | 4 | 11 | 0 | 6 | 17 | 8 | 1 | 0 | 1 | 11 | 0 | 0 | 3 | 10 | 4 | 0 | 1 | 1 |
| 336 | E | 3 | 2 | 2 | 14 | 0 | 14 | 51 | 3 | 2 | 0 | 1 | 2 | 2 | 1 | 0 | 1 | 2 | 1 | 0 | 1 |
| 337 | F | 2 | 0 | 0 | 0 | 1 | 1 | 0 | 0 | 2 | 7 | 11 | 0 | 3 | 24 | 0 | 0 | 1 | 27 | 15 | 5 |
| 338 | E | 11 | 19 | 2 | 5 | 1 | 5 | 18 | 2 | 3 | 4 | 4 | 9 | 1 | 1 | 0 | 4 | 5 | 0 | 1 | 5 |
| 339 | A | 19 | 8 | 5 | 11 | 0 | 8 | 15 | 6 | 2 | 0 | 2 | 8 | 1 | 0 | 1 | 7 | 5 | 0 | 1 | 1 |
| 340 | L | 3 | 1 | 0 | 0 | 0 | 0 | 1 | 0 | 0 | 7 | 69 | 1 | 5 | 1 | 0 | 0 | 1 | 5 | 1 | 4 |
| 341 | A | 14 | 0 | 0 | 0 | 3 | 0 | 0 | 3 | 0 | 7 | 39 | 1 | 0 | 5 | 19 | 0 | 1 | 1 | 0 | 6 |
| 342 | K | 14 | 11 | 3 | 5 | 0 | 5 | 18 | 4 | 2 | 1 | 3 | 12 | 1 | 0 | 1 | 8 | 8 | 0 | 1 | 2 |
| 343 | A | 17 | 10 | 3 | 9 | 0 | 9 | 17 | 3 | 1 | 0 | 2 | 12 | 1 | 0 | 1 | 9 | 3 | 0 | 0 | 1 |
| 344 | A | 60 | 1 | 2 | 0 | 3 | 1 | 1 | 3 | 2 | 2 | 2 | 0 | 0 | 0 | 2 | 10 | 4 | 0 | 1 | 7 |
| 345 | G | 0 | 3 | 2 | 3 | 0 | 1 | 1 | 86 | 0 | 0 | 0 | 1 | 0 | 1 | 1 | 1 | 0 | 0 | 0 | 0 |

TABLE Ts1-continued

| pos | wildtype | A | R | N | D | C | Q | E | G | H | I | L | K | M | F | P | S | T | W | Y | V |
|---|---|---|---|---|---|---|---|---|---|---|---|---|---|---|---|---|---|---|---|---|---|
| 346 | F | 0 | 0 | 0 | 0 | 1 | 0 | 0 | 0 | 0 | 0 | 22 | 0 | 1 | 68 | 0 | 0 | 0 | 4 | 2 | 0 |
| 347 | K | 6 | 14 | 2 | 4 | 1 | 5 | 13 | 3 | 2 | 2 | 1 | 21 | 1 | 0 | 0 | 9 | 11 | 0 | 1 | 5 |
| 348 | G | 3 | 6 | 5 | 10 | 1 | 2 | 4 | 4 | 2 | 14 | 14 | 4 | 1 | 3 | 3 | 5 | 2 | 0 | 1 | 16 |
| 349 | F | 5 | 4 | 2 | 3 | 2 | 3 | 7 | 1 | 2 | 13 | 6 | 4 | 1 | 7 | 3 | 3 | 8 | 0 | 3 | 25 |
| 350 | N | 5 | 20 | 6 | 7 | 1 | 6 | 13 | 4 | 2 | 2 | 1 | 13 | 0 | 1 | 1 | 8 | 6 | 0 | 1 | 3 |
| 351 | K | 4 | 7 | 1 | 1 | 3 | 2 | 4 | 1 | 2 | 15 | 6 | 5 | 2 | 3 | 1 | 5 | 8 | 2 | 3 | 25 |
| 352 | A | 7 | 9 | 1 | 2 | 0 | 3 | 3 | 2 | 7 | 10 | 7 | 7 | 1 | 3 | 2 | 4 | 8 | 5 | 4 | 15 |
| 353 | A | 8 | 9 | 4 | 6 | 2 | 3 | 8 | 3 | 3 | 1 | 2 | 7 | 1 | 2 | 17 | 5 | 6 | 3 | 5 | 3 |
| 354 | C | 5 | 4 | 2 | 3 | 3 | 2 | 3 | 2 | 1 | 11 | 18 | 3 | 3 | 4 | 5 | 6 | 12 | 0 | 3 | 10 |
| 355 | A | 11 | 8 | 3 | 7 | 1 | 3 | 6 | 13 | 1 | 4 | 4 | 3 | 1 | 2 | 16 | 6 | 3 | 0 | 3 | 4 |
| 356 | L | 9 | 3 | 2 | 6 | 1 | 2 | 3 | 19 | 3 | 1 | 7 | 3 | 2 | 5 | 6 | 11 | 5 | 4 | 5 | 3 |
| 357 | N | 4 | 2 | 10 | 6 | 1 | 2 | 4 | 14 | 3 | 3 | 6 | 2 | 2 | 6 | 8 | 8 | 7 | 0 | 5 | 4 |
| 358 | T | 3 | 7 | 3 | 3 | 1 | 5 | 6 | 1 | 6 | 4 | 8 | 2 | 8 | 12 | 2 | 5 | 9 | 1 | 9 | 5 |
| 359 | W | 11 | 3 | 2 | 1 | 3 | 2 | 1 | 12 | 2 | 1 | 2 | 1 | 1 | 4 | 1 | 28 | 8 | 6 | 5 | 5 |
| 360 | V | 2 | 1 | 0 | 0 | 1 | 0 | 0 | 1 | 1 | 19 | 27 | 0 | 3 | 2 | 0 | 2 | 1 | 0 | 2 | 37 |
| 361 | M | 1 | 0 | 0 | 0 | 1 | 1 | 0 | 1 | 1 | 30 | 22 | 1 | 11 | 8 | 1 | 1 | 2 | 1 | 4 | 14 |
| 362 | E | 2 | 2 | 1 | 1 | 0 | 1 | 68 | 1 | 1 | 2 | 3 | 2 | 0 | 1 | 0 | 1 | 4 | 1 | 1 | 7 |
| 363 | F | 24 | 1 | 0 | 0 | 7 | 0 | 1 | 5 | 0 | 4 | 15 | 1 | 3 | 23 | 0 | 3 | 1 | 1 | 2 | 9 |
| 364 | C | 3 | 18 | 1 | 1 | 6 | 3 | 6 | 2 | 5 | 5 | 3 | 6 | 2 | 5 | 1 | 7 | 6 | 1 | 10 | 8 |
| 365 | K | 3 | 5 | 2 | 0 | 0 | 0 | 1 | 1 | 1 | 1 | 3 | 65 | 0 | 0 | 14 | 2 | 0 | 0 | 0 | 1 |

TABLE Ts2

| positions | most preferred | preferred, sorted in decreasing order of preference | to be avoided | score |
|---|---|---|---|---|
| 253 + 256 | DE | RQ, ND, NE, DA, DR, DN, DQ, DH, DL, DK, DS, DT, DV, EA, LA, KQ, PS, SD, SE, TD | AE, AK, NA, NR, NQ, NK, NV, DD, DG, DI, DP, EK, LE, SA, SR, SQ, SS, ST, TA | 0.37 |
| 217 + 229 | LG | AA, AC, AI, AV, CF, EF, GV, IG, LL, LM, MG, PI, SA, SF, SS, SV, TA, TY, VF | AG, AL, AM, AF, AS, CI, CV, GA, GF, IA, II, IV, LI, LF, LV, MA, SG, SY, TL, TF | 0.3 |
| 279 + 343 | LA | AT, RD, RE, RS, DR, QP, QS, ER, EK, IA, IQ, IK, LR, LQ, LK, KD, KE, KS, VR, VE | AR, AE, AK, RR, RN, RK, QR, QE, ED, EE, ID, IS, LS, KR, KQ, KK, VA, VG, VS | 0.3 |
| 286 + 346 | YF | AI, AL, AM, RF, RW, RY, NF, EY, GW, HF, IL, LA, FF, SL, TL, WF, VE, VL, VP | AF, AW, RC, RL, NL, CF, EF, GF, HL, IW, LL, KF, FL, SF, WL, YL, YW, YY, VF, VW | 0.28 |
| 334 + 338 | EE | AA, AD, AM, RD, RE, RV, QL, ER, EK, LD, LQ, LG, LI, KE, KF, KY, PK, TT, WE, YE | AK, RR, RI, RK, QR, ED, EQ, ES, EV, IE, LA, LR, LT, KA, KR, KK, FT, PV, VD | 0.28 |
| 284 + 287 | NK | AP, RD, RQ, RE, RG, NA, NN, NP, ER, HA, HN, HD, HT, LS, KD, KE, PE, SP, SS | AD, AT, RR, RN, RK, RP, ND, NE, NG, QD, QE, ED, EE, EK, HE, HP, LR, KQ, SA, SD | 0.27 |
| 289 + 293 | LG | AA, AT, CC, GR, GL, HQ, IG, IV, LA, LD, MN, MS, FR, FQ, PV, ST, SW, TG, VG | AG, AS, GG, IA, IS, IT, LR, LS, LT, KG, MA, MR, MG, MT, MV, FA, FG, SA, SG, VS | 0.26 |
| 221 + 229 | TG | AC, AI, AL, AF, AV, RG, RI, RM, CA, CC, CS, HL, IA, LA, LG, MG, TA, YY, VA, VG | AA, AG, AM, AS, RA, RC, RV, CG, CI, CV, LI, LL, LF, LV, KV, SA, SG, YG, VC, VF | 0.25 |
| 272 + 273 | DW | RR, RL, NH, NW, DM, CF, QL, EI, GF, HI, HL, IY, LL, MQ, MF, FT, SE, YF, VF | AW, RW, NF, DE, DI, DL, DF, CW, QW, EF, GW, HT, LW, LY, FW, SW, TW, YW, YY, VW | 0.25 |
| 198 + 201 | DS | RP, NQ, DA, DN, DG, DT, GR, GG, GK, HN, LG, PA, PD, PE, PP, SA, SQ, SK, VL | AA, AE, RA, RS, NK, NP, DD, DE, DL, DP, QK, GS, GT, LS, PR, PG, PS, PT, TS, VS | 0.24 |
| 205 + 230 | TI | AC, RA, RD, RV, NT, DR, DH, ET, HT, II, LI, LL, KY, KV, FI, ST, SY, TV, VV | RI, RT, RY, NV, DI, DV, EI, EV, HI, HV, IT, LT, KI, KT, SI, SV, TH, TL, TT, VT | 0.23 |
| 217 + 231 | LN | AV, CI, EI, GF, IN, IG, IL, LE, LG, LL, LY, MC, MS, PV, SA, SV, TC, TI, VV | AN, AL, AS, DV, CV, GG, II, IV, LA, LI, LS, LV, ML, PL, SN, SG, SL, SF, TV, VL | 0.23 |
| 125 + 127 | SA | AL, AF, AV, NS, NV, DR, DS, GD, GL, GK, GS, FG, SR, SQ, SH, SK, TE, TP, YG | AA, AR, AG, NG, DA, DL, GA, GR, GG, LG, FA, SN, SE, SG, SS, TG, TS, YR, YL, YT | 0.22 |
| 165 + 272 | FD | AF, RY, DR, QM, ES, HH, LR, LN, LE, LG, FV, SD, SG, WD, WF, YA, YN, YI, VE | AN, AD, EN, HN, IN, LD, FN, FE, FI, FK, FS, TD, WN, WE, WH, WS, WV, YD, YE, YH | 0.22 |
| 110 + 114 | VC | AT, NN, ND, NQ, NE, NS, NV, QS, HS, IG, LG, MA, FA, PC, PT, SL, ST, TY, VA, VG | AG, AS, NR, NC, NG, NL, HA, HG, HT, IT, LL, LS, LT, PG, PS, SA, SG, SS, TS, VS | 0.22 |
| 232 + 252 | FG | AL, AV, CG, CL, QR, QH, QY, EY, IA, IG, LG, LF, MG, TR, WK, YG, VA, VD, VT | AG, CG, QC, QG, EG, IH, IL, LI, LY, FA, FR, FC, FH, FL, SG, TG, YA, VG, VH, VF | 0.22 |
| 277 + 280 | LQ | AD, RE, NK, DR, DH, DK, QQ, QE, EQ, EG, ET, KE, KI, KL, SK, TQ, TM, YR, YK, VK | AK, RR, NQ, NE, DD, DQ, DE, DG, QR, QK, ED, EE, EH, LT, KR, KK, KT, YE, VR, VQ | 0.22 |
| 205 + 228 | TK | AH, RE, NN, NS, EN, HT, IK, LR, LP, LS, KE, KH, KT, SR, SK, ST, TN, VR, VK | RR, RN, RK, NR, DK, HQ, HH, IS, IE, LK, LT, KR, KK, SE, TR, TE, TS, TT, VN, VE | 0.22 |
| 234 + 235 | LP | RG, RP, ND, QA, QQ, QS, EA, HE, IA, ID, IK, IS, ME, FQ, PD, SE, WA, YH, VD | RQ, RS, NP, QD, QP, EP, GP, IQ, IP, LA, LD, LH, LL, LT, MS, FP, PA, SP, TP, VP | 0.21 |
| 274 + 277 | SL | AD, NN, ND, DR, DG, DH, DS, DT, QD, GA, GE, PA, PE, PK, PV, SY, TQ, TE, TM, VD | AR, NA, NE, NH, NY, DD, DQ, DE, DK, DY, DV, GN, GQ, PR, PN, PG, PH, SG, SS, TG | 0.2 |
| 238 + 249 | IH | AA, AI, AV, RF, CT, QF, EF, IE, IG, IM, IT, IY, LL, LK, KF, TV, VA, VC, VI, VV | AL, AF, AT, CL, EL, EV, IC, II, IV, LA, LI, LF, LV, PF, SF, VL, VM, VF, VP, VT | 0.2 |
| 81 + 319 | RD | AH, AT, DE, QS, IA, IS, LA, KD, FG, PE, SN, SG, TA, TS, YY, VA, VS, VY | AA, AD, RA, RR, RE, RG, RS, RY, DD, CD, HD, ID, LD, KG, MD, FD, PD, SD, TD, VD | 0.2 |
| 40 + 86 | AL | AC, DI, CV, GA, GQ, GM, GF, GY, IA, LA, LG, LT, LV, MG, FS, SL, TL, VC, VV | AA, AQ, AG, AM, AF, AP, AS, AT, AY, AV, CA, GC, GL, IL, IV, LL, LS, SA, TA, VA | 0.2 |
| 213 + 215 | TA | AH, RN, RH, DF, DT, GQ, HR, HD, HL, IS, LQ, LG, KQ, PT, SA, SI, SY, SV, VS | AA, AL, NV, DQ, HQ, HE, HH, HS, HT, IL, PA, PH, SN, SQ, SS, ST, TQ, TV, YH, VQ | 0.2 |

TABLE Ts2-continued

| positions | most preferred | preferred, sorted in decreasing order of preference | to be avoided | score |
|---|---|---|---|---|
| 206 + 227 | LL | AV, IA, IR, IC, IF, IP, IS, IT, LI, LM, LW, MI, ML, MM, FG, VC, VG, VL, VV | AI, II, IL, IM, LA, LC, LQ, LG, LS, LT, LV, MA, MV, FV, VI, VM, VF, VS, VW, VY | 0.19 |
| 44 + 47 | DE | RD, RE, NG, NK, NM, NS, DR, DN, DG, DS, DT, EK, GA, GR, GD, GK, HE, KD, KE, KH | RA, RR, RN, RK, RS, RT, ND, DD, DH, DK, ED, GG, GH, GS, GT, KA, KR, KQ, KK | 0.19 |
| 245 + 246 | HG | AA, AG, AP, NI, DR, QQ, EN, GR, GV, LD, LE, LP, KN, PA, PN, PP, SS, TN, TG | AN, AK, RR, NG, NA, DD, DK, QN, EA, EE, GA, GG, GK, LR, KG, PR, PQ, SG, TR, WR | 0.18 |
| 93 + 109 | TG | AT, RA, RE, RV, NS, NT, DR, CA, QS, ER, EK, EW, GF, GV, HS, IK, SQ, TA, TE, | RR, RK, NA, DE, DT, QR, EQ, EE, EG, EI, ES, ET, EV, GA, HA, KK, SR, TR, TS, TV | 0.18 |
| 211 + 231 | GN | AA, AL, AM, AF, CA, CD, CE, CG, CF, GQ, GI, GV, HI, PG, SN, SC, ST, TG, VA | AG, AI, AV, RV, CN, CC, CI, CL, CT, CV, GA, GR, GE, GG, GM, GF, GY, SV, TL, VL | 0.18 |
| 219 + 222 | MS | AR, RA, RD, RE, NK, DR, QL, ER, EK, ES, GQ, HS, LQ, KQ, KE, KS, MK, PR, SR, TA | AG, AL, AS, RR, RK, NR, QA, QQ, ED, EQ, EE, GK, HR, LS, KR, KK, SE, SK, SS, YR | 0.18 |
| 338 + 342 | EK | AA, RA, RE, RV, NN, DR, DQ, DK, CE, ER, GA, HD, IK, LS, KE, KL, SS, TD, YE | AQ, AL, AS, RR, RN, RD, RQ, RG, RK, DE, QN, QK, EE, ET, IA, LA, LT, KR, KK, SR | 0.18 |
| 202 + 203 | SL | AG, AH, RF, RY, NV, DR, DT, DV, QF, QY, EG, GR, GL, GV, KP, PG, PF, PY, TA | AA, RA, RV, DH, DL, DP, DY, QV, EA, GG, GF, GY, KR, PA, PR, PL, PV, SG, SV, TF | 0.18 |
| 304 + 335 | EK | AG, RD, RE, NK, NS, DR, DN, DS, EA, EG, ES, LR, KD, PA, PN, PE, SD, SE, YG | AS, RA, RQ, RK, DE, DK, ER, ED, EE, EP, GR, PR, PD, PS, PT, SR, SG, SK, SS, TS | 0.18 |
| 228 + 248 | KE | RD, RQ, RE, NR, NN, QR, QQ, ER, EH, EK, HT, KQ, KS, PE, SS, TA, TN, TK, TV | RR, RK, RF, NE, NV, DE, DS, QE, EN, ED, EE, HQ, KR, KK, KT, PS, SD, SQ, TQ, TE | 0.18 |
| 255 + 273 | FW | RC, RL, NY, DL, EI, ET, GQ, GL, HE, HY, LL, LF, LW, KE, MY, SQ, WY, YN, VL | AW, RY, NL, NW, DW, EL, GW, HL, HW, LM, KF, KW, FA, FE, FL, FY, FV, TW, YW, VW | 0.17 |
| 203 + 204 | LE | AR, NA, DV, GA, GE, GI, LG, KG, MK, FN, FE, FS, PL, SG, SV, YR, YH, VK, VS, VT | AL, RS, DR, DK, GR, GK, GT, IA, LK, FA, FR, FG, FV, PG, PS, YA, YG, YT, VA, VV | 0.17 |
| 238 + 251 | IG | AR, CE, CP, EP, IA, IL, IK, IV, LE, LH, LP, LY, FP, ST, TS, YN, VA, VC, VG, VT | AP, CA, EE, IR, IE, IH, IP, IT, LD, LG, LL, LS, LT, LV, MP, SA, TE, TV, VP | 0.17 |
| 266 + 269 | MI | AL, AS, NM, CA, CS, GI, IA, IC, IT, LI, LV, MF, FQ, FV, SA, TC, TT, YH, VV | AA, AM, CC, CV, GV, II, LA, LC, LF, LS, LT, MS, MV, FC, SI, SL, SS, SV, TI, VI | 0.17 |
| 221 + 246 | TG | AR, AN, AQ, RG, RS, ND, CR, QG, GN, LA, LR, KD, KG, MG, SA, SN, YN, VG, VK, VV | AA, AD, AG, AK, AS, RR, CG, CK, QR, HR, IR, LN, LQ, LG, KR, KN, SR, SG, TN, VN | 0.17 |
| 330 + 336 | KE | AR, AD, RD, RE, DE, QQ, QV, ER, EH, EP, LR, LQ, MQ, PD, SG, TQ, TK, YE, VQ | RR, RQ, RH, RK, NE, DQ, QD, QE, ED, EE, LE, KR, KQ, KH, ME, FE, PE, SE, TE, VD | 0.17 |
| 195 + 223 | DK | AA, AQ, RA, RQ, DR, DH, QN, QT, ER, EK, GA, GE, GS, II, KD, KE, KF, SA, SL | AH, RR, RK, DA, DN, DQ, DL, DT, QA, QE, EA, EN, EE, GH, GK, HR, KR, SR, TA, TK | 0.17 |
| 61 + 76 | SP | AQ, AE, RE, NK, DA, DR, DK, QV, EA, EG, EL, EP, ES, ET, GE, GP, HE, KE, SE, SL | AR, AK, AT, RA, NA, NE, DP, QL, EE, GA, GV, IP, KK, KP, KS, SG, YP, VE | 0.17 |
| 218 + 222 | NS | AR, AS, RA, RE, NL, DR, QE, GA, IR, IN, IQ, IK, LQ, LK, KD, MD, SA, VE, VK | AN, AD, AE, AK, RR, NQ, NE, IA, ID, IE, IS, IT, LS, KK, MQ, SR, SS, VA, VN, VD | 0.16 |
| 339 + 343 | AA | AQ, AS, RD, RE, DR, DQ, DK, DS, QD, EN, EK, ES, KD, KE, SR, SE, ST, TA, TD | AN, AD, AL, AK, RR, AR, RQ, RK, NE, DD, DE, DT, QQ, ED, EE, KS, SA, SQ, TR, TQ | 0.16 |
| 42 + 146 | EK | RD, RE, RH, RY, NE, DA, DR, DG, DT, QP, EA, ES, ET, HV, KD, KE, KL, SE, TP | RA, RR, RL, RK, RT, DD, DE, DV, QE, QK, QT, EN, ED, EE, EG, EL, KA, KK, KT, SA | 0.16 |
| 290 + 292 | PN | AD, RA, RG, NN, NG, DR, DE, EG, EK, GN, GQ, KG, KY, PH, PT, SN, SD, ST, TK, TS | AR, AG, RN, RE, RK, RT, DG, GG, GT, GY, HG, KA, KD, KQ, KS, PD, PQ, SG, TG, TH | 0.16 |
| 207 + 261 | VG | AA, AL, AV, CC, IG, LE, LG, LH, LF, LY, MA, MN, FS, SC, TS, TT, VA, VR, VK | AG, CG, CS, IC, IF, IS, LA, LN, LC, LL, LP, TA, VN, VC, VE, VH, VI, VF, VY, VV | 0.16 |
| 286 + 287 | YK | AA, AE, AG, AM, RN, RD, RE, RS, HR, HG, HH, IP, LP, KA, SK, SS, TP, YN, YD, VP | AD, AP, AS, RA, RH, RP, HD, HE, HP, IR, ID, LE, KQ, FS, SR, SP, YA, YP, VN, VK | 0.16 |
| 162 + 170 | MK | AD, AS, RA, RD, DR, DK, QG, QS, ER, EK, GE, IE, LQ, KN, KE, MA, MS, FK, TQ, TK | AQ, RQ, RK, DE, DS, QQ, EA, EE, EG, ET, LD, LE, LK, KR, KQ, KK, KS, ME, TA, VE | 0.16 |
| 254 + 273 | MW | AQ, AM, AF, CY, IF, IT, IV, LL, FH, FW, PL, WP, YN, YE, YH, VR, VI, VF, VY | AE, AL, LH, LW, MN, ML, FE, FL, FM, FF, FS, FT, FY, FV, WW, YF, YW, VQ, VE, VW | 0.15 |
| 224 + 227 | HL | AA, AS, RL, RV, NI, NL, CI, HM, MA, FA, FL, FS, SR, ST, YH, YL, YM, VG, VV | AI, AL, NA, NS, CL, QL, GL, HA, HS, HV, LL, ML, FR, FG, FT, FV, SI, YF, YV, VL | 0.15 |
| 48 + 66 | TQ | AR, AK, AT, RE, DR, ER, EK, HA, HD, HL, LA, LS, KE, KL, KS, FH, TK, WG, VA, VR | AA, AG, AL, RR, RQ, RL, RK, QE, EE, HR, HE, HS, IA, KA, KR, KK, TR, TE, YR, YE | 0.15 |
| 290 + 291 | PK | AE, AP, RK, RP, NH, DG, DT, EP, ES, GY, LD, LP, KR, KP, PA, PE, SD, SL, TD | AR, AQ, AK, RA, RD, RQ, RE, DP, EK, GP, HP, KA, KD, KG, PP, SP, TR, TE, TK, VP | 0.15 |
| 240 + 243 | DT | AA, RA, NK, DD, QG, QT, EI, EK, GG, HA, HP, IR, LQ, MK, SP, TA, TR, TK, TT, VE | AK, AT, RR, RK, QA, EA, EE, EP, GA, GR, IA, IP, IS, LA, LK, KA, KK, SR, TE, VA | 0.15 |
| 163 + 166 | PE | RT, DA, DS, DT, QG, EA, GE, GG, HA, KD, KE, PR, PN, PQ, SD, SE, SK, TD, TQ, TE | DD, DE, DP, QE, EQ, GD, GQ, GS, KS, PD, PS, SA, SG, SP, SS, ST, TA, TS, TT, VD | 0.15 |
| 218 + 221 | NT | AL, NI, DR, CA, QR, ER, EL, IA, IC, IK, LA, LQ, LS, KL, MH, FA, SV, TV, VA, VC | AA, AR, AS, NR, CL, EA, EC, IQ, IL, IV, LR, LL, LV, KA, KV, ML, SA, SC, VL, VV | 0.15 |
| 221 + 247 | TI | AV, RI, RV, CI, GS, HI, II, LA, LC, LL, LM, LY, KI, MF, MY, PV, SA, SV, TV, VI | AC, AI, AL, AM, AS, NV, CC, CV, HV, IV, LI, LF, LV, KL, MI, MV, SI, TL, YV, VC | 0.15 |
| 175 + 179 | NN | AA, AD, AH, AT, RD, DT, QN, EQ, GA, GR, GN, LQ, LH, LL, KD, ML, SD, TA, VS | AN, AI, AL, RQ, ND, NQ, DQ, QA, QH, QL, GQ, GH, GI, LA, LD, LT, KN, MN, MD, TD | 0.15 |
| 216 + 265 | SF | AF, AY, DW, CF, QY, GF, HF, IV, LI, LT, LV, MI, ML, FV, SY, TL, YL, YF, VL | AI, AL, DI, DL, DV, QF, IT, LL, LF, LW, LY, MF, FL, FM, SI, SV, TY, YV, VF, VT | 0.15 |
| 236 + 239 | HE | AD, AG, DL, DS, DV, CD, QA, EA, ER, EQ, HD, LS, KE, PE, SN, SE, SS, VD, VK | AA, AR, AN, AS, NS, DD, DQ, DE, QE, EN, ED, GE, HR, KK, KP, PS, SA, SK, TE, VA | 0.15 |
| 164 + 168 | AY | AA, RL, CL, EA, GI, IM, IF, IY, LL, LF, LY, MF, FI, FL, FK, FV, PQ, SS, YL, YV | AL, AM, EL, LA, LR, LI, LM, LW, LV, ML, FA, FH, FF, FY, SL, TL, WL, YF, YY, VL | 0.15 |
| 248 + 250 | EV | AQ, AH, RE, RV, NI, DV, QR, QM, QV, ER, EI, HT, KI, SA, SQ, TQ, TK, TT, VE | AV, RA, RR, RH, RI, RK, RT, NQ, DH, DM, QQ, QE, EE, HQ, KK, FV, SI, TR, TV, VI | 0.15 |

TABLE Ts2-continued

| positions | most preferred | preferred, sorted in decreasing order of preference | to be avoided | score |
|---|---|---|---|---|
| 239 + 242 | ET | AA, AP, RR, RE, RK, DR, DM, DP, EA, ER, EK, GD, GK, KQ, KE, KL, PE, TR, TN, TT | AQ, AL, AK, AT, NR, NE, DA, DE, EN, ED, EE, EP, KA, KK, PK, PP, SR, SQ, TE, TK | 0.15 |
| 235 + 251 | PG | AA, AE, AT, AV, NC, DR, DN, DH, QA, EA, EP, ES, GQ, LQ, KE, KV, PP, SH, SV | AG, AP, AS, RA, DQ, DP, QP, EQ, EE, EG, LA, KA, KP, PR, PN, PH, PI, PT, PV, SG | 0.15 |
| 276 + 277 | AL | AD, AE, AS, DD, DK, QA, ER, EN, EQ, EG, EH, EK, ET, GR, GK, KY, MR, PV, SS, TA | AA, AR, DN, DQ, DH, DS, ED, EE, EY, EV, KA, KR, KK, KV, PR, PE, PG, PK, SK, TD | 0.15 |
| 327 + 329 | LG | AE, AG, RY, DT, CS, GS, GV, HS, IG, LA, MG, FA, FS, PA, PG, SV, TQ, TG, YA, VA | RA, RV, DA, CA, GG, HG, HT, IA, LR, LS, MA, MS, FC, FG, SG, SS, TA, TR, TS, WG | 0.15 |
| 181 + 182 | AM | CG, EH, EL, GL, GK, ML, FD, FL, PE, PG, SQ, SK, TL, WM, YL, YF, YV, VA, VL | AQ, AL, AS, AY, RL, DM, CL, QM, EM, GT, LQ, LI, KM, FM, PM, SI, SM, YQ, YI, VV | 0.14 |
| 151 + 153 | DG | AG, RH, NN, ND, NG, QQ, QY, ER, ET, GP, HR, KE, KG, KP, MK, SK, ST, TE, TI, TK | AN, AQ, NR, NE, DR, DE, ED, EH, GR, GK, HE, HK, KD, KK, SG, SH, TD, TG, TL, TP | 0.14 |
| 258 + 260 | VK | AE, QI, QV, IN, IQ, IS, LR, LE, LK, MQ, FA, FD, FT, PG, FG, PP, TL, WN, YD, VA, VS | QA, QN, QE, QP, QS, IA, IE, IV, LQ, LG, LI, LS, FQ, FG, FP, FV, WG, YT, VQ, VV | 0.14 |
| 244 + 245 | YH | AA, AG, RA, DG, DS, EQ, ET, HK, IK, IP, LE, LK, LP, KL, MS, PD, SH, TD, YI, VE | AP, RK, RT, NS, DD, DE, ED, EE, EP, HD, ID, IS, LD, KG, KH, KK, FS, TG, YP, VP | 0.14 |
| 298 + 300 | AC | AQ, AI, NI, NF, NW, CT, HF, IN, IM, IP, IS, IT, LR, LG, LS, FS, ST, TY, VA, VP | AR, AS, AT, NH, NP, NS, HT, IQ, IL, IF, IV, LI, LL, MH, FI, SA, SF, TM, VM, VY | 0.14 |
| 232 + 250 | FV | AE, RQ, CL, CK, QQ, QM, EI, EV, IE, LD, LI, LV, FA, FH, FF, SE, VR, VI, VL | QR, QH, QI, QL, QV, EQ, EE, EM, LQ, LE, LH, LM, LT, FE, FL, TV, YA, VD, VK, VM | 0.14 |
| 252 + 258 | GV | AF, AP, RA, RQ, NQ, DT, QN, QL, GI, GL, GF, GY, HQ, LA, KL, MP, YN, YQ, VA | AQ, AL, QF, QV, GA, GN, GQ, GG, GK, HI, HL, HF, HP, HS, HV, LQ, KQ, SL, TQ, YL | 0.14 |
| 220 + 227 | IL | AG, AL, CC, CV, IA, II, IV, LR, LL, LM, LF, MS, MY, FA, FH, FW, TV, WS, VS, VT | AI, AS, CL, IR, IC, IS, IW, LA, LG, LH, LI, LS, LT, LV, MV, FL, FM, WL, VL | 0.14 |
| 204 + 205 | ET | RN, DR, DV, EH, GS, HR, IE, LR, LK, KK, KT, FV, PL, PF, SS, TC, TS, VA, VM | AA, AD, AH, RR, RL, DL, DK, EL, ES, GR, LS, LT, KH, KL, KS, PS, PT, SK, TA, TT | 0.14 |
| 303 + 304 | SE | NQ, NE, DR, DD, DK, EH, EP, GR, GG, GT, HA, LP, KP, PE, PS, PV, SN, SD, VP | AN, AT, RE, DA, DE, DS, EA, ED, GD, GE, GK, GP, KE, PN, PD, PG, PH, PP, SP, TE | 0.14 |
| 348 + 349 | GF | NI, NV, DI, DY, DV, QV, EI, EP, EV, IE, IT, LR, LE, MT, SF, VR, VQ, VE, VS, VT | DR, DE, DK, DT, HV, IA, II, IF, IV, LL, LF, LT, LV, SE, VI, VL, VF, VP, VY, VV | 0.14 |
| 265 + 267 | FK | HG, IA, IS, LI, LL, LK, LS, MN, MC, FH, SG, TK, TF, TY, WR, WS, YR, VR, VG, VT | IR, LR, LQ, LG, LH, LF, MR, MG, MS, SK, SS, TR, TS, WK, YA, YF, YS, YT, VI, VF | 0.14 |
| 118 + 120 | TN | AA, AD, AE, RD, DR, CP, ED, IN, IG, LE, LK, LP, LS, KD, MS, SN, SP, TT, VG, VT | AG, AS, AT, RA, RN, RK, RP, DD, DP, CE, IP, LN, LD, LG, SD, SG, VD, VK, VP | 0.14 |
| 279 + 283 | LK | AA, RA, RL, DA, QD, ER, EH, GE, GG, IN, IK, LR, LG, KQ, KE, SQ, TK, VQ, VK | AK, RH, RK, RS, EQ, GR, GK, HR, IA, IG, LA, LQ, LS, LT, KR, KK, PR, VA, VN, VG | 0.14 |
| 60 + 79 | SV | AI, AF, AT, DV, CL, CV, QF, ES, GV, HM, IL, LL, FV, PA, PV, ST, TL, VA, VL | AL, DL, CT, QL, EL, GL, IA, IT, IV, LI, LV, FL, PL, SA, SL, TI, VI, VF, VT, VV | 0.14 |
| 35 + 139 | MM | AR, AK, AM, RW, RY, NS, DR, CQ, QW, QY, EK, GW, HN, LL, LS, KY, SV, YI, VM | AA, AM, AS, AY, RI, RK, RM, RV, QL, EW, EY, GA, GY, HW, LW, LY, KL, MY, SL, ST | 0.14 |
| 144 + 147 | FD | AQ, RD, RE, DG, QA, QH, ER, ES, ET, GA, GE, HR, HD, HE, KQ, KE, SQ, SS, YD, YS | AD, AS, RR, RS, RT, NT, DD, DQ, DE, CE, QD, QE, ED, EQ, EE, HA, HQ, HS, KN, SR | 0.14 |
| 265 + 266 | FM | AY, IN, IL, IV, LA, LL, MI, FF, FS, SA, TO, TI, TM, WI, YV, VL, VM, VS, VT | CL, IM, LM, LS, LT, ML, FL, FV, TA, TL, TS, WL, YA, YL, VC, VI, VF, VV | 0.14 |
| 151 + 152 | DG | AA, AK, RG, RL, NK, NP, DD, DP, QN, EP, GA, GN, GE, KD, KS, PA, PT, SG, TG, VS | AG, RD, NE, NH, ES, ET, GG, HA, LG, KR, KE, KG, KK, KP, PG, TA, TN, TP, TT | 0.14 |
| 250 + 260 | VK | AA, RD, RE, QT, QV, EA, ER, EH, EP, HD, IN, IG, LP, KS, MI, MV, SN, TV, VA, VQ | RA, QH, EE, EI, EK, EV, HS, IR, ID, IQ, LA, LR, LT, KP, KV, MA, VN, VE, VG, VV | 0.14 |
| 201 + 202 | SS | AG, AS, NQ, DK, DS, QP, EG, EI, ET, GQ, IK, KN, KD, PA, PD, PE, SA, SR, SP, VD | AR, AK, AT, RA, RS, DT, QK, EA, ED, GD, GG, KA, KE, KP, PR, PG, PP, SD, SQ, TR | 0.14 |
| 140 + 143 | EY | AD, RQ, RE, RL, DR, DK, QG, EN, EK, LH, KA, KD, KE, PN, PL, PM, PY, SP, TL, YE | AN, AE, AL, AK, AY, RA, RR, RH, RK, RS, DA, DD, DE, DG, QS, EE, KR, KT, PE, SD | 0.14 |
| 259 + 260 | PK | AD, RT, DG, QT, EN, GD, GE, GS, LG, LP, KN, FG, PA, PE, PI, PV, SE, SG, TR | AK, EE, GG, GP, LA, LR, LD, LE, LV, KI, PR, PN, PC, PG, PP, PT, SK, SV, TV, VD | 0.14 |
| 223 + 224 | KH | AG, AF, RH, RF, RW, RY, DH, QF, QY, EN, EC, ET, EY, GS, LN, LV, KY, SA, TH, VV | AL, AW, AY, RR, RQ, RL, RT, DN, DF, EH, ES, GF, GY, LH, LF, KC, KF, SH, SY | 0.14 |
| 297 + 341 | VA | AG, AF, AW, CM, HF, IC, II, IL, IV, LC, LI, LL, MA, FL, TM, TF, WF, VF, VY | AC, AL, AM, DF, CL, IA, IF, IW, IY, LA, LG, LF, MI, MM, TL, VC, VI, VL, VM, VV | 0.14 |
| 77 + 330 | VK | RD, RQ, RE, RI, DR, DK, EK, EP, HK, IT, KA, KQ, PR, PF, PS, SN, SK, TM, VL, VV | RR, RH, RK, RF, DA, DG, DI, DM, QK, EQ, EI, ES, HR, LK, KK, KM, PK, SR, SV, TK | 0.14 |
| 83 + 108 | CY | AI, AL, CA, CF, IR, II, IL, IV, LF, LW, LY, MF, MY, FL, TI, TL, YF, VI, VL, VV | AF, AY, CV, QY, IF, IY, LI, LL, LT, LV, MA, MI, ML, MW, MV, TY, YY, VF, VW, VY | 0.14 |
| 75 + 78 | AM | AR, AP, ND, DA, DI, DL, DK, QP, EL, HN, HS, HT, LR, KY, PR, PQ, PH, PV, SG | AS, NP, NS, DR, DD, DG, DH, DP, QA, EG, EV, HR, HL, HP, KA, PA, PL, PP, SK, SS | 0.14 |
| 47 + 118 | ET | AA, AD, AH, RA, RC, RI, NT, DR, DQ, DT, DV, QA, QG, EL, GV, HH, KA, SM, TD, TV | AR, AV, NL, DA, DN, DD, DG, DL, DM, DF, QR, EA, ES, EV, HV, KT, SR, TR, TL, TT | 0.14 |
| 176 + 180 | KS | AA, AR, AQ, AK, RG, RL, RM, NE, DR, QD, QE, QT, ER, EN, GC, HT, KD, PR, TQ, TL | AN, AE, AL, AM, RR, RN, RK, RT, NR, DA, DQ, DE, QQ, QG, QS, ED, EE, KR, KK, TA | 0.14 |
| 257 + 284 | SN | AR, AS, DR, DK, QT, ER, EL, EK, GE, IQ, LA, LQ, FK, PA, PQ, PE, PH, SI, SS | AE, DN, DH, EQ, EE, EH, ET, LN, LE, LH, PR, PI, PL, PK, SR, SQ, SK, TE, VE, VK | 0.14 |
| 179 + 240 | ND | AA, RA, NE, NS, DA, DR, DN, DT, QA, EL, GQ, GE, HL, HK, MM, SR, SQ, VA, VV | AH, NA, NR, NL, NK, NM, DD, DQ, DL, DV, QD, GR, GG, HT, IL, MV, SA, SE, SI, SL | 0.14 |
| 264 + 293 | IG | AG, RR, RQ, DN, GL, HG, II, LA, LK, FD, FC, FT, YA, YP, YS, YV, VR, VD, VG | AA, RG, RS, HA, IA, IR, IS, LS, FG, FS, WG, YR, YE, YG, YK, YT, VA, VK, VS, VT | 0.14 |
| 197 + 198 | YD | AG, CK, GG, GV, HD, IS, LN, LE, MP, FR, FD, FP, TG, TS, YP, VR, VN, VD, VT | AP, ED, GD, GP, HP, LG, KD, FL, FK, PD, TD, TP, YN, YE, YG, YL, VA, VG, VP, VS | 0.13 |

TABLE Ts2-continued

| positions | most preferred | preferred, sorted in decreasing order of preference | to be avoided | score |
|---|---|---|---|---|
| 215 + 300 | AC | AL, AF, AT, QT, ER, GY, HH, IV, LQ, LH, KS, MI, SN, ST, SW, SY, TF, VA, VM, VS | AN, AI, AS, AY, NF, QR, QH, HP, HT, IY, LP, LT, SS, SV, TA, TS, YF, VH, VL, VT | 0.13 |
| 192 + 196 | KL | AA, AD, AG, DR, DG, QN, ER, EL, EK, GD, HG, FY, PM, SD, SS, TD, TV, VL, VK | AR, AH, AI, AL, AM, NA, DL, ED, GK, HV, IA, IG, LG, FL, PD, SY, TG, VA, VR, VG | 0.13 |
| 47 + 119 | EK | AN, AD, AP, RV, DR, DQ, DH, DS, DT, EA, EP, GE, GP, HP, KD, SK, TD, TE, TK | AK, AS, RR, DN, DD, DE, DK, DP, DV, QT, ED, EH, ET, KR, SD, SG, TL, TP, TS, TT | 0.13 |
| 266 + 270 | ML | AI, AV, CF, IL, IT, LC, LI, LL, LV, MA, MM, FF, PP, SI, SV, TI, WL, YA, YF | AL, CL, CV, II, IM, IF, IV, LA, LF, LP, MI, MF, FI, FM, FT, FV, SL, TF, YL, VA | 0.13 |
| 215 + 218 | AN | NV, DV, QI, QV, EG, EL, GL, HA, HM, IN, IS, LI, KR, MS, SA, SY, TS, YF, VD, VT | AI, AM, RL, DR, QS, HR, HQ, HG, HS, IE, II, IV, LV, FA, SK, SM, SS, VA, VI, VL | 0.13 |
| 332 + 340 | RL | AC, RI, RV, QV, EW, HW, II, LA, LM, KI, ML, FL, PA, PQ, WF, YM, YF, YW, VE | RA, RR, RK, RS, RT, RW, RY, DL, QL, HL, IL, LI, LL, LW, KL, FM, WI, YR, YL, YV | 0.13 |
| 239 + 243 | ET | AA, AR, AE, NA, ND, DP, QS, ER, EQ, EG, EH, EK, IK, LE, ED, KE, KT, PA, SS, TE | AQ, AK, AT, AV, RA, NR, NQ, NK, DA, DE, DS, QE, EA, EE, KP, PD, PK, SA, TK | 0.13 |
| 62 + 65 | EA | AE, AT, NS, NT, DA, DR, DK, DS, QD, QQ, QE, EQ, EG, EK, EV, HR, LE, KA, SG, VE | AG, AK, NA, DD, DQ, DE, DG, QA, QR, QG, QH, QL, QK, QS, EE, EM, EP, ET, KE, TR | 0.13 |
| 216 + 267 | SK | AR, DH, DK, QR, HS, IS, LS, MS, MT, FG, FI, SR, TR, TE, WA, WG, YN, YS, VR, VC | AA, AS, NR, DR, QK, LR, LE, LI, LF, MG, FR, FS, SS, TS, WS, YR, YC, YK, VA, VK | 0.13 |
| 300 + 321 | CI | AH, RA, RH, NI, QQ, QT, GC, GS, HT, IM, ME, ML, FQ, FM, PF, SN, SV, TI, YT, YY | AN, AF, RN, RS, GA, GL, IN, IH, MI, MF, MT, FA, FS, SL, TF, YM, YS, YV, VL, VT | 0.13 |
| 203 + 263 | LA | AI, AV, RI, RV, DV, GY, GV, HL, IA, ML, FA, FC, FL, SI, ST, YI, YL, VG, VL | AA, AC, AL, NA, DA, DI, CV, GA, GL, IV, LV, KL, MV, FI, FT, FV, SL, TL, YV, VI | 0.13 |
| 257 + 258 | SV | AV, NI, EQ, EI, EL, GV, HI, IP, LA, LD, KN, FI, PN, PQ, PL, PF, PY, TI, VP | AI, DQ, DW, EY, EV, GQ, LL, LF, PA, PI, PK, PP, PS, PT, PV, SA, SQ, SP, TL, VF | 0.13 |
| 198 + 202 | DS | AA, NA, NT, DR, DQ, DG, DK, DP, ED, EP, GE, GG, KN, KE, PD, PQ, PE, SG, TG | AG, RE, RK, NP, DN, DD, DE, DH, DT, EE, GR, GQ, GS, KP, PR, PN, PG, PK, PP, SA | 0.13 |
| 131 + 133 | LN | RG, NI, QN, QV, EA, EN, EQ, EF, GY, GV, LR, LE, LH, ML, FN, FV, PA, SI, SP, VM | AN, RN, RF, QQ, QL, ES, EV, GA, GG, II, IM, LI, LL, LF, LV, KQ, FL, SQ, TA, VV | 0.13 |
| 334 + 335 | EK | AE, AS, RA, RE, QS, EA, ER, EQ, EM, IG, LD, LP, LT, KK, FN, FG, FP, PS, VL | AK, RD, RG, QK, ED, EE, ES, GS, LA, LR, LQ, LE, KA, KG, FA, PD, SE, SS, VA, VR | 0.13 |
| 59 + 62 | SE | AD, AE, RD, DG, DS, DT, GE, HQ, HL, KD, PR, PK, SN, SD, SQ, TA, TQ, TE, TK, TS | AQ, NE, DD, DQ, DE, DK, EE, GQ, PD, PE, PG, SG, SK, ST, TR, TN, TD, TL, TT, TV | 0.13 |
| 213 + 240 | TD | RD, RG, RF, NR, DR, ER, HA, HE, HS, IQ, LL, LK, MK, PV, SI, TQ, TV, YR, YN, VQ | RR, RQ, RI, RK, RT, DE, HQ, HI, IV, PA, SA, SE, SH, SF, TR, YL, VG, VS, VT | 0.13 |
| 279 + 344 | LA | AR, RC, RE, RV, DH, DY, EQ, EV, IA, IC, IS, KI, KT, KV, MA, SN, TA, VA, VS | RA, RH, DA, DS, DV, QA, GA, HS, IH, IT, LC, LT, KA, KH, PA, SA, SV, TS, VI, VV | 0.13 |
| 232 + 258 | FV | RQ, CF, QN, QQ, QS, EQ, HV, IW, LD, LW, LY, MP, FI, FL, YF, YV, VL, VK, VM | CL, QI, QL, QF, QV, EL, IQ, IV, LA, LN, LQ, FA, FN, FQ, FF, FW, YQ, VQ, VW, VV | 0.13 |
| 38 + 42 | KE | AR, RQ, RE, RG, RH, RT, NK, DQ, QK, EK, GR, GD, HA, HV, LE, KD, ME, YK, VN | AQ, AK, RR, RN, RD, RK, DD, DE, QR, QE, EE, GE, HR, HD, KR, KK, MD, TE, YE | 0.13 |
| 58 + 66 | LQ | AR, AD, RE, RI, RV, NA, CR, IK, LR, LN, LT, KE, KL, MA, ME, SG, TA, VA, VK | AI, RR, RK, CA, QE, IA, IE, IL, IV, LA, LD, LE, LL, KQ, KH, KK, MS, MT, SA, VR | 0.13 |
| 268 + 300 | WC | AV, RM, RF, NI, NY, DP, QI, QS, EE, HL, LQ, LF, MI, FR, FC, FV, SR, SF, TI, WA | AR, AF, RI, RY, RV, NR, DG, QM, HR, HE, HI, LL, LY, MF, FM, FF, SQ, SH, SV, WI | 0.13 |
| 231 + 249 | NH | AV, ND, NE, CF, GI, GL, GF, IL, LR, LC, LI, LK, LP, LT, VA, VF, VW, VY, VV | AF, NA, NI, NL, NF, NV, GA, GT, GV, LH, LF, LW, LY, VR, VC, VE, VH, VI, VL, VK | 0.13 |
| 224 + 225 | HT | NR, NP, DA, EP, GE, GF, HA, HR, HS, LK, LS, MD, FP, SL, SS, TK, YG, YP, VE, VG | ND, NQ, NG, DP, GP, HE, KP, FA, FR, FE, FK, FS, SP, TP, YA, YR, YN, YK, YS, VP | 0.13 |
| 306 + 307 | PD | AG, RR, RT, RV, NP, QD, EQ, GA, GT, ID, LE, LG, LK, PA, PE, PL, PW, SS, VE, VG | RA, RD, RE, RG, NG, NS, DK, GR, GN, GD, GE, GP, KG, PG, PP, PT, ST, TA, VA, VS | 0.13 |
| 269 + 272 | ID | AH, AF, NY, ON, IG, IS, LH, MM, FC, FH, FM, PS, SH, TN, YL, VD, VE, VG, VV | AG, CD, CH, IQ, IE, IH, IT, IV, LN, LD, FD, PD, SN, SD, TD, VC, VH, VM, VS, VY | 0.13 |
| 238 + 239 | IE | AA, AP, CQ, CV, QQ, EP, ES, IN, ID, IS, LD, LK, LP, MI, TN, VA, VR, VL, VS | AD, AQ, AS, CA, CP, EE, IA, IR, II, IL, IP, IT, LR, LE, LS, LV, VD, VH, VI, VP | 0.13 |
| 218 + 244 | NY | AH, AL, AF, AT, RH, DR, QI, ER, EK, IR, IN, IK, IP, IV, LQ, KH, MF, MV, YQ, VP | AR, AP, RR, NR, QR, QL, EF, ID, IQ, IE, IH, II, IL, LV, KF, MA, MP, TR, VH, VY | 0.13 |
| 283 + 287 | KK | AR, RG, RP, RS, RT, NN, NK, DE, QL, ER, GD, HE, KA, KD, KE, KP, SA, SD, TH, TK | AD, AS, RR, RK, NA, ND, DA, QA, QR, ED, EE, GQ, GP, KR, KT, SE, SP, TR, TP | 0.13 |
| 76 + 77 | PV | AA, AP, QR, QS, ER, EQ, EH, EK, EF, GM, LI, PA, PD, PE, PP, PS, SR, TA, VA, VL, VT | AR, AL, EA, ED, EE, EG, EI, ET, GD, LD, LE, PR, PG, PQ, PS, SN, SE, SG, TF | 0.13 |
| 88 + 89 | SY | AA, AN, AI, AM, AF, AS, DL, CG, QR, GL, GM, PY, SC, SI, ST, SV, TQ, TL, VN, VS | AR, AL, AK, AT, AY, AV, NL, GV, IL, SN, SG, SL, SF, SS, TE, TI, TM, TT, VA, VL | 0.13 |
| 179 + 213 | NT | AA, AP, NI, NL, NK, DR, DN, DD, QE, QP, ED, GI, GV, HR, LT, KH, SN, SE, SK, TS | AR, AN, AI, NN, ND, NS, DG, DH, DS, DV, QR, ES, GR, GS, HT, IT, LH, SA, SQ, SH | 0.13 |
| 271 + 331 | HE | AV, RE, DM, QA, GL, HC, HQ, HT, LR, LL, MS, PG, SH, SS, SW, TP, YA, YF, VI | AE, DE, QE, EE, GE, HR, HH, HI, HM, HP, HS, HW, HV, LE, ME, SA, SE, SL, YE | 0.13 |
| 105 + 106 | ER | AA, AG, AH, RA, RD, NN, NQ, NS, DQ, DG, EI, GD, GE, GK, HG, KE, PN, PE, PG, SA | AN, RG, NA, NE, NG, DR, DN, DD, DE, DK, EG, GN, GG, GI, KG, PA, PD, TD, TG | 0.13 |
| 201 + 203 | SL | AG, RA, RL, NG, DD, DV, QG, QL, QV, EG, GK, GY, KS, PA, PR, PK, SF, SY, TA, TD | AF, AY, RP, NL, DA, DG, DK, QF, EA, ES, GL, PD, PF, PY, PV, SA, SN, SE, SG, TF | 0.13 |
| 203 + 294 | LK | AS, RL, RV, DR, CK, GR, GQ, GT, HT, IK, KL, KS, FA, FG, PT, SK, TR, YA, VR | AR, RK, DL, DV, EK, GK, GV, HK, IR, KK, FR, FL, PR, PL, SR, YR, YL, VA, VS, VT | 0.13 |
| 254 + 269 | MI | AL, AM, AF, AS, DP, CF, II, IV, LA, LV, MV, FC, FI, PS, SL, SP, YS, YT, VA, VF | AI, AV, CV, GI, IS, LC, LM, LS, MF, MS, FL, FM, FF, FS, PI, YA, YI, YF, VI, VV | 0.13 |
| 57 + 109 | SG | AR, DR, QA, QK, ER, GA, GH, GF, GT, KQ, PA, PE, PL, PT, PW, PV, SI, SS, TR, VK | AA, AK, RK, QS, EE, GR, GQ, GG, GK, GS, KR, KT, PR, PK, PF, PY, SF, SV, TT, VA | 0.13 |

TABLE Ts2-continued

| positions | most preferred | preferred, sorted in decreasing order of preference | to be avoided | score |
|---|---|---|---|---|
| 205 + 261 | TG | AK, RG, RF, RS, RY, NF, NY, EF, EY, HA, LA, LK, LV, KN, KF, KY, SA, SH, TA, VA | AA, RA, RC, RP, NA, EA, HG, HF, LF, LY, KA, KG, KV, MA, SG, SF, TF, TY, VF | 0.13 |
| 44 + 48 | DT | RH, RL, NI, NL, NF, NT, DK, DW, QR, QC, ER, GA, GQ, GE, GK, GM, GS, GV, KI, SH | RA, RE, RT, NA, NR, NQ, NK, DH, DL, DF, QA, EA, GC, GH, GI, GP, GT, GY, KR, KE | 0.13 |
| 298 + 321 | AI | AT, NI, NM, CA, CQ, GG, HA, HN, IL, IF, LR, LV, MQ, MV, ST, TY, YK, VN, VE, VH | AM, NN, NQ, NE, NG, CL, CV, HL, HF, IQ, IG, IS, IT, MA, MN, MH, SH, SL, VA, VM | 0.12 |
| 179 + 183 | NF | AQ, AE, AG, NA, NK, NT, DS, QR, QM, ET, GQ, HS, HV, IH, LN, KS, PR, TE, YA, YD | AD, AS, ND, NG, NH, NS, DG, DH, QA, QD, QH, GA, GE, GS, HR, HQ, HK, LS, SN, TT | 0.12 |
| 264 + 285 | IC | AL, AV, CI, HS, IA, IL, IM, LA, LF, FI, FL, FV, SC, YQ, YH, YI, YV, VA, VI | AA, AC, HA, HI, HV, II, IS, IV, LI, LV, FA, FC, YA, YM, YF, YS, VC, VL, VF, VV | 0.12 |
| 120 + 122 | NS | AG, AP, RS, NE, DH, DM, ES, GR, GK, GP, LG, KS, PA, PI, PF, SG, SS, TA, TD, TS | AA, AH, NA, DD, DG, DL, DK, DS, ER, EL, GS, PD, PE, PG, PP, PS, SN, SH, TG, TH | 0.12 |
| 243 + 244 | TY | AA, AK, AV, RR, RT, DL, DV, QA, QR, EL, EF, KT, PI, PL, PV, SL, TF, TS, VD, VP | AI, AL, AF, AP, AT, RG, RF, RS, RY, EP, ES, ET, EV, GR, GL, KA, KR, KP, TA, TL | 0.12 |
| 174 + 175 | FN | AA, AN, AT, RA, RL, NL, DF, QA, EG, GL, GM, LQ, LG, LS, KA, FD, FS, SL, VH, VY | AG, AL, AK, AS, AW, RD, RG, RS, DL, QE, QS, EA, ED, LA, LL, LF, KN, MQ, FL, FV | 0.12 |
| 171 + 174 | DF | RM, RV, NA, NL, DA, DR, DL, QL, QV, ER, EF, GY, HE, HK, HT, KY, PR, SE, SH | AA, RR, NM, NS, DN, DD, DE, DH, DS, DV, QA, GR, GL, HA, HL, KR, FL, PL, SY, YA | 0.12 |
| 35 + 38 | MK | AR, AN, AQ, RH, RL, RM, QH, QF, QY, IR, LE, LG, KL, KF, MR, FK, PT, SK, VR | AL, AF, AY, RR, RK, RF, RT, QR, QK, EL, GL, LY, KR, KQ, KK, KY, PR, SQ, VH, VK | 0.12 |
| 196 + 305 | LA | AD, AG, AI, RE, NE, DN, DT, EA, EE, EK, GA, HH, HT, LQ, LK, LP, SM, ST, TQ, VR | AE, AL, AK, AS, AT, RR, RD, NA, DR, DD, EN, GR, GQ, GK, HG, LE, LT, SG, VD, VT | 0.12 |
| 83 + 92 | CL | AL, CN, EM, EY, GL, IM, IF, IY, LI, LV, MA, MF, FH, FI, FL, SL, TA, YM, VL | AF, CF, CV, EF, IL, IV, LA, LN, LL, LM, LF, LY, MI, ML, FF, TF, YL, YF, VA, VV | 0.12 |
| 234 + 236 | LH | AG, RQ, RE, DR, QH, IS, LQ, LG, LP, LT, KD, FD, FE, FK, PA, SD, TA, WN, VD | AE, RN, RG, RH, RK, NE, QD, QE, IH, LA, LR, LN, LD, LI, FA, FH, FS, PP, TH, WE | 0.12 |
| 283 + 343 | KA | AA, AG, AT, RD, RQ, RE, QD, QQ, ER, ES, GR, GS, HK, IR, LS, KQ, KE, SK, SP, TA | AQ, AE, RG, RK, RS, NE, DA, DE, QR, QE, EQ, GD, HA, KR, KD, KK, KP, SR, SE, SS | 0.12 |
| 222 + 228 | SK | AR, RS, RT, NS, DA, DE, DT, EA, ED, EE, EP, GR, HR, LT, KN, KQ, KK, KS, TR | AE, AT, RA, RR, NR, NN, NE, DQ, QR, EN, ES, LR, LK, KR, KD, KE, KP, KT, SQ, TK | 0.12 |
| 201 + 204 | SE | AQ, AL, RD, NN, ND, DQ, DT, EI, ES, EV, GT, KG, KK, KV, PA, PG, SQ, SK, SS | AS, AT, RK, RS, NR, DP, QK, EA, EG, GQ, GG, KA, KP, PD, PT, SA, SD, SV, TA | 0.12 |
| 195 + 215 | DA | AQ, AS, RA, DH, DL, DP, QY, EQ, EG, ET, GH, HA, HN, KA, PL, PV, SF, SW, TA, TS | AL, AT, RV, NA, DD, DQ, DG, DV, EA, EE, EH, EF, GS, KG, SA, SQ, SH, TH, TT | 0.12 |
| 241 + 249 | AH | AN, AI, AF, RF, NE, GF, GW, IR, IP, LL, FF, SK, SW, TL, TT, TV, YF, VA, VL | AA, AD, AG, AK, AP, AW, NF, GA, GI, GT, GV, IL, IF, IY, LF, LV, FL, SF, TF, VF | 0.12 |
| 77 + 81 | VR | AA, AR, AK, AS, RA, RE, RI, RV, DR, DP, QL, ER, GR, HD, HQ, PD, SS, TQ, VL, VK | AI, AV, RR, RK, DA, DD, DQ, DK, DS, QA, QK, EA, ED, EQ, GS, HR, IR, TR, TS, YR | 0.12 |
| 236 + 251 | HG | AG, AH, AN, AP, ND, DS, QG, EA, EP, GQ, EN, GD, HA, HV, KA, PQ, PK, PV, SA, TE, VQ | AA, AE, NE, DA, DE, QQ, QV, EN, ED, GS, GV, HP, HT, PR, PG, PI, SE, TP, TV, VP | 0.12 |
| 176 + 244 | KY | AQ, AE, AT, RG, RH, RI, RL, DR, DQ, DI, QK, EN, EE, GA, GR, GT, IL, KA, KD, | AA, AG, AL, AK, AM, RN, RD, RF, RT, RY, DE, DL, QR, QL, EH, EP, KQ, KK, KT, SA | 0.12 |
| 300 + 327 | CL | AG, AM, QI, QF, QV, EP, GL, GM, ID, LC, MN, MG, FP, FY, PR, PQ, SS, TT, YY, VQ | AF, CF, QT, LR, LL, KL, MA, MC, FH, FM, FT, PL, PF, SM, SF, YG, VR, VG, VF | 0.12 |
| 119 + 120 | KN | AD, RN, RD, DA, DP, QP, ER, EN, EG, GA, GN, IP, LP, KD, PG, SD, SS, ST, TT | AN, RP, DG, DS, QD, EA, ED, EP, GD, GG, LD, KR, KT, PP, PT, SN, SE, SP, TN, TP | 0.12 |
| 240 + 242 | DT | AP, RR, NS, DK, QR, EG, EV, GD, GE, HR, HQ, IQ, IE, IK, LR, KT, FD, SF, TA, VR | AK, RK, DR, DD, DE, QQ, QE, ER, ED, EL, GR, GP, HE, HK, IR, IT, LP, SE, SK, TR | 0.12 |
| 226 + 242 | ST | AR, RR, RQ, NE, NK, DN, DI, DT, EK, GM, GV, HP, HT, LK, KN, KK, KS, SS, TA, TN | AA, AQ, RE, NR, ND, NV, DR, DK, DV, QK, EA, ER, EP, GS, GT, HK, HS, KQ, KP, SE | 0.12 |
| 131 + 177 | LV | AG, RI, RV, ND, DS, DV, ER, GA, GR, LN, LQ, LL, MG, MI, ML, PA, SI, TS, TT, VL | AL, RR, RN, RQ, DL, QN, EL, ET, GL, GT, HA, IR, LE, LG, LS, KR, MR, SL, TV | 0.12 |
| 273 + 281 | WV | AM, AF, RV, EL, IL, LA, LL, LT, MA, MV, FA, FI, FF, FV, PK, WI, WL, YM, VA, VF | AL, RI, EI, EV, II, IF, IV, LI, LM, LF, MI, ML, FL, FS, WA, WE, WM, YA, VL | 0.12 |
| 63 + 79 | LV | AA, AT, CL, IA, IE, II, IL, IF, IP, LR, LC, LE, LT, ML, FT, FV, PA, SL, SM, VA, VT | AI, CA, FI, FL, VI, VL, VP | 0.12 |
| 178 + 182 | FM | AF, EK, GI, HI, IS, LL, FV, SQ, TT, WT, WV, YD, YQ, YG, YF, YW, VC, VL, VF | AM, RM, EM, HM, IM, LQ, ML, FA, FG, FI, FK, FF, FS, FW, WL, WM, YA, YL, YV, VM | 0.12 |
| 180 + 185 | SH | AA, AG, AF, RQ, RM, RF, NY, NV, DR, DD, QR, QE, QI, EV, GL, IS, KI, KT, SA, VW | AI, AL, AW, AV, RR, RD, RY, DM, DT, QL, QW, ER, EF, LL, KR, KN, KQ, KF, SV, TF | 0.12 |
| 215 + 244 | AY | AF, NH, DA, DP, GR, GG, GV, HL, LN, LF, LY, ML, FK, PK, SK, SY, TR, TT, YQ, VD | AE, AT, RL, QF, GK, HR, HH, IK, LR, LI, LK, LP, SD, SE, SF, TL, TF, VP, VS | 0.12 |
| 239 + 251 | EG | AA, AR, AD, AG, AL, RA, RE, DK, QI, QP, EA, EP, ES, EV, GA, KE, KL, PA, PG, TP | AK, AP, AS, AV, RG, RP, RS, NA, DE, QA, QS, ER, EQ, EE, EI, EL, GP, KP, KT, PE | 0.12 |
| 159 + 160 | AY | AN, AC, AM, AF, AV, RA, RD, DM, EL, GH, LR, LG, LT, KH, PA, SL, TK, TF, VH | AA, AD, AG, AK, AS, NL, DF, QF, EH, ET, GN, GF, LH, KF, PH, SF, TT, TY, VR, VG | 0.12 |
| 267 + 268 | KW | AR, RF, RY, ND, QK, EA, ES, GH, GF, HS, ID, KH, KS, KY, SR, SN, SQ, SL, TN, VD | AA, AD, RN, RK, RS, CH, GR, GN, GD, GQ, HR, KR, KK, FS, SD, SE, SH, SS, SW, TA | 0.12 |
| 139 + 143 | MY | AD, AV, NA, QT, GR, LN, LQ, ML, FE, SE, TH, WG, WP, WS, WT, YG, VA, VF, VP | AN, AG, GE, IG, LA, LG, LS, KA, MA, FT, SG, WA, WR, WQ, YH, YT, YV, VG, VL, VS | 0.12 |
| 245 + 305 | HA | AA, AR, AT, RS, DR, DN, DP, ET, GA, GN, GP, HD, KI, PE, PY, SD, SP, TT, WA, VG | AN, AD, AP, RD, NE, DA, DK, QA, QD, EI, EP, GR, GD, GG, HE, KP, KT, PN, PT, SA | 0.12 |
| 183 + 213 | FT | AA, AT, RD, RM, NG, NS, DR, QR, QP, EN, EK, HS, HT, SD, SE, TQ, TE, TH, TV, VL | AQ, AV, RK, RY, RV, DH, DT, QH, QT, QV, ED, GS, KK, ST, SV, TP, TT, VN, VS, VT | 0.12 |
| 280 + 284 | QN | AR, AT, RA, RE, RS, DG, QR, QD, QT, EK, GR, GH, IH, IK, LN, KN, KQ, MK, FK, TN | AN, AG, AH, AK, RK, RT, NK, QK, EQ, ES, GN, HN, IN, LR, KR, KE, KH, TA, TQ, TE | 0.12 |

TABLE Ts2-continued

| positions | most preferred | preferred, sorted in decreasing order of preference | to be avoided | score |
|---|---|---|---|---|
| 204 + 248 | EE | AQ, AE, AL, RR, RG, DK, ET, GN, GD, GT, GV, HR, LE, MR, PR, SS, ST, TE, TH, VE | AR, AK, AT, RQ, RE, NT, DR, DE, QT, ER, EN, GA, GE, GH, KN, PE, SR, TD, VS | 0.12 |
| 80 + 108 | DY | AI, AY, RY, RV, DL, DT, QF, EA, EY, GF, GW, HY, LF, LV, KY, ML, FF, SA, TI, YF | AF, AV, RI, RF, DF, EI, EW, EV, GI, GY, GV, HV, LY, KF, KW, FY, SF, TL, TF, YY | 0.12 |
| 196 + 197 | LY | AL, AV, RL, DM, DF, DY, CV, QL, EI, GF, GY, HH, HP, LA, LG, LK, FV, TI, VL, VY | AG, AP, QF, QY, EF, GI, GL, GV, HL, HY, IV, LI, LF, KV, FY, SA, WY, YL, VF | 0.12 |
| 122 + 124 | SV | AI, RD, DR, DP, QG, GA, HQ, HL, HS, LA, KS, KT, PS, SQ, SF, SW, SY, VD, VG | AH, AS, RA, DD, DE, DG, GE, GG, GP, HD, HG, PG, PL, SD, SG, SL, SP, SS, VE, VS | 0.12 |
| 250 + 252 | VG | AV, RG, QG, QH, QY, EA, EY, IG, LR, LQ, LL, KL, MH, MI, FE, TH, VA, VE, VS | RA, QQ, EG, HH, IQ, IE, IV, LG, KG, MG, ML, FH, SG, TG, TY, YG, VH, VL, VK, VY | 0.12 |
| 174 + 183 | FF | AT, RR, RD, RQ, RK, QA, EV, GR, GY, HE, IS, LA, LT, KE, KG, KS, FA, YK, VR, VQ | AA, RN, RG, RS, RV, QQ, QS, EA, EE, IA, LQ, LH, KA, MT, FE, FK, FS, YA, YR, YQ | 0.12 |
| 218 + 245 | NH | AR, AK, AF, RQ, NP, EA, EP, GP, HS, ID, IE, II, LW, LV, MG, MT, MW, SG, VD, VE | AS, RR, RN, NE, EG, IG, IK, IP, IT, IW, LA, LE, KD, MA, FD, SA, SQ, SK, VK, VP | 0.12 |
| 300 + 330 | CK | AR, AK, RG, RS, CC, QK, GQ, HR, HE, IK, LR, MM, FD, FL, FV, PH, SR, TT, YH, VR | AE, AG, RK, GR, HK, HM, IR, IF, MG, ML, FA, FR, FT, SK, TR, TH, WK, YR, VI, VK | 0.12 |
| 146 + 150 | KL | AR, AK, RD, DE, DK, ER, HL, LR, LT, KQ, KV, PA, PL, PK, SN, TR, TL, YK, VR, VQ | AQ, RR, NR, DQ, QR, EE, ES, EV, HK, LE, KR, KK, KT, PR, PD, SE, TQ, YR, VD, VL | 0.12 |
| 274 + 300 | SC | AQ, AG, AT, RW, NR, NV, DF, DP, QM, EQ, GP, PN, PH, PL, PS, PT, SP, SY, SV, TI | AP, AS, NW, NY, DR, DQ, DT, GA, GR, PQ, PF, PP, PW, PY, PV, SN, SL, SK, SM, TV | 0.12 |
| 336 + 339 | EA | RD, RQ, NE, NG, DA, DR, DN, QA, QQ, QT, ED, ET, EY, GA, GK, KE, ME, TS, VE, VK | RA, RR, DD, DQ, DE, DT, QR, QG, QK, QS, ER, EQ, EK, GQ, GE, GG, HA, KR, SD, VA | 0.12 |
| 144 + 146 | FK | AP, RG, NK, NT, DV, QA, EP, GA, GR, GL, HA, HE, KD, KP, FR, FE, SL, TP, YK, YT | AA, AE, AK, RA, RS, RT, NP, DE, DP, QV, EG, GD, GP, KA, KT, FP, SE, YL, YP, YV | 0.12 |
| 304 + 334 | EE | AE, NK, DK, DP, DT, DW, QF, EL, EP, EV, GK, LL, PA, PS, SR, SE, TE, YR, YL | AI, AK, DA, DD, DE, DY, DV, ER, ED, EK, ES, GL, KR, PL, PF, PP, SQ, SI, SS, YE | 0.12 |
| 115 + 339 | KA | AA, RA, RG, RL, QQ, QE, EN, ET, GE, LK, KN, KD, KQ, KK, PE, SK, SS, TA, TE, VS | AH, AK, AS, RN, RD, RK, RT, DA, QA, QN, QK, EQ, EK, LA, KR, KE, KG, PA, TD | 0.12 |
| 318 + 321 | II | AQ, RT, QN, IL, IM, IF, LQ, LT, MN, MI, MS, MT, FH, FI, FY, PL, SN, WH, VA, VE | RI, RL, IN, IQ, LN, LI, LL, LF, MA, MQ, MH, MM, MV, FN, FD, FF, FS, TT, VN, VT | 0.12 |
| 240 + 318 | DI | AV, RR, RS, NM, NT, DT, QV, EV, IW, LQ, LL, LY, KI, ML, PL, SL, TA, VH, VL, VF | AL, AF, RL, RF, NV, DM, QL, QT, ES, HF, II, IV, LR, LI, LM, LV, KL, SY, VA, VS | 0.12 |
| 301 + 337 | IF | AY, DL, CF, CY, IT, IW, IV, LL, LM, LF, KA, MV, FF, FT, FV, PY, YI, YW, VW | AL, AF, NW, DY, CL, HY, IA, IY, LH, LT, LW, KF, MW, FL, WL, TF, YF, VL, VM, VV | 0.12 |
| 270 + 278 | LC | AN, AL, AF, CN, CT, QR, IA, IK, IS, LA, LR, LQ, LK, LM, MC, FC, FV, PL, VV | AA, AC, AK, CV, IR, IC, IQ, IL, IV, LN, LD, LL, LT, MS, FA, FR, FI, FK, TA, VC | 0.12 |
| 266 + 285 | MC | AI, AY, NY, CL, CM, CV, IA, II, LC, LL, LV, MT, FA, FQ, FT, SI, TI, YS, VC, VI | AA, CA, CC, CI, IC, IV, LQ, LM, LF, LT, LY, ML, FC, FI, FL, FV, SA, TV, YI, VA | 0.12 |
| 268 + 342 | WK | AN, AQ, AV, RD, RS, NI, DR, QD, QK, HA, HR, HE, LK, LP, KS, MD, FE, SR, SE, SK | AE, AK, RR, RT, NA, NE, DD, DE, QA, HS, LE, MR, ME, FR, FK, SA, SS, ST, WA, YS | 0.12 |
| 260 + 261 | KG | AA, AP, RY, NI, DN, DG, QV, EC, EF, GG, GY, IA, LV, KA, PA, SY, TG, TF, VA, VQ | AH, AV, RA, NA, NF, DA, DF, DY, EA, EK, GA, IG, KP, PG, PY, TA, VG, VF, VP, VV | 0.12 |
| 263 + 296 | AI | AL, AY, DY, CF, IM, IV, LA, LC, LM, LV, KI, FL, SI, TI, WT, YL, YS, VV | AA, AV, RI, DL, CL, IL, LI, LF, LS, LY, KL, FI, SV, WL, YV, VL, VM, VF, VS, VY | 0.12 |
| 183 + 185 | FH | AN, AD, AE, AG, AH, AS, AT, RS, RV, DV, EV, GA, GF, GY, HR, MQ, SF, SY, YH, VW | AA, AQ, AK, AF, AY, AV, RH, RF, RW, NA, QT, GQ, GS, HN, HT, SG, SS, ST, TN, TH | 0.12 |
| 238 + 242 | IT | AR, AE, AG, RE, RL, CE, QE, EH, GL, IR, IK, IP, LR, KE, MA, FS, VI, VK, VY | AD, AL, AK, RR, RK, QK, EE, IA, IE, II, IL, LL, KK, SE, TE, TP, VR, VE, VG, VH | 0.12 |
| 285 + 287 | CK | AQ, CN, CE, IN, ID, IG, IK, IT, LD, LP, MR, FE, FL, SE, TA, VA, VR, VQ, VS | AP, CG, CP, IA, IR, IQ, IL, IS, IV, LA, LR, LQ, LE, LK, FR, TD, TP, VD, VG, VP | 0.12 |
| 255 + 277 | FL | AI, RD, RE, NN, QE, EA, EK, EV, LE, LM, LT, MI, FD, FQ, FK, FS, FY, SR, WK, YL | AD, AR, RR, DD, DE, ED, EE, EG, ET, LR, LL, LK, MK, FI, FM, FT, FV, YD, YE | 0.12 |
| 50 + 58 | AL | AR, RV, DT, DV, QQ, ED, ET, GA, GH, GK, HA, HM, LM, KM, PI, PV, SV, YA, YR | AA, AM, AT, AV, RI, DK, DM, EL, EV, GQ, GI, GM, LA, LV, KL, PL, PK, SI, TL, VR | 0.12 |
| 215 + 219 | AM | AR, AQ, AG, RE, DD, EQ, QR, GR, GH, HA, HK, IT, LM, LF, MA, FE, SA, SI, TK, YK, VE | AK, AT, RT, NE, DR, DE, DL, EA, GA, GL, HG, HI, IA, LE, FA, SD, SE, TQ, TS, VK | 0.12 |
| 171 + 173 | DR | NQ, DA, DN, DG, DK, DV, QG, QK, EF, EP, HD, HE, MA, MD, MQ, FK, SR, SE, TE, YS | RG, NG, NH, DD, DE, DL, QA, EE, HA, HR, HN, HT, KK, ME, FA, PD, PE, SA, SV, TQ | 0.12 |
| 213 + 216 | TS | RL, DI, EL, GV, HF, HY, IS, KA, KD, MA, PV, SL, SF, SW, SS, TL, TM, TT, TW, VV | AF, RQ, RI, RT, NS, DY, HL, IV, LL, KF, PF, SA, SM, SN, SV, TD, TY, TV, VL, VF | 0.12 |
| 39 + 146 | TK | AA, AP, AV, CP, QG, EG, IV, LA, LQ, LE, LK, SS, ST, TH, TT, YE, VE, VL, VW | AE, AG, AL, AK, IT, LP, LV, SE, SL, SV, TE, TG, TL, TV, VD, VG, VH, VI, VS, VT | 0.12 |
| 264 + 289 | IL | AS, AT, AV, RK, CV, HL, LL, LF, ML, FA, FM, FS, SI, YA, YC, YI, YM, VI, VV | AA, RL, RM, HM, IA, II, IM, LM, LV, FC, FL, SL, TL, YL, YK, YT, YV, VL, VM, VS | 0.12 |
| 203 + 290 | LP | AR, AS, RA, RV, NE, DK, DT, GA, GR, HG, HP, FR, PS, SK, TT, YP, YS, VG, VP, VT | AE, AP, RR, RK, RT, NP, DN, DP, DS, GD, GP, GS, LA, KP, FS, ST, YA, YK, VR, VK | 0.12 |
| 218 + 219 | NM | AQ, AG, AY, EL, EK, ES, GR, GL, HL, IA, IG, IP, LP, KI, MA, ST, TT, VA, VP | AD, AK, AP, RK, RS, EA, GA, IQ, II, IL, IT, IY, LQ, MG, MM, SA, SE, YA, VR, VE | 0.12 |
| 185 + 188 | HM | AI, RK, DM, CG, EV, GA, LG, LL, LP, LS, LY, KG, FR, FS, SA, SL, WL, WV, YG, VL | AG, AL, RL, QM, GL, IA, LA, LD, LM, LT, LV, FG, FL, SG, SI, SS, WG, VR, VF, VM | 0.12 |
| 242 + 300 | TC | AH, AF, RN, RG, RT, NT, NV, DF, QW, EE, EY, HP, LT, KI, KM, KS, PL, SM, SF, VY | AL, AT, RA, RI, RM, RF, NM, QV, EN, EI, EM, ET, LF, KG, KF, KY, PR, PH, PS, TS | 0.12 |
| 240 + 300 | DC | AM, RP, NM, DN, QQ, QP, EN, EQ, EP, HR, IM, IS, IW, LR, KL, YF, YP, VQ, VH | AH, AF, RY, RV, NR, NP, DI, DP, QN, QM, QS, EM, EF, GY, IA, IP, LP, LT, KQ, KM | 0.12 |
| 265 + 298 | FA | II, IL, IY, LI, LL, LS, MF, MV, FN, FC, FQ, FM, WQ, YN, YD, YH, YT, VI, VF, VV | IQ, LC, LG, LT, LY, MN, FD, FH, FI, FF, TH, YC, YI, YL, YM, YF, YY, YV, VH, VS | 0.12 |

TABLE Ts2-continued

| positions | most preferred | preferred, sorted in decreasing order of preference | to be avoided | score |
|---|---|---|---|---|
| 258 + 259 | VP | NQ, DI, DL, QP, QT, EA, IG, IP, LP, KL, FD, FE, FS, PI, PL, SF, WG, YG, YK, | NP, DP, QA, QG, QI, EP, II, IL, IS, LL, LS, KP, FL, FP, PP, TP, YD, VE, VL, VT | 0.12 |
| 268 + 301 | WI | AH, RM, NI, NF, DD, DW, EN, HM, HS, HV, LG, LV, MI, FV, SE, TD, TL, TK, WL, YI | RC, ND, NG, NL, NV, DI, DV, HC, HI, HL, LC, LI, ML, FL, FM, SL, SF, TV, WV, YF | 0.12 |
| 236 + 248 | HE | AQ, AS, RT, NK, DD, DT, QR, QS, ES, EV, GG, HK, LS, KR, KD, PS, PT, SD, TT, VR | NR, DK, QK, QT, ED, EG, EK, ET, GR, GQ, HS, LT, KE, KS, PQ, PE, SA, SS, TR, VT | 0.12 |
| 203 + 300 | LC | AQ, AF, AW, DN, DL, GI, GP, HK, LT, KI, MM, FA, FG, PT, SA, SV, TH, YS, VR, VH | AA, AI, AL, AK, DT, GA, GN, LI, FR, FN, FH, FI, FV, PM, SN, SM, SS, YQ, VA, VY | 0.12 |
| 191 + 192 | KK | AG, AV, RL, NG, DR, DV, QN, EA, EN, EI, IP, LA, LP, KE, FA, SS, SY, TR, VS | AL, RP, NA, DK, DP, QD, EE, EK, GH, LR, LV, KA, KS, PR, PN, PP, PS, SA, SE, SG | 0.12 |
| 127 + 128 | AP | AA, AS, AW, RA, RN, RD, QA, GD, GG, IN, LT, KF, FT, PA, SS, TG, TP, VH, VP | AN, AG, AH, RG, RL, RP, RT, NP, GA, GR, GN, GP, GS, IS, LD, LQ, FA, FS, SG, VG | 0.12 |
| 192 + 242 | KT | AQ, AP, NP, DH, QQ, QV, ED, EE, EG, EM, IA, LR, KK, PR, PS, SQ, SE, TI, TT, YN | AR, AG, AK, NT, DD, QR, QE, EQ, EK, EP, GP, HN, IE, KA, KE, PA, PT, SK, TR, VK | 0.12 |
| 137 + 140 | VE | AA, AD, RA, QP, ER, EQ, GV, IG, IK, LN, LP, MR, SN, SQ, SG, TA, TE, WK, YD, VP | AQ, AP, RP, DQ, EK, EP, GQ, GK, GP, HA, LA, LS, ME, SA, SR, SP, TR, VA, VN, VL | 0.12 |
| 218 + 240 | ND | AR, RA, RR, RY, EL, GS, HT, II, LQ, LM, KN, KG, MA, MQ, FL, FV, TR, YA, YV, VE | AI, AM, RD, RI, RL, QQ, EA, EN, EQ, IQ, IH, IM, LA, LR, LL, LS, KV, MR, MG, MV | 0.11 |
| 213 + 236 | TH | AY, ND, NS, DP, DS, EA, GL, HG, IG, IH, KA, PA, SG, SP, TA, TR, TQ, TT, WS, VN | AG, AH, NA, NR, NQ, DE, QA, ES, GP, HS, FE, PD, SA, SE, TN, TL, TP, TS, YD, VE | 0.11 |
| 271 + 272 | HD | AF, RE, RF, DC, CD, QN, HN, HH, IA, LN, LH, MD, PS, SV, TM, YA, YL, YY, VI | AH, DD, QD, HA, HR, HQ, HI, HL, HF, HS, HT, HY, LD, MN, PN, SN, SD, TH, YD, YH | 0.11 |
| 32 + 142 | VW | AW, RW, CF, CW, QW, IL, IF, LA, LP, LS, MF, FE, SS, SW, TL, WW, YD, YC, YV, VI | AM, AS, AY, HL, IW, LH, LW, LV, MV, FW, SL, TW, WL, WF, WS, YL, YF, YW, VM, | 0.11 |
| 286 + 292 | YN | AQ, AG, RA, RD, RE, RH, RT, ES, HD, IG, LG, KS, FG, SN, ST, TD, TG, YG, VD, VG | AD, RG, RK, RS, CG, GD, HA, HN, LD, KA, KG, KH, FD, SE, TG, YQ, YS, YT, VS, VT | 0.11 |
| 204 + 260 | EK | AG, AV, RA, RG, RS, NS, DD, DS, GR, HN, IV, KK, KS, ML, PD, SQ, TN, TG, VI | AR, AN, AD, AK, RE, RI, RK, DG, QV, ES, GE, GG, GS, KP, SR, TS, TV, VA, VS, VT | 0.11 |
| 129 + 133 | LN | AR, AF, AW, DQ, CF, GA, HV, IN, LS, LT, LY, FC, FV, SF, TL, TT, WN, WM, VL | AA, AN, AC, AI, AS, GV, IA, IT, LL, LM, LF, LV, FR, FN, FH, WL, WF, YN, YY, VT | 0.11 |
| 202 + 279 | SL | AR, AL, RA, RR, RT, DQ, DI, DV, ER, EQ, EL, GV, KG, KI, PR, SD, ST, TE, TK | AQ, AI, AV, RL, RV, DR, DE, DT, QR, QI, EE, EV, GQ, KL, KT, PL, PV, SI, SK, TR | 0.11 |
| 46 + 92 | LL | AF, CF, QM, IA, IC, IV, LC, LV, MM, FI, FL, FM, PF, SY, TY, WV, YI, YL, VV | AI, AL, AM, AV, IL, IF, LF, FA, FC, FF, FY, PI, PY, PV, SL, SV, TF, WF, YV, VL | 0.11 |
| 204 + 215 | EA | AH, RA, RR, RE, RL, DS, QQ, QT, EH, GA, LI, LY, KA, KE, KK, KM, PQ, PL, SS, VH | AA, AT, RQ, RV, DH, QA, EN, GG, GS, GV, LA, LH, KR, KQ, KH, KS, KV, PS, SH, TL | 0.11 |
| 203 + 205 | LT | AS, RA, RL, NR, NL, DL, DV, GV, HQ, IS, LS, KE, KL, FS, PR, SH, SL, TR, YR, VT | AR, AL, AV, RT, NT, DS, DT, GN, GL, GS, GT, IL, LV, MR, FV, SS, TS, VI, VL, VV | 0.11 |
| 177 + 185 | VH | AR, AD, AI, RA, RL, RM, RW, NI, NT, DF, QY, GL, LQ, PS, SG, TG, TM, VF, VV | AH, AY, AV, RR, RD, RG, RK, RT, NA, DA, DS, IM, LR, SI, SY, TD, TS, VR, VD, VL | 0.11 |
| 128 + 131 | PL | AE, AG, AK, NH, NK, DR, DG, DL, EL, HM, KL, PA, PM, SE, SL, SV, TE, TF, YM, VQ | AI, AL, AM, RL, NQ, NE, NS, DE, DF, DS, GL, GS, HR, HL, FL, PD, PG, PF, SG, VL | 0.11 |
| 201 + 226 | SS | AA, AD, AK, RA, RT, NK, DH, DK, QG, EN, GG, HH, KN, KE, KH, PD, SR, SN, TQ, VA | AN, AE, AG, AH, RE, NG, DD, DQ, ED, EH, GD, HN, LH, KG, PH, PK, SA, SD, SK, TN | 0.11 |
| 180 + 240 | SD | AD, AF, AS, RA, RG, RH, NK, DL, QA, QT, EW, GM, HI, LI, KN, KH, FA, SE, SS, TQ | AN, AQ, AT, RD, RK, RS, NR, NH, DE, DG, QL, QK, QV, ER, EE, HL, KI, SA, SI, TA | 0.11 |
| 268 + 318 | WI | AK, RA, RQ, NF, NS, NY, QE, GM, HL, LR, LW, MV, FL, FV, SS, TV, WG, WL, YR | AQ, AV, RL, RM, RS, NQ, NW, NV, DL, HS, HW, LE, LM, LV, ML, FM, SA, SV, TL, YL | 0.11 |
| 80 + 106 | DR | AN, AD, RD, RE, RL, RP, RT, RV, DQ, QE, ER, EQ, ES, GD, GG, KN, TG, YR, VE | AR, AE, RR, RN, RQ, RG, QD, ED, EE, EG, GE, HD, KR, FR, FG, SR, TE, YD, YG, VD | 0.11 |
| 339 + 342 | AK | AD, AT, RA, RN, RQ, NL, DA, DR, DQ, QR, QG, ER, EI, ES, GD, GP, KE, TR, TS | AR, AL, RR, RG, RS, DE, DK, DS, QA, QN, QD, EE, ET, GQ, SR, SN, SQ, SK, TD, TT | 0.11 |
| 268 + 298 | WA | AR, AH, RA, ND, DK, QQ, QH, GN, HA, HH, HY, HV, LA, LI, FL, SN, SC, TN, WN, WQ | AN, AI, AV, RH, NA, NN, DA, DN, QV, GI, GV, HQ, HI, HT, LL, LS, MA, SM, WH, WM | 0.11 |
| 188 + 240 | MD | AF, AS, DQ, QH, QL, EV, GQ, IE, LR, LK, KI, FQ, PR, PV, ST, TA, YN, YL, VQ, VT | AV, RQ, QA, ER, EQ, GE, GT, II, IK, LQ, LL, LT, KV, FE, FG, PQ, TQ, TV, VE, VL | 0.11 |
| 140 + 144 | EF | AR, AW, RQ, RY, NK, NY, DA, QN, ER, EH, EM, LE, LG, KA, KF, KY, PA, PE, PK, ST | AN, AG, AS, AY, RG, RK, NR, NF, EA, EQ, EE, GH, LA, KQ, KG, PR, PN, PH, SF, TD | 0.11 |
| 203 + 227 | LL | AL, AP, RI, RL, DA, GG, GS, HL, II, IV, LF, KR, FK, FM, PA, PV, TI, VI, VM | AA, RA, RV, DI, DS, EA, EI, GM, IL, IS, LA, LI, LS, KI, FL, PL, PM, VA, VS, VT | 0.11 |
| 50 + 114 | AC | AA, RE, DR, DG, QT, ES, EV, GG, GK, HS, LR, KA, PS, SD, SC, SE, TN, WG, VI, VT | AE, AG, AK, RS, RT, DS, QA, EA, EG, ET, GS, LS, PA, PG, PT, SS, ST, TS, VG, VS | 0.11 |
| 258 + 284 | VN | AL, AT, DR, QA, QQ, QH, EL, IN, IK, LR, LL, MN, FE, FK, PQ, YE, YK, VS, VT | AK, QN, QE, QT, EK, IH, IL, LN, LQ, LH, LT, LV, FA, FN, FL, YR, YN, VR, VQ, VK | 0.11 |
| 38 + 134 | KQ | AV, RH, RL, RF, RT, RY, NQ, NS, GS, HA, HG, HV, KL, KF, MD, FN, SS, YG, YM | AC, AM, RR, RN, RG, RK, RV, NL, EG, GG, HL, HS, HT, LG, KG, FT, SA, YS, YT, VS | 0.11 |
| 196 + 215 | LA | AR, AQ, AH, RT, DA, DG, DS, EA, EV, GF, GT, IQ, LV, MQ, SQ, SL, WH, YH, YT, VH | AL, AF, AT, AV, RA, RL, RV, NA, DH, EH, ES, GQ, HH, LT, KH, SA, SD, SH, TT, VT | 0.11 |
| 204 + 228 | EK | AR, AS, AT, RE, NE, DK, QQ, GR, GQ, LE, KE, KH, PR, PP, TL, VA, VK, VP | AQ, AE, AK, RK, RT, NR, DQ, QR, ES, GH, GK, GT, HR, KR, PE, PK, SE, TE, VR, VS | 0.11 |
| 243 + 248 | TE | AR, AG, RR, RN, ND, NQ, DK, QA, QS, EA, EE, GK, GS, LD, KI, KS, PQ, TQ, TK, VQ | AD, AQ, AK, RD, RQ, NS, DA, DE, DT, ER, EQ, ES, GQ, GE, GT, HE, KR, KN, KV, PS | 0.11 |
| 268 + 276 | WA | AQ, AE, RQ, RE, NA, NE, DP, QA, QK, GA, HD, HT, LD, KE, FS, SP, WD, WH, WK, YD | AD, AH, AS, RA, ND, NI, NP, DK, QE, GK, GS, HA, HE, HK, HS, LP, ME, FD, SA, YA | 0.11 |
| 226 + 243 | ST | AD, AP, RA, NN, NS, NT, DR, DE, DK, QQ, QS, ER, EE, EK, GA, GD, HG, HH, KS, SS | RK, NA, NR, ND, DA, DL, DS, QE, EG, ES, ET, GE, GK, GP, HR, HE, KD, SA, SV, TE | 0.11 |

TABLE Ts2-continued

| positions | most preferred | preferred, sorted in decreasing order of preference | to be avoided | score |
|---|---|---|---|---|
| 184 + 187 | NT | AA, AR, AN, AK, DR, CR, QN, QL, ER, EV, GQ, GV, HL, IR, LG, SF, SS, TR, YS, VA | AQ, AG, AM, ND, NS, DV, QR, EA, ED, GR, GF, GS, IA, LR, SR, SN, SG, TS, YG, VS | 0.11 |
| 279 + 286 | LY | AH, AI, RA, RF, NH, DY, QF, EL, EY, GR, LR, KC, KY, PA, SS, SV, TH, VR, VV | AR, AY, RK, RY, RV, QY, HR, IL, IY, LA, LL, LF, KA, KH, PF, SR, TV, VA, VH, VF | 0.11 |
| 192 + 277 | KL | AA, RD, RY, ND, NQ, DN, DE, QR, ED, EE, GK, GT, HN, IS, LK, FT, PS, SA, TK, YY | AN, AQ, NA, NK, DK, QE, EK, GD, GQ, GS, HR, ID, LE, FD, PK, PT, SE, SK, VR, VK | 0.11 |
| 138 + 139 | FM | AY, QW, ER, HW, HY, IE, IM, IV, LA, LF, MG, MW, FK, FY, TA, TV, WQ, YA, YF, VL | AT, QA, HV, IF, IW, IY, LG, LW, MA, MY, FI, FF, FW, SA, TL, YM, YT, YY, VM | 0.11 |
| 202 + 300 | SC | AG, AF, RA, NE, DA, DF, QM, EG, EL, EF, ES, EV, GR, GQ, KI, PY, SE, SS, TH, TP | AA, AY, AV, NV, DG, DI, QV, EA, ER, EQ, EP, GA, GG, GS, KQ, KM, PH, PV, SL, SP | 0.11 |
| 253 + 255 | DF | AA, AE, RE, NQ, NL, NF, DR, DN, DC, DH, DM, DS, DT, GD, LT, FQ, SD, SL, SF | AF, NR, NN, NE, NT, NW, DD, DQ, DE, DG, DL, DP, DV, EF, LF, PF, SR, SH, ST, TF | 0.11 |
| 215 + 240 | AD | AA, AQ, RA, RD, DS, QK, EV, GL, HD, HQ, HP, IV, LD, LV, SY, TI, TL, YK, VA, VR | AI, AS, AV, RL, DQ, DV, QT, QV, EE, GD, HR, HN, HK, IL, IK, LA, LI, SD, TA, YA | 0.11 |
| 244 + 321 | YI | AA, AF, AP, RY, NI, NP, DQ, EL, ES, GY, IF, LN, LI, LV, KR, FN, FD, SQ, TN, VT | AN, AQ, AE, AV, RV, NA, DN, DT, QN, EN, GT, LS, KL, KM, KV, FH, FI, VH, VI, VS | 0.11 |
| 177 + 181 | VA | AT, AV, RA, NF, DW, DY, QH, EQ, GL, HT, IA, IS, LA, LG, KA, MA, SG, SL, SF, | AA, RF, RY, NA, NT, DA, DS, QV, EA, GG, HG, IG, IF, IT, LL, MG, SA, SS, SY, TT | 0.11 |
| 235 + 236 | PH | AK, AP, AS, RE, DT, QH, QP, EN, ET, HA, HP, PA, PD, PQ, PG, SE, SS, SY, TP | AN, AQ, AH, AT, DN, DK, DP, DS, QA, QD, EE, EL, EV, HE, LA, KP, PN, PP, SQ, SK | 0.11 |
| 218 + 249 | NH | AR, AI, AM, RA, RY, NM, CW, HL, IA, IT, IV, LF, LS, KL, KK, ML, MT, FF, TV, VL | AA, AF, AY, RV, DF, QF, EY, IL, IF, IY, LR, LH, LW, LV, KA, KF, MV, FL, SI, ST | 0.11 |
| 230 + 250 | IV | AH, AI, DI, DF, ER, ET, HH, IA, IQ, IM, LE, KK, FI, SI, TV, YV, VD, VQ, VE, VL | AR, AM, RV, EQ, EV, HV, II, IL, IF, IS, LT, TI, TM, YR, YQ, YH, VA, VH, VI, VT | 0.11 |
| 266 + 295 | MV | AL, AM, AF, NL, CF, EF, GY, IV, LI, LV, ML, FI, FV, SF, TF, TW, TY, YL, VA, VR | AI, CI, CV, GL, IM, LA, LL, LF, LY, MI, FL, FF, SI, SL, SV, TI, TL, YV, VF | 0.11 |
| 191 + 239 | KE | AA, RQ, RE, DA, DG, QE, ED, EP, GD, GS, HE, LD, KQ, FE, PE, PG, PP, SE, TP, WE | AD, AG, AK, RA, RG, DQ, QA, QP, EE, EG, GP, KS, ME, PA, PD, PQ, SA, TD, TE | 0.11 |
| 156 + 160 | SY | AF, RD, DA, QK, GL, LM, KE, FN, FH, FK, FF, FY, PL, TD, TL, TF, WH, WT, YH | AN, AH, AY, QY, LF, MH, FR, FD, FE, FI, FL, FP, FS, FV, SH, SF, TH, WL, YD, YL | 0.11 |
| 277 + 328 | LG | AN, AD, AQ, AK, DD, DG, DT, QD, QS, EN, EG, GR, HN, IG, KA, KE, SH, SS, TK, YN | AH, AS, RD, DN, DQ, DH, QA, QE, QK, ED, EE, ES, HG, KR, KK, KS, SG, TR, YG, VD | 0.11 |
| 254 + 255 | MF | AR, AQ, AE, AG, CL, GE, IS, IV, LK, LF, LS, MW, FM, FF, YN, VA, VD, VH, VT | AH, AF, AS, AY, IN, LN, LT, LY, ML, MT, FA, FR, FE, FL, FV, SF, WF, YF, VQ, VL | 0.11 |
| 173 + 176 | RK | AA, AQ, AT, RE, DA, DR, DP, QK, ER, EH, ES, EV, GE, KN, KE, SD, SP, TN, TG, WR | AR, AD, AG, AK, RN, RD, DE, DG, DV, QT, EA, EN, EE, KK, KP, KV, SA, TR, TQ, WA | 0.11 |
| 156 + 167 | SY | AF, AS, RW, CA, QQ, EK, ES, HT, HY, LW, FF, FW, FY, SE, WD, YA, YD, YE, YH, VI | AW, GY, IY, LE, LS, FD, FQ, FE, FH, FI, FT, SW, TW, WF, YL, YF, YW, YY, VY, VV | 0.11 |
| 242 + 244 | TY | AD, AL, RE, RS, NL, DF, QA, QK, EQ, EK, GA, HR, LT, KQ, KH, KI, MK, PL, PV, SL | AR, AH, AV, RQ, RL, RV, DA, DN, QG, QL, EP, KR, KG, KK, PE, PS, PT, SK, TA, TT | 0.11 |
| 188 + 196 | ML | AA, AD, AH, NM, NY, DY, QE, QF, EN, EL, GS, LA, FS, PR, PG, PM, SG, TG, WA | AE, AS, NG, QA, EA, ES, GA, GR, HA, IG, LG, LL, LV, KG, PA, PQ, PL, SK, TL, YL | 0.11 |
| 187 + 188 | TM | AF, AP, RL, NA, DG, QE, QG, GW, IR, IG, KL, MA, PT, PY, SR, SV, TS, WQ, YA, VA | AR, AH, AL, RQ, RG, RM, RY, NR, NP, DS, QI, QL, EE, GG, GV, LA, KI, SA, ST, TL | 0.11 |
| 204 + 206 | EL | AV, RA, RM, NL, DV, CL, QL, EV, GL, GV, LV, KI, MI, PI, PF, SI, SF, TA, TL, VM | AL, AM, AF, RI, NV, DI, DF, QV, GF, HV, II, LM, KV, PM, PV, SL, TI, TV, VI, VL | 0.11 |
| 204 + 242 | ET | AQ, AS, RE, RS, DR, QQ, QR, GH, HE, IK, IT, LK, KK, MA, SA, ST, TA, TH, VP, VS | AA, AN, RK, DQ, DT, QR, EK, GA, GL, GS, HR, KQ, KH, KV, MK, PE, SQ, TS, VL, VK | 0.11 |
| 251 + 257 | GS | AD, AE, AP, AV, RA, NQ, DE, ER, EG, EK, ET, GA, KP, PD, SE, SS, TL, VL, VM, VP | AA, AK, AS, NE, NP, CP, ED, EE, ES, GV, IP, KD, PA, PP, SA, SD, SK, TA, VE, VK | 0.11 |
| 252 + 285 | GQ | AA, AI, RH, DA, CI, QA, QL, EV, GV, HI, HL, II, KW, MI, SL, TV, YQ, YT, VA | AL, AV, RI, DL, CV, GQ, GL, HA, HC, HQ, HT, HV, IL, ML, SA, SV, YI, YL, VL | 0.11 |
| 172 + 173 | QR | AA, AG, NL, DA, ER, EK, EV, GR, GW, KE, PA, PD, PQ, PE, PV, SP, SS, TG, VD | AD, EA, ED, EG, EL, EP, GK, IE, PR, PN, PG, PP, PS, PT, PW, PY, SA, SE, TD, VE | 0.11 |
| 254 + 272 | MD | AD, AH, AM, CI, IC, IG, IK, IF, LL, MA, FN, FD, PN, TR, WE, YA, YQ, VE, VY | AN, AE, AG, IN, ID, IH, LA, LD, FA, FR, FC, FE, FH, FL, FM, FF, FV, PD, YD, VN | 0.11 |
| 287 + 303 | KS | AA, AD, AT, RD, RP, DA, DQ, DV, QE, ER, EG, EL, ES, EV, LD, KN, KD, KQ, KK, PP | AE, AG, RA, RR, RQ, RG, RL, RS, NE, DP, QD, QP, EA, ED, EQ, EP, KE, KP, PD, PQ | 0.11 |
| 230 + 248 | IE | AL, RE, NN, DT, CV, HF, IT, LQ, KE, FE, TA, TH, TK, YK, VR, VD, VL, VS, VT | AQ, DE, EE, HS, IA, IN, ID, IH, LD, FS, SS, TQ, TE, YT, VN, VE, VG, VH, VK, VF | 0.11 |
| 192 + 236 | KH | AA, AP, RK, RV, DA, DH, DK, QE, QS, ED, GA, GN, HE, LG, SE, SG, TQ, WE, VQ, VL | AN, AK, RD, DG, DP, QA, QG, EN, GE, HA, IP, LE, LP, KA, PT, SA, SV, TE, VA, VE | 0.11 |
| 300 + 338 | CE | AE, AG, AK, RI, RV, GA, GR, HA, IE, KQ, ME, FA, FK, PR, SQ, TE, WA, YQ, VE, VT | AQ, AI, RR, EE, GE, IA, IQ, KE, MR, MK, FE, FG, FS, SE, SV, TA, TR, YA, VR, VI | 0.11 |
| 277 + 279 | LL | AI, AM, RA, RR, NI, DI, DT, DV, QR, QQ, QL, EA, EL, EK, GR, HR, KQ, MQ, QL, YK | RI, NR, DA, DR, DD, DQ, DG, DL, QK, ER, EM, IV, LR, KA, KI, MR, TI, YV, VL, VV | 0.11 |
| 341 + 346 | AF | AL, AS, AY, CA, CL, QL, GL, II, IK, IF, LC, LF, LW, MV, FL, FY, YL, YW, VE, VM | AM, CF, CY, QF, IL, IW, LI, LL, LK, LT, LV, MF, FC, FF, FP, SL, SW, YF, VW | 0.11 |
| 219 + 251 | MG | AA, AK, AP, AS, RD, RQ, RP, NG, NP, DP, EE, EG, HA, LD, LA, LE, KG, KP, SE, SV, TQ | AD, AQ, AG, RA, RV, DE, QA, EA, ED, EI, EK, GG, IA, LA, LE, KP, SE, SV, TQ | 0.11 |
| 204 + 240 | ED | RA, RG, RL, NN, QI, EA, GE, GF, HI, IQ, LV, KI, MQ, PD, PH, PM, TS, VK, VT | AD, AQ, AE, RH, RT, RV, DA, DI, EK, ET, GI, GL, II, KA, KR, PN, PS, SV, TR, VH | 0.11 |
| 128 + 184 | PN | AG, RD, RG, ND, NE, DA, DN, DS, GS, LV, KA, FV, PA, PC, PM, PS, SD, SP, TT, YG | AN, AD, AI, NA, NS, DD, DE, QS, ES, GA, GQ, GG, HA, FS, PD, PE, PG, PV, SA, SS | 0.11 |
| 283 + 344 | KA | AN, AG, RE, RG, NC, NT, DH, DS, QN, EA, EL, ET, GV, KN, PY, SH, SS, SV, TS | AT, RN, RH, RS, NA, NS, DA, DV, QS, ES, GA, KG, KH, KL, KS, SA, SC, SL, ST, TA | 0.11 |

TABLE Ts2-continued

| positions | most preferred | preferred, sorted in decreasing order of preference | to be avoided | score |
|---|---|---|---|---|
| 257 + 300 | SC | DQ, DH, ER, EG, EK, GD, GL, IS, LQ, LT, FI, PA, PM, PF, PV, SM, SS, SV, TF, VY | AS, AY, DA, DM, EH, EF, EV, GI, LM, LF, PR, PQ, PE, PI, PL, PK, PY, SQ, SF, TI | 0.11 |
| 179 + 192 | NK | AY, NT, NV, DE, DK, QD, QP, GG, GF, HN, IQ, IE, IS, LA, LE, FS, FV, SH, SV, TA | AQ, ND, NH, NF, QA, QG, GR, GD, GK, HA, HL, IA, LV, SA, SN, SG, SK, TE, TS | 0.11 |
| 226 + 338 | SE | AL, AT, NI, NL, DQ, DK, DT, QQ, QY, ED, EL, ES, GA, GR, GG, GK, HT, KL, TR | AK, ND, NQ, DR, DE, DL, QL, QK, EQ, EK, ET, GI, GT, HA, HD, HE, KS, KV, ST, SV | 0.11 |
| 240 + 280 | DQ | AK, RA, DK, QE, QT, GQ, HT, IH, LL, LT, KQ, KE, FK, PK, SR, SE, TD, VA, VI, VL | AR, AT, RK, RT, NA, QQ, QI, EA, EQ, GE, LQ, LK, KA, KK, SK, TE, TL, VD, VK, VT | 0.11 |
| 180 + 244 | SY | AN, AQ, RA, RF, ND, NS, DR, DG, QE, QL, EV, GF, IP, LL, KE, KK, KP, MI, SK, ST | AV, RN, RQ, RP, RS, DL, QR, QS, EQ, EG, EL, GK, GS, GT, HL, KF, TE, TL, TP | 0.11 |
| 202 + 218 | SN | AM, RA, NI, DD, QK, QS, EE, EV, GA, GL, HE, IE, LI, KN, PC, PL, PK, PF, SL, TT | AT, RE, NL, DL, QA, QR, QV, EK, EM, GI, GS, GT, KA, KE, KL, KS, PA, PE, PM, SK | 0.11 |
| 305 + 339 | AA | AQ, AG, RA, RE, NK, DR, DD, DG, QD, EQ, GR, HS, LA, KT, PN, SN, SE, TK, VE | AN, AE, AK, RQ, NT, DQ, DK, DS, QR, QQ, GA, HD, LR, KA, PD, SS, TR, TG, TT, VA | 0.11 |
| 279 + 339 | LA | AN, AH, RA, RD, QQ, QT, EA, EE, HA, IN, IT, IY, LG, KE, SN, TD, TQ, VA, VR, VK | AE, AS, RR, RQ, DQ, QA, QG, EG, GA, GD, IA, IR, LR, KD, KK, TA, TG, TS, VQ, VT | 0.11 |
| 267 + 298 | KA | AA, AV, RA, RN, RD, RC, RT, NG, EH, GY, HH, HT, IS, LL, FI, SC, SE, SG, SI, SL, TI | AC, AH, RG, RH, RK, RW, RY, GG, GH, GF, HV, KS, FH, FI, SC, SE, SG, SI, SL, TI | 0.11 |
| 222 + 300 | SC | AA, AD, RI, RY, NV, DM, QW, EN, EC, EM, EP, LA, LV, KM, KF, KS, SM, ST, TR, TP | AR, AI, AY, RN, RM, RV, NM, DF, DT, QP, QV, EA, EL, ES, HF, LM, KA, KN, KI, KW | 0.11 |
| 65 + 66 | AQ | AA, AE, AV, RE, RT, DS, QQ, ER, EK, ES, GH, GK, LK, KA, KD, KE, SD, SI, TA, TT | AH, AI, AK, RK, NA, DA, DK, QR, EA, ED, EE, EL, GQ, GS, KQ, KG, KK, KS, SA, TR | 0.11 |
| 338 + 347 | EK | AA, AR, AE, RA, RE, RT, QT, ER, EH, ES, GT, KQ, KE, KV, MG, SD, TE, TK, YK, VD | AG, AK, AS, RR, RK, RV, DE, DT, QA, QD, EA, ED, EE, IT, LD, LE, KK, KT, SE, VS | 0.11 |
| 206 + 263 | LA | AL, AW, IG, IL, IT, IY, LG, LS, MR, ML, MF, FI, FM, FY, WF, VC, VI, VL, VV | AV, IR, IC, IF, IW, IV, LI, LL, LK, LF, MA, MC, MV, FL, FF, VA, VG, VM, VT, VY | 0.11 |
| 256 + 302 | EL | AE, AL, NG, DA, DN, DI, QI, QK, QM, EP, EV, IL, LL, KA, KI, FV, TL, TV, VV | AG, AI, AV, NV, DL, DP, DS, QL, QS, QV, EI, KL, TA, TG, TI, TM, TP, TY, VI, VL | 0.11 |
| 260 + 287 | KK | AA, NR, DR, ER, EK, GA, GD, GT, IP, KN, KD, KE, PQ, PE, SH, TN, TP, VG, VL, VP | AE, AP, NA, DN, DQ, DG, QD, EA, EE, GR, KR, KQ, PR, PD, PT, SA, VR, VN, VD, VK | 0.11 |
| 275 + 340 | DL | AM, AT, AW, RI, NL, DV, EF, EW, GW, LA, LC, KL, PR, PM, PW, SA, SE, TW, VI | AL, RL, NW, DA, DE, DH, DM, DF, DW, DY, EL, GI, LM, LW, KW, PL, SI, SM, TL, VM | 0.11 |
| 217 + 221 | LT | AA, AS, AV, CQ, EL, GA, GI, IL, LR, LN, LL, SA, SC, ST, TI, TL, TV, VC, VS, VV | AR, AL, CC, CL, EA, GL, IA, LA, LC, MA, SQ, SH, SI, SL, TA, TK, TS, TT, VA, VR | 0.11 |
| 192 + 300 | KC | AP, AT, AY, RL, DR, DM, ER, EY, GT, HF, IM, KI, FA, PD, PM, SH, SI, SV, VA, VV | AI, AM, AF, NA, NL, DF, DT, QI, EI, EM, GA, HR, HL, KT, FM, PS, PV, SR, SF, TT | 0.11 |
| 321 + 324 | IV | AT, AV, RV, NI, NV, DL, QL, QM, QT, ER, HC, HT, LN, FT, PL, SI, TA, WF, VP, VS | AM, AS, NA, NC, NL, QC, QQ, EL, HI, IA, LL, LV, MA, FS, FV, SN, SC, SF, VI, VV | 0.11 |
| 226 + 260 | SK | AA, RG, RS, NN, NE, DA, DG, EA, EE, EV, GP, GV, HD, HK, HT, KT, KV, ST, TD, TI | AE, RA, NR, ND, NP, NT, DP, QE, QK, EN, EP, GA, GE, GI, GT, HV, KG, KS, TA, TK | 0.11 |
| 240 + 244 | DY | AR, AG, RR, NL, DD, QD, QF, EL, HT, LG, LK, LS, LT, KL, SD, TA, VA, VN, VY | AD, RK, RS, DE, DF, QA, QR, QH, ER, EI, ET, IS, IY, LE, LL, LV, SN, TT, VR, VI | 0.11 |
| 350 + 352 | NA | AH, RA, RI, RL, RV, NK, NY, DW, DV, QH, QL, ER, EK, EF, KW, SR, SS, ST, TI, VG | AL, AT, AV, RR, RH, RK, RS, RT, NR, NW, DA, DT, EY, GI, KR, KK, SH, SL, SW, TV | 0.11 |
| 133 + 185 | NH | AR, AN, AV, CL, QV, EI, GM, HF, IS, LN, LS, MQ, FV, SR, TL, WA, WY, YD, VM | AG, AI, AF, AY, NS, NV, DL, IL, IF, IT, IV, LL, MF, MS, MY, SI, TM, YR, YM, VS | 0.11 |
| 240 + 298 | DA | AG, AL, AN, RN, RL, NA, NI, QH, EI, EM, IH, II, IT, LC, LK, LY, KI, YL, VS | AA, AM, AH, RI, NL, NS, DN, DI, QQ, QL, QF, EA, GA, GN, IL, LQ, LV, MI, VH, VI | 0.11 |
| 244 + 300 | YC | AG, AF, RE, RT, NS, EA, HR, HP, IM, LA, LH, KC, KG, FQ, PA, SM, SV, TI, TM, YL | AH, RA, RG, NY, NV, QR, QM, HI, LC, FA, FT, SQ, SF, TA, TF, YA, YR, YS, VR, VM | 0.11 |
| 243 + 283 | TK | AQ, AK, AS, RA, RR, RD, DE, DS, QL, QK, QT, EA, EE, HH, KD, KK, SQ, SS, VG | RN, RQ, RE, RK, NR, DR, DK, QS, ED, GS, HA, KA, KR, KQ, PE, SA, SR, SK, TS, VS | 0.11 |
| 327 + 342 | LK | AG, NE, NV, DT, QK, GE, HA, IS, LR, LT, MK, FN, FD, FQ, FE, FH, SS, TA, TG, VE | AR, NA, DK, QE, EA, EE, GT, HE, IE, LA, KE, ME, FR, FG, FK, FS, FT, PS, SQ, TS | 0.11 |
| 119 + 213 | KT | AR, AD, RE, NQ, NI, DE, DT, QS, ES, LA, KS, PN, SG, SH, ST, TG, TL, TY, TV, VF | AT, RH, DR, DN, DI, DY, QI, ET, HT, KR, KD, KE, PS, SN, SS, TE, TH, TK, TS, VS | 0.11 |
| 256 + 280 | EQ | AQ, AL, AV, NR, DA, DR, DK, QT, ER, EE, EK, GA, IK, LL, KA, KQ, SD, SS, TE, TT | AD, AE, RK, NA, DE, DT, QL, QK, EA, EN, ED, EG, EV, KR, KT, SR, ST, TI, TL, VK | 0.11 |
| 206 + 229 | LG | AT, AV, HS, IC, II, IL, LA, LC, LP, MG, MS, FG, FI, YG, FL, VM, VF, VW, VY, VN | AA, IA, IG, IF, IS, IY, LL, LM, LF, LV, MI, MV, FA, FL, FV, VA, VC, VI, VS | 0.11 |
| 327 + 328 | LG | AQ, AH, RG, NG, DG, EG, GA, HS, IN, IG, LA, LL, LS, MW, FN, FS, PG, SH, ST, YA | AG, QD, ED, EE, ES, GG, HA, LQ, LE, LH, KN, MG, FA, FH, PS, SA, SK, TD, TG, TS | 0.11 |
| 238 + 240 | ID | AI, CR, CI, CT, IQ, IE, IH, IM, IF, IS, LG, LI, LK, LV, SL, TL, VA, VR, VM | AD, AG, CA, EI, IA, IG, II, IK, LE, LH, LF, LP, LS, TI, VE, VF, VP, VS, VV | 0.11 |
| 177 + 236 | VH | AA, AT, RE, RV, NA, DE, GQ, GE, GV, HE, HG, LH, KY, MR, PH, SE, TN, TD, TE, VP | AH, RA, RT, NE, NG, DN, CE, QE, EG, GH, LA, LG, KE, KS, MP, PE, TR, TH, TT, VE | 0.11 |
| 268 + 269 | WI | AM, RV, NI, NL, DA, DC, QC, QI, GR, GV, HF, IP, LM, KT, MH, ST, SV, TV, YI | RI, NA, NC, NS, DI, DT, QV, GI, HC, HT, IV, LI, LV, MV, PV, SI, SS, WV, YA, YV | 0.11 |
| 180 + 283 | SK | AA, AK, RR, RE, RK, NR, DQ, DS, CR, QH, QK, ET, GA, HP, IT, KS, PR, SA, TN | AH, RA, RN, RQ, RG, RS, RT, NK, DE, DK, QR, ES, GQ, LR, KQ, QE, SS, TR, TK, VR | 0.11 |
| 85 + 317 | LH | AI, AL, AW, GM, HA, HD, HG, HS, IN, IW, LR, MA, MQ, PM, TA, YQ, YE, YS, YT, VL | AA, AC, AQ, AE, AH, AK, AS, HI, HL, HM, IG, LA, LL, LS, LT, FL, FV, YN, YL, YW | 0.11 |
| 215 + 276 | AA | AE, ND, DQ, DS, CA, QQ, GD, HS, HT, IQ, LG, MD, FD, FP, SD, TE, TS, YD, VE | AD, RD, NA, DE, QA, GP, HA, HD, HQ, HE, KD, ME, FE, SE, TD, TP, WE, YE, VR, VK | 0.11 |
| 317 + 321 | HI | AL, AF, NI, CL, QE, EG, EL, GL, IG, LN, LE, LH, LY, MN, MS, FL, FS, PP, SV, VD | AG, AY, QQ, QH, EN, GN, HN, IA, LA, LL, LF, LV, ML, MM, SS, WA, WQ, YT, VN, VL | 0.11 |

TABLE Ts2-continued

| positions | most preferred | preferred, sorted in decreasing order of preference | to be avoided | score |
|---|---|---|---|---|
| 195 + 236 | DH | AA, AE, AP, RA, RP, NS, DD, DE, DS, QV, EQ, EL, EK, ET, GE, HA, KN, PE, SS, TH | AR, AS, RE, NA, NE, DA, DR, DG, DL, DP, QE, QG, EA, EE, EV, GA, KH, PD, PP, SP | 0.11 |
| 191 + 196 | KL | AA, AE, AG, RD, ND, DR, DC, QG, EA, EH, GA, IH, KG, KI, MV, PS, PW, SN, SH, TQ | AK, AV, RA, NG, DA, DQ, DH, DY, QR, QD, EE, GV, LG, KA, PL, PT, SG, TL, VV | 0.11 |
| 301 + 302 | IL | AI, AF, AV, NG, CL, GK, IN, IM, IS, LA, LL, LT, LY, KK, FC, TP, VA, VI, VL, VM | AL, AV, DL, CL, CG, CI, IA, IT, LR, LI, KL, ML, FI, SL, TA, VR, VC, VG, VH, VV | 0.11 |
| 174 + 192 | FK | AQ, RE, RP, NE, QV, EA, EV, LA, LG, KA, KN, MR, FS, SD, SE, TP, YA, VD, VG | RA, RS, QG, ED, EE, HG, HV, IS, LP, KL, MN, MS, FA, FD, FE, FG, FT, TA, YD, VA | 0.11 |
| 133 + 222 | NS | AS, RK, NA, DG, CR, CS, CT, EK, GK, GS, HR, IK, LH, LK, MA, FN, FE, SE, WT, VR | AE, AK, CQ, CK, QE, EA, GQ, HS, IR, IE, LR, LE, MR, MG, SR, TN, TS, WK, YK, VT | 0.11 |
| 193 + 298 | IA | AL, AV, HA, IC, II, LH, LM, LF, LY, MS, MV, FM, TT, WN, WD, VG, VI, VM, VV | AI, IN, IG, IH, IS, LD, LG, LL, LV, FA, FV, WA, WC, WI, VA, VN, VC, VH, VF, VY | 0.11 |
| 287 + 300 | KC | AA, AE, AT, RE, RF, RW, NN, DA, DQ, DL, QF, GM, KH, KF, KY, PI, PK, PY, PV, TT | AG, AS, AV, RH, RM, RY, RV, DF, DP, DY, EF, GA, GR, KQ, KL, KT, PA, PQ, PT, SY | 0.11 |
| 303 + 305 | SA | AR, RD, NQ, NE, NK, DN, DE, EP, GG, GS, LA, FN, PR, PG, PK, PP, PT, PV, SD, VG | AN, AE, RS, NG, NP, DR, DG, DP, DV, EN, ET, GD, GP, PN, PD, PQ, PE, ST, TG, VD | 0.11 |
| 245 + 274 | HS | NA, NT, DS, QP, ES, GD, GG, GP, HG, LD, KR, KN, PA, PD, PQ, PE, PP, ST, TP | AD, AS, NS, DA, DD, DE, QS, EG, EP, GS, HP, LS, KE, PN, PG, PS, PT, SN, SP, TD | 0.11 |
| 268 + 317 | WH | AI, AK, RW, NQ, NH, NF, DA, HR, HF, LL, MQ, MV, FL, FS, SG, TN, WS, WY, YM, YS | RS, RT, RV, NA, NW, DR, QR, QF, GI, HS, HV, LQ, LI, MA, ML, SL, SY, TL, WQ, WG | 0.11 |
| 230 + 232 | IF | RV, DL, DY, IQ, IH, LI, MV, FL, SL, SM, TI, TL, TM, YL, YF, VQ, VE, VM, VY | AQ, HQ, IE, II, IL, IM, IV, LY, LV, MI, FI, SQ, TE, TF, TY, YQ, YY, VI, VL, VS | 0.11 |
| 203 + 213 | LT | AH, RK, NN, DG, GR, GN, GI, HA, HE, IN, LI, FR, FN, FP, PS, PT, TS, YS, VG, VV | AP, AS, NH, NT, DN, GA, GH, HH, IR, IH, IT, LR, FI, FL, FS, FV, PR, SS, TH | 0.11 |
| 49 + 58 | IL | IA, ID, IH, II, IV, LR, LL, LK, LM, MN, MI, MV, FA, FR, FC, WQ, WM, VI, VP, VT | IR, IC, IK, IM, LN, LD, LC, LI, LT, LV, MR, ML, FI, FM, WI, WV, VA, VQ, VL | 0.11 |
| 240 + 274 | DS | AG, AP, RD, NP, QN, QS, QT, ED, GN, GK, IR, LP, KN, MG, MT, TG, YN, VA, VD | AS, RA, RN, RP, NA, DP, QD, QG, QP, ET, GS, IN, LD, LS, LT, KT, FP, TS, VN, VT | 0.11 |
| 139 + 140 | ME | AS, AV, RE, RS, QA, EL, GG, HR, IP, LP, KA, MR, FP, PA, TG, WN, WD, WK, YR, YQ | AA, RK, QG, QP, IR, IS, LL, LT, KK, MQ, ML, FE, PP, SP, WA, WR, WL, YS, VA, VP | 0.11 |
| 193 + 216 | IS | AM, AW, CF, EF, HF, IL, LA, LN, LI, LT, LV, MI, FV, WD, WQ, WE, WH, VL, VY | AL, EL, ID, IQ, IY, LL, LF, MM, FI, FL, WA, WI, WL, WM, WF, WV, VN, VI, VW, VV | 0.11 |
| 119 + 248 | KE | AD, AS, RS, RT, DQ, DE, QE, EA, EE, GR, HV, IE, KK, PD, PH, SD, SE, SK, ST, TS | AE, RN, RE, RK, DS, DT, QQ, EH, ES, GE, GT, KR, KD, KH, KT, PK, SA, SS, TE | 0.11 |
| 142 + 146 | WK | AI, AP, AT, DK, CS, EV, LD, LP, MA, FQ, FE, FG, PA, SL, SV, TV, WD, WH, WF, WT | AD, AE, DA, LA, LS, LT, LV, MS, FA, FR, FT, FV, PP, PT, SE, SK, ST, WR, WL, WV | 0.11 |
| 236 + 240 | HD | AQ, AV, RS, NG, NL, DA, DR, QN, QG, EI, EL, EM, HQ, KG, PR, SD, SI, ST, TS, YE | AL, AF, RV, NR, NE, DI, DL, QI, QL, ER, ET, EV, GG, GI, PN, PQ, PG, SR, SQ, SE | 0.11 |
| 41 + 46 | IL | AA, AS, RL, DY, CF, QF, EL, GL, II, IF, IP, LL, LF, KM, FF, SF, TP, WL, VP, VV | AI, AL, AF, AP, DA, DF, EF, HL, HP, IA, LA, LV, MA, FA, TL, TF, VA, VL, VF, VY | 0.11 |
| 201 + 236 | SH | AN, AE, AV, RD, RG, RH, NA, NS, DH, DK, QA, ES, HQ, IE, KA, PP, SR, TP, TT, VP | AA, AD, AT, RE, RS, NE, DP, QP, EA, EH, EV, GA, GH, PN, PK, SQ, SV, TD, TE, TH | 0.11 |
| 198 + 203 | DL | AI, AP, RG, NS, DH, DF, DY, DV, QI, GG, GV, KN, KE, FP, PD, PC, PK, SP, VA, VF | AG, AF, NA, NR, NG, NA, DN, DQ, DG, DP, EL, GN, GI, GF, KG, PH, PI, PF, PY, PV | 0.11 |
| 280 + 287 | QK | AE, AG, RP, RT, DK, DT, QE, QP, EA, ER, EK, GS, LR, KN, KQ, KE, MK, SA, TD, TL | AQ, AS, RR, RN, RK, DE, QA, QS, ED, EQ, EE, IP, LE, KA, KP, KT, SR, TR, TE, VE | 0.11 |
| 236 + 245 | HH | AE, AS, ND, NK, DE, QQ, QG, QL, QK, ED, EP, ES, GA, GH, HR, PG, SA, SD, VA, VG | AG, RK, NA, NE, DK, DP, QA, QE, QS, EG, EH, EL, GD, GP, PT, SR, SQ, SE, VE | 0.11 |
| 134 + 191 | QK | AA, AP, NE, DG, EE, GQ, GP, IL, IK, LD, KP, MS, PQ, SS, ST, SV, TN, TQ, TK, VE | AV, NQ, DP, CK, GD, IR, LQ, LG, LP, MP, FA, FQ, SR, SQ, TE, TL, TS, VA, VQ, VP | 0.11 |
| 338 + 348 | EG | AL, AT, RE, RM, RV, DR, DI, QS, EQ, EI, GV, HI, HP, IE, IF, LA, KI, KY, SG, TV | AA, AI, RI, RT, NI, DD, DL, QE, QI, QV, ED, IN, II, LL, KR, KE, KV, SR, TI | 0.11 |
| 215 + 318 | AI | AS, AW, AV, NL, DM, QE, EW, EV, GF, HN, HQ, HL, IL, LR, LL, KL, SF, SY, TA, VM | AQ, AL, AF, NF, DR, QL, ER, EL, EY, GL, GT, GY, HA, HF, LF, KM, SI, TM, YF, VV | 0.11 |
| 177 + 180 | VS | AG, AK, RR, RH, RM, NK, DA, QR, QQ, GD, IR, IN, IE, LR, SQ, ST, TE, YL, VQ, | AA, RD, RQ, RS, RT, NQ, NS, DR, QE, QL, EG, HR, IK, LA, SR, SE, SS, TQ, VR, VG | 0.11 |
| 92 + 114 | LC | AT, AY, NV, CG, CT, IN, IG, II, LQ, LG, LM, MC, FA, FS, YS, VR, VG, VH, VF, VT | AA, AS, CS, IC, LH, LI, LF, LT, LY, FR, FG, FT, FV, TS, VA, VN, VQ, VI, VK, VS | 0.11 |
| 202 + 287 | SK | AQ, AE, NN, NH, DN, DG, DP, QA, EA, EL, GA, GE, KR, KK, PR, PK, SG, TQ, TE | AD, AK, AS, RA, RP, NA, NG, DA, DE, ER, EK, EP, ES, GN, GK, KA, KE, PN, SQ, TK | 0.11 |
| 196 + 198 | LD | AR, AD, AG, ND, NP, DH, DP, QA, EE, EL, GD, GQ, IE, LG, KE, SD, SK, TA, TG, VP | AN, AE, AL, AK, AP, AV, RG, NG, DD, QP, EP, GP, GS, ID, IG, LR, KD, KG, SE | 0.11 |
| 260 + 290 | KP | AR, AP, RL, DR, DK, QG, ER, EK, GA, IK, KA, KD, KI, KT, PH, PP, SN, SS, VG, VK | RR, NA, DN, EA, ED, EE, EG, ES, GR, GT, HK, IP, KK, PA, SR, SG, TK, TT, VR, VS | 0.11 |
| 269 + 273 | IW | AQ, AM, AF, AV, DL, CN, CM, AH, HH, IY, LL, LF, ME, FF, PS, SY, TF, TY, VL, VW | AL, AY, NW, CH, CL, IL, IM, IS, LH, LW, MF, FW, SI, SF, TW, VN, VQ, VM, VF, VY | 0.11 |
| 205 + 215 | TA | RC, RS, RV, QQ, ET, IQ, LN, LL, KG, KI, KL, MH, PS, SN, SG, TG, TS, TT, VA, VH | RD, RG, RT, RY, NL, NS, IH, LQ, LS, LT, KA, KQ, KH, KT, SM, TQ, TH, TL, VN, VI | 0.11 |
| 215 + 248 | AE | AR, AN, RH, RV, NQ, DR, QE, ED, ET, GS, HE, HV, IG, LV, MQ, FK, SE, TD, YE, VS | AD, RK, RT, NE, NS, EE, EK, ES, GT, HS, IR, LE, KK, FE, SR, SD, YQ, VQ, VE | 0.11 |
| 196 + 244 | LY | AR, AH, AL, AS, RR, DF, DV, EQ, GQ, GK, HA, LE, MI, ML, FG, SQ, YS, VT | AA, AQ, AI, AK, AT, AV, DQ, DL, DK, CL, QR, GL, GS, GY, LF, LS, SI, SK, YL, VR | 0.11 |
| 256 + 257 | ES | AG, AP, DA, DL, DV, QP, QT, QV, EH, ET, IP, KD, KQ, KM, SD, TD, TE, VR, VS | AD, AS, DN, DD, DP, DT, QE, QL, ED, EG, EL, EV, KA, KR, KL, KP, KV, SR, SE, TS | 0.11 |
| 250 + 258 | VV | AG, AL, RL, DY, QQ, QT, EF, IL, IW, IV, LA, LE, LI, MQ, MI, FL, TL, VF, VS, | RF, RV, QI, QW, QY, EL, HL, IY, LS, LV, KQ, KL, ML, MF, MV, FQ, TF, VA, VQ, VE | 0.11 |

TABLE Ts2-continued

| positions | most preferred | preferred, sorted in decreasing order of preference | to be avoided | score |
|---|---|---|---|---|
| 185 + 187 | HT | AD, AG, RQ, RL, DS, QM, IA, IT, LR, MS, MV, SQ, SI, TR, TM, WE, YR, YQ, YL, VA | AN, RR, RS, NK, QK, GQ, IR, IQ, LQ, LV, KR, MR, MN, MD, SE, SS, TN, TS, WA, VD | 0.11 |
| 321 + 339 | IA | AE, AG, RG, NA, NQ, NG, DD, QS, HG, HT, LR, LD, LE, MA, FK, SK, ST, TH, YD, YS | AA, RK, RS, NS, NT, QE, QK, ED, GR, HE, LG, LS, LT, MD, FA, FD, SD, VD, VQ | 0.11 |
| 195 + 342 | DK | AQ, AE, AS, AT, RR, RS, NN, NE, DA, EE, EK, GD, IR, LA, SR, SG, SI, SK, VN, VG | AR, AN, AK, RD, RE, RK, NA, NR, NK, DE, DS, ER, EQ, ET, GT, KE, SA, SQ, SE, ST | 0.11 |
| 320 + 321 | AI | AA, AL, IA, IE, IK, IM, LN, LH, LT, LW, LY, LV, MR, MQ, MI, ML, MW, VA, VN, VM | AN, AH, AM, AT, IQ, IL, IY, LA, LC, LE, LI, LL, LM, MA, MF, MS, MY, FR, FL, VV | 0.11 |
| 335 + 338 | KE | AR, AD, AQ, RR, RG, DK, QA, QL, EA, EG, EL, GE, KD, KL, KT, SN, SE, SF, VI | AG, AI, AK, AV, RI, RK, NA, ND, NQ, DE, QE, ER, EN, ED, GL, LE, KR, SA, SH, TT | 0.11 |
| 218 + 321 | NI | AH, AT, RL, NL, QF, QS, EG, EH, EW, LC, LP, KI, MN, FI, FY, SE, TG, TF, YE, VL | AL, AS, RE, RF, RT, QA, QQ, EF, EY, IG, LN, LH, LL, LY, KS, MF, MV, SI, TS, VV | 0.11 |
| 141 + 144 | SF | AA, AG, AS, GD, HR, IN, IS, LH, LY, MG, MY, FF, PD, PS, SA, SQ, SK, ST, TE, YH | AR, AD, AK, AY, GS, IE, LD, LK, LS, MQ, PA, PN, PG, PH, SR, SD, TR, TG, VS, VY | 0.11 |
| 204 + 280 | EQ | AA, AR, RS, RV, QQ, QL, EE, GA, GK, GM, KD, KK, KS, KT, MA, SN, SE, TR, VN, VS | AD, AQ, RK, QE, QK, QS, GR, GN, GS, IA, KR, KQ, PE, SA, SI, ST, TA, TK, VR, VK | 0.11 |
| 277 + 321 | LI | AV, RN, RH, DC, DG, DF, QM, QT, ET, HN, KQ, KE, KS, KT, SH, TQ, TE, TI, YQ, VN | AN, AS, NV, DN, DQ, DE, DT, QN, QE, EQ, EI, ES, GN, HH, HV, KG, KH, KV, SL, YH | 0.11 |
| 237 + 238 | VI | AR, AL, RY, EL, EM, GI, IT, LQ, LE, LL, KE, MM, SI, SV, TR, TI, VA, VC, VV | AA, DV, QI, GL, GV, IA, II, LI, LV, KV, FI, FV, PV, SL, VR, VQ, VE, VL, VM, VF | 0.11 |
| 218 + 304 | NE | AD, RR, RE, NP, CA, CP, QT, EA, GV, IN, ID, LA, LT, KS, MS, SG, SP, TE, YQ, VE | AT, CE, QE, ED, EE, GE, HE, IE, IP, IT, LS, KD, KP, MD, MG, SD, TP, VD, VP | 0.11 |
| 279 + 340 | LL | AA, AM, AV, RL, RW, DK, DM, QM, QW, EM, HA, II, IV, LR, KW, SL, TA, VI, VV | AL, AW, RA, RI, RM, RV, NL, DW, QA, QI, QL, GW, IA, IM, LI, LV, TW, VL, VM, VW | 0.11 |
| 179 + 212 | NG | AS, RN, NN, DG, DV, QN, QG, GA, GG, GF, HG, HS, IS, LA, MA, ML, FG, SA, SS | AA, AN, AG, RG, NA, NS, DA, DS, QS, GS, HA, HN, IN, LN, LG, MG, SG, TA, TS, VG | 0.11 |
| 133 + 184 | NN | RA, ND, DA, CV, QF, HT, IL, IM, LR, LE, LS, MS, FQ, PV, SG, TG, TV, YA, VL, VP | AN, AG, NV, DS, CE, QL, QT, EN, GG, HA, IG, LA, LG, MA, FS, SD, SE, TA, VE, VS | 0.11 |
| 202 + 242 | ST | AR, RN, NQ, DA, DE, DK, QK, QS, EG, EK, GH, GL, GV, HA, LQ, PD, PE, SI, SK, TR | AQ, AT, RR, NK, DR, DQ, QD, QP, QT, ER, ET, GQ, GK, GP, KI, PK, SE, TA, TD, TK | 0.11 |
| 183 + 244 | FY | AD, AT, AY, RA, RN, DL, QI, EP, GL, HI, HF, HY, IF, KR, KK, SE, TA, TD, WV, VS | AR, AF, AS, AV, RR, NA, DA, ET, GN, GF, HA, HN, KI, KL, SL, TQ, TH, TK, TS | 0.11 |
| 251 + 283 | GK | AQ, AG, AK, DR, DG, ER, EE, ET, GG, GT, HH, IK, KR, PR, PE, SQ, SS, TA, VD | AA, AR, AD, AS, EA, EG, EK, GR, GN, GQ, GE, IE, PA, PG, PK, SG, TT, VR, VQ, VK | 0.11 |
| 174 + 177 | FV | AE, RR, RN, DA, QG, QI, EW, HV, IV, LQ, LS, MR, MT, FE, FL, FK, FS, YD, VN, VM | AL, RG, RL, NR, DN, QR, QN, QD, QS, EK, IA, LN, LE, LG, MN, FR, FN, SV, TA, YE | 0.11 |
| 203 + 280 | LQ | AA, AR, RD, DQ, GA, GG, GH, HK, ID, LK, FE, FP, FS, PE, SA, SN, TR, WD, YH, VK | AN, AQ, AL, RA, RK, NT, GR, GE, GT, LL, LS, FR, FI, FV, PK, SQ, TK, TS, YR, VA | 0.11 |
| 244 + 268 | YW | AH, AM, RM, RS, NR, QN, EN, EQ, EM, IN, LL, KI, KL, FN, FG, FL, SW, TF, YH, VT | AN, AQ, AW, RR, RN, RL, NG, DH, ER, EY, IH, LQ, LW, KD, KH, FH, FS, TN, YQ, YM | 0.11 |
| 213 + 244 | TY | AR, AQ, AL, AT, RE, RL, NP, NT, QS, GR, HY, IY, IV, LH, PN, PS, SQ, TG, TK, TF | RN, RS, NK, NF, NY, QA, QT, HE, HI, HV, LT, PA, PQ, SR, SL, TN, TE, TL, TV, YE | 0.11 |
| 189 + 196 | TL | AA, NK, QR, QN, EE, ET, GA, GM, HG, IV, LD, KG, MG, PV, SW, TE, TT, TV, VA, VS | AG, AH, AT, RK, RS, DD, DV, QS, GL, IA, LA, LG, KA, MA, PG, SE, SK, ST, TA, TS | 0.11 |
| 192 + 342 | KK | AA, AR, AS, RA, RR, NT, QQ, EN, EK, GE, HT, PA, PT, SD, SS, TK, WE, YK, VE, VM | AE, AH, AT, RE, NK, DT, EA, EG, ET, GA, GS, HA, LR, KA, FR, PE, PK, SN, TS, VT | 0.11 |
| 146 + 148 | KA | AR, AN, AT, DT, EL, ES, GW, LT, KG, KI, MT, PL, PF, PY, SI, SS, SY, TA, VA, VV | AC, AH, AL, AM, AV, RA, ET, GT, HT, KS, KT, KY, PN, PG, PP, PT, SA, SV, TS, VG | 0.11 |
| 191 + 256 | KE | AA, AS, AT, RR, RD, NE, DE, QQ, EA, EH, EK, GQ, IT, KL, KK, MK, PD, PQ, PT, YE | AD, AQ, AK, RQ, RE, RS, DQ, DK, QA, QS, EQ, GT, KQ, PA, PE, PK, PS, SD, TE | 0.11 |
| 66 + 185 | QH | AQ, AG, AL, AV, RA, RD, RL, RW, NL, QF, ES, IV, LR, LS, KI, KF, MF, SN, SL, TF | AE, AL, AM, AF, RR, RN, RG, RF, QL, EA, EY, EV, LL, KD, KM, KS, KW, SQ, SF, TV | 0.11 |
| 184 + 298 | NA | AC, AH, AI, AT, RL, RV, NH, DS, DV, CG, QI, EV, GN, GH, LI, PA, SM, SV, TH, VD | AQ, AG, AV, QA, QS, EN, EH, EI, GD, GI, GL, GF, GT, HV, IV, LH, LL, SN, VA, VV | 0.11 |
| 205 + 290 | TP | RA, RE, RG, RS, DR, CP, EK, HP, HV, ID, LA, LD, KN, KE, KK, SN, SK, TN, TK | RR, RK, HA, HN, IK, LE, LP, LS, KR, KP, SA, SE, ST, TA, TG, TL, TV, VR, VD, VS | 0.11 |
| 113 + 115 | VK | AQ, RH, DA, QA, EL, EP, IQ, IS, IT, LR, LN, LE, LS, LT, FD, PE, TA, TK, VR, | AE, AL, DE, ER, EK, GR, HR, ID, IL, LQ, LH, LK, LP, MA, FA, FR, SA, TS, VN, VS | 0.11 |
| 318 + 327 | IL | RI, NS, ED, GL, ID, IF, IS, LL, LF, MC, FQ, FK, FM, ST, YQ, YT, YV, VG, VL, VY | NF, QT, GF, IE, IG, LQ, LE, LT, MH, ML, FA, FI, FF, FS, FY, SV, YL, YF, VF, VV | 0.11 |
| 168 + 185 | YH | AV, GA, GH, II, IS, IV, LD, LL, LT, ME, MI, MF, FG, FW, PH, SI, TM, YW, YV, VQ | AQ, AL, IA, IH, LR, LE, LI, LK, LS, LW, MA, MH, MT, FH, FV, WL, YS, YY, VR, VL | 0.11 |
| 298 + 318 | AI | AM, RF, CS, QT, GM, HS, HY, IM, IP, LA, LN, LL, KQ, MV, FG, FI, TF, VL, VS, VV | AE, AV, NA, DS, CM, QL, HV, IL, IF, LR, LQ, LM, LS, LY, MF, FL, SQ, SY, VR, VM | 0.11 |
| 290 + 300 | PC | AR, AQ, RA, RL, NK, DF, DV, GA, IV, LM, KN, KG, KI, KF, KY, PR, PL, ST, TN, TT | AL, AP, AV, RR, RT, RW, NF, NY, DI, DM, GT, KA, KR, KQ, KE, KL, PH, PF, SQ, TV | 0.11 |
| 231 + 241 | NA | AL, AT, AV, NN, NK, GA, IG, IT, IV, LA, LI, LS, LV, MV, SK, VC, VG, VM, VF, VT | AA, NT, CA, GV, IA, II, IS, LR, LC, LG, LL, LF, LT, MA, FA, VA, VI, VK, VY, VV | 0.11 |
| 194 + 224 | IH | AR, AN, AH, AT, RF, CF, HF, IN, IF, LD, LF, LY, FF, FY, TH, VN, VC, VE, VY, VV | AC, AF, AY, QY, IR, IY, LN, LH, LT, FN, FH, PN, PF, SY, TY, YF, VD, VL, VF, VS | 0.11 |
| 226 + 228 | SK | AT, RR, NL, NT, DD, DH, DP, QN, QK, ER, ET, GA, GR, GS, HE, HK, LQ, KN, KK, TQ | AN, RT, NR, NK, DR, DE, DK, QP, QS, QT, EN, EQ, EP, ES, GN, HQ, HH, HP, KR, KT | 0.1 |
| 204 + 226 | ES | AR, AD, RE, RH, RY, DE, QH, EA, GG, HN, HH, IN, KD, KG, ME, PD, SH, SS, TS, TW | AE, AG, RN, RG, RK, DG, EE, GD, GH, IH, IS, LH, KA, KR, KK, PN, SD, TN, TE, TH | 0.1 |
| 257 + 260 | SK | AP, NK, DE, DH, DP, EG, EI, EK, EV, LT, LV, KN, KE, PA, PR, PD, PQ, SE, SS, VV | AI, DA, DR, DQ, DV, ED, EE, ES, GP, LD, KS, PG, PK, PP, PS, PV, SD, SG, TT, VK | 0.1 |

TABLE Ts2-continued

| positions | most preferred | preferred, sorted in decreasing order of preference | to be avoided | score |
|---|---|---|---|---|
| 183 + 215 | FA | AL, RD, RH, RL, NN, DN, DS, GV, HC, HS, HT, IH, KH, SD, SG, TA, TE, TI, VQ, VM | AA, AN, AQ, AW, RI, RY, RV, NH, DL, DT, EG, HD, HH, HL, SA, SQ, SH, TD, TQ, VI | 0.1 |
| 240 + 324 | DV | AR, AC, RA, RC, RI, QI, EV, GV, HL, HM, II, LT, LV, KM, MV, SA, VA, VE, VL, VS | AI, AL, RN, RV, NV, QS, QT, EA, EL, GA, HA, IL, LA, LM, KA, KL, KV, SC, SI, VV | 0.1 |
| 228 + 243 | KT | AP, RA, RP, NK, NS, DQ, DK, EA, HV, KN, KD, KL, KK, PS, SR, SD, ST, TE, YE, VR | AK, RD, RK, NE, NP, QA, QR, ER, EN, EK, HK, KR, KP, KS, PA, PQ, SE, SK, TD | 0.1 |
| 183 + 203 | FL | AA, AQ, AI, RD, RG, NP, DN, QD, EP, HY, HV, KG, KL, SL, TH, TK, TF, TS, YA, VF | AG, AL, AP, AY, RH, RS, RV, NG, DA, QF, EA, HG, HP, KD, SE, SF, TG, TL, TP, VY | 0.1 |
| 242 + 283 | TK | AR, AK, RA, RR, NK, DR, DK, QQ, EA, EE, GA, IQ, LR, LS, KE, KP, KT, PQ, PG, TH | AN, AE, RG, RI, RS, DQ, DE, DS, QR, ER, EQ, EK, LK, KA, KR, KQ, MR, PA, SA, | 0.1 |
| 191 + 223 | KK | AR, RA, RE, NK, DL, DK, DM, DS, QQ, EA, ER, EM, GR, HV, IA, PA, SA, TQ, YK, VI | AA, AQ, AH, NR, DA, DN, DE, QR, EE, EK, GA, HR, LA, LS, KR, PR, PL, SR, TA, VR | 0.1 |
| 268 + 272 | WD | AM, RD, NC, NG, NL, NY, DY, QN, QC, GR, GE, HN, HM, IS, LH, FD, FE, SF, TG, WN | AD, NR, ND, NH, NF, NS, DE, DS, QD, GD, GS, HD, HY, MN, FN, SA, SH, TH, WH, VN | 0.1 |
| 239 + 321 | EI | AR, AE, AH, RI, NS, DH, DS, QA, EN, EG, EL, EV, GA, GY, IN, KH, PV, SY, TQ, TP | AI, AF, AS, AV, RS, NN, NI, NV, DF, ER, EH, EM, EW, GQ, KA, KI, KL, PL, SN, TV | 0.1 |
| 283 + 300 | KC | AG, AL, AY, RR, RH, RF, RV, NY, QF, ER, EQ, EM, GE, LW, KI, KL, KM, SQ, SP, TP | AH, AM, AF, RN, RG, RI, RL, RM, RP, QQ, QM, EA, ET, EW, GS, GY, KH, KV, SF, TH | 0.1 |
| 250 + 251 | VG | AP, CP, QA, EI, EV, GT, HE, IQ, IE, IG, IH, LA, LP, KQ, MA, ME, TS, VA, VC, | AA, QP, EQ, EE, EG, EP, HA, IR, II, IP, IV, LS, LV, KE, KG, MG, MV, VQ, VP, VT | 0.1 |
| 183 + 195 | FD | AR, AD, RD, RI, RK, RS, DT, QA, ET, GE, GK, HE, HT, KQ, TA, TG, TS, YA, YP, VE | AN, AQ, AE, AT, RA, RE, RG, RT, DD, QD, EP, GQ, GT, HA, HD, HK, KN, TE, TK, VK | 0.1 |
| 61 + 131 | SL | AQ, AL, AK, RS, DN, DV, QE, EK, EF, GR, GS, KD, KS, PR, PE, SG, SY, TR, YS, VL | AE, AG, AS, AY, DE, DL, DK, QA, QG, ER, EQ, EE, ET, EY, KL, KK, PL, PS, SI, TK | 0.1 |
| 240 + 334 | DE | AR, AF, RE, NL, DT, DV, QA, QK, QP, EE, GQ, GE, HR, IG, KE, ML, SL, ST, TP, VF | AL, RR, NE, DA, QE, QF, QV, EA, GK, IE, II, IL, IK, IF, LR, LK, KP, SP, SV, VE | 0.1 |
| 284 + 288 | NS | AS, RA, RS, RT, RW, NA, NG, NM, QV, EV, GR, GL, HA, LK, KA, KK, KW, TH, TL, TS | AT, AV, RL, RK, RV, NR, NL, NV, QS, EA, ES, GA, HG, KR, KG, KL, KV, TA, TV | 0.1 |
| 185 + 240 | HD | AE, RA, RI, DS, CQ, QS, ED, GI, HT, IQ, LA, LK, MG, FQ, SD, TT, WI, YN, YI, VM | RE, RS, RT, DL, QG, GR, HV, IS, LQ, LG, LI, LS, MA, MD, FN, FD, SK, SS, YA, VS | 0.1 |
| 277 + 335 | LK | RR, RD, ND, NE, DA, DG, QK, QS, EE, GE, HD, LE, KN, MD, SA, TK, YD, YL, VA, VK | AN, AD, RQ, RK, DR, DS, DK, QD, QE, QG, EA, EK, GA, HS, LG, KA, KG, SE, YK, VE | 0.1 |
| 133 + 137 | NV | NM, DF, QI, EG, EI, GA, HH, IS, IV, LP, ML, FN, FS, FV, TA, YA, YE, VT, VW | AL, NE, NS, QD, ET, EV, HI, IR, LF, ME, MV, FL, SA, SL, SF, SS, ST, YG, YT, VV | 0.1 |
| 48 + 67 | TL | AI, AT, AV, RV, DR, DH, EL, HT, IC, IT, LA, LL, LS, LT, KL, KY, MT, FF, FS, | AC, AL, AS, RT, DL, ET, HL, HV, IS, IV, LC, LI, LV, KA, KT, FL, FT, TA, YL, VA | 0.1 |
| 129 + 305 | LA | AD, AG, RT, NQ, DD, IN, LE, LH, MN, MT, FQ, TP, WA, WG, WP, YA, YE, YT, VP | AA, AR, AP, HT, IR, IT, LD, LG, LV, MD, MK, MP, FN, SP, TD, WE, WT, YN, YK, VD | 0.1 |
| 146 + 147 | KD | AA, AR, AD, RQ, RK, DY, EA, GD, GE, GK, HE, IE, LD, LH, KE, PE, SS, TE, VE, VP | AH, AP, AS, AY, RD, DD, DE, QE, EE, GQ, GS, LR, LE, KQ, ME, PD, SN, SE, VQ | 0.1 |
| 229 + 230 | GI | AI, AV, CH, CF, CS, GA, GL, GV, II, IT, LK, LV, FE, FV, PE, YY, VD, VM, VT | CI, CV, GD, GE, GH, GM, GT, GY, IY, IV, LA, LI, MT, FA, SV, YI, VA, VQ, VI, VV | 0.1 |
| 112 + 113 | PV | AA, AS, RI, RL, RP, NR, DT, DV, EA, EL, EK, GL, KT, PE, PG, PH, SV, TA, VD | AE, AH, AL, AV, RA, RK, RV, DA, DR, EM, EF, ES, ET, GA, KI, PI, PK, PT, SE, VL | 0.1 |
| 243 + 277 | TL | AI, RA, RR, DD, DV, QA, QR, EE, EG, ES, ET, EY, LQ, KQ, KE, KT, SK, VG, VK, VV | AT, RE, RK, NE, DE, QD, QQ, QK, EA, ED, EI, EK, GQ, LE, KA, KR, KK, KV, PR, VQ | 0.1 |
| 50 + 51 | AK | AA, AG, AH, RE, DA, QN, QG, EK, ES, ET, GD, LA, LE, KN, PI, PL, PT, VA, VD | AN, AT, RA, DN, QD, ED, EE, GA, GG, GK, HD, KQ, PD, PE, PK, PS, SE, TA, TD, VK | 0.1 |
| 222 + 338 | SE | AR, AQ, RA, RE, RS, NT, DL, QA, QQ, QG, QM, EE, GT, LR, KK, KV, PI, SD, SL, TD | AE, AK, AT, RD, RH, RL, RK, QR, QD, QI, QL, QT, ER, ES, GA, HE, LA, KA, KN, KQ | 0.1 |
| 240 + 277 | DL | AE, RK, RS, NQ, DD, DY, QQ, EK, GD, ID, LN, KK, ME, FM, PD, SG, SV, TD, VA, VT | AD, AS, RT, NK, DA, DQ, QK, ED, EQ, GQ, IQ, IE, IK, LA, LE, KR, KE, FK, VD, VY | 0.1 |
| 183 + 189 | FT | AR, AM, AF, AV, RS, NG, NI, QA, EP, GA, HP, HT, IT, SD, SQ, TE, TL, WP, YL, VT | AA, AN, AQ, AH, RA, RI, RM, QE, EA, EK, ET, GD, GV, HF, KA, SP, ST, TI, VD, VS | 0.1 |
| 59 + 60 | SS | RV, NA, NQ, DI, DL, EL, HI, HY, HV, KV, PL, PV, SC, SL, SY, TA, TF, TP, TS | AS, NL, DA, GL, HA, HL, HS, LV, KA, PA, PS, PY, SE, SP, ST, SV, TQ, TI, TL, TY | 0.1 |
| 119 + 127 | KA | AR, RG, NV, DA, DQ, DS, ER, EK, HF, LG, KG, KY, KV, PG, SA, SH, SV, TE, TL, VT | AG, RT, NG, DY, EG, GL, IR, KR, KL, PR, PL, SR, SE, SL, SF, TA, TQ, TG, TK | 0.1 |
| 33 + 89 | LY | AL, RL, RT, DQ, QL, QM, EM, IA, IV, LG, LH, KV, FH, TA, TR, TS, YI, VC, VF, VY | AE, AS, DA, DF, DV, QH, EH, EL, GL, IR, II, IM, LI, LL, KA, TL, TM, TF, VL, VM | 0.1 |
| 183 + 218 | FN | AA, AR, AG, RE, NV, DA, ER, GN, HI, IL, IM, KE, MK, FI, FK, SI, TQ, TS, WV, VG | AQ, AE, AI, AL, AM, RR, RN, NL, DI, QV, EQ, GR, GE, GI, SS, TA, TR, TV, VA, VR | 0.1 |
| 190 + 213 | MT | AQ, AE, AI, AS, RR, NQ, NI, QA, QL, EA, GT, LY, MM, MS, ST, TL, TM, YT, VH, VS | AL, AK, AT, RS, QR, QH, ET, GQ, IN, IE, II, LS, LT, SR, TA, TP, TS, TT, VE | 0.1 |
| 242 + 243 | TT | AK, RQ, NN, DE, DG, QQ, QA, QK, ER, EK, EF, GL, LA, KN, KD, KG, KS, PA, PP, TG, TS | AE, RD, RG, RK, DA, DD, QT, EE, ES, KA, KQ, KP, KV, PR, PK, SE, SK, TE, TP, VE | 0.1 |
| 324 + 327 | VL | AN, AG, AP, RS, NR, CV, QH, QL, EF, GY, HT, IE, IV, LG, SI, SF, TL, WR, VC, | AF, AT, RL, CT, GT, IG, IF, LL, LF, LP, FL, SC, SV, TM, TV, VG, VI, VF, VS, VT | 0.1 |
| 334 + 339 | EA | AA, AL, AT, RS, QR, EN, EE, EK, ID, LA, LT, KN, KE, KK, LG, FK, PS, SG, SK, VR | AR, AN, AD, AG, RA, RK, QE, ER, ES, ET, IA, LR, LE, GN, FD, FQ, PQ, PK, SD, VN, VE | 0.1 |
| 240 + 306 | DP | AR, AQ, RP, ND, QE, EP, GV, ID, IK, LD, LS, KN, KI, MP, FR, SA, TQ, TG, VR, VL | AG, AK, RD, NG, QK, ER, GP, HK, IP, LA, LL, KE, KG, KS, FG, SR, SD, TR, TP, VD | 0.1 |
| 87 + 92 | AL | AI, AY, AV, RI, CA, CF, QV, EI, EV, GL, HL, IF, LI, LV, KV, MF, TA, TF, VL | AA, AF, AT, RL, RF, DL, DF, CV, QL, QF, EL, GF, II, IV, LL, KL, ML, TV, VI, VV | 0.1 |
| 175 + 213 | NT | AR, AN, AP, RI, QL, EY, GN, GH, LR, LI, LV, KQ, MF, FT, SD, SH, TS, WH, YT, VP | AI, AV, RT, NN, ND, QN, EP, ES, GR, GL, GP, IH, LN, LH, LL, KT, MR, SR, SS, TI | 0.1 |

TABLE Ts2-continued

| positions | most preferred | preferred, sorted in decreasing order of preference | to be avoided | score |
|---|---|---|---|---|
| 277 + 318 | LI | AR, RL, RS, NI, DA, DD, DM, DV, QI, QV, EC, EE, HR, HM, IF, KM, FM, SF, TM, VL | AM, RR, RM, DQ, DG, DI, DL, DF, DW, DY, QM, QF, EA, EG, GL, HL, KR, KN, KF, ML | 0.1 |
| 274 + 330 | SK | AM, AF, RP, NR, NK, DR, DD, ES, GA, GK, LR, KV, PH, PL, PM, PS, SQ, SG, SS, TA | AR, AQ, AK, NG, NH, NS, DE, DI, DL, DS, GS, PR, PD, PK, PF, SA, SR, SH, SL, | 0.1 |
| 266 + 268 | MW | AG, AS, NA, CF, IQ, IH, LA, LN, LD, MN, FR, FN, SL, SF, SS, SY, YH, VH, VM | AN, AH, IN, IL, IM, LC, LQ, LM, LW, MA, MH, MS, FD, SA, SN, SG, SH, TN, VL, VS | 0.1 |
| 216 + 256 | SE | AD, AE, NA, NE, DT, IV, LA, LD, LG, LH, LS, MQ, ME, FE, FK, WD, YK, YT, VR, VS | AQ, AK, NQ, DE, DK, QT, IA, IS, LQ, LE, LT, MS, MT, FR, FD, SD, TD, YA, YD, VA | 0.1 |
| 107 + 109 | FG | RA, RR, RG, RV, EL, EY, GR, GV, IK, LG, LL, LS, KK, TA, TR, WG, YN, YS, VA, VT | RC, RE, RK, RS, RT, QA, ES, EV, GG, LA, LE, LT, KR, FR, SE, TG, TI, TL, YR, YV | 0.1 |
| 201 + 239 | SE | AQ, AT, RA, NI, DN, DD, QE, EQ, EK, GG, GL, GP, HS, KA, KN, PT, TK, TS, VD | AN, AE, AL, RD, RP, DA, DR, QN, EE, GA, GQ, GS, KK, KS, PE, SD, SS, ST, TD, TE | 0.1 |
| 190 + 216 | MS | AF, AY, RD, DL, EQ, II, LF, LV, KM, MA, FA, FL, PV, SF, ST, TN, TY, YL, VA, VT | AA, AD, AT, AV, RL, RF, NV, QL, EF, GI, IA, LL, KL, MY, PL, SA, SI, TI, TF, VS | 0.1 |
| 175 + 185 | NH | AN, AF, NF, DH, DV, QG, EA, EI, GV, LQ, LS, KL, MA, SQ, SH, SF, TL, TV, YN, VV | AA, AD, AH, AL, AY, QL, GA, GL, GT, LN, LV, MI, FS, SA, SN, SL, TI, TS, YL, VL | 0.1 |
| 185 + 268 | HW | RS, QR, QN, GR, GT, GY, HN, IQ, LF, KE, FN, FT, PA, SR, SE, TR, YH, YS, VQ, VH | RR, RW, DN, QH, QW, GH, GS, IR, IF, LR, LN, MS, FR, FL, SM, TH, TS, VN, VD, VF | 0.1 |
| 93 + 236 | TH | AE, AL, RA, RT, RV, DQ, QP, ES, ET, HY, KE, KK, FE, SD, SH, TR, TN, TG, YG, VG | AS, RP, DN, DH, QQ, QE, EQ, EG, EH, EL, EK, EP, LE, LP, KD, SG, SP, TA, TE, VE | 0.1 |
| 50 + 110 | AV | AL, RL, RP, NI, NL, DV, EN, EK, GN, HL, LI, KT, FH, PH, SN, SL, SS, TA, WL, VP | AH, AS, AT, RN, RH, DL, QL, EL, EV, HH, LN, KA, PA, PN, PL, SH, SP, TL, VN, VH | 0.1 |
| 222 + 244 | SY | AR, AE, AL, RG, RP, NS, QF, QY, ER, EK, ET, GE, HG, LL, KN, KP, KS, KV, TE | AA, AN, RH, RK, NF, NY, QE, EN, EE, EL, EF, ES, EV, GT, LK, KE, KH, KT, SL, SS | 0.1 |
| 167 + 171 | YD | AD, RD, RS, DT, QA, ED, HL, IN, IE, MD, FN, TD, WR, WN, WK, WP, YR, YN, YS, VQ | AN, RN, RE, DN, DD, EH, HR, IH, FE, TH, WD, WG, WM, WV, WF, WS, YK, YM, YS, YY | 0.1 |
| 200 + 203 | FL | AE, DR, QP, EA, EP, LR, LG, LS, KP, FH, FI, FM, FF, FY, PA, TN, WL, WV, YV, VG | AV, EF, IA, LE, LL, LP, KG, FR, FN, FE, FG, FP, FS, PF, PV, WA, WR, WG, WI, VF | 0.1 |
| 191 + 300 | KC | AV, RI, RL, DY, CA, QA, EH, ES, EW, GI, LQ, KR, KF, PE, PM, SI, SP, TM, VM, VT | AI, AM, AF, RM, NV, DF, DP, QY, EA, ER, EQ, EM, GS, GT, KA, KM, PH, PV, SF, TI | 0.1 |
| 239 + 240 | ED | AQ, AE, AT, RR, RN, RV, DM, DS, QK, ER, EN, EQ, EH, GL, KI, PH, PF, ST, TL, TK | AA, AK, RK, DQ, DI, QR, QN, QD, EF, ES, KR, KQ, KE, KS, PR, PN, PD, PE, SL, TS | 0.1 |
| 93 + 146 | TK | AD, RQ, RT, NP, DL, CV, QL, EE, GR, HL, IK, LA, KA, KP, SP, SS, TE, TP, VP, VT | AR, AL, RA, RK, RP, DE, DG, EP, ES, IL, IP, LV, KR, KT, SA, SD, SK, TL, VA | 0.1 |
| 213 + 267 | TK | AS, AV, RA, RK, NC, DI, DL, QQ, QK, HF, LR, PR, PS, SS, TA, TS, TT, YK, VG, VF | AK, AR, RH, RS, NT, HA, HR, HG, HS, IK, LS, KR, KK, FS, SR, ST, TR, TF, VS | 0.1 |
| 177 + 179 | VN | AR, AN, AQ, RA, RG, NN, NI, NL, DH, DI, QA, QV, EF, GT, HN, LD, LS, TA, TQ, VS | AL, RD, RH, RP, NQ, NS, DA, DN, DG, QD, QQ, QG, QS, EH, GN, HS, LH, LI, TS, VA | 0.1 |
| 197 + 200 | YF | AL, GN, HF, IR, IL, IS, LA, LL, LP, LT, FW, TE, YD, YE, YG, YW, VL, VK, VP | AW, EF, GW, HL, II, IF, IW, LG, LM, LF, FA, FL, PL, YR, YL, YP, YT, YV, VF, VW | 0.1 |
| 195 + 196 | DL | AA, AE, RR, NN, NG, DI, DF, QG, EH, EI, EK, ET, GL, GM, KM, PV, SK, TA, TD | AR, AI, AM, RN, RD, DA, DD, DS, DT, EA, ED, EE, EL, EV, GG, HA, KG, SN, TH, TK | 0.1 |
| 215 + 277 | AL | AE, AK, RA, NL, DH, QA, QN, EL, GN, GD, GQ, HR, IE, LE, SD, TA, TR, TV, YD, YK | AN, AD, AT, NA, QE, GR, GK, GV, HD, HL, IQ, LA, LD, LT, SA, SN, SK, TD, TE, VE | 0.1 |
| 106 + 107 | RF | AY, RG, RS, RV, NQ, NT, DR, DE, DK, DT, QG, QT, ET, GA, GR, GI, GY, KL, SL, TG | AT, RK, NR, NG, DQ, DI, DL, DF, DY, QL, ER, EH, EL, EY, GE, GG, GT, KT, SR, SK | 0.1 |
| 277 + 286 | LY | AH, AV, RW, NS, NY, DR, DH, DK, QR, ER, EG, HY, IF, KE, KF, KS, SK, TV, YI, VA | AR, AK, RI, NR, NK, DF, DY, DV, QV, HH, HK, LA, KA, KR, KH, KL, SY, TR, VR, VI | 0.1 |
| 218 + 298 | NA | AW, AY, RA, RT, CC, QG, GV, ID, IH, IK, LC, LH, LV, KL, MA, MQ, MH, FT, SI, VM | AC, AQ, AH, QI, QV, EH, GL, IC, II, IY, IV, LA, LT, LY, MS, YA, YV, VC, VI, VV | 0.1 |
| 218 + 317 | NH | AR, AD, AG, AL, RL, RF, NI, DE, QM, EG, GA, IA, IS, IV, LQ, KI, MR, FN, SF, VG | AA, AI, AW, QA, EV, IH, II, IL, IF, LE, LG, LV, KM, MA, ML, SL, SV, VE, VL, VW | 0.1 |
| 204 + 300 | EC | AE, RR, RW, QA, ER, EP, ES, GG, GI, GV, HS, II, KK, PM, PV, SH, ST, TY, VI, VW | AR, AT, AV, RQ, RM, QV, EI, EV, GH, GM, GY, KI, KF, KV, SA, SI, TA, VA, VM, VS | 0.1 |
| 191 + 244 | KY | AR, AE, AH, AP, RG, NK, DG, DK, CN, QA, ER, EN, ES, GR, IY, KQ, PL, PF, PS, TP | AN, AS, RR, RN, RQ, RS, DA, DH, DY, EL, EP, GK, GY, LE, KR, KT, PA, PQ, PE, SR | 0.1 |
| 142 + 321 | WI | AE, RL, CM, EM, IW, LA, LI, LP, LY, MA, ML, FG, FL, FF, FY, PA, WN, WD, WH, YD | AG, LN, LH, LL, MN, MV, FM, FV, PH, PY, SA, SF, WA, WL, WM, WF, WP, WV, VM | 0.1 |
| 58 + 59 | LS | AD, AT, RN, RT, QE, QK, QS, GT, IA, IS, LR, LH, LP, KT, MT, SG, TA, VP, VS | AH, AP, RR, HT, IT, LA, LN, LE, LL, LT, KP, KS, MS, PS, PT, ST, TN, TD, TS, VT | 0.1 |
| 244 + 339 | YA | AS, RA, RD, NQ, QR, EE, GD, HV, IR, IK, LK, KQ, KG, MA, FS, PR, PE, SD, TQ, VD | RG, RK, RT, ND, NE, DD, EA, HS, IA, ID, LR, LQ, KA, KK, FN, PQ, SR, TD, TS, VE | 0.1 |
| 215 + 298 | AA | AI, AY, NA, NG, NY, QS, EA, GL, GT, HN, HM, HV, ML, FV, ST, SV, TH, WW, VI, VF | AN, AL, AV, RV, NV, DA, QF, EH, GA, HL, HF, IA, LH, LL, SS, TF, TS, WV, VM | 0.1 |
| 300 + 343 | CA | AK, RA, NR, NE, QD, QQ, GG, HE, IQ, IE, IS, LG, MA, MQ, FA, FS, SK, TA, WE, VR | AD, RQ, NA, NS, EA, IA, IG, IK, LQ, MR, MS, FR, FQ, FE, PE, SD, SQ, WK, YR, VG | 0.1 |
| 271 + 299 | HE | AE, RD, RE, NN, DS, CD, QG, QS, EA, GT, HD, LD, MD, PG, SQ, TE, YH, YT, VS | NE, DD, CE, QD, EE, GD, HN, HG, HH, HI, HK, HS, HT, PD, PE, SE, TD, YD, YE, YG | 0.1 |
| 204 + 251 | EG | AA, AK, RG, NS, DV, QV, EA, GR, GP, GT, II, LA, LP, KG, ME, PA, SS, TG, TI, VK | AQ, AS, AV, RP, NP, EP, GA, GI, IA, LE, KK, KV, MA, PS, PT, SE, SV, TA, TE, VK | 0.1 |
| 185 + 239 | HE | RN, NN, NP, DA, DD, QD, QS, ER, HK, IP, LE, ME, MI, FG, FK, TE, YA, YD, VS | AA, AE, RQ, RG, QA, ED, HA, ID, IS, LN, LK, MD, MK, FD, FE, SE, TA, YS, VK | 0.1 |
| 162 + 166 | ME | AE, AV, RD, ND, DS, DT, CE, EQ, ET, GA, LE, KE, MQ, ST, TA, TR, TP, TS, YD, VE | RQ, RS, DA, DD, DE, QT, ED, EE, GQ, LA, LS, LT, KA, KS, KT, SD, TD, TE, TT, VS | 0.1 |
| 205 + 260 | TK | AQ, RT, NN, CP, QA, HQ, HE, IA, LV, KD, KS, MV, FI, SN, SK, SS, TG, TV, VI, VP | AE, RR, RI, RK, NE, QG, QV, HR, HP, LK, LS, KA, KN, KQ, SR, SG, TD, VA, VE, VG | 0.1 |

TABLE Ts2-continued

| positions | most preferred | preferred, sorted in decreasing order of preference | to be avoided | score |
|---|---|---|---|---|
| 183 + 192 | FK | AR, AV, RG, RT, DE, DS, QG, EL, GQ, HA, MP, FA, SD, SQ, SG, SF, TA, TN, VA, VD | AN, AQ, AG, AK, RL, NE, DA, QA, QQ, QP, ER, EE, GV, HD, HP, KA, KE, MA, SA, SS | 0.1 |
| 176 + 219 | KM | AA, AG, RQ, RL, NL, DE, DS, QK, EE, IA, LA, KD, KQ, KK, KY, KV, PA, SE, TT, VL | AD, AQ, AL, AV, RE, RS, RY, NE, DL, QG, EA, EQ, EV, KA, KE, KS, PE, SA, TE, VA | 0.1 |
| 206 + 220 | LI | AL, NR, CL, II, IL, LA, LF, LT, MA, MF, MV, FA, FS, FV, TG, YF, VI, VM, VV | AA, AI, AF, AV, CF, IA, IM, IT, IV, LL, LM, LS, LV, ML, FI, FM, FF, VA, VL, VF | 0.1 |
| 192 + 194 | KI | AA, RA, RI, NV, DA, DL, EL, HI, HV, KF, FA, PT, SE, SI, SM, TI, TL, WL, VR | AE, AM, RL, NA, QL, EF, EV, GI, HA, LI, KL, MV, FL, PA, SF, SV, TA, YL, VL, VV | 0.1 |
| 298 + 342 | AK | AR, AH, NN, NK, DD, CA, QR, ET, HR, HE, HT, IK, LL, MA, SD, TS, WE, VA, VG, VS | AQ, AE, AT, NQ, NT, GT, HA, HK, IA, IR, IL, LR, LK, LT, ME, SG, YE, VD, VE, VK | 0.1 |
| 204 + 347 | EK | AR, AQ, AH, RR, RG, DD, DS, EQ, EE, GR, GS, GT, HR, LD, KK, MK, PR, PT, SK, SS | AK, AS, AT, RE, RK, DA, DR, QR, EA, HK, HS, LS, KA, KR, KE, KV, SR, SG, ST, VR | 0.1 |
| 133 + 176 | NK | AR, RQ, NR, NL, CN, QA, QD, GG, HE, LR, LG, LL, LT, KE, MR, MH, FQ, FK, VA | AN, AK, NE, NS, CR, QR, HA, HT, LQ, LE, LK, MA, ME, FA, FD, FS, SG, TR, VR, VG | 0.1 |
| 204 + 245 | EH | AW, RA, RE, DD, DH, QQ, EE, GA, GS, HT, IG, IK, LH, KD, KI, MR, PE, TD, TV, VA | AD, AE, AK, RD, DE, QH, QK, ED, EG, ES, GN, GD, GQ, IA, KA, KP, PH, PT, TA, TK | 0.1 |
| 107 + 115 | FK | AD, AS, RR, RE, RP, RY, QE, ET, GR, HH, IR, LL, KQ, KK, SR, TH, TK, VE, VI, VS | AE, AK, RA, RN, RQ, RK, RS, RT, GK, HR, HE, IK, KR, KE, FE, TR, TE, VR, VL, VP | 0.1 |
| 175 + 177 | NV | RI, NS, QA, QN, EI, EL, GR, HA, IN, LP, KQ, KT, FE, TR, TL, WD, WT, VR, VV | AE, AV, RR, RT, NA, NR, DR, DI, QR, ER, GI, GT, IL, LA, LG, LV, MI, ML, VQ, VT | 0.1 |
| 204 + 244 | EY | AA, RR, NS, DK, QR, QE, EI, GT, IL, IF, LY, KF, KV, PI, SN, SH, SV, TE, TG, VN | AR, AD, AK, AS, AY, NR, EV, GN, GE, GH, LA, KR, KH, KL, SA, SK, TK, TT, TY, VI | 0.1 |
| 226 + 236 | SH | AP, RA, NA, DQ, DP, CP, QQ, QS, QT, EA, EG, GG, GP, HN, HE, HH, KD, SC, SE, TK | AS, NQ, NP, DD, DE, DS, DT, QD, QE, EQ, GN, GD, HD, HG, HP, HT, KA, KG, KH, SP | 0.1 |
| 196 + 321 | LI | AR, AE, AT, AV, RH, RF, QA, EA, EL, GT, HM, IT, LN, KN, KL, FW, SQ, TS, VN, VQ | AA, AN, AQ, AF, NL, QN, EN, GA, GR, GL, GV, HV, IA, LH, FL, SM, ST, SY, TH, VS | 0.1 |
| 283 + 286 | KY | AA, RI, RY, RV, NY, DR, QT, EG, EK, EY, GR, GH, HL, IA, KH, KV, SA, SS, TR | AR, AH, AS, AY, RK, RF, DA, QR, QH, EA, GK, GY, KA, KR, KC, SI, SL, ST, TA, TV | 0.1 |
| 180 + 236 | SH | AA, AD, NN, ND, DE, DK, CG, QA, QQ, QH, EQ, EK, GD, GH, GT, KE, ME, SE, SG, TV | AN, AQ, AG, AH, AT, RA, RG, RS, NQ, NE, DQ, DG, QE, QV, EG, EP, GK, GP, KH, SA | 0.1 |
| 203 + 226 | LS | AD, RN, RG, NN, ND, DR, DG, EK, GA, GR, GK, LD, KD, KQ, KE, FN, PS, TE, VH | AN, AK, RQ, NH, DN, DD, GD, GQ, GS, IG, LG, KH, KS, FH, SN, TD, TK, VR, VN, VD | 0.1 |
| 203 + 216 | LS | AY, DI, ED, GA, GG, GP, GS, GT, HL, LI, LL, KF, FL, FF, PY, SM, YL, VC, VT, VV | AL, RL, RF, DL, EL, GH, GI, GL, GM, GF, HV, IF, LQ, KV, ML, FY, SA, SV, VA, VD | 0.1 |
| 286 + 298 | YA | AA, AI, RH, RI, RL, RV, HL, HV, LM, LV, KI, SE, SF, SV, YK, YY, YV, VN, VD, VM | AH, AL, AV, RA, RD, RE, RK, CI, GV, HI, LN, KH, KF, KV, FV, SI, YH, VA, VV | 0.1 |
| 303 + 306 | SP | AP, RG, NR, NH, NK, DR, DH, QR, QV, EQ, EM, EP, GS, IN, LT, PA, PG, SD, VA | NN, NG, NP, DA, DG, DP, ED, EG, ES, GN, GG, GL, PR, PH, PK, PM, PP, PS, SE, SG | 0.1 |
| 205 + 218 | TN | AL, NE, ES, IN, LR, LH, LK, KC, KI, KL, MA, SQ, SH, SK, TR, TG, TT, VE, VM, VS | AR, AI, RN, NL, HR, HK, IL, LA, LM, KR, KE, KS, SR, SE, SI, SL, TQ, TK, TV, VI | 0.1 |

The invention claimed is:

1. A method for conferring, increasing or modifying resistance in a plant, a plant part, or a plant cell as compared to a wild type plant, a wild type plant part or a wild type plant cell against soybean rust, comprising providing a transgenic plant, plant part or plant cell comprising an exogenous nucleic acid encoding an O-methyltransferase 3 (OMT3) protein having 100% identity to SEQ ID NO: 2, wherein the transgenic plant, plant part or plant cell produces scoparone.

2. The method of claim 1, wherein said plant is more resistant than said wildtype plant to infection caused by soybean rust.

* * * * *